US012173343B2

(12) United States Patent
Gabant

(10) Patent No.: US 12,173,343 B2
(45) Date of Patent: Dec. 24, 2024

(54) ENGINEERING ANTIMICROBIAL PEPTIDES

(71) Applicant: Syngulon SA, Seraing (BE)

(72) Inventor: Philippe Gabant, Ottignies Louvain-La-Neuve (BE)

(73) Assignee: Syngulon SA, Seraing (BE)

( * ) Notice: Subject to any disclaimer, the term of this patent is extended or adjusted under 35 U.S.C. 154(b) by 187 days.

(21) Appl. No.: 16/972,553

(22) PCT Filed: Jun. 5, 2019

(86) PCT No.: PCT/US2019/035666
§ 371 (c)(1),
(2) Date: Dec. 4, 2020

(87) PCT Pub. No.: WO2019/236761
PCT Pub. Date: Dec. 12, 2019

(65) Prior Publication Data

US 2021/0238645 A1 Aug. 5, 2021

Related U.S. Application Data

(60) Provisional application No. 62/681,529, filed on Jun. 6, 2018.

(51) Int. Cl.

| | |
|---|---|
| ***C12Q 1/6869*** | (2018.01) |
| ***A61K 35/74*** | (2015.01) |
| ***C07K 14/195*** | (2006.01) |
| ***C12P 21/02*** | (2006.01) |

(52) U.S. Cl.
CPC ............ *C12P 21/02* (2013.01); *C07K 14/195* (2013.01)

(58) Field of Classification Search
CPC ........... G01N 2500/00; G01N 2500/10; G01N 2500/20; C12Q 1/6869; A61K 35/66
See application file for complete search history.

(56) References Cited

U.S. PATENT DOCUMENTS

| | | | |
|---|---|---|---|
| 5,910,438 | A | 6/1999 | Bernard et al. |
| 6,180,407 | B1 | 1/2001 | Bernard et al. |
| 6,653,124 | B1 | 11/2003 | Freeman |
| 7,176,029 | B2 | 2/2007 | Bernard et al. |
| 7,183,097 | B1 | 2/2007 | Gerdes et al. |
| 8,835,604 | B2 | 9/2014 | Hoegenhaug et al. |
| 9,333,227 | B2 | 5/2016 | Gabant |
| 10,188,114 | B2 | 1/2019 | Gabant |
| 11,427,800 | B2 | 8/2022 | Gabant |
| 11,492,651 | B2 | 11/2022 | Gabant |
| 2001/0039014 | A1 | 11/2001 | Bass et al. |
| 2003/0033088 | A1 | 2/2003 | Agrafiotis et al. |
| 2004/0052814 | A1 | 3/2004 | Shi et al. |
| 2009/0118132 | A1 | 5/2009 | Haferlach et al. |
| 2010/0076173 | A1 | 3/2010 | Stephanopoulos et al. |
| 2013/0052182 | A1 | 2/2013 | Miller |
| 2015/0050253 | A1 | 2/2015 | Gabant |
| 2016/0002611 | A1 | 1/2016 | Mershin et al. |
| 2017/0282133 | A1 | 10/2017 | Griffiths et al. |
| 2018/0135095 | A1 | 5/2018 | Davies et al. |
| 2018/0237847 | A1* | 8/2018 | Culler ...................... C12N 5/16 |
| 2019/0191709 | A1 | 6/2019 | Gabant |
| 2020/0263221 | A1 | 8/2020 | Gabant |
| 2021/0070812 | A1 | 3/2021 | Gabant et al. |
| 2021/0238645 | A1 | 8/2021 | Gabant |
| 2022/0017573 | A1 | 1/2022 | Mignolet et al. |
| 2023/0414707 | A1 | 12/2023 | Gabant |
| 2023/0416797 | A1 | 12/2023 | Gabant |

FOREIGN PATENT DOCUMENTS

| | | | |
|---|---|---|---|
| CN | 1807645 | A | 7/2006 |
| CN | 101974546 | A | 2/2011 |
| EP | 1262556 | A2 | 12/2002 |
| WO | WO 2015/144859 | A2 | 10/2015 |
| WO | WO 2016028700 | | 2/2016 |
| WO | WO 2017/031399 | A1 | 2/2017 |
| WO | WO 2019046577 | A1 | 3/2019 |
| WO | WO 2022/104320 | | 5/2022 |
| WO | WO 2022/104321 | | 5/2022 |

OTHER PUBLICATIONS

Soliman et al., J. Med. Chem., 54, 2399-2408, 2011.*
Supplementary European Search Report Dated Feb. 28, 2022 in European Application No. 19814401.6 in 10 pages.
International Search Report with written Opinion Dated Aug. 19, 2019 in International Application No. PCT/US2019/035666 in 16 pages.
Acuña L., A new hybrid bacteriocin, Ent35-MccV, displays antimicrobial activity against pathogenic Gram-positive and Gram-negative bacteria, FEBS Openbio, vol. 2, No. 1 , pp. 12-19, 2012.
Chong, S., Overview of Cell-Free Protein Synthesis: Historic Landmarks, commercial systems, and Expanding Applications, Current Protocols in Molecular Biology, vol. 108, No. 16, pp. 1-16, 2014.
Gibson, D. G., et al. Creation of a bacterial cell controlled by a chemically synthesized genome, Science, Vo, 329, No. 5978, pp. 52-56, 2010.
Hols et al. Mobilization of Microbiota Commensals and Their Bactericicins for Therapeutics. Trends in Microbiology, vol. 27, No. 8, pp. 690-702, 2019.
Jin, X. et al., Rapid Production and Characterization of Antimicrobial Colicins Using *Escherichia coli*-Based Cell-Free Protein Synthesis, Synthetic Biology, vol. 3, No. 1, 2018.

(Continued)

*Primary Examiner* — Maryam Monshipouri
(74) *Attorney, Agent, or Firm* — KNOBBE, MARTENS, OLSON & BEAR, LLP

(57) ABSTRACT

Embodiments herein relate to methods, systems and kits for engineering antimicrobial peptides such as bacteriocins, for example to have a desired range of activity in a desired range of culture conditions. The antimicrobial peptides may be engineered to have a particular activity for a particular culture, environmental conditions or a range of conditions. Some embodiments include screening an antimicrobial peptides or several candidate antimicrobial peptides for a desired activity. Some embodiments include an iterative process for engineering antimicrobial peptides such as bacteriocins. In some embodiments, the process is performed by automated machine learning.

15 Claims, 2 Drawing Sheets

Specification includes a Sequence Listing.

(56) References Cited

OTHER PUBLICATIONS

Kuipers, 2015, Design and Production of Novel Antimicrobials by Synthetic Biology and high Throughput Screening. Available at http://sciencecafewageningen.nl/wp-content/uploads/2015/11/Kenniscafe2015Kuipers.pdf.
Muller S. et al., Functional single-cell analyses: flow cytometry and cell sorting of microbial populations and communities, FEMS Microbiology Reviews, vol. 34, No. 4, Jul. 2010, pp. 554-587, 2010.
Schmitt et al., Analysis of modular bioengineered antimicrobial lanthipeptides at nanoliter scale, Nature Chemical Biology, May 2019, vol. 15, No. 5, pp. 437-443.
Wang, et al., APD3: the antimicrobial peptide database as a tool for research and education, Nucleic Acids Research, vol. 44, Issue D1, pp. D1087-D1093, 2016.
Wright O. et al, building-in biosafety for synthetic biology, Microbiology, vol. 159, No. 7, pp. 1221-1235, 2013.
Bar-Ziv R. "Programmable on-chip DNA compartments as Artificial Cells" Nov. 14, 2019. https://www.youtube.com/watch?v=EKIBvROhx6g, Screenshot acquired Apr. 23, 2018.
Adetunji et al., Fungicidal effect of bacteriocins harvested from *Bacillus* spp., Malaysian Journal of Microbiology, vol. 9, No. 2, pp. 130-134, 2013.
Altschul, S.F., et al. Basic local alignment search tool, Journal of Molecular Biology, vol. 215, pp. 403-410, 1990.
Cotter, P.D. et al., Bacteriocins—a viable alternative to antibiotics, Nature Reviews Microbiology, vol. 11, pp. 95-105, 2013.
Extended European Search Report in European Application No. 18852336.9 in 17 pages.
Goñi-Moreno, et al., Multicellular Computing Using Conjugation for Wiring. PLoS ONE, vol. 8, No. 6, e65986, 2013.
International Search Report and Written Opinion in International Application No. PCT/US2018/048846 Dated Dec. 20, 2018 in 12 pages.
Jain et al. Current ADC Linker Chemistry, Pharmaceutical Research, vol. 32, pp. 3526-3540, 2015.
Jaramillo A., et al., Engineered Stable Ecosystems, Synthetic Biology, No. 2, vol. 17119, 2017.
Leonardo Acuna et al., A new hybrid bacteriocin, Ent35-MccV, displays antimicrobial activity against pathogenic Gram-positive and Gram-negative bacteria, FEBS Open Bio, vol. 2, No. 1, Jan. 1, 2012, pp. 12-19.
Li. Recombinant production of antimicrobial peptides in *Escherichia coli*: a review. Protein Expr Purif, Dec. 2011, vol. 80, No. 2, pp. 260-267.
Lohans Christopher T. et al., Development 1-4,6-H of Class lla Bacteriocins as Therapeutic Agents, International Journal of Microbiology, vol. 2012, 386410, Jan. 1, 2012, pp. 1-13.
Mead et al. Nucleic Acids Res. Dec. 11, 1990; 18(23): 7167.
Michael Klocke et al., Heterologous Expression of Enterocin A, a Bacteriocin From Enterococcus Faecium, Fused to a Cellulose-Binding Domain in *Escherichia coli* Results in a Functional Protein With Inhibitory Activity Against Listeria., Applied Microbiology and Biotechnology, vol. 67, No. 4, Jun. 1, 2005, pp. 532-538.
Montalban-Lopez Manuel et al., Employing the promiscuity of lantibiotic biosynthetic machineries to produce novel antimicrobials FEMS Microbiology Reviews, vol. 41, No. 1, Sep. 2, 2016, pp. 5-18.
Nielsen et al., Genetic circuit design automation, Science, vol. 352, No. 6281, aac7341, 2016.
Office Action with English Translation dated Jul. 22, 2022, in Japanese Patent Application No. 2020-512860 in 11 pages.
Qingshan Ma et al., Expression and purification of lacticin Q by small ubiquitin-related modifier fusion in *Escherichia coli*, The Journal of Microbiology, the Microbiological Society of Korea, Heidelberg, vol. 50, No. 2, Apr. 27, 2012, pp. 326-331.
Rajput A. et al., Prediction and Analysis of Quorum Sensing Peptides Based on Sequence Features, PLoS One, vol. 10, No. 3, 2015.
Sahl et al. Biosynthesis and biological activities of lantibiotics with unique post-translational modifications. Eur J Biochem, Jun. 15, 1995, vol. 230, No. 3, pp. 827-853.
Shekh, R.M. et al., Biochemical characterization of an anti-Candida factor produced by Enterococcus, BMC Microbiology, vol. 12, No. 132, 2012.
Shenin et al., "Characteristics of Alirin B1, the major component of a fungicidal substance produced by Bacillus subtilis 10-VIZR". Antibiot Khimioter, vol. 50: pp. 3-7, 1995.
Srivastava, S. et al., Antifungal Activity of Pseudomonas fluorescens Against Different Plant Pathogenic Fungi, The Internet Journal of Microbiology, vol. 7 No. 2, 2008.
Tomita et al. Twenty-Five Years of Research on Bovine Lactoferrin Applications, Biochimie, vol. 91, No. 1, pp. 52-57, 2009.
Van Heel Auke J. et al., Discovery, Production and Modification of Five Novel Lantibiotics Using the Promiscuous Nisin Modification Machinery, ACS Synthetic Biology, vol. 5, No. 10, Jul. 7, 2016, pp. 1146-1154.
Wang et al. Genome Mining Demonstrates the Widespread Occurrence of Gene Clusters Encoding Bacteriocins in Cyanobacteria, PLoS ONE 6(7): e22384, 2011.
Zuber, P et al. Peptide Antibiotics, Bacillus subtilis and Other Gram-Positive Bacteria: Biochemistry, Physiology, and Molecular Genetics ed Sonenshein et al., pp. 897-916, American Society for Microbiology, 1993.
File History of U.S. Appl. No. 18/052,519, filed Nov. 3, 2022.
File History of U.S. Appl. No. 17/822,663, filed Aug. 26, 2022.
File History of U.S. Appl. No. 14/459,810, filed Aug. 14, 2014.
File History of U.S. Appl. No. 15/087,706, filed Mar. 31, 2016.
File History of U.S. Appl. No. 16/227,371, filed Dec. 20, 2018.
File History of U.S. Appl. No. 16/642,342, filed Feb. 26, 2020.
Office Action with English Translation dated Jun. 7, 2023 in Japanese Application No. 2020-567524 in 7 pages.
Hong, S. H. Bacteriocin Production and Screening Using Cell-Free Protein Synthesis, 2016 Sythetic Biology: Engineering, Evolution & Design (SEED), https://www.aiche.org/sbe/confenrences/synthetic-biology-enineering-evolution-design-seed/2016/proceedings/paper/bacterocin-production-and-screening-using-cell-free-protein-synthesis.
Office Action with English Translation dated Mar. 28, 2023 in Brazilian Application No. BR1120200041491 in 10 pages.
Office Action with English Summary dated Oct. 20, 2023 in Chinese Patent Application No. 201880060807.0 in 10 pages.
Pandi, A. et al., Cell-free biosynthesis combined with deep learning accelerates de novo-development of antimicrobial peptides, Nature Communications, vol. 14, No. 7197, 2023.
King, A. M. Systematic mining of the human microbiome identifies antimicrobial peptides with diverse activity spectra, Nature Microbiology, 2023.
Gabant, P. et al., PARAGEN 1.0: A Standardized Synthetic Gene Library for Fast Cell-Free Bacteriocin Synthesis, Frontiers in Bioengineering and Biotechnology, vol. 7, No. 213, 2013.
Office Action with English Translation dated Dec. 8, 2022, in Japanese Patent Application No. 2020-512860 in 11 pages.
Lohans Christopher T. et al, "Development of Class lla Bacteriocins as Therapeutic Agents", International Journal of Microbiology, vol. 2012, ISSN 1687-918X, Database accession No. 386410, pp. 1-13, dated Nov. 30, 2011. DOI: http://dx.doi.org/10.1155/2012/386410.
Office Action with English Translation dated Feb. 6, 2024 in Brazilian Application No. BR1120200041491 in 13 pages.
Office Action with English Translation dated Oct. 23, 2023 in Japanese Application No. 2020-567524 in 11 pages.
Office Action with English Translation dated Mar. 29, 2024 in Japanese Application No. 2020-567524 in 6 pages.
Office Action with English Translation dated Jun. 18, 2024 in Brazilian Application No. BR1120200041491 in 12 pages.
Office Action with English Summary dated Jun. 18, 2024 in Chinese Patent Application No. 201880060807.0 in 8 pages.
Notice of Allowance dated May 9, 2024 in U.S. Appl. No. 18/052,519 in 28 pages.

(56) References Cited

OTHER PUBLICATIONS

Office Action with English Translation dated Apr. 26, 2024 in 6 pages, in Japanese Patent Application No. 2023-066616.
V. Georgi, et al., Lab on a Chip, vol. 16, p. 269-281, 2016.

* cited by examiner

SEQUENCE LISTING

```
<160> NUMBER OF SEQ ID NOS: 750

<210> SEQ ID NO 1
<211> LENGTH: 40
<212> TYPE: PRT
<213> ORGANISM: Enterococcus faecalis

<400> SEQUENCE: 1

Trp Leu Pro Pro Ala Gly Leu Leu Gly Arg Cys Gly Arg Trp Phe Arg
1               5                   10                  15
```

```
Pro Trp Leu Leu Trp Leu Gln Ser Gly Ala Gln Tyr Lys Trp Leu Gly
            20                  25                  30

Asn Leu Phe Gly Leu Gly Pro Lys
        35                  40


<210> SEQ ID NO 2
<211> LENGTH: 5
<212> TYPE: PRT
<213> ORGANISM: Artificial Sequence
<220> FEATURE:
<223> OTHER INFORMATION: N-terminal motif of class terminal IIa
<220> FEATURE:
<221> NAME/KEY: VARIANT
<222> LOCATION: 3
<223> OTHER INFORMATION: Xaa = any amino acid

<400> SEQUENCE: 2

Tyr Gly Xaa Gly Val
1               5


<210> SEQ ID NO 3
<211> LENGTH: 135
<212> TYPE: PRT
<213> ORGANISM: Artificial Sequence
<220> FEATURE:
<223> OTHER INFORMATION: Hybrid bacteriocin Ent35-MccV

<400> SEQUENCE: 3

Gly Lys Tyr Tyr Gly Asn Gly Val Ser Cys Asn Lys Lys Gly Cys Ser
1               5                   10                  15

Val Asp Trp Gly Arg Ala Ile Gly Ile Ile Gly Asn Asn Ser Ala Ala
            20                  25                  30

Asn Leu Ala Thr Gly Gly Ala Ala Gly Trp Lys Ser Gly Gly Gly Ala
        35                  40                  45

Ser Gly Arg Asp Ile Ala Met Ala Ile Gly Thr Leu Ser Gly Gln Phe
    50                  55                  60

Val Ala Gly Gly Ile Gly Ala Ala Ala Gly Gly Val Ala Gly Gly Ala
65                  70                  75                  80

Ile Tyr Asp Tyr Ala Ser Thr His Lys Pro Asn Pro Ala Met Ser Pro
                85                  90                  95

Ser Gly Leu Gly Gly Thr Ile Lys Gln Lys Pro Glu Gly Ile Pro Ser
            100                 105                 110

Glu Ala Trp Asn Tyr Ala Ala Gly Arg Leu Cys Asn Trp Ser Pro Asn
        115                 120                 125

Asn Leu Ser Asp Val Cys Leu
    130                 135


<210> SEQ ID NO 4
<211> LENGTH: 46
<212> TYPE: PRT
<213> ORGANISM: Lactobacillus acidophilus

<400> SEQUENCE: 4

Met Ile Ser Ser His Gln Lys Thr Leu Thr Asp Lys Glu Leu Ala Leu
1               5                   10                  15

Ile Ser Gly Gly Lys Thr His Tyr Pro Thr Asn Ala Trp Lys Ser Leu
            20                  25                  30

Trp Lys Gly Phe Trp Glu Ser Leu Arg Tyr Thr Asp Gly Phe
        35                  40                  45
```

<210> SEQ ID NO 5
<211> LENGTH: 141
<212> TYPE: DNA
<213> ORGANISM: Lactobacillus acidophilus

<400> SEQUENCE: 5
atgatttcat ctcatcaaaa aacgttaact gataaagaat tagcattaat ttctgggggg 60
aaaacgcact acccgactaa tgcatggaaa agtctttgga aaggtttctg ggaaagcctt 120
cgttatactg acggttttta g 141

<210> SEQ ID NO 6
<211> LENGTH: 81
<212> TYPE: PRT
<213> ORGANISM: Lactobacillus acidophilus

<400> SEQUENCE: 6

Met Ile Ser Met Ile Ser Ser His Gln Lys Thr Leu Thr Asp Lys Glu
1 5 10 15

Leu Ala Leu Ile Ser Gly Gly Lys Thr Tyr Tyr Gly Thr Asn Gly Val
20 25 30

His Cys Thr Lys Lys Ser Leu Trp Gly Lys Val Arg Leu Lys Asn Val
35 40 45

Ile Pro Gly Thr Leu Cys Arg Lys Gln Ser Leu Pro Ile Lys Gln Asp
50 55 60

Leu Lys Ile Leu Leu Gly Trp Ala Thr Gly Ala Phe Gly Lys Thr Phe
65 70 75 80

His

<210> SEQ ID NO 7
<211> LENGTH: 246
<212> TYPE: DNA
<213> ORGANISM: Lactobacillus acidophilus

<400> SEQUENCE: 7
atgatttcaa tgatttcatc tcatcaaaaa acgttaactg ataaagaatt agcattaatt 60
tctgggggga aaacgtacta tggtactaat ggtgtgcatt gtactaaaaa gagtctttgg 120
ggtaaagtac gcttaaaaaa cgtgattcct ggaactcttt gtcgtaagca atcgttgccg 180
atcaaacagg atttaaaaat tttactgggc tgggctacag gtgcttttgg caagacattt 240
cattaa 246

<210> SEQ ID NO 8
<211> LENGTH: 60
<212> TYPE: PRT
<213> ORGANISM: Lactobacillus acidophilus

<400> SEQUENCE: 8

Met Asp Lys Lys Thr Lys Ile Leu Phe Glu Val Leu Tyr Ile Ile Cys
1 5 10 15

Ile Ile Gly Pro Gln Phe Ile Leu Phe Val Thr Ala Lys Asn Asn Met
20 25 30

Tyr Gln Leu Val Gly Ser Phe Val Gly Ile Val Trp Phe Ser Tyr Ile
35 40 45

Phe Trp Tyr Ile Phe Phe Lys Gln His Lys Lys Met
50 55 60

<210> SEQ ID NO 9
<211> LENGTH: 183

```
<212> TYPE: DNA
<213> ORGANISM: Lactobacillus acidophilus

<400> SEQUENCE: 9

atggataaga aaacaaaaat attatttgaa gtattataca tcatctgtat aataggccct      60

caatttatat tatttgtgac tgcaaaaaac aatatgtatc agttggtggg ttcgtttgtt     120

ggaatagtat ggttttcgta tattttttgg tatatttttt tcaaacaaca taaaaaaatg     180

tag                                                                   183


<210> SEQ ID NO 10
<211> LENGTH: 65
<212> TYPE: PRT
<213> ORGANISM: Lactobacillus gasseri

<400> SEQUENCE: 10

Met Ala Leu Lys Thr Leu Glu Lys His Glu Leu Arg Asn Val Met Gly
1               5                   10                  15

Gly Asn Lys Trp Gly Asn Ala Val Ile Gly Ala Ala Thr Gly Ala Thr
            20                  25                  30

Arg Gly Val Ser Trp Cys Arg Gly Phe Gly Pro Trp Gly Met Thr Ala
        35                  40                  45

Cys Ala Leu Gly Gly Ala Ala Ile Gly Gly Tyr Leu Gly Tyr Lys Ser
    50                  55                  60

Asn
65


<210> SEQ ID NO 11
<211> LENGTH: 198
<212> TYPE: DNA
<213> ORGANISM: Lactobacillus gasseri

<400> SEQUENCE: 11

atggctttaa aaacattaga aaaacatgaa ttaagaaatg taatgggtgg aaacaagtgg      60

gggaatgctg taataggagc tgctacggga gctactcgcg gagtaagttg gtgcagagga     120

ttcggaccat ggggaatgac tgcctgtgcg ttaggaggtg ctgcaattgg aggatatctg     180

ggatataaga gtaattaa                                                   198


<210> SEQ ID NO 12
<211> LENGTH: 51
<212> TYPE: PRT
<213> ORGANISM: Staphylococcus aureus

<400> SEQUENCE: 12

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50


<210> SEQ ID NO 13
<211> LENGTH: 156
<212> TYPE: DNA
<213> ORGANISM: Staphylococcus aureus
```

<400> SEQUENCE: 13

```
atgagttggt taaatttttt aaaatacatc gctaaatatg gcaaaaaagc ggtatctgct     60

gcttggaagt acaaaggtaa agtattagaa tggcttaatg ttggtcctac tcttgaatgg    120

gtatggcaaa aattaaagaa aattgctgga ttataa                              156
```

<210> SEQ ID NO 14
<211> LENGTH: 61
<212> TYPE: PRT
<213> ORGANISM: Enterococcus avium

<400> SEQUENCE: 14

```
Met Thr Arg Ser Lys Lys Leu Asn Leu Arg Glu Met Lys Asn Val Val
1               5                   10                  15

Gly Gly Thr Tyr Tyr Gly Asn Gly Val Ser Cys Asn Lys Lys Gly Cys
            20                  25                  30

Ser Val Asp Trp Gly Lys Ala Ile Ser Ile Ile Gly Asn Asn Ser Ala
        35                  40                  45

Ala Asn Leu Ala Thr Gly Gly Ala Ala Gly Trp Lys Ser
    50                  55                  60
```

<210> SEQ ID NO 15
<211> LENGTH: 186
<212> TYPE: DNA
<213> ORGANISM: Enterococcus avium

<400> SEQUENCE: 15

```
atgacaagat caaaaaaatt aaatttacgc gaaatgaaga atgttgttgg tggtacctac     60

tatggaaatg gtgtatcttg taacaagaaa ggctgttcag ttgactgggg caaagccatc    120

agtattatag gaaataattc cgcagcaaac ttagcaactg gtggtgctgc tggttggaag    180

tcataa                                                               186
```

<210> SEQ ID NO 16
<211> LENGTH: 67
<212> TYPE: PRT
<213> ORGANISM: Enterococcus faecalis

<400> SEQUENCE: 16

```
Met Lys Lys Lys Leu Val Ile Cys Gly Ile Ile Gly Ile Gly Phe Thr
1               5                   10                  15

Ala Leu Gly Thr Asn Val Glu Ala Ala Thr Tyr Tyr Gly Asn Gly Leu
            20                  25                  30

Tyr Cys Asn Lys Gln Lys Cys Trp Val Asp Trp Asn Lys Ala Ser Arg
        35                  40                  45

Glu Ile Gly Lys Ile Ile Val Asn Gly Trp Val Gln His Gly Pro Trp
    50                  55                  60

Ala Pro Arg
65
```

<210> SEQ ID NO 17
<211> LENGTH: 204
<212> TYPE: DNA
<213> ORGANISM: Enterococcus faecalis

<400> SEQUENCE: 17

```
atgaaaaaga aattagttat ttgtggcatt attgggattg gttttacagc attaggaaca     60

aatgtagaag ctgctacgta ttacggaaat ggtttatatt gtaataagca aaaatgttgg    120
```

```
gtagactgga ataaagcttc aagggaaatt ggaaaaatta ttgttaatgg ttgggtacaa    180

catggccctt gggctcctag atag                                            204


<210> SEQ ID NO 18
<211> LENGTH: 51
<212> TYPE: PRT
<213> ORGANISM: Lactococcus lactis

<400> SEQUENCE: 18

Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Val Ile Tyr Asn Ser Trp Asn Phe Val Phe Thr
        35                  40                  45

Cys Cys Ser
    50


<210> SEQ ID NO 19
<211> LENGTH: 156
<212> TYPE: DNA
<213> ORGANISM: Lactococcus lactis

<400> SEQUENCE: 19

atgaaagaac aaaactcttt taatcttctt caagaagtga cagaaagtga attggacctt     60

attttaggtg caaaaggcgg cagtggagtt attcatacaa tttctcatga agtaatatat    120

aatagctgga actttgtatt tacttgctgc tcttaa                              156


<210> SEQ ID NO 20
<211> LENGTH: 74
<212> TYPE: PRT
<213> ORGANISM: Enterococcus faecium

<400> SEQUENCE: 20

Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
            20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70


<210> SEQ ID NO 21
<211> LENGTH: 225
<212> TYPE: DNA
<213> ORGANISM: Enterococcus faecium

<400> SEQUENCE: 21

atgaaaaaga aagtattaaa acattgtgtt attctaggaa tattaggaac ttgtctagct     60

ggcatcggta caggaataaa agttgatgca gctacttact atggaaatgg tctttattgt    120

aacaaagaaa aatgttgggt agattggaat caagctaaag gagaaattgg aaaaattatt    180

gttaatggtt gggttaatca tggtccatgg gcacctagaa ggtag                    225
```

<210> SEQ ID NO 22
<211> LENGTH: 50
<212> TYPE: PRT
<213> ORGANISM: Clostridium botulinum

<400> SEQUENCE: 22

Met Gln Lys Pro Glu Ile Ile Ser Ala Asp Leu Gly Leu Cys Ala Val
1 5 10 15

Asn Glu Phe Val Ala Leu Ala Ala Ile Pro Gly Gly Ala Ala Thr Phe
20 25 30

Ala Val Cys Gln Met Pro Asn Leu Asp Glu Ile Val Ser Asn Ala Ala
35 40 45

Tyr Val
50

<210> SEQ ID NO 23
<211> LENGTH: 153
<212> TYPE: DNA
<213> ORGANISM: Clostridium botulinum

<400> SEQUENCE: 23
atgcaaaaac cagaaattat tagtgctgat ttagggcttt gtgcagttaa tgaatttgta 60
gctcttgctg ccattcctgg tggtgctgct acatttgcag tatgccaaat gccaaacttg 120
gatgagattg ttagtaatgc agcatatgtt taa 153

<210> SEQ ID NO 24
<211> LENGTH: 58
<212> TYPE: PRT
<213> ORGANISM: Streptococcus equinus

<400> SEQUENCE: 24

Met Met Asn Ala Thr Glu Asn Gln Ile Phe Val Glu Thr Val Ser Asp
1 5 10 15

Gln Glu Leu Glu Met Leu Ile Gly Gly Ala Asp Arg Gly Trp Ile Lys
20 25 30

Thr Leu Thr Lys Asp Cys Pro Asn Val Ile Ser Ser Ile Cys Ala Gly
35 40 45

Thr Ile Ile Thr Ala Cys Lys Asn Cys Ala
50 55

<210> SEQ ID NO 25
<211> LENGTH: 177
<212> TYPE: DNA
<213> ORGANISM: Streptococcus equinus

<400> SEQUENCE: 25
atgatgaatg ctactgaaaa ccaaattttt gttgagactg tgagtgacca agaattagaa 60
atgttaattg gtggtgcaga tcgtggatgg attaagactt taacaaaaga ttgtccaaat 120
gtaatttctt caatttgtgc aggtacaatt attacagctt gtaaaaattg tgcttaa 177

<210> SEQ ID NO 26
<211> LENGTH: 77
<212> TYPE: PRT
<213> ORGANISM: Brochothrix campestris

<400> SEQUENCE: 26

Met His Lys Val Lys Lys Leu Asn Asn Gln Glu Leu Gln Gln Ile Val
1 5 10 15

```
Gly Gly Tyr Ser Ser Lys Asp Cys Leu Lys Asp Ile Gly Lys Gly Ile
            20                  25                  30

Gly Ala Gly Thr Val Ala Gly Ala Ala Gly Gly Gly Leu Ala Ala Gly
        35                  40                  45

Leu Gly Ala Ile Pro Gly Ala Phe Val Gly Ala His Phe Gly Val Ile
    50                  55                  60

Gly Gly Ser Ala Ala Cys Ile Gly Gly Leu Leu Gly Asn
65                  70                  75


<210> SEQ ID NO 27
<211> LENGTH: 234
<212> TYPE: DNA
<213> ORGANISM: Brochothrix campestris

<400> SEQUENCE: 27

atgcacaagg taaaaaaatt aaacaatcaa gagttacaac agatcgtggg aggttacagt      60

tcaaaagatt gtctaaaaga tattggtaaa ggaattggtg ctggtacagt agctggggca     120

gccggcggtg gcctagctgc aggattaggt gctatcccag gagcattcgt tggagcacat     180

tttggagtaa tcggcggatc tgccgcatgc attggtggat tattaggtaa ctag           234


<210> SEQ ID NO 28
<211> LENGTH: 80
<212> TYPE: PRT
<213> ORGANISM: Butyrivibrio fibrisolvens

<400> SEQUENCE: 28

Met Ser Lys Lys Gln Ile Met Ser Asn Cys Ile Ser Ile Ala Leu Leu
1               5                   10                  15

Ile Ala Leu Ile Pro Asn Ile Tyr Phe Ile Ala Asp Lys Met Gly Ile
            20                  25                  30

Gln Leu Ala Pro Ala Trp Tyr Gln Asp Ile Val Asn Trp Val Ser Ala
        35                  40                  45

Gly Gly Thr Leu Thr Thr Gly Phe Ala Ile Ile Val Gly Val Thr Val
    50                  55                  60

Pro Ala Trp Ile Ala Glu Ala Ala Ala Ala Phe Gly Ile Ala Ser Ala
65                  70                  75                  80


<210> SEQ ID NO 29
<211> LENGTH: 243
<212> TYPE: DNA
<213> ORGANISM: Butyrivibrio fibrisolvens

<400> SEQUENCE: 29

atgagtaaaa aacaaattat gagtaactgt atatcaattg cattattaat agcactaatt      60

cctaatatct attttattgc agataaaatg ggaattcagt tagcacctgc ttggtatcaa     120

gatattgtga attgggtatc tgctggtgga acacttacta ctggttttgc gattattgta     180

ggagttacag taccggcatg gatagcagaa gcagctgcag cttttggtat agcttcagca     240

tga                                                                   243


<210> SEQ ID NO 30
<211> LENGTH: 48
<212> TYPE: PRT
<213> ORGANISM: Butyrivibrio fibrisolvens
```

<400> SEQUENCE: 30

```
Met Asn Lys Glu Leu Asn Ala Leu Thr Asn Pro Ile Asp Glu Lys Glu
1               5                   10                  15

Leu Glu Gln Ile Leu Gly Gly Gly Asn Gly Val Ile Lys Thr Ile Ser
            20                  25                  30

His Glu Cys His Met Asn Thr Trp Gln Phe Ile Phe Thr Cys Cys Ser
        35                  40                  45
```

<210> SEQ ID NO 31
<211> LENGTH: 147
<212> TYPE: DNA
<213> ORGANISM: Butyrivibrio fibrisolvens

<400> SEQUENCE: 31

```
atgaacaaag aacttaatgc acttacaaat cctattgacg agaaggagct tgagcagatc     60

ctcggtggtg gcaatggtgt catcaagaca atcagccacg agtgccacat gaacacatgg    120

cagttcattt tcacatgttg ctcttaa                                        147
```

<210> SEQ ID NO 32
<211> LENGTH: 66
<212> TYPE: PRT
<213> ORGANISM: Carnobacterium maltaromaticum

<400> SEQUENCE: 32

```
Met Asn Ser Val Lys Glu Leu Asn Val Lys Glu Met Lys Gln Leu His
1               5                   10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
    50                  55                  60

Arg Pro
65
```

<210> SEQ ID NO 33
<211> LENGTH: 201
<212> TYPE: DNA
<213> ORGANISM: Carnobacterium maltaromaticum

<400> SEQUENCE: 33

```
atgaatagcg taaaagaatt aaacgtgaaa gaaatgaaac aattacacgg tggagtaaat     60

tatggtaatg gtgtttcttg cagtaaaaca aaatgttcag ttaactgggg acaagccttt    120

caagaaagat acacagctgg aattaactca tttgtaagtg gagtcgcttc tggggcagga    180

tccattggta ggagaccgta a                                              201
```

<210> SEQ ID NO 34
<211> LENGTH: 61
<212> TYPE: PRT
<213> ORGANISM: Carnobacterium maltaromaticum

<400> SEQUENCE: 34

```
Met Lys Ser Val Lys Glu Leu Asn Lys Lys Glu Met Gln Gln Ile Asn
1               5                   10                  15

Gly Gly Ala Ile Ser Tyr Gly Asn Gly Val Tyr Cys Asn Lys Glu Lys
            20                  25                  30
```

```
Cys Trp Val Asn Lys Ala Glu Asn Lys Gln Ala Ile Thr Gly Ile Val
        35                  40                  45

Ile Gly Gly Trp Ala Ser Ser Leu Ala Gly Met Gly His
    50                  55                  60


<210> SEQ ID NO 35
<211> LENGTH: 186
<212> TYPE: DNA
<213> ORGANISM: Carnobacterium maltaromaticum

<400> SEQUENCE: 35

atgaaaagcg ttaaagaact aaataaaaaa gaaatgcaac aaattaatgg tggagctatc      60

tcttatggca atggtgttta ttgtaacaaa gagaaatgtt gggtaaacaa ggcagaaaac     120

aaacaagcta ttactggaat agttatcggt ggatgggctt ctagtttagc aggaatggga     180

cattaa                                                                186


<210> SEQ ID NO 36
<211> LENGTH: 71
<212> TYPE: PRT
<213> ORGANISM: Carnobacterium maltaromaticum

<400> SEQUENCE: 36

Met Asn Asn Val Lys Glu Leu Ser Ile Lys Glu Met Gln Gln Val Thr
1               5                   10                  15

Gly Gly Asp Gln Met Ser Asp Gly Val Asn Tyr Gly Lys Gly Ser Ser
            20                  25                  30

Leu Ser Lys Gly Gly Ala Lys Cys Gly Leu Gly Ile Val Gly Gly Leu
        35                  40                  45

Ala Thr Ile Pro Ser Gly Pro Leu Gly Trp Leu Ala Gly Ala Ala Gly
    50                  55                  60

Val Ile Asn Ser Cys Met Lys
65                  70


<210> SEQ ID NO 37
<211> LENGTH: 216
<212> TYPE: DNA
<213> ORGANISM: Carnobacterium maltaromaticum

<400> SEQUENCE: 37

atgaataatg taaaagagtt aagtattaaa gaaatgcaac aagttactgg tggagaccaa      60

atgtcagatg gtgtaaatta tggaaaaggc tctagcttat caaaaggtgg tgccaaatgt     120

ggtttaggga tcgtcggcgg attagctact atcccttcag gtcctttagg ctggttagcc     180

ggagcagcag gtgtaattaa tagctgtatg aaataa                               216


<210> SEQ ID NO 38
<211> LENGTH: 64
<212> TYPE: PRT
<213> ORGANISM: Carnobacterium maltaromaticum

<400> SEQUENCE: 38

Met Leu Tyr Glu Leu Val Ala Tyr Gly Ile Ala Gln Gly Thr Ala Glu
1               5                   10                  15

Lys Val Val Ser Leu Ile Asn Ala Gly Leu Thr Val Gly Ser Ile Ile
            20                  25                  30

Ser Ile Leu Gly Gly Val Thr Val Gly Leu Ser Gly Val Phe Thr Ala
        35                  40                  45
```

```
Val Lys Ala Ala Ile Ala Lys Gln Gly Ile Lys Lys Ala Ile Gln Leu
    50                  55                  60


<210> SEQ ID NO 39
<211> LENGTH: 195
<212> TYPE: DNA
<213> ORGANISM: Carnobacterium maltaromaticum

<400> SEQUENCE: 39

atgttatatg aattagttgc atatggtatc gcacaaggta cagctgaaaa ggttgtaagt      60

ctaattaacg caggtttaac agtagggtct attatttcaa ttttgggtgg ggtcacagtc     120

ggtttatcag gtgtcttcac agcagttaaa gcagcaattg ctaaacaagg aataaaaaaa     180

gcaattcaat tataa                                                      195


<210> SEQ ID NO 40
<211> LENGTH: 836
<212> TYPE: PRT
<213> ORGANISM: Pectobacterium carotovorum subsp. carotovorum

<400> SEQUENCE: 40

Met Ile Lys Tyr Arg Leu Tyr Ala Pro Asn Asp Gly Asp Thr Met Thr
1               5                   10                  15

Val Ser Gly Gly Gly Gly Trp Val Ser Asn Asp Asp Arg Lys Gly Gly
            20                  25                  30

Asn Asp Arg Asp Asn Gly Lys Gly Gly Ser Ala Val Asp Phe Ser Lys
        35                  40                  45

Asn Pro Glu Lys Gln Ala Ile Val Asn Pro Tyr Leu Ala Ile Ala Ile
    50                  55                  60

Pro Met Pro Val Tyr Pro Leu Tyr Gly Lys Leu Gly Phe Thr Ile Asn
65                  70                  75                  80

Thr Thr Ala Ile Glu Thr Glu Leu Ala Asn Val Arg Ala Ala Ile Asn
                85                  90                  95

Thr Lys Leu Ala Thr Leu Ser Ala Val Ile Gly Arg Ser Leu Pro Val
            100                 105                 110

Val Gly Arg Val Phe Gly Val Thr Ala Ala Gly Met Trp Pro Ser Ser
        115                 120                 125

Thr Ala Pro Ser Ser Leu Asp Ser Ile Tyr Asn Gln Ala His Gln Gln
    130                 135                 140

Ala Leu Ala Gln Leu Ala Ala Gln Gln Gly Val Leu Asn Lys Gly Tyr
145                 150                 155                 160

Asn Val Thr Ala Met Pro Ala Gly Phe Val Ser Ser Leu Pro Val Ser
                165                 170                 175

Glu Ile Lys Ser Leu Pro Thr Ala Pro Ala Ser Leu Leu Ala Gln Ser
            180                 185                 190

Val Ile Asn Thr Glu Leu Ser Gln Arg Gln Leu Ala Leu Thr Gln Pro
        195                 200                 205

Thr Thr Asn Ala Pro Val Ala Asn Ile Pro Val Val Lys Ala Glu Lys
    210                 215                 220

Thr Ala Met Pro Gly Val Tyr Ser Ala Lys Ile Ile Ala Gly Glu Pro
225                 230                 235                 240

Ala Phe Gln Ile Lys Val Asp Asn Thr Lys Pro Ala Leu Ala Gln Asn
                245                 250                 255

Pro Pro Lys Val Lys Asp Asp Ile Gln Val Ser Ser Phe Leu Ser Ser
            260                 265                 270
```

```
Pro Val Ala Asp Thr His His Ala Phe Ile Asp Phe Gly Ser Asp His
        275                 280                 285

Glu Pro Val Tyr Val Ser Leu Ser Lys Ile Val Thr Ala Glu Glu Glu
    290                 295                 300

Lys Lys Gln Val Glu Glu Ala Lys Arg Arg Glu Gln Glu Trp Leu Leu
305                 310                 315                 320

Arg His Pro Ile Thr Ala Ala Glu Arg Lys Leu Thr Glu Ile Arg Gln
                325                 330                 335

Val Ile Ser Phe Ala Gln Gln Leu Lys Glu Ser Ser Val Ala Thr Ile
            340                 345                 350

Ser Glu Lys Thr Lys Thr Val Ala Val Tyr Gln Glu Gln Val Asn Thr
        355                 360                 365

Ala Ala Lys Asn Arg Asp Asn Phe Tyr Asn Gln Asn Arg Gly Leu Leu
    370                 375                 380

Ser Ala Gly Ile Thr Gly Gly Pro Gly Tyr Pro Ile Tyr Leu Ala Leu
385                 390                 395                 400

Trp Gln Thr Met Asn Asn Phe His Gln Ala Tyr Phe Arg Ala Asn Asn
                405                 410                 415

Ala Leu Glu Gln Glu Ser His Val Leu Asn Leu Ala Arg Ser Asp Leu
            420                 425                 430

Ala Lys Ala Glu Gln Leu Leu Ala Glu Asn Asn Arg Leu Gln Val Glu
        435                 440                 445

Thr Glu Arg Thr Leu Ala Glu Glu Lys Glu Ile Lys Arg Asn Arg Val
    450                 455                 460

Asn Val Ser Thr Phe Gly Thr Val Gln Thr Gln Leu Ser Lys Leu Leu
465                 470                 475                 480

Ser Asp Phe Tyr Ala Val Thr Ser Leu Ser Gln Ser Val Pro Ser Gly
                485                 490                 495

Ala Leu Ala Ser Phe Ser Tyr Asn Pro Gln Gly Met Ile Gly Ser Gly
            500                 505                 510

Lys Ile Val Gly Lys Asp Val Asp Val Leu Phe Ser Ile Pro Val Lys
        515                 520                 525

Asp Ile Pro Gly Tyr Lys Ser Pro Ile Asn Leu Asp Asp Leu Ala Lys
    530                 535                 540

Lys Asn Gly Ser Leu Asp Leu Pro Ile Arg Leu Ala Phe Ser Asp Glu
545                 550                 555                 560

Asn Gly Glu Arg Val Leu Arg Ala Phe Lys Ala Asp Ser Leu Arg Ile
                565                 570                 575

Pro Ser Ser Val Arg Gly Val Ala Gly Ser Tyr Asp Lys Asn Thr Gly
            580                 585                 590

Ile Phe Ser Ala Glu Ile Asp Gly Val Ser Ser Arg Leu Val Leu Glu
        595                 600                 605

Asn Pro Ala Phe Pro Pro Thr Gly Asn Val Gly Asn Thr Gly Asn Thr
    610                 615                 620

Ala Pro Asp Tyr Lys Ala Leu Leu Asn Thr Gly Val Asp Val Lys Pro
625                 630                 635                 640

Val Asp Lys Ile Thr Val Thr Val Thr Pro Val Ala Asp Pro Val Asp
                645                 650                 655

Ile Asp Asp Tyr Ile Ile Trp Leu Pro Thr Ala Ser Gly Ser Gly Val
            660                 665                 670

Glu Pro Ile Tyr Val Val Phe Asn Ser Asn Pro Tyr Gly Gly Thr Glu
        675                 680                 685
```

```
Lys Gly Lys Tyr Ser Lys Arg Tyr Tyr Asn Pro Asp Lys Ala Gly Gly
    690                 695                 700

Pro Ile Leu Glu Leu Asp Trp Lys Asn Val Lys Ile Asp His Ala Gly
705                 710                 715                 720

Val Asp Asn Val Lys Leu His Thr Gly Arg Phe Lys Ala Ser Val Glu
                725                 730                 735

Asn Lys Val Met Ile Glu Arg Leu Glu Asn Ile Leu Asn Gly Gln Ile
            740                 745                 750

Thr Ala Thr Asp Thr Asp Lys Arg Phe Tyr Thr His Glu Leu Arg Glu
        755                 760                 765

Leu Asn Arg Tyr Arg Asn Leu Gly Ile Lys Asp Gly Glu Val Pro Ser
    770                 775                 780

Ser Ile Gln Glu Glu Ser Ala Val Trp Asn Asp Thr His Thr Ala Thr
785                 790                 795                 800

Leu Glu Asp Tyr Lys Ile Asn Glu Lys Glu Gln Pro Leu Tyr Thr Asp
                805                 810                 815

Ala Ala Leu Gln Ala Ala Tyr Glu Gln Glu Leu Lys Asp Ala Leu Gly
            820                 825                 830

Gly Lys His Gly
        835
```

<210> SEQ ID NO 41
<211> LENGTH: 2511
<212> TYPE: DNA
<213> ORGANISM: Pectobacterium carotovorum subsp. carotovorum

<400> SEQUENCE: 41

```
atgattaaat accgtttata tgctccaaat gatggagaca ccatgacagt gagtggtggt      60

ggtggttggg tttcaaacga tgatcgcaaa ggtggtaatg acagggacaa tggcaaaggt     120

ggttctgccg ttgattttag taaaaatcca gaaaagcagg ctatcgttaa tccctatttg     180

gcaatcgcga taccgatgcc ggtctaccct ctttatggaa agctagggtt cacaataaat     240

acgacggcaa ttgagactga actcgcaaat gtcagagcag caattaacac taaacttgca     300

acactcagtg cagtgattgg cagatcactt ccggtcgttg ggcgggtatt tggtgttact     360

gccgccggaa tgtggccttc tagtaccgct cccagtagtc tcgattctat atacaatcaa     420

gcacatcagc aggctttagc ccagttagct gctcaacagg gagtattaaa taaagggtat     480

aacgttacag caatgcctgc aggtttcgtc agcagtttgc ctgttagtga aatcaaatca     540

ttgccaacag ctcccgccag tttactggca caaagtgtga ttaataccga actttcccag     600

cgtcaactgg ctcttactca gcccacgacg aatgcaccag tcgcgaatat tcccgtagtt     660

aaagcagaga aaacagcaat gccaggtgtg tattcagcga aaattattgc tggtgagcct     720

gcattccaaa tcaaggtcga taataccaaa cctgctttgg cacagaatcc gccgaaagta     780

aaagatgata ttcaggtatc ttctttcctt tcctcgccag tagctgatac gcaccatgca     840

tttattgatt ttggcagcga tcatgaaccg gtatacgtgt ctctttcaaa gatcgtgaca     900

gccgaggagg agaaaaaaca ggttgaagag gccaagcgcc gtgagcagga gtggttgttg     960

cgtcatccaa ttacagctgc ggagcgaaaa ttaactgaaa tccgccaagt gatctctttt    1020

gctcaacagc taaaagaaag ctctgtcgca accatttcag aaaaaactaa aactgttgcg    1080

gtttaccaag aacaggtgaa taccgctgca aaaaatcgcg acaattttta taatcaaaat    1140

agaggtctgt taagtgcggg tataactggg ggaccgggat atcctattta tcttgcttta    1200
```

```
tggcaaacga tgaataactt tcatcaggct tatttcagag caaataatgc attggaacaa   1260
gagagtcatg ttctgaacct ggctcgttct gatctggcta aggctgagca attgcttgct   1320
gagaataatc gacttcaggt tgaaacggag cgaacgcttg ccgaagaaaa agagataaaa   1380
cgcaacaggg ttaatgtatc aacatttggc acagtgcaaa ctcaacttag taaattgctg   1440
tcagattttt atgctgttac atcactttcc caaagtgttc cttcgggggc attagcctct   1500
ttttcatata atccacaagg gatgattggc agcggtaaga ttgttgggaa ggatgtcgat   1560
gttttatttt ccatcccagt aaaagatatt ccgggatata aatctcctat taacttggac   1620
gatttagcca agaaaaatgg aagtctggat cttcccattc gtctggcatt ttctgatgag   1680
aatggagaaa gggttcttcg ggcattcaaa gcggatagtc tgcgaatccc ttcgagtgtc   1740
agaggtgtag cgggcagtta tgacaaaaat acgggtattt ttagtgcaga aattgatggt   1800
gtttcatctc gccttgtact ggaaaaccca gcgtttcctc cgaccggaaa tgtcggtaat   1860
acgggtaata ctgcacctga ctataaagca ttactgaata ctggtgttga tgttaaacct   1920
gttgataaaa tcacagttac ggtaacacca gttgctgatc cagtggatat tgatgactat   1980
ataatctggt tgccaactgc gtctggttct ggcgtggaac ccatttatgt cgtgtttaac   2040
agtaatccgt atggtgggac ggaaaaagga aaatatagca aacgttatta taatccagat   2100
aaggcaggcg gtccgatctt ggagctggat tggaaaaacg ttaagattga ccatgcaggt   2160
gtggacaatg ttaaattaca cacagggcgt ttcaaagcgt cggttgaaaa caaagtgatg   2220
attgaacgtt tggaaaacat actgaatggt caaatcacgg ccacggatac tgacaagcga   2280
ttctatacgc atgaattaag agagttaaac cgctacagaa atttaggcat caaagacggt   2340
gaagtgccta gtagcattca agaagaaagc gctgtttgga acgacacaca cacagcgacg   2400
cttgaagact acaaaattaa tgagaaagag caaccgttgt acactgatgc tgctttgcag   2460
gcagcctacg aacaggaact caaagacgca ttaggaggga aacatggcta a            2511
```

```
<210> SEQ ID NO 42
<211> LENGTH: 74
<212> TYPE: PRT
<213> ORGANISM: Bacillus cereus

<400> SEQUENCE: 42

Met Glu Asn Leu Gln Met Leu Thr Glu Glu Glu Leu Met Glu Ile Glu
1               5                   10                  15

Gly Gly Gly Trp Trp Asn Ser Trp Gly Lys Cys Val Ala Gly Thr Ile
            20                  25                  30

Gly Gly Ala Gly Thr Gly Gly Leu Gly Gly Ala Ala Ala Gly Ser Ala
        35                  40                  45

Val Pro Val Ile Gly Thr Gly Ile Gly Gly Ala Ile Gly Gly Val Ser
    50                  55                  60

Gly Gly Leu Thr Gly Ala Ala Thr Phe Cys
65                  70


<210> SEQ ID NO 43
<211> LENGTH: 225
<212> TYPE: DNA
<213> ORGANISM: Bacillus cereus

<400> SEQUENCE: 43

atggaaaact tacaaatgtt aactgaagaa gaattaatgg aaattgaagg tggaggctgg     60

tggaatagct ggggtaaatg tgttgctgga actatcggtg gagctggaac tggtggttta    120
```

ggtggagctg ctgcaggttc agctgttccg gttattggta ctggtattgg tggcgctatt 180
ggtggagtta gcggtggcct tacaggtgca gctacttttt gctaa 225

<210> SEQ ID NO 44
<211> LENGTH: 78
<212> TYPE: PRT
<213> ORGANISM: Streptoverticillium griseoverticillatum

<400> SEQUENCE: 44

```
Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
            20                  25                  30

Leu Pro Thr Pro Val Glu Ala Gln Asp Gln Ala Ser Leu Asp Phe Trp
        35                  40                  45

Thr Lys Asp Ile Ala Ala Thr Glu Ala Phe Ala Cys Arg Gln Ser Cys
    50                  55                  60

Ser Phe Gly Pro Phe Thr Phe Val Cys Asp Gly Asn Thr Lys
65                  70                  75
```

<210> SEQ ID NO 45
<211> LENGTH: 237
<212> TYPE: DNA
<213> ORGANISM: Streptoverticillium griseoverticillatum

<400> SEQUENCE: 45
atgaccgctt ccattcttca gcagtccgtc gtggacgccg acttccgcgc ggcgctgctt 60
gagaaccccg ccgccttcgg cgcttccgcc gcggccctgc ccacgcccgt cgaggcccag 120
gaccaggcgt cccttgactt ctggaccaag gacatcgccg ccacggaagc cttcgcctgc 180
cgccagagct gcagcttcgg cccgttcacc ttcgtgtgcg acggcaacac caagtaa 237

<210> SEQ ID NO 46
<211> LENGTH: 76
<212> TYPE: PRT
<213> ORGANISM: Geobacillus kaustophilus

<400> SEQUENCE: 46

```
Met Ser Leu Leu Ala Leu Val Ala Gly Thr Leu Gly Val Ser Gln Ser
1               5                   10                  15

Ile Ala Thr Thr Val Val Ser Ile Val Leu Thr Gly Ser Thr Leu Ile
            20                  25                  30

Ser Ile Ile Leu Gly Ile Thr Ala Ile Leu Ser Gly Gly Val Asp Ala
        35                  40                  45

Ile Leu Glu Ile Gly Trp Ser Ala Phe Val Ala Thr Val Lys Lys Ile
    50                  55                  60

Val Ala Glu Arg Gly Lys Ala Ala Ala Ile Ala Trp
65                  70                  75
```

<210> SEQ ID NO 47
<211> LENGTH: 231
<212> TYPE: DNA
<213> ORGANISM: Geobacillus kaustophilus

<400> SEQUENCE: 47
atgagtttgc tggcgcttgt tgccgggacg ctcggcgtgt cacagtcaat cgcgacgacg 60
gttgtttcga ttgtgttgac cggctccact ctcatttcta ttattcttgg gatcaccgct 120

```
atttttgtcag gtggagtcga cgccattttg gaaattgggt ggtcagcttt tgtcgcgacg    180

gtgaaaaaaa tagtggcgga acgaggaaaa gcggcagcga ttgcatggta a              231


<210> SEQ ID NO 48
<211> LENGTH: 309
<212> TYPE: PRT
<213> ORGANISM: Clostridium tyrobutyricum

<400> SEQUENCE: 48

Met Arg Lys Val Phe Leu Arg Ser Ile Ile Ser Thr Leu Val Met Cys
1               5                   10                  15

Ala Phe Val Ser Ser Ser Phe Ser Val Asn Ala Asp Glu Ser Lys Pro
            20                  25                  30

Asn Asp Glu Lys Ile Ile Asn Asn Ile Glu Asn Val Thr Thr Thr Lys
        35                  40                  45

Asp Ile Val Lys Ser Asn Lys Asn Asn Ile Val Tyr Leu Asp Glu Gly
    50                  55                  60

Val Met Ser Ile Pro Leu Ser Gly Arg Lys Pro Ile Ala Ile Lys Asp
65                  70                  75                  80

Asp Asn Asn Lys Glu Asp Leu Thr Val Thr Leu Pro Ile Lys Asn Thr
                85                  90                  95

Gly Asp Ile Ser Lys Ile Ser Ser Asn Gly Thr Ile Leu Tyr Lys Asn
            100                 105                 110

Asn Ser Ser Asn Ser Ser Asn Ile Ala Leu Gln Pro Lys Asn Asp Gly
        115                 120                 125

Phe Lys Ala Leu Ile Asn Ile Asn Asp Lys Leu Ala Asn Lys Glu Tyr
    130                 135                 140

Glu Phe Thr Phe Asn Leu Pro Lys Asn Ser Lys Leu Ile Ser Ala Ala
145                 150                 155                 160

Thr Tyr Leu Gly Lys Glu Tyr Asp Thr Lys Glu Val Phe Val Val Asp
                165                 170                 175

Lys Asn Asn Ile Ile Thr Ser Ile Ile Ser Pro Ala Trp Ala Lys Asp
            180                 185                 190

Ala Asn Gly His Asn Val Ser Thr Tyr Tyr Lys Ile Val Ser Asn Asn
        195                 200                 205

Lys Leu Val Gln Val Val Glu Phe Thr Glu Asn Thr Ala Phe Pro Val
    210                 215                 220

Val Ala Asp Pro Asn Trp Thr Lys Ile Gly Lys Cys Ala Gly Ser Ile
225                 230                 235                 240

Ala Trp Ala Ile Gly Ser Gly Leu Phe Gly Gly Ala Lys Leu Ile Lys
                245                 250                 255

Ile Lys Lys Tyr Ile Ala Glu Leu Gly Gly Leu Gln Lys Ala Ala Lys
            260                 265                 270

Leu Leu Val Gly Ala Thr Thr Trp Glu Glu Lys Leu His Ala Gly Gly
        275                 280                 285

Tyr Ala Leu Ile Asn Leu Ala Ala Glu Leu Thr Gly Val Ala Gly Ile
    290                 295                 300

Gln Ala Asn Cys Phe
305


<210> SEQ ID NO 49
<211> LENGTH: 930
<212> TYPE: DNA
<213> ORGANISM: Clostridium tyrobutyricum
```

<400> SEQUENCE: 49

```
ttgagaaaag tatttttaag atcaataatt tcaacattag ttatgtgtgc atttgtttca     60

agcagctttt cagtaaatgc ggatgaaagc aaaccaaatg atgaaaaaat aattaataac    120

atagaaaacg ttactactac taaagatatt gtaaaaagta ataaaaataa tattgtatat    180

ttagatgaag gtgtaatgag tattccattg tctgggagaa aacccattgc tattaaagat    240

gataataata aagaagattt aactgttaca ttacctatta agaatactgg agatatatct    300

aaaattagta gtaatggtac tattctgtat aaaaataata gtagtaattc atctaatata    360

gctttacaac ctaaaaatga tggatttaag gctttaataa atattaatga taagttagct    420

aataaagaat atgaatttac atttaattta cccaaaaaca gtaaattaat tagtgctgcc    480

acatatttgg gtaaagaata tgatacaaaa gaagtatttg tagtagacaa aaataatata    540

attacgagta ttattagtcc agcttgggct aaagatgcaa atggacataa tgtttctact    600

tattataaga tagtatcgaa taataaatta gtacaagttg ttgaattcac agaaaatact    660

gcattcccgg tggtagctga tcctaattgg actaaaattg ggaaatgcgc tgggtcaata    720

gcatgggcta taggttctgg cctttttggt ggagcaaagc taattaaaat aaaaaaatat    780

atagcagagc ttggaggact tcaaaaagca gctaaattat tagttggtgc aaccacttgg    840

gaagaaaaat tacacgcagg cggttatgca ttaattaact tagctgctga gctaacaggt    900

gtagcaggta tacaagcaaa ttgtttttaa                                     930
```

<210> SEQ ID NO 50
<211> LENGTH: 62
<212> TYPE: PRT
<213> ORGANISM: Bacillus coagulans

<400> SEQUENCE: 50

```
Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Thr His Lys Cys
    50                  55                  60
```

<210> SEQ ID NO 51
<211> LENGTH: 189
<212> TYPE: DNA
<213> ORGANISM: Bacillus coagulans

<400> SEQUENCE: 51

```
atgaaaaaaa ttgaaaaatt aactgaaaaa gaaatggcca atatcattgg tggtaaatac     60

tacggtaatg gggttacttg tggcaaacat tcctgctctg ttgactgggg taaggctacc    120

acctgcataa tcaataatgg agctatggca tgggctactg gtggacatca aggtactcat    180

aaatgctag                                                            189
```

<210> SEQ ID NO 52
<211> LENGTH: 490
<212> TYPE: PRT
<213> ORGANISM: Escherichia coli

<400> SEQUENCE: 52

```
Met Asp Lys Val Thr Asp Asn Ser Pro Asp Val Glu Ser Thr Glu Ser
1               5                   10                  15

Thr Glu Gly Ser Phe Pro Thr Val Gly Val Asp Thr Gly Asp Thr Ile
            20                  25                  30

Thr Ala Thr Leu Ala Thr Gly Thr Glu Asn Val Gly Gly Gly Gly Gly
        35                  40                  45

Ala Phe Gly Gly Ala Ser Glu Ser Ser Ala Ala Ile His Ala Thr Ala
    50                  55                  60

Lys Trp Ser Thr Ala Gln Leu Lys Lys His Gln Ala Glu Gln Ala Ala
65                  70                  75                  80

Arg Ala Ala Ala Ala Glu Ala Ala Leu Ala Lys Ala Lys Ser Gln Arg
                85                  90                  95

Asp Ala Leu Thr Gln Arg Leu Lys Asp Ile Val Asn Asp Ala Leu Arg
            100                 105                 110

Ala Asn Ala Ala Arg Ser Pro Ser Val Thr Asp Leu Ala His Ala Asn
        115                 120                 125

Asn Met Ala Met Gln Ala Glu Ala Glu Arg Leu Arg Leu Ala Lys Ala
    130                 135                 140

Glu Gln Lys Ala Arg Glu Glu Ala Glu Ala Ala Glu Lys Ala Leu Arg
145                 150                 155                 160

Glu Ala Glu Arg Gln Arg Asp Glu Ile Ala Arg Gln Gln Ala Glu Thr
                165                 170                 175

Ala His Leu Leu Ala Met Ala Glu Ala Ala Glu Ala Glu Lys Asn Arg
            180                 185                 190

Gln Asp Ser Leu Asp Glu Glu His Arg Ala Val Glu Val Ala Glu Lys
        195                 200                 205

Lys Leu Ala Glu Ala Lys Ala Glu Leu Ala Lys Ala Glu Ser Asp Val
    210                 215                 220

Gln Ser Lys Gln Ala Ile Val Ser Arg Val Ala Gly Glu Leu Glu Asn
225                 230                 235                 240

Ala Gln Lys Ser Val Asp Val Lys Val Thr Gly Phe Pro Gly Trp Arg
                245                 250                 255

Asp Val Gln Lys Lys Leu Glu Arg Gln Leu Gln Asp Lys Lys Asn Glu
            260                 265                 270

Tyr Ser Ser Val Thr Asn Ala Leu Asn Ser Ala Val Ser Ile Arg Asp
        275                 280                 285

Ala Lys Lys Thr Glu Val Gln Asn Ala Glu Ile Lys Leu Lys Glu Ala
    290                 295                 300

Lys Asp Ala Leu Glu Lys Ser Gln Val Lys Asp Ser Val Asp Thr Met
305                 310                 315                 320

Val Gly Phe Tyr Gln Tyr Ile Thr Glu Gln Tyr Gly Glu Lys Tyr Ser
                325                 330                 335

Arg Ile Ala Gln Asp Leu Ala Glu Lys Ala Lys Gly Ser Lys Phe Asn
            340                 345                 350

Ser Val Asp Glu Ala Leu Ala Ala Phe Glu Lys Tyr Lys Asn Val Leu
        355                 360                 365

Asp Lys Lys Phe Ser Lys Val Asp Arg Asp Asp Ile Phe Asn Ala Leu
    370                 375                 380

Glu Ser Ile Thr Tyr Asp Glu Trp Ala Lys His Leu Glu Lys Ile Ser
385                 390                 395                 400
```

```
Arg Ala Leu Lys Val Thr Gly Tyr Leu Ser Phe Gly Tyr Asp Val Trp
                405                 410                 415

Asp Gly Thr Leu Lys Gly Leu Lys Thr Gly Asp Trp Lys Pro Leu Phe
            420                 425                 430

Val Thr Leu Glu Lys Ser Ala Val Asp Phe Gly Val Ala Lys Ile Val
        435                 440                 445

Ala Leu Met Phe Ser Phe Ile Val Gly Ala Pro Leu Gly Phe Trp Gly
    450                 455                 460

Ile Ala Ile Ile Thr Gly Ile Val Ser Ser Tyr Ile Gly Asp Asp Glu
465                 470                 475                 480

Leu Asn Lys Leu Asn Glu Leu Leu Gly Ile
                485                 490


<210> SEQ ID NO 53
<211> LENGTH: 1473
<212> TYPE: DNA
<213> ORGANISM: Escherichia coli

<400> SEQUENCE: 53

atggataaag tcactgataa ttctccagat gtggagagca cagaatctac tgaggggtca     60

ttcccaactg ttggggttga tactggcgat acgattacag cgacgcttgc aactggaact    120

gaaaatgttg gtggaggcgg tggagcattt ggtggggcca gtgaaagttc tgctgcgata    180

catgcaaccg ctaaatggtc taccgcgcag ttgaaaaaac atcaggctga acaggctgcc    240

cgtgctgctg cggctgaggc agcattggca aaagcgaaat ctcagcgtga tgccctgact    300

caacgtctca aggatattgt taatgacgct ttacgtgcta atgccgctcg tagtccatca    360

gtaactgacc ttgctcatgc caataatatg gcaatgcagg cagaggctga gcgtttgcgc    420

cttgcgaagg cagagcaaaa agcccgtgaa gaagctgaag cagcagaaaa agcgctccgg    480

gaagcagaac gccaacgtga tgagattgcc cgccaacagg ctgaaaccgc gcatttgtta    540

gcaatggcgg aggcagcaga ggctgagaaa aatcgacagg attctcttga tgaagagcat    600

cgggctgtgg aagtggcaga gaagaagctg gctgaggcta aagctgaact ggcgaaggcc    660

gaaagcgatg tacagagtaa gcaagcgatt gtttccagag ttgcagggga gcttgaaaac    720

gctcaaaaaa gtgttgatgt gaaggttacc ggatttcctg gatggcgtga tgttcagaaa    780

aaactggaga gacaattgca ggataagaag aatgaatatt cgtcagtgac gaatgctctt    840

aattctgctg ttagcattag agatgctaaa aaaacagaag ttcagaatgc tgagataaaa    900

ttaaaagaag ctaaggatgc tcttgagaag agtcaggtaa aagactctgt tgatactatg    960

gttgggtttt atcaatatat aaccgaacaa tatggggaaa aatattccag aatagctcag   1020

gatttagctg aaaaggcgaa gggtagtaaa tttaatagtg ttgatgaagc acttgctgca   1080

tttgaaaagt ataaaaatgt actggataag aaattcagta aggttgatag ggatgatatt   1140

tttaatgctt tagagtctat tacttatgat gagtgggcca agcatctaga aaagatctct   1200

agggctctta aggttactgg atatttgtct ttcgggtatg atgtatggga tggtacccta   1260

aagggattaa aaacaggaga ctggaagcct ttatttgtca ctctggagaa gagcgcggta   1320

gatttcggcg tggcaaaaat tgtggcatta atgtttagtt ttattgttgg tgcgcctctt   1380

ggcttctggg gaattgcaat tatcacaggt attgtttctt cttacatagg ggatgatgag   1440

ttgaacaagc ttaatgaatt actaggtatt taa                                1473


<210> SEQ ID NO 54
```

```
<211> LENGTH: 522
<212> TYPE: PRT
<213> ORGANISM: Escherichia coli

<400> SEQUENCE: 54

Met Glu Thr Ala Val Ala Tyr Tyr Lys Asp Gly Val Pro Tyr Asp Asp
1               5                   10                  15

Lys Gly Gln Val Ile Ile Thr Leu Leu Asn Gly Thr Pro Asp Gly Ser
            20                  25                  30

Gly Ser Gly Gly Gly Gly Gly Lys Gly Gly Ser Lys Ser Glu Ser Ser
        35                  40                  45

Ala Ala Ile His Ala Thr Ala Lys Trp Ser Thr Ala Gln Leu Lys Lys
    50                  55                  60

Thr Gln Ala Glu Gln Ala Ala Arg Ala Lys Ala Ala Ala Glu Ala Gln
65                  70                  75                  80

Ala Lys Ala Lys Ala Asn Arg Asp Ala Leu Thr Gln Arg Leu Lys Asp
                85                  90                  95

Ile Val Asn Glu Ala Leu Arg His Asn Ala Ser Arg Thr Pro Ser Ala
            100                 105                 110

Thr Glu Leu Ala His Ala Asn Asn Ala Ala Met Gln Ala Glu Asp Glu
        115                 120                 125

Arg Leu Arg Leu Ala Lys Ala Glu Glu Lys Ala Arg Lys Glu Ala Glu
    130                 135                 140

Ala Ala Glu Lys Ala Phe Gln Glu Ala Glu Gln Arg Arg Lys Glu Ile
145                 150                 155                 160

Glu Arg Glu Lys Ala Glu Thr Glu Arg Gln Leu Lys Leu Ala Glu Ala
                165                 170                 175

Glu Glu Lys Arg Leu Ala Ala Leu Ser Glu Glu Ala Lys Ala Val Glu
            180                 185                 190

Ile Ala Gln Lys Lys Leu Ser Ala Ala Gln Ser Glu Val Val Lys Met
        195                 200                 205

Asp Gly Glu Ile Lys Thr Leu Asn Ser Arg Leu Ser Ser Ser Ile His
    210                 215                 220

Ala Arg Asp Ala Glu Met Lys Thr Leu Ala Gly Lys Arg Asn Glu Leu
225                 230                 235                 240

Ala Gln Ala Ser Ala Lys Tyr Lys Glu Leu Asp Glu Leu Val Lys Lys
                245                 250                 255

Leu Ser Pro Arg Ala Asn Asp Pro Leu Gln Asn Arg Pro Phe Phe Glu
            260                 265                 270

Ala Thr Arg Arg Arg Val Gly Ala Gly Lys Ile Arg Glu Glu Lys Gln
        275                 280                 285

Lys Gln Val Thr Ala Ser Glu Thr Arg Ile Asn Arg Ile Asn Ala Asp
    290                 295                 300

Ile Thr Gln Ile Gln Lys Ala Ile Ser Gln Val Ser Asn Asn Arg Asn
305                 310                 315                 320

Ala Gly Ile Ala Arg Val His Glu Ala Glu Glu Asn Leu Lys Lys Ala
                325                 330                 335

Gln Asn Asn Leu Leu Asn Ser Gln Ile Lys Asp Ala Val Asp Ala Thr
            340                 345                 350

Val Ser Phe Tyr Gln Thr Leu Thr Glu Lys Tyr Gly Glu Lys Tyr Ser
        355                 360                 365

Lys Met Ala Gln Glu Leu Ala Asp Lys Ser Lys Gly Lys Lys Ile Gly
    370                 375                 380
```

```
Asn Val Asn Glu Ala Leu Ala Ala Phe Glu Lys Tyr Lys Asp Val Leu
385                 390                 395                 400

Asn Lys Lys Phe Ser Lys Ala Asp Arg Asp Ala Ile Phe Asn Ala Leu
                405                 410                 415

Ala Ser Val Lys Tyr Asp Asp Trp Ala Lys His Leu Asp Gln Phe Ala
            420                 425                 430

Lys Tyr Leu Lys Ile Thr Gly His Val Ser Phe Gly Tyr Asp Val Val
        435                 440                 445

Ser Asp Ile Leu Lys Ile Lys Asp Thr Gly Asp Trp Lys Pro Leu Phe
    450                 455                 460

Leu Thr Leu Glu Lys Lys Ala Ala Asp Ala Gly Val Ser Tyr Val Val
465                 470                 475                 480

Ala Leu Leu Phe Ser Leu Leu Ala Gly Thr Thr Leu Gly Ile Trp Gly
                485                 490                 495

Ile Ala Ile Val Thr Gly Ile Leu Cys Ser Tyr Ile Asp Lys Asn Lys
            500                 505                 510

Leu Asn Thr Ile Asn Glu Val Leu Gly Ile
        515                 520


<210> SEQ ID NO 55
<211> LENGTH: 1569
<212> TYPE: DNA
<213> ORGANISM: Escherichia coli

<400> SEQUENCE: 55

atggaaaccg cggtagcgta ctataaagat ggtgttcctt atgatgataa gggacaggta     60

attattactc ttttgaatgg tactcctgac gggagtggct ctggcggcgg aggtggaaaa    120

ggaggcagta aaagtgaaag ttctgcagct attcatgcaa ctgctaaatg gtctactgct    180

caattaaaga aaacacaggc agagcaggct gcccgggcaa aagctgcagc ggaagcacag    240

gcgaaagcaa aggcaaacag ggatgcgctg actcagcgcc tgaaggatat cgtgaatgag    300

gctcttcgtc acaatgcctc acgtacgcct tcagcaacag agcttgctca tgctaataat    360

gcagctatgc aggcggaaga cgagcgtttg cgccttgcga aagcagaaga aaaagcccgt    420

aaagaagcgg aagcagcaga aaaggctttt caggaagcag aacaacgacg taaagagatt    480

gaacgggaga aggctgaaac agaacgccag ttgaaactgg ctgaagctga agagaaacga    540

ctggctgcat tgagtgaaga agctaaagct gttgagatcg cccaaaaaaa actttctgct    600

gcacaatctg aagtggtgaa aatggatgga gagattaaga ctctcaattc tcgtttaagc    660

tccagtatcc atgcccgtga tgcagaaatg aaaacgctcg ctggaaaacg aaatgaactg    720

gctcaggcat ccgctaaata taaagaactg gatgagctgg tcaaaaaact atcaccaaga    780

gccaatgatc cgcttcagaa ccgtcctttt tttgaagcaa ccagacgacg ggttggggcc    840

ggtaagatta gagaagaaaa acaaaaacag gtaacagcat cagaaacacg tattaaccgg    900

ataaatgctg atataactca gatccagaag gctatttctc aggtcagtaa taatcgtaat    960

gccggtatcg ctcgtgttca tgaagctgaa gaaaatttga aaaaagcaca gaataatctc   1020

cttaattcac agattaagga tgctgttgat gcaacagtta gcttttatca aacgctgact   1080

gaaaaatatg gtgaaaaata ttcgaaaatg gcacaggaac ttgctgataa gtctaaaggt   1140

aagaaaatcg gcaatgtgaa tgaagctctc gctgcttttg aaaaatacaa ggatgtttta   1200

aataagaaat tcagcaaagc cgatcgtgat gctattttta atgcgttggc atcggtgaag   1260

tatgatgact gggctaaaca tttagatcag tttgccaagt acttgaagat tacggggcat   1320
```

```
gtttcttttg gatatgatgt ggtatctgat atcctaaaaa ttaaggatac aggtgactgg   1380

aagccactat ttcttacatt agagaagaaa gctgcagatg caggggtgag ttatgttgtt   1440

gctttacttt ttagcttgct tgctggaact acattaggta tttggggtat tgctattgtt   1500

acaggaattc tatgctccta tattgataag aataaactta atactataaa tgaggtgtta   1560

gggatttaa                                                           1569
```

<210> SEQ ID NO 56
<211> LENGTH: 626
<212> TYPE: PRT
<213> ORGANISM: Escherichia coli

<400> SEQUENCE: 56

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Asn Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320
```

```
Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn
                405                 410                 415

Ala Leu Leu Lys Glu Lys Glu Asn Ile Arg Asn Gln Leu Ser Gly Ile
            420                 425                 430

Asn Gln Lys Ile Ala Glu Glu Lys Arg Lys Gln Asp Glu Leu Lys Ala
        435                 440                 445

Thr Lys Asp Ala Ile Asn Phe Thr Thr Glu Phe Leu Lys Ser Val Ser
    450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
        595                 600                 605

Gly Ala Leu Ile Asp Glu Ser Leu Val Glu Lys Ala Asn Lys Phe Trp
    610                 615                 620

Gly Ile
625


<210> SEQ ID NO 57
<211> LENGTH: 1881
<212> TYPE: DNA
<213> ORGANISM: Escherichia coli

<400> SEQUENCE: 57

atgtctgacc ctgtacgtat tacaaatccc ggtgcagaat cgctggggta tgattcagat      60

ggccatgaaa ttatggccgt tgatatttat gtaaaccctc cacgtgtcga tgtctttcat     120

ggtaccccgc ctgcatggag ttccttcggg aacaaaacca tctggggcgg aaacgagtgg     180

gttgatgatt ccccaacccg aagtgatatc gaaaaaaggg acaaggaaat cacagcgtac     240

aaaaacacgc tcagcgcgca gcagaaagag aatgagaata agcgtactga agccggaaaa     300

cgcctctctg cggcgattgc tgcaagggaa aaagatgaaa acacactgaa aacactccgt     360
```

```
gccggaaacg cagatgccgc tgatattaca cgacaggagt tcagactcct gcaggcagag    420

ctgagagaat acggattccg tactgaaatc gccggatatg acgccctccg gctgcataca    480

gagagccgga tgctgtttgc tgatgctgat tctcttcgta tatctccccg ggaggccagg    540

tcgttaatcg aacaggctga aaaacggcag aaggatgcgc agaacgcaga caagaaggcc    600

gctgatatgc ttgctgaata cgagcgcaga aaaggtattc tggacacccg gttgtcagag    660

ctggaaaaaa atggcggggc agcccttgcc gttcttgatg cacaacaggc ccgtctgctc    720

gggcagcaga cacggaatga cagggccatt tcagaggccc ggaataaact cagttcagtg    780

acggaatcgc ttaacacggc ccgtaatgca ttaaccagag ctgaacaaca gctgacgcaa    840

cagaaaaaca cgcctgacgg caaaacgata gtttcccctg aaaaattccc ggggcgttca    900

tcaacaaatg attctattgt tgtgagcggt gatccgagat ttgccggtac gataaaaatc    960

acaaccagcg cagtcatcga taaccgtgca aacctgaatt atcttctgag ccattccggt   1020

ctggactata aacgcaatat tctgaatgac cggaatccgg tggtgacaga ggatgtggaa   1080

ggtgacaaga aaatttataa tgctgaagtt gctgaatggg ataagttacg gcaaagattg   1140

cttgatgcca gaaataaaat cacctctgct gaatctgcgg taaattcggc gagaaataac   1200

ctcagtgcca gaacaaatga gcaaaagcat gcaaatgacg ctcttaatgc cctgttgaag   1260

gaaaaagaga atatccgtaa ccagctttcc ggcatcaatc agaagatagc ggaagagaaa   1320

agaaaacagg atgaactgaa ggcaacgaaa gacgcaatta atttcacaac agagttcctg   1380

aaatcagttt cagaaaaata tggtgcaaaa gctgagcagt tagccagaga gatggccggg   1440

caggctaaag ggaagaaaat acgtaatgtt gaagaggcat taaaaacgta tgaaaagtac   1500

cgggctgaca ttaacaaaaa aattaatgca aaagatcgtg cagcgattgc cgcagccctt   1560

gagtctgtga agctgtctga tatatcgtct aatctgaaca gattcagtcg gggactggga   1620

tatgcaggaa aatttacaag tcttgctgac tggatcactg agtttggtaa ggctgtccgg   1680

acagagaact ggcgtcctct tttgttaaa acagaaacca tcatagcagg caatgccgca   1740

acggctcttg tggcactggt cttcagtatt cttaccggaa gcgctttagg cattatcggg   1800

tatggtttac tgatggctgt caccggtgcg ctgattgatg aatcgcttgt ggaaaaagcg   1860

aataagttct ggggtattta a                                              1881
```

<210> SEQ ID NO 58
<211> LENGTH: 626
<212> TYPE: PRT
<213> ORGANISM: Escherichia coli

<400> SEQUENCE: 58

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95
```

```
Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Lys Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Thr His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Ile Asn Ser Ala Arg Asn Asn
385                 390                 395                 400

Val Ser Ala Arg Thr Asn Glu Gln Lys His Ala Asn Asp Ala Leu Asn
                405                 410                 415

Ala Leu Leu Lys Glu Lys Glu Asn Ile Arg Ser Gln Leu Ala Asp Ile
            420                 425                 430

Asn Gln Lys Ile Ala Glu Glu Lys Arg Lys Arg Asp Glu Ile Asn Met
        435                 440                 445

Val Lys Asp Ala Ile Lys Leu Thr Ser Asp Phe Tyr Arg Thr Ile Tyr
    450                 455                 460

Asp Glu Phe Gly Lys Gln Ala Ser Glu Leu Ala Lys Glu Leu Ala Ser
465                 470                 475                 480

Val Ser Gln Gly Lys Gln Ile Lys Ser Val Asp Asp Ala Leu Asn Ala
                485                 490                 495

Phe Asp Lys Phe Arg Asn Asn Leu Asn Lys Lys Tyr Asn Ile Gln Asp
            500                 505                 510
```

```
Arg Met Ala Ile Ser Lys Ala Leu Glu Ala Ile Asn Gln Val His Met
        515                 520                 525

Ala Glu Asn Phe Lys Leu Phe Ser Lys Ala Phe Gly Phe Thr Gly Lys
    530                 535                 540

Val Ile Glu Arg Tyr Asp Val Ala Val Glu Leu Gln Lys Ala Val Lys
545                 550                 555                 560

Thr Asp Asn Trp Arg Pro Phe Phe Val Lys Leu Glu Ser Leu Ala Ala
                565                 570                 575

Gly Arg Ala Ala Ser Ala Val Thr Ala Trp Ala Phe Ser Val Met Leu
            580                 585                 590

Gly Thr Pro Val Gly Ile Leu Gly Phe Ala Ile Ile Met Ala Ala Val
        595                 600                 605

Ser Ala Leu Val Asn Asp Lys Phe Ile Glu Gln Val Asn Lys Leu Ile
    610                 615                 620

Gly Ile
625


<210> SEQ ID NO 59
<211> LENGTH: 1881
<212> TYPE: DNA
<213> ORGANISM: Escherichia coli

<400> SEQUENCE: 59

atgtctgacc ctgtacgtat tacaaatccc ggtgcagaat cgctgggata tgattcagat      60

ggccatgaaa ttatggccgt tgatatttat gtaaaccctc cacgtgtcga tgtctttcat     120

ggtaccccgc ctgcatggag ttccttcggg aacaaaacca tctggggtgg aaacgagtgg     180

gtcgatgatt ccccaacccg aagtgatatc gaaaaaaggg acaaggaaat cacagcgtac     240

aaaaacacgc tcagcgcgca gcagaaagag aatgagaata agcgtactga agctggaaaa     300

cgcctttctg cggcaattgc tgcaagggaa aaagatgaaa acacactgaa aacactccgt     360

gccggaaacg cagatgccgc tgatattaca cgacaggagt tcagactcct gcaggcagag     420

ctgagagaat acggattccg tactgaaatc gccggatatg atgccctccg gctgcataca     480

gagagccgga tgctgtttgc tgatgctgat tctcttcgta tatctccccg cgaggccagg     540

tcgttaatcg aacaggctga aaaacggcag aaggatgcgc agaacgcaga caagaaggcc     600

gctgatatgc ttgctgaata cgagcgcaga aaaggtattc tggacacgcg gttgtcagag     660

ctggaaaaaa atggcggggc agcccttgcc gttcttgatg cacaacaggc ccgtctgctc     720

gggcagcaga cacggaatga cagggccatt tcagaggccc ggaataaact cagttcggtg     780

acggaatcgc ttaagacggc ccgtaatgca ttaaccagag ctgaacaaca gctgacgcaa     840

cagaaaaaca cgcctgacgg caaaacgata gtttcccctg aaaaattccc ggggcgttca     900

tcaacaaatc attctattgt tgtgagtggt gatccgaggt ttgccggtac gataaaaatc     960

acaaccagcg cggtcatcga taaccgtgca aacctgaatt atcttctgac ccattccggt    1020

ctggactata aacgcaatat tctgaatgac cggaatccgg tggtgacaga ggatgtggaa    1080

ggtgacaaga aaatttataa tgctgaagtt gctgaatggg ataagttacg gcaacgattg    1140

cttgatgcca gaaataaaat cacctctgct gaatctgcga taaattcggc gagaaataac    1200

gtcagtgcca gaacaaatga acaaaagcat gcaaatgacg ctcttaatgc cctgttgaag    1260

gaaaaagaga atatccgtag ccagcttgct gacatcaatc agaaaatagc tgaagagaaa    1320

agaaaaaggg atgaaataaa tatggtaaag gatgccataa aactcacctc tgatttctac    1380
```

```
agaacgatat atgatgagtt cggtaaacaa gcatccgaac ttgctaagga gctggcttct   1440

gtatctcaag ggaaacagat taagagtgtg gatgatgcac tgaacgcttt tgataaattc   1500

cgtaataatc tgaacaagaa atataacata caagatcgca tggccatttc taaagccctg   1560

gaagctatta atcaggtcca tatggcggag aattttaagc tgttcagtaa ggcatttggt   1620

tttaccggaa aagttattga acgttatgat gttgctgtgg agttacaaaa ggctgtaaaa   1680

acggacaact ggcgtccatt ttttgtaaaa cttgaatcac tggcagcagg aagagctgct   1740

tcagcagtta cagcatgggc gttttccgtc atgctgggaa cccctgtagg tattctgggt   1800

tttgcaatta ttatggcggc tgtgagtgcg cttgttaatg ataagtttat tgagcaggtc   1860

aataaactta ttggtatctg a                                             1881
```

<210> SEQ ID NO 60
<211> LENGTH: 271
<212> TYPE: PRT
<213> ORGANISM: Escherichia coli

<400> SEQUENCE: 60

```
Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro Leu Leu Val Gln Val Val Tyr Ser Phe Phe Gln Ser Pro
        35                  40                  45

Asn Met Cys Leu Gln Ala Leu Thr Gln Leu Glu Asp Tyr Ile Lys Lys
    50                  55                  60

His Gly Ala Ser Asn Pro Leu Thr Leu Gln Ile Ile Ser Thr Asn Ile
65                  70                  75                  80

Gly Tyr Phe Cys Asn Ala Asp Arg Asn Leu Val Leu His Pro Gly Ile
                85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
        115                 120                 125

Pro Ile Val Ala Leu Ala His Tyr Leu Trp Gly Asn Gly Ala Glu Arg
    130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
        195                 200                 205

Ile Ser Ala Asn Gly Ser Trp Thr Tyr Asn Gly Val Val Arg Ser Tyr
    210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
                245                 250                 255

Ile Leu Leu Pro Gly Glu Ile His Ile Lys Glu Ser Gly Lys Arg
            260                 265                 270
```

<210> SEQ ID NO 61

<211> LENGTH: 816
<212> TYPE: DNA
<213> ORGANISM: Escherichia coli

<400> SEQUENCE: 61

```
atggaaacct taactgttca tgcaccatca ccatcaacta acttaccaag ttatggcaat     60

ggtgcatttt ctctttcagc accacatgtg cctggtgctg gccctctttt agtccaggtt    120

gtttatagtt ttttccagag tccaaacatg tgtcttcagg ctttaactca acttgaggat    180

tacatcaaaa aacatggggc cagcaaccct ctcacattgc agatcatatc gacaaatatt    240

ggttacttct gtaacgccga ccgaaatctg gttcttcacc ctggaataag cgtttatgac    300

gcttaccact tcgcaaaacc agcgccaagt caatatgact atcgctcaat gaatatgaaa    360

caaatgagcg gtaatgtcac tacaccaatt gtggcgcttg ctcactattt atggggtaat    420

ggcgctgaaa ggagcgttaa tatcgccaac attggtctta aaatttcccc tatgaaaatt    480

aatcagataa aagacattat aaaatctggt gtagtaggca cattccctgt ttctacaaag    540

ttcacacatg ccactggtga ttataatgtt attaccggtg catatcttgg taatatcaca    600

ctgaaaacag aaggtacttt aactatctct gccaatggct cctggactta caatggcgtt    660

gttcgttcat atgatgataa atacgatttt aacgccagca ctcaccgtgg cattatcgga    720

gagtcgctca caaggctcgg ggcgatgttt tctggtaaag agtaccagat actgcttcct    780

ggtgaaattc acattaaaga aagtggtaag cgataa                               816
```

<210> SEQ ID NO 62
<211> LENGTH: 387
<212> TYPE: PRT
<213> ORGANISM: Escherichia coli

<400> SEQUENCE: 62

```
Met Gly Ser Asn Gly Ala Asp Asn Ala His Asn Asn Ala Phe Gly Gly
1               5                   10                  15

Gly Lys Asn Pro Gly Ile Gly Asn Thr Ser Gly Ala Gly Ser Asn Gly
            20                  25                  30

Ser Ala Ser Ser Asn Arg Gly Asn Ser Asn Gly Trp Ser Trp Ser Asn
        35                  40                  45

Lys Pro His Lys Asn Asp Gly Phe His Ser Asp Gly Ser Tyr His Ile
    50                  55                  60

Thr Phe His Gly Asp Asn Asn Ser Lys Pro Lys Pro Gly Gly Asn Ser
65                  70                  75                  80

Gly Asn Arg Gly Asn Asn Gly Asp Gly Ala Ser Ala Lys Val Gly Glu
                85                  90                  95

Ile Thr Ile Thr Pro Asp Asn Ser Lys Pro Gly Arg Tyr Ile Ser Ser
            100                 105                 110

Asn Pro Glu Tyr Ser Leu Leu Ala Lys Leu Ile Asp Ala Glu Ser Ile
        115                 120                 125

Lys Gly Thr Glu Val Tyr Thr Phe His Thr Arg Lys Gly Gln Tyr Val
    130                 135                 140

Lys Val Thr Val Pro Asp Ser Asn Ile Asp Lys Met Arg Val Asp Tyr
145                 150                 155                 160

Val Asn Trp Lys Gly Pro Lys Tyr Asn Asn Lys Leu Val Lys Arg Phe
                165                 170                 175

Val Ser Gln Phe Leu Leu Phe Arg Lys Glu Glu Lys Glu Lys Asn Glu
            180                 185                 190
```

```
Lys Glu Ala Leu Leu Lys Ala Ser Glu Leu Val Ser Gly Met Gly Asp
        195                 200                 205

Lys Leu Gly Glu Tyr Leu Gly Val Lys Tyr Lys Asn Val Ala Lys Glu
    210                 215                 220

Val Ala Asn Asp Ile Lys Asn Phe His Gly Arg Asn Ile Arg Ser Tyr
225                 230                 235                 240

Asn Glu Ala Met Ala Ser Leu Asn Lys Val Leu Ala Asn Pro Lys Met
                245                 250                 255

Lys Val Asn Lys Ser Asp Lys Asp Ala Ile Val Asn Ala Trp Lys Gln
            260                 265                 270

Val Asn Ala Lys Asp Met Ala Asn Lys Ile Gly Asn Leu Gly Lys Ala
        275                 280                 285

Phe Lys Val Ala Asp Leu Ala Ile Lys Val Glu Lys Ile Arg Glu Lys
    290                 295                 300

Ser Ile Glu Gly Tyr Asn Thr Gly Asn Trp Gly Pro Leu Leu Leu Glu
305                 310                 315                 320

Val Glu Ser Trp Ile Ile Gly Gly Val Val Ala Gly Val Ala Ile Ser
                325                 330                 335

Leu Phe Gly Ala Val Leu Ser Phe Leu Pro Ile Ser Gly Leu Ala Val
            340                 345                 350

Thr Ala Leu Gly Val Ile Gly Ile Met Thr Ile Ser Tyr Leu Ser Ser
        355                 360                 365

Phe Ile Asp Ala Asn Arg Val Ser Asn Ile Asn Asn Ile Ile Ser Ser
    370                 375                 380

Val Ile Arg
385


<210> SEQ ID NO 63
<211> LENGTH: 51
<212> TYPE: DNA
<213> ORGANISM: Escherichia coli

<400> SEQUENCE: 63

gcaaatcgag tttcgaatat aaataacatt atatctagtg ttattcgatg a              51


<210> SEQ ID NO 64
<211> LENGTH: 103
<212> TYPE: PRT
<213> ORGANISM: Escherichia coli

<400> SEQUENCE: 64

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Ala Gly Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100
```

<210> SEQ ID NO 65
<211> LENGTH: 312
<212> TYPE: DNA
<213> ORGANISM: Escherichia coli

<400> SEQUENCE: 65
atgagaactc tgactctaaa tgaattagat tctgtttctg gtggtgcttc agggcgtgat 60
attgcgatgg ctataggaac actatccgga caatttgttg caggaggaat tggagcagct 120
gctgggggtg tggctggagg tgcaatatat gactatgcat ccactcacaa acctaatcct 180
gcaatgtctc catccggttt aggaggaaca attaagcaaa aacccgaagg gataccttca 240
gaagcatgga actatgctgc gggaagattg tgtaattgga gtccaaataa tcttagtgat 300
gtttgtttat aa 312

<210> SEQ ID NO 66
<211> LENGTH: 58
<212> TYPE: PRT
<213> ORGANISM: Enterococcus columbae

<400> SEQUENCE: 66

Met Met Asn Ala Thr Glu Asn Gln Ile Phe Val Glu Thr Val Ser Asp
1 5 10 15

Gln Glu Leu Glu Met Leu Ile Gly Gly Ala Gly Arg Gly Trp Ile Lys
20 25 30

Thr Leu Thr Lys Asp Cys Pro Asn Val Ile Ser Ser Ile Cys Ala Gly
35 40 45

Thr Ile Ile Thr Ala Cys Lys Asn Cys Ala
50 55

<210> SEQ ID NO 67
<211> LENGTH: 177
<212> TYPE: DNA
<213> ORGANISM: Enterococcus columbae

<400> SEQUENCE: 67
atgatgaatg ctactgaaaa ccaaattttt gttgagactg tgagtgacca agaattagaa 60
atgttaattg gtggtgcagg tcgtggatgg attaagactt taacaaaaga ttgtccaaat 120
gtgatttctt caatttgtgc aggtacaatt attacagctt gtaaaaattg tgcttaa 177

<210> SEQ ID NO 68
<211> LENGTH: 59
<212> TYPE: PRT
<213> ORGANISM: Lactobacillus curvatus

<400> SEQUENCE: 68

Met Asn Asn Val Lys Glu Leu Ser Met Thr Glu Leu Gln Thr Ile Thr
1 5 10 15

Gly Gly Ala Arg Ser Tyr Gly Asn Gly Val Tyr Cys Asn Asn Lys Lys
20 25 30

Cys Trp Val Asn Arg Gly Glu Ala Thr Gln Ser Ile Ile Gly Gly Met
35 40 45

Ile Ser Gly Trp Ala Ser Gly Leu Ala Gly Met
50 55

<210> SEQ ID NO 69
<211> LENGTH: 180
<212> TYPE: DNA
<213> ORGANISM: Lactobacillus curvatus

<400> SEQUENCE: 69
atgaataatg taaaagaatt aagtatgaca gaattacaaa caattaccgg cggtgctaga 60
tcatatggca acggtgttta ctgtaataat aaaaaatgtt gggtaaatcg ggtgaagca 120 acgcaaagta ttattggtgg tatgattagc ggctgggcta gtggtttagc tggaatgtaa 180

<210> SEQ ID NO 70
<211> LENGTH: 64
<212> TYPE: PRT
<213> ORGANISM: Streptomyces sp.

<400> SEQUENCE: 70

Met Arg Ser Glu Met Thr Leu Thr Ser Thr Asn Ser Ala Glu Ala Leu
1 5 10 15

Ala Ala Gln Asp Phe Ala Asn Thr Val Leu Ser Ala Ala Ala Pro Gly
20 25 30

Phe His Ala Asp Cys Glu Thr Pro Ala Met Ala Thr Pro Ala Thr Pro
35 40 45

Thr Val Ala Gln Phe Val Ile Gln Gly Ser Thr Ile Cys Leu Val Cys
50 55 60

<210> SEQ ID NO 71
<211> LENGTH: 195
<212> TYPE: DNA
<213> ORGANISM: Streptomyces sp.

<400> SEQUENCE: 71
gtgcgatctg agatgactct tacgagcacg aattccgctg aggctctggc ggcgcaggac 60
tttgcgaaca ccgttctcag cgcggcggcc ccgggcttcc acgcggactg cgagacgccg 120
gccatggcca ccccggccac gccgaccgtc gcccagttcg tgatccaggg cagcacgatc 180
tgcctggtct gctga 195

<210> SEQ ID NO 72
<211> LENGTH: 65
<212> TYPE: PRT
<213> ORGANISM: Bacillus halodurans

<400> SEQUENCE: 72

Met Val Asn Ser Lys Asp Leu Arg Asn Pro Glu Phe Arg Lys Ala Gln
1 5 10 15

Gly Leu Gln Phe Val Asp Glu Val Asn Glu Lys Glu Leu Ser Ser Leu
20 25 30

Ala Gly Ser Gly Asp Val His Ala Gln Thr Thr Trp Pro Cys Ala Thr
35 40 45

Val Gly Val Ser Val Ala Leu Cys Pro Thr Thr Lys Cys Thr Ser Gln
50 55 60

Cys
65

<210> SEQ ID NO 73
<211> LENGTH: 198
<212> TYPE: DNA
<213> ORGANISM: Bacillus halodurans

<400> SEQUENCE: 73
atggtaaatt caaaagattt gcgtaatcct gaattccgca aagcccaagg tctacaattc 60
gttgacgagg tgaacgagaa ggaactttcg tctctagctg gttcaggaga tgtgcatgca 120

```
caaacaactt ggccttgcgc tacagttggt gtctccgtag ccttgtgccc aactacaaag    180

tgtacaagcc agtgctaa                                                  198


<210> SEQ ID NO 74
<211> LENGTH: 66
<212> TYPE: PRT
<213> ORGANISM: Carnobacterium divergens

<400> SEQUENCE: 74

Met Lys Asn Leu Lys Glu Gly Ser Tyr Thr Ala Val Asn Thr Asp Glu
1               5                   10                  15

Leu Lys Ser Ile Asn Gly Gly Thr Lys Tyr Tyr Gly Asn Gly Val Tyr
            20                  25                  30

Cys Asn Ser Lys Lys Cys Trp Val Asp Trp Gly Gln Ala Ser Gly Cys
        35                  40                  45

Ile Gly Gln Thr Val Val Gly Gly Trp Leu Gly Gly Ala Ile Pro Gly
    50                  55                  60

Lys Cys
65


<210> SEQ ID NO 75
<211> LENGTH: 201
<212> TYPE: DNA
<213> ORGANISM: Carnobacterium divergens

<400> SEQUENCE: 75

atgaaaaact taaaagaagg ttcatacact gctgttaata ctgatgaatt aaaaagtatc     60

aatggtggaa caaaatatta tggaatggc gtttattgca attctaaaaa atgttgggta    120

gattggggac aagcttcagg ttgtatcggt caaactgttg ttggcggatg gctaggcgga    180

gctataccag gtaaatgcta a                                              201


<210> SEQ ID NO 76
<211> LENGTH: 63
<212> TYPE: PRT
<213> ORGANISM: Carnobacterium divergens

<400> SEQUENCE: 76

Met Ile Lys Arg Glu Lys Asn Arg Thr Ile Ser Ser Leu Gly Tyr Glu
1               5                   10                  15

Glu Ile Ser Asn His Lys Leu Gln Glu Ile Gln Gly Gly Lys Gly Ile
            20                  25                  30

Leu Gly Lys Leu Gly Val Val Gln Ala Gly Val Asp Phe Val Ser Gly
        35                  40                  45

Val Trp Ala Gly Ile Lys Gln Ser Ala Lys Asp His Pro Asn Ala
    50                  55                  60


<210> SEQ ID NO 77
<211> LENGTH: 192
<212> TYPE: DNA
<213> ORGANISM: Carnobacterium divergens

<400> SEQUENCE: 77

atgattaaaa gagaaaagaa cagaacaatt tcttcccttg gttatgaaga aatttctaat     60

cataaattgc aagaaataca aggtggaaaa ggaattcttg gtaaactagg agtagtacag    120

gcaggagtgg attttgtatc aggagtgtgg gctggaataa aacagtctgc caaagatcat    180

cctaatgcgt aa                                                        192
```

<210> SEQ ID NO 78
<211> LENGTH: 75
<212> TYPE: PRT
<213> ORGANISM: Carnobacterium divergens

<400> SEQUENCE: 78

```
Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Ala Ala Pro
            20                  25                  30

Lys Ile Thr Gln Lys Gln Lys Asn Cys Val Asn Gly Gln Leu Gly Gly
        35                  40                  45

Met Leu Ala Gly Ala Leu Gly Gly Pro Gly Gly Val Val Leu Gly Gly
    50                  55                  60

Ile Gly Gly Ala Ile Ala Gly Gly Cys Phe Asn
65                  70                  75
```

<210> SEQ ID NO 79
<211> LENGTH: 228
<212> TYPE: DNA
<213> ORGANISM: Carnobacterium divergens

<400> SEQUENCE: 79

```
atgaaaaaac aaattttaaa agggttggtt atagttgttt gtttatctgg ggcaacattt      60

ttctcaacac cacaacaagc ttctgctgct gcaccgaaaa ttactcaaaa acaaaaaaat     120

tgtgttaatg gacaattagg tggaatgctt gctggagctt tgggtggacc tggcggagtt     180

gtgttaggtg gtataggtgg tgcaatagca ggaggttgtt ttaattaa                  228
```

<210> SEQ ID NO 80
<211> LENGTH: 72
<212> TYPE: PRT
<213> ORGANISM: Enterococcus durans

<400> SEQUENCE: 80

```
Met Gln Thr Ile Lys Glu Leu Asn Thr Met Glu Leu Gln Glu Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Gly Pro Gly Gly Phe Ile Ser Ala Gly
    50                  55                  60

Ile Ser Ala Val Leu Gly Cys Met
65                  70
```

<210> SEQ ID NO 81
<211> LENGTH: 219
<212> TYPE: DNA
<213> ORGANISM: Enterococcus durans

<400> SEQUENCE: 81

```
atgcaaacga tcaaagaatt gaacacgatg gaattacaag aaataattgg aggtgaaaat      60

gaccatcgga tgccttacga attgaaccgt ccaaataatt tatccaaagg tggggctaag     120

tgtgctgctg gaatacttgg cgctggacta ggcgcagtag gcggtggacc tggcggattt     180

attagtgccg gaatcagtgc tgttcttggt tgtatgtaa                            219
```

<210> SEQ ID NO 82
<211> LENGTH: 72
<212> TYPE: PRT
<213> ORGANISM: Enterococcus durans

<400> SEQUENCE: 82

```
Met Gln Thr Ile Lys Glu Leu Asn Thr Met Glu Leu Gln Lys Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Gly Pro Gly Gly Phe Ile Ser Ala Gly
    50                  55                  60

Ile Ser Ala Val Leu Gly Cys Met
65                  70
```

<210> SEQ ID NO 83
<211> LENGTH: 219
<212> TYPE: DNA
<213> ORGANISM: Enterococcus durans

<400> SEQUENCE: 83

```
atgcaaacga tcaaagaatt gaacacgatg gaattacaaa aaataattgg aggtgaaaat     60

gaccatcgga tgccttacga attgaaccgt ccaaataatt tatccaaagg tggagctaag    120

tgcgctgccg gaatacttgg tgctggatta ggcgcagtag gcggtggacc tggcggattt    180

attagtgccg gaatcagtgc tgttcttggt tgtatgtaa                           219
```

<210> SEQ ID NO 84
<211> LENGTH: 220
<212> TYPE: PRT
<213> ORGANISM: Streptococcus dysgalactiae subsp. equisimilis

<400> SEQUENCE: 84

```
Met Lys Lys Leu Lys Arg Leu Val Ile Ser Leu Val Thr Ser Leu Leu
1               5                   10                  15

Val Ile Ser Ser Thr Val Pro Ala Leu Val Tyr Ala Asn Glu Thr Asn
            20                  25                  30

Asn Phe Ala Glu Thr Gln Lys Glu Ile Thr Thr Asn Ser Glu Ala Thr
        35                  40                  45

Leu Thr Asn Glu Asp Tyr Thr Lys Leu Thr Ser Glu Val Lys Thr Ile
    50                  55                  60

Tyr Thr Asn Leu Ile Gln Tyr Asp Gln Thr Lys Asn Lys Phe Tyr Val
65                  70                  75                  80

Asp Glu Asp Lys Thr Glu Gln Tyr Tyr Asn Tyr Asp Asp Glu Ser Ile
                85                  90                  95

Lys Gly Val Tyr Leu Met Lys Asp Ser Leu Asn Asp Glu Leu Asn Asn
            100                 105                 110

Asn Asn Ser Ser Asn Tyr Ser Glu Ile Ile Asn Gln Lys Ile Ser Glu
        115                 120                 125

Ile Asp Tyr Val Leu Gln Gly Asn Asp Ile Asn Asn Leu Ile Pro Ser
    130                 135                 140

Asn Thr Arg Val Lys Arg Ser Ala Asp Phe Ser Trp Ile Gln Arg Cys
145                 150                 155                 160

Leu Glu Glu Ala Trp Gly Tyr Ala Ile Ser Leu Val Thr Leu Lys Gly
                165                 170                 175
```

```
Ile Ile Asn Leu Phe Lys Ala Gly Lys Phe Glu Ala Ala Ala Ala Lys
            180                 185                 190

Leu Ala Ser Ala Thr Ala Gly Arg Ile Ala Gly Met Ala Ala Leu Phe
        195                 200                 205

Ala Phe Val Ala Thr Cys Gly Ala Thr Thr Val Ser
    210                 215                 220


<210> SEQ ID NO 85
<211> LENGTH: 663
<212> TYPE: DNA
<213> ORGANISM: Streptococcus dysgalactiae subsp. equisimilis

<400> SEQUENCE: 85

atgaaaaaat taaaacgtct tgttatctct cttgttactt cattactagt aatttcaagt     60

acagttccag cacttgttta cgctaatgaa acaaataact ttgcagaaac tcaaaaagaa    120

attacaacaa attcagaagc aacattaacc aatgaagact acactaaatt aacttccgaa    180

gtaaaaacaa tttatacaaa tctgattcaa tacgaccaaa caaaaaacaa attttacgtc    240

gatgaagaca aaactgaaca atattataac tacgatgatg aaagtataaa aggggtttat    300

ctcatgaaag atagtttgaa cgatgagtta aacaataata actcttcaaa ctattctgaa    360

ataattaatc aaaaaatctc tgaaattgac tatgtccttc aaggaaacga tataaataat    420

ttaattccta gcaataccag agtaaaaaga tcagcagatt tttcttggat tcaaagatgt    480

ctagaagaag catggggata tgctattagt ctagttactc taaaaggaat aatcaatcta    540

tttaaagcag gaaaatttga agctgctgct gctaaattag cttctgctac agcaggtaga    600

atcgctggaa tggctgcctt atttgctttc gtagcaactt gcggtgcgac aactgtatca    660

taa                                                                  663


<210> SEQ ID NO 86
<211> LENGTH: 57
<212> TYPE: PRT
<213> ORGANISM: Enterococcus faecalis

<400> SEQUENCE: 86

Met Lys Gln Tyr Lys Val Leu Asn Glu Lys Glu Met Lys Lys Pro Ile
1               5                   10                  15

Gly Gly Glu Ser Val Phe Ser Lys Ile Gly Asn Ala Val Gly Pro Ala
            20                  25                  30

Ala Tyr Trp Ile Leu Lys Gly Leu Gly Asn Met Ser Asp Val Asn Gln
        35                  40                  45

Ala Asp Arg Ile Asn Arg Lys Lys His
    50                  55


<210> SEQ ID NO 87
<211> LENGTH: 174
<212> TYPE: DNA
<213> ORGANISM: Enterococcus faecalis

<400> SEQUENCE: 87

atgaagcaat ataaagtatt gaatgaaaaa gaaatgaaaa aacctattgg gggagagtcg     60

gtttttagta aaataggtaa tgctgtaggt ccagctgctt attggatttt aaaaggatta    120

ggtaatatga gtgatgtaaa ccaagctgat agaattaata gaaagaaaca ttaa          174


<210> SEQ ID NO 88
<211> LENGTH: 44
```

<212> TYPE: PRT
<213> ORGANISM: Enterococcus faecalis

<400> SEQUENCE: 88

```
Met Gly Ala Ile Ala Lys Leu Val Ala Lys Phe Gly Trp Pro Ile Val
1               5                   10                  15

Lys Lys Tyr Tyr Lys Gln Ile Met Gln Phe Ile Gly Glu Gly Trp Ala
            20                  25                  30

Ile Asn Lys Ile Ile Asp Trp Ile Lys Lys His Ile
        35                  40
```

<210> SEQ ID NO 89
<211> LENGTH: 135
<212> TYPE: DNA
<213> ORGANISM: Enterococcus faecalis

<400> SEQUENCE: 89

```
atgggagcaa tcgcaaaatt agtagcaaag tttggatggc caattgttaa aaagtattac     60

aaacaaatta tgcaatttat tggagaagga tgggcaatta acaaaattat tgattggatc    120

aaaaaacata tttaa                                                     135
```

<210> SEQ ID NO 90
<211> LENGTH: 43
<212> TYPE: PRT
<213> ORGANISM: Enterococcus faecalis

<400> SEQUENCE: 90

```
Met Gly Ala Ile Ala Lys Leu Val Ala Lys Phe Gly Trp Pro Phe Ile
1               5                   10                  15

Lys Lys Phe Tyr Lys Gln Ile Met Gln Phe Ile Gly Gln Gly Trp Thr
            20                  25                  30

Ile Asp Gln Ile Glu Lys Trp Leu Lys Arg His
        35                  40
```

<210> SEQ ID NO 91
<211> LENGTH: 132
<212> TYPE: DNA
<213> ORGANISM: Enterococcus faecalis

<400> SEQUENCE: 91

```
atgggagcaa tcgcaaaatt agtagcaaag tttggatggc catttattaa aaaattctac     60

aaacaaatta tgcagtttat cggacaagga tggacaatag atcaaattga aaaatggtta    120

aaaagacatt ga                                                        132
```

<210> SEQ ID NO 92
<211> LENGTH: 74
<212> TYPE: PRT
<213> ORGANISM: Enterococcus faecalis

<400> SEQUENCE: 92

```
Met Leu Asn Lys Lys Leu Leu Glu Asn Gly Val Val Asn Ala Val Thr
1               5                   10                  15

Ile Asp Glu Leu Asp Ala Gln Phe Gly Gly Met Ser Lys Arg Asp Cys
            20                  25                  30

Asn Leu Met Lys Ala Cys Cys Ala Gly Gln Ala Val Thr Tyr Ala Ile
        35                  40                  45

His Ser Leu Leu Asn Arg Leu Gly Gly Asp Ser Ser Asp Pro Ala Gly
    50                  55                  60
```

```
Cys Asn Asp Ile Val Arg Lys Tyr Cys Lys
65                  70


<210> SEQ ID NO 93
<211> LENGTH: 225
<212> TYPE: DNA
<213> ORGANISM: Enterococcus faecalis

<400> SEQUENCE: 93

atgttaaata aaaaattatt agaaaatggt gtagtaaatg ctgtaacaat tgatgaactt      60

gatgctcaat ttggtggaat gagcaaacgt gattgtaact tgatgaaggc gtgttgtgct     120

ggacaagcag taacatatgc tattcatagt cttttaaatc gattaggtgg agactctagt     180

gatccagctg gttgtaatga tattgtaaga aaatattgta aataa                     225


<210> SEQ ID NO 94
<211> LENGTH: 65
<212> TYPE: PRT
<213> ORGANISM: Enterococcus faecium

<400> SEQUENCE: 94

Met Lys His Leu Lys Ile Leu Ser Ile Lys Glu Thr Gln Leu Ile Tyr
1               5                   10                  15

Gly Gly Thr Thr His Ser Gly Lys Tyr Tyr Gly Asn Gly Val Tyr Cys
            20                  25                  30

Thr Lys Asn Lys Cys Thr Val Asp Trp Ala Lys Ala Thr Thr Cys Ile
        35                  40                  45

Ala Gly Met Ser Ile Gly Gly Phe Leu Gly Gly Ala Ile Pro Gly Lys
    50                  55                  60

Cys
65


<210> SEQ ID NO 95
<211> LENGTH: 195
<212> TYPE: DNA
<213> ORGANISM: Enterococcus faecium

<400> SEQUENCE: 95

atgaaacatt taaaaatttt gtctattaaa gagacacaac ttatctatgg gggtaccact      60

catagtggaa aatattatgg aaatggagtg tattgcacta aaaataaatg tacggtcgat     120

tgggccaagg caactacttg tattgcagga atgtctatag gtggtttttt aggtggagca     180

attccaggga agtgc                                                      195


<210> SEQ ID NO 96
<211> LENGTH: 105
<212> TYPE: PRT
<213> ORGANISM: Enterococcus faecalis

<400> SEQUENCE: 96

Met Val Lys Glu Asn Lys Phe Ser Lys Ile Phe Ile Leu Met Ala Leu
1               5                   10                  15

Ser Phe Leu Gly Leu Ala Leu Phe Ser Ala Ser Leu Gln Phe Leu Pro
            20                  25                  30

Ile Ala His Met Ala Lys Glu Phe Gly Ile Pro Ala Ala Val Ala Gly
        35                  40                  45

Thr Val Leu Asn Val Val Glu Ala Gly Gly Trp Val Thr Thr Ile Val
    50                  55                  60
```

```
Ser Ile Leu Thr Ala Val Gly Ser Gly Gly Leu Ser Leu Leu Ala Ala
65                  70                  75                  80

Ala Gly Arg Glu Ser Ile Lys Ala Tyr Leu Lys Lys Glu Ile Lys Lys
                85                  90                  95

Lys Gly Lys Arg Ala Val Ile Ala Trp
            100                 105


<210> SEQ ID NO 97
<211> LENGTH: 318
<212> TYPE: DNA
<213> ORGANISM: Enterococcus faecalis

<400> SEQUENCE: 97

atggttaaag aaaataaatt ttctaagatt tttattttaa tggctttgag ttttttgggg      60

ttagccttgt ttagtgcaag tcttcagttt ttgcccattg cacatatggc taaagagttc     120

ggtataccag cagcagttgc aggaactgtg cttaatgtag ttgaagctgg tggatgggtc     180

actactattg tatcaattct tactgctgta ggtagcggag gtctttcttt actcgctgca     240

gcaggaagag agtcaattaa agcatacctt aagaaagaaa ttaagaaaaa aggaaaaaga     300

gcagttattg cttggtaa                                                   318


<210> SEQ ID NO 98
<211> LENGTH: 71
<212> TYPE: PRT
<213> ORGANISM: Enterococcus faecium

<400> SEQUENCE: 98

Met Gln Asn Val Lys Glu Leu Ser Thr Lys Glu Met Lys Gln Ile Ile
1               5                   10                  15

Gly Gly Glu Asn Asp His Arg Met Pro Asn Glu Leu Asn Arg Pro Asn
            20                  25                  30

Asn Leu Ser Lys Gly Gly Ala Lys Cys Gly Ala Ala Ile Ala Gly Gly
        35                  40                  45

Leu Phe Gly Ile Pro Lys Gly Pro Leu Ala Trp Ala Ala Gly Leu Ala
    50                  55                  60

Asn Val Tyr Ser Lys Cys Asn
65                  70


<210> SEQ ID NO 99
<211> LENGTH: 216
<212> TYPE: DNA
<213> ORGANISM: Enterococcus faecium

<400> SEQUENCE: 99

atgcaaaatg taaaagaatt aagtacgaaa gagatgaaac aaattatcgg tggagaaaat      60

gatcacagaa tgcctaatga gttaaataga cctaacaact tatctaaagg tggagcaaaa     120

tgtggtgctg caattgctgg gggattattt ggaatcccaa aaggaccact agcatgggct     180

gctgggttag caaatgtata ctctaaatgc aactaa                               216


<210> SEQ ID NO 100
<211> LENGTH: 58
<212> TYPE: PRT
<213> ORGANISM: Enterococcus mundtii

<400> SEQUENCE: 100

Met Lys Lys Leu Thr Ser Lys Glu Met Ala Gln Val Val Gly Gly Lys
1               5                   10                  15
```

```
Tyr Tyr Gly Asn Gly Val Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55


<210> SEQ ID NO 101
<211> LENGTH: 177
<212> TYPE: DNA
<213> ORGANISM: Enterococcus mundtii

<400> SEQUENCE: 101

ttgaagaaat taacatcaaa agaaatggca caagtagtag gtggaaaata ctacggtaat      60

ggagtctcat gtaataaaaa agggtgcagt gttgattggg gaaaagctat tggcattatt     120

ggaaataatt ctgctgcgaa tttagctact ggtggagcag ctggttggaa aagttaa        177


<210> SEQ ID NO 102
<211> LENGTH: 44
<212> TYPE: PRT
<213> ORGANISM: Enterococcus faecalis

<400> SEQUENCE: 102

Met Leu Ala Lys Ile Lys Ala Met Ile Lys Lys Phe Pro Asn Pro Tyr
1               5                   10                  15

Thr Leu Ala Ala Lys Leu Thr Thr Tyr Glu Ile Asn Trp Tyr Lys Gln
            20                  25                  30

Gln Tyr Gly Arg Tyr Pro Trp Glu Arg Pro Val Ala
        35                  40


<210> SEQ ID NO 103
<211> LENGTH: 135
<212> TYPE: DNA
<213> ORGANISM: Enterococcus faecalis

<400> SEQUENCE: 103

atgttagcaa aaattaaagc gatgattaag aagtttccga acccttatac tttagcagct      60

aagctaacga cttacgaaat taattggtat aaacaacaat acggtcgtta tccttgggag     120

cgccctgtag cataa                                                      135


<210> SEQ ID NO 104
<211> LENGTH: 71
<212> TYPE: PRT
<213> ORGANISM: Enterococcus faecium

<400> SEQUENCE: 104

Met Arg Lys Lys Leu Phe Ser Leu Ala Leu Ile Gly Ile Phe Gly Leu
1               5                   10                  15

Val Val Thr Asn Phe Gly Thr Lys Val Asp Ala Ala Thr Arg Ser Tyr
            20                  25                  30

Gly Asn Gly Val Tyr Cys Asn Asn Ser Lys Cys Trp Val Asn Trp Gly
        35                  40                  45

Glu Ala Lys Glu Asn Ile Ala Gly Ile Val Ile Ser Gly Trp Ala Ser
    50                  55                  60

Gly Leu Ala Gly Met Gly His
65                  70
```

<210> SEQ ID NO 105
<211> LENGTH: 216
<212> TYPE: DNA
<213> ORGANISM: Enterococcus faecium

<400> SEQUENCE: 105

```
atgagaaaaa aattatttag tttagctctt attggaatat ttgggttagt tgtgacaaat     60

tttggtacaa aagttgatgc agctacgcgt tcatatggta atggtgttta ttgtaataat    120

agtaaatgct gggttaactg gggagaagct aaagagaata ttgcaggaat cgttattagt    180

ggctgggctt ctggtttggc aggtatggga cattaa                              216
```

<210> SEQ ID NO 106
<211> LENGTH: 34
<212> TYPE: PRT
<213> ORGANISM: Enterococcus faecium

<400> SEQUENCE: 106

```
Met Asn Phe Leu Lys Asn Gly Ile Ala Lys Trp Met Thr Gly Ala Glu
1               5                   10                  15

Leu Gln Ala Tyr Lys Lys Lys Tyr Gly Cys Leu Pro Trp Glu Lys Ile
            20                  25                  30

Ser Cys
```

<210> SEQ ID NO 107
<211> LENGTH: 105
<212> TYPE: DNA
<213> ORGANISM: Enterococcus faecium

<400> SEQUENCE: 107

```
atgaattttc ttaaaaatgg tatcgcaaaa tggatgaccg gtgctgaatt gcaagcgtat     60

aaaaagaaat atggatgctt gccatgggaa aaaatttctt gttaa                    105
```

<210> SEQ ID NO 108
<211> LENGTH: 76
<212> TYPE: PRT
<213> ORGANISM: Enterococcus faecalis

<400> SEQUENCE: 108

```
Met Lys Lys Lys Leu Val Lys Gly Leu Val Ile Cys Gly Met Ile Gly
1               5                   10                  15

Ile Gly Phe Thr Ala Leu Gly Thr Asn Val Glu Ala Ala Thr Tyr Tyr
            20                  25                  30

Gly Asn Gly Val Tyr Cys Asn Lys Gln Lys Cys Trp Val Asp Trp Ser
        35                  40                  45

Arg Ala Arg Ser Glu Ile Ile Asp Arg Gly Val Lys Ala Tyr Val Asn
    50                  55                  60

Gly Phe Thr Lys Val Leu Gly Gly Ile Gly Gly Arg
65                  70                  75
```

<210> SEQ ID NO 109
<211> LENGTH: 231
<212> TYPE: DNA
<213> ORGANISM: Enterococcus faecalis

<400> SEQUENCE: 109

```
atgaaaaaga aattagttaa aggcttagtt atttgtggca tgattgggat tggttttaca     60

gcattaggaa caaatgtaga agccgccacg tattacggaa atggtgtcta ttgcaataag    120
```

```
caaaaatgtt gggtagattg gagtagagca cgttctgaaa ttatagacag aggcgtaaaa    180

gcatacgtca atggatttac gaaagtgtta ggtggtatag gtggaagata a             231


<210> SEQ ID NO 110
<211> LENGTH: 60
<212> TYPE: PRT
<213> ORGANISM: Enterococcus faecalis

<400> SEQUENCE: 110

Met Lys Lys Glu Glu Leu Val Gly Met Ala Lys Glu Asp Phe Leu Asn
1               5                   10                  15

Val Ile Cys Glu Asn Asp Asn Lys Leu Glu Asn Ser Gly Ala Lys Cys
            20                  25                  30

Pro Trp Trp Asn Leu Ser Cys His Leu Gly Asn Asp Gly Lys Ile Cys
        35                  40                  45

Thr Tyr Ser His Glu Cys Thr Ala Gly Cys Asn Ala
    50                  55                  60


<210> SEQ ID NO 111
<211> LENGTH: 183
<212> TYPE: DNA
<213> ORGANISM: Enterococcus faecalis

<400> SEQUENCE: 111

atgaaaaaag aagaattagt aggaatggct aaggaagact tttaaaatgt tatttgtgaa     60

aatgacaaca aactagaaaa tagtggagca aaatgtcctt ggtggaatct ttcttgtcat    120

ttaggcaatg atggtaaaat ttgcacttat tcacatgaat gtaccgcagg ttgtaatgca    180

taa                                                                  183


<210> SEQ ID NO 112
<211> LENGTH: 61
<212> TYPE: PRT
<213> ORGANISM: Enterococcus faecalis

<400> SEQUENCE: 112

Met Thr Glu Leu Asn Lys Arg Leu Gln Leu Lys Arg Asp Val Ser Thr
1               5                   10                  15

Glu Asn Ser Leu Lys Lys Ile Ser Asn Thr Asp Glu Thr His Gly Gly
            20                  25                  30

Val Thr Thr Ser Ile Pro Cys Thr Val Met Val Ser Ala Ala Val Cys
        35                  40                  45

Pro Thr Leu Val Cys Ser Asn Lys Cys Gly Gly Arg Gly
    50                  55                  60


<210> SEQ ID NO 113
<211> LENGTH: 186
<212> TYPE: DNA
<213> ORGANISM: Enterococcus faecalis

<400> SEQUENCE: 113

atgactgaac ttaacaaaag attacaatta aaaagagatg tttcaacaga aaatagtttg     60

aaaaaaattt ctaatactga tgaaacacat gggggagtta ctacatcaat tccatgtaca    120

gtaatggtta gtgcggcagt atgtcctacc cttgtttgct cgaataaatg tggcggtaga    180

ggctag                                                               186


<210> SEQ ID NO 114
```

```
<211> LENGTH: 58
<212> TYPE: PRT
<213> ORGANISM: Enterococcus faecium

<400> SEQUENCE: 114

Met Gln Asn Val Lys Glu Val Ser Val Lys Glu Met Lys Gln Ile Ile
1               5                   10                  15

Gly Gly Ser Asn Asp Ser Leu Trp Tyr Gly Val Gly Gln Phe Met Gly
            20                  25                  30

Lys Gln Ala Asn Cys Ile Thr Asn His Pro Val Lys His Met Ile Ile
        35                  40                  45

Pro Gly Tyr Cys Leu Ser Lys Ile Leu Gly
    50                  55


<210> SEQ ID NO 115
<211> LENGTH: 177
<212> TYPE: DNA
<213> ORGANISM: Enterococcus faecium

<400> SEQUENCE: 115

atgcaaaatg taaaagaagt ttctgtaaaa gagatgaaac aaattatcgg tggttctaat      60

gatagtcttt ggtatggtgt aggacaattt atgggtaaac aagcaaactg tataacaaac     120

catcctgtta aacacatgat aattcctgga tattgtttat cgaaaatttt agggtaa        177


<210> SEQ ID NO 116
<211> LENGTH: 55
<212> TYPE: PRT
<213> ORGANISM: Enterococcus faecium

<400> SEQUENCE: 116

Met Lys Lys Tyr Asn Glu Leu Ser Lys Lys Glu Leu Leu Gln Ile Gln
1               5                   10                  15

Gly Gly Ile Ala Pro Ile Ile Val Ala Gly Leu Gly Tyr Leu Val Lys
            20                  25                  30

Asp Ala Trp Asp His Ser Asp Gln Ile Ile Ser Gly Phe Lys Lys Gly
        35                  40                  45

Trp Asn Gly Gly Arg Arg Lys
    50                  55


<210> SEQ ID NO 117
<211> LENGTH: 168
<212> TYPE: DNA
<213> ORGANISM: Enterococcus faecium

<400> SEQUENCE: 117

atgaaaaaat ataatgagtt atctaaaaaa gaacttctac agattcaagg aggaatagca      60

cctattatag ttgctggcct tggctattta gtaaaagatg catgggatca ctcagatcaa     120

ataatctcag gatttaaaaa aggttggaat ggtggacgta gaaaataa                  168


<210> SEQ ID NO 118
<211> LENGTH: 343
<212> TYPE: PRT
<213> ORGANISM: Enterococcus faecalis

<400> SEQUENCE: 118

Met Lys Asn Ile Leu Leu Ser Ile Leu Gly Val Leu Ser Ile Val Val
1               5                   10                  15

Ser Leu Ala Phe Ser Ser Tyr Ser Val Asn Ala Ala Ser Asn Glu Trp
            20                  25                  30
```

```
Ser Trp Pro Leu Gly Lys Pro Tyr Ala Gly Arg Tyr Glu Glu Gly Gln
        35                  40                  45

Gln Phe Gly Asn Thr Ala Phe Asn Arg Gly Gly Thr Tyr Phe His Asp
    50                  55                  60

Gly Phe Asp Phe Gly Ser Ala Ile Tyr Gly Asn Gly Ser Val Tyr Ala
65                  70                  75                  80

Val His Asp Gly Lys Ile Leu Tyr Ala Gly Trp Asp Pro Val Gly Gly
                85                  90                  95

Gly Ser Leu Gly Ala Phe Ile Val Leu Gln Ala Gly Asn Thr Asn Val
            100                 105                 110

Ile Tyr Gln Glu Phe Ser Arg Asn Val Gly Asp Ile Lys Val Ser Thr
        115                 120                 125

Gly Gln Thr Val Lys Lys Gly Gln Leu Ile Gly Lys Phe Thr Ser Ser
    130                 135                 140

His Leu His Leu Gly Met Thr Lys Lys Glu Trp Arg Ser Ala His Ser
145                 150                 155                 160

Ser Trp Asn Lys Asp Asp Gly Thr Trp Phe Asn Pro Ile Pro Ile Leu
                165                 170                 175

Gln Gly Gly Ser Thr Pro Thr Pro Pro Asn Pro Gly Pro Lys Asn Phe
            180                 185                 190

Thr Thr Asn Val Arg Tyr Gly Leu Arg Val Leu Gly Gly Ser Trp Leu
        195                 200                 205

Pro Glu Val Thr Asn Phe Asn Asn Thr Asn Asp Gly Phe Ala Gly Tyr
    210                 215                 220

Pro Asn Arg Gln His Asp Met Leu Tyr Ile Lys Val Asp Lys Gly Gln
225                 230                 235                 240

Met Lys Tyr Arg Val His Thr Ala Gln Ser Gly Trp Leu Pro Trp Val
                245                 250                 255

Ser Lys Gly Asp Lys Ser Asp Thr Val Asn Gly Ala Ala Gly Met Pro
            260                 265                 270

Gly Gln Ala Ile Asp Gly Val Gln Leu Asn Tyr Ile Thr Pro Lys Gly
        275                 280                 285

Glu Lys Leu Ser Gln Ala Tyr Tyr Arg Ser Gln Thr Thr Lys Arg Ser
    290                 295                 300

Gly Trp Leu Lys Val Ser Ala Asp Asn Gly Ser Ile Pro Gly Leu Asp
305                 310                 315                 320

Ser Tyr Ala Gly Ile Phe Gly Glu Pro Leu Asp Arg Leu Gln Ile Gly
                325                 330                 335

Ile Ser Gln Ser Asn Pro Phe
            340
```

<210> SEQ ID NO 119
<211> LENGTH: 1032
<212> TYPE: DNA
<213> ORGANISM: Enterococcus faecalis

<400> SEQUENCE: 119

```
atgaaaaata ttttactttc tattctaggg gtattatcta tcgttgtttc tttggcgttt      60

tcttcttatt ctgtcaacgc agcttctaat gagtggtcgt ggccactggg caaaccatat     120

gcgggaagat atgaagaagg acaacaattc gggaacactg catttaaccg aggaggtact     180

tatttccatg atgggtttga ctttggttct gctatttatg gaaatggcag tgtgtatgct     240

gtgcatgatg gtaaaatttt atatgctggt tgggatcctg taggtggagg ctcattaggt     300
```

```
gcatttattg tactacaagc gggaaacaca aatgtgattt atcaagaatt tagccgaaat    360

gttggagata ttaaagttag cactggacaa actgttaaaa aaggacagct gataggaaag    420

tttacttcta gtcatttaca tttaggaatg acaaaaaaag aatggcgttc tgctcattct    480

tcttggaata aagatgatgg cacttggttt aacccaattc ctatacttca aggaggatct    540

acgcctacgc ctccaaatcc aggaccaaaa aatttcacaa caaatgttcg ttacggattg    600

cgggtcctcg gaggttcatg gttaccagaa gtaaccaact ttaacaatac caatgatggt    660

ttcgcaggtt accctaatcg tcaacatgat atgctttata taaaggtaga taaagggcaa    720

atgaaatatc gtgttcacac ggctcaaagt ggatggttgc cttgggtaag taaaggggat    780

aagagcgata cagtaaatgg agcggcaggt atgcctggac aagcaattga tggtgttcag    840

ctaaactata taactcctaa gggagaaaaa ttatcacagg cttactatcg ttcacaaact    900

acgaaacgat caggctggtt aaaagtaagt gcagataatg gttctattcc tggactagac    960

agttatgcag gaatctttgg agaaccgttg gatcgcttgc aaataggtat ttcacagtca   1020

aatccatttt aa                                                       1032


<210> SEQ ID NO 120
<211> LENGTH: 56
<212> TYPE: PRT
<213> ORGANISM: Staphylococcus epidermidis

<400> SEQUENCE: 120

Met Glu Asn Lys Lys Asp Leu Phe Asp Leu Glu Ile Lys Lys Asp Asn
1               5                   10                  15

Met Glu Asn Asn Asn Glu Leu Glu Ala Gln Ser Leu Gly Pro Ala Ile
            20                  25                  30

Lys Ala Thr Arg Gln Val Cys Pro Lys Ala Thr Arg Phe Val Thr Val
        35                  40                  45

Ser Cys Lys Lys Ser Asp Cys Gln
    50                  55


<210> SEQ ID NO 121
<211> LENGTH: 171
<212> TYPE: DNA
<213> ORGANISM: Staphylococcus epidermidis

<400> SEQUENCE: 121

atggaaaaca aaaaagattt atttgattta gaaatcaaaa aagataatat ggaaaataat     60

aatgaattag aagctcaatc tcttggtcct gcaattaagg caactagaca ggtatgtcct    120

aaagcaacac gttttgttac agtttcttgt aaaaaaagtg attgtcaata g             171


<210> SEQ ID NO 122
<211> LENGTH: 51
<212> TYPE: PRT
<213> ORGANISM: Staphylococcus epidermidis

<400> SEQUENCE: 122

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln Ser Phe Glu Trp Ile Tyr Lys Gln Ile Lys Lys
        35                  40                  45

Leu Trp Ala
    50
```

<210> SEQ ID NO 123
<211> LENGTH: 156
<212> TYPE: DNA
<213> ORGANISM: Staphylococcus epidermidis

<400> SEQUENCE: 123
atggcagcat ttatgaagtt aattcagttc ttagcaacta aaggtcaaaa gtatgtttca 60
cttgcatgga aacataaagg tactatttta aaatggatta acgccggtca aagttttgaa 120
tggatttata aacaaatcaa aaaattatgg gcataa 156

<210> SEQ ID NO 124
<211> LENGTH: 52
<212> TYPE: PRT
<213> ORGANISM: Staphylococcus epidermidis

<400> SEQUENCE: 124

Met Glu Ala Val Lys Glu Lys Asn Asp Leu Phe Asn Leu Asp Val Lys
1 5 10 15

Val Asn Ala Lys Glu Ser Asn Asp Ser Gly Ala Glu Pro Arg Ile Ala
20 25 30

Ser Lys Phe Ile Cys Thr Pro Gly Cys Ala Lys Thr Gly Ser Phe Asn
35 40 45

Ser Tyr Cys Cys
50

<210> SEQ ID NO 125
<211> LENGTH: 159
<212> TYPE: DNA
<213> ORGANISM: Staphylococcus epidermidis

<400> SEQUENCE: 125
atggaagcag taaaagaaaa aaatgatctt tttaatcttg atgttaaagt taatgcaaaa 60
gaatctaacg attcaggagc tgaaccaaga attgctagta aatttatatg tactcctgga 120
tgtgcaaaaa caggtagttt taacagttat tgttgttaa 159

<210> SEQ ID NO 126
<211> LENGTH: 55
<212> TYPE: PRT
<213> ORGANISM: Staphylococcus epidermidis

<400> SEQUENCE: 126

Met Asn Asn Ser Leu Phe Asp Leu Asn Leu Asn Lys Gly Val Glu Thr
1 5 10 15

Gln Lys Ser Asp Leu Ser Pro Gln Ser Ala Ser Val Leu Lys Thr Ser
20 25 30

Ile Lys Val Ser Lys Lys Tyr Cys Lys Gly Val Thr Leu Thr Cys Gly
35 40 45

Cys Asn Ile Thr Gly Gly Lys
50 55

<210> SEQ ID NO 127
<211> LENGTH: 168
<212> TYPE: DNA
<213> ORGANISM: Staphylococcus epidermidis

<400> SEQUENCE: 127
atgaataact cattattcga tttaaaccta aacaaaggtg tagaaactca aaagagtgat 60
ttaagtccgc aatctgctag tgtcttgaag acttctatta aagtatctaa aaaatattgt 120
aaaggtgtta ctttaacatg cggttgcaat attactggtg gtaaataa 168

<210> SEQ ID NO 128
<211> LENGTH: 52
<212> TYPE: PRT
<213> ORGANISM: Staphylococcus gallinarum

<400> SEQUENCE: 128

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
        35                  40                  45

Ser Tyr Cys Cys
    50

<210> SEQ ID NO 129
<211> LENGTH: 159
<212> TYPE: DNA
<213> ORGANISM: Staphylococcus gallinarum

<400> SEQUENCE: 129
atggaagcag taaaagagaa aaatgaactt tttgatcttg acgttaaagt aaatgcaaaa 60
gagtctaatg attcaggcgc agaaccacga attgctagta aatttttatg tactcctgga 120
tgtgccaaaa caggtagctt caatagctac tgttgttaa 159

<210> SEQ ID NO 130
<211> LENGTH: 63
<212> TYPE: PRT
<213> ORGANISM: Lactococcus garvieae

<400> SEQUENCE: 130

Met Glu Asn Asn Asn Tyr Thr Val Leu Ser Asp Glu Glu Leu Gln Lys
1               5                   10                  15

Ile Asp Gly Gly Ile Gly Gly Ala Leu Gly Asn Ala Leu Asn Gly Leu
            20                  25                  30

Gly Thr Trp Ala Asn Met Met Asn Gly Gly Gly Phe Val Asn Gln Trp
        35                  40                  45

Gln Val Tyr Ala Asn Lys Gly Lys Ile Asn Gln Tyr Arg Pro Tyr
    50                  55                  60

<210> SEQ ID NO 131
<211> LENGTH: 192
<212> TYPE: DNA
<213> ORGANISM: Lactococcus garvieae

<400> SEQUENCE: 131
atggaaaaca acaattacac agtactttca gatgaagaac tacaaaaaat tgatggtgga 60
atcggcgggg ctcttggtaa tgctctcaac ggattaggta cctgggcaaa catgatgaac 120
ggtggaggat ttgttaatca gtggcaagtt tatgctaata aaggaaaaat aaatcaatac 180
cgtccgtatt aa 192

<210> SEQ ID NO 132
<211> LENGTH: 63
<212> TYPE: PRT
<213> ORGANISM: Lactococcus garvieae

<400> SEQUENCE: 132

```
Met Phe Asp Leu Val Ala Thr Gly Met Ala Ala Gly Val Ala Lys Thr
1               5                   10                  15

Ile Val Asn Ala Val Ser Ala Gly Met Asp Ile Ala Thr Ala Leu Ser
            20                  25                  30

Leu Phe Ser Gly Ala Phe Thr Ala Ala Gly Gly Ile Met Ala Leu Ile
        35                  40                  45

Lys Lys Tyr Ala Gln Lys Lys Leu Trp Lys Gln Leu Ile Ala Ala
    50                  55                  60
```

<210> SEQ ID NO 133
<211> LENGTH: 192
<212> TYPE: DNA
<213> ORGANISM: Lactococcus garvieae

<400> SEQUENCE: 133

```
atgtttgatt tagtcgcgac tggaatggct gcaggtgtag caaaaactat tgttaatgcc      60

gttagtgctg gtatggatat tgccactgct ttatcattgt tctcaggagc ttttactgca     120

gctgggggaa ttatggcact cattaaaaaa tatgctcaaa agaaattatg gaaacagctt     180

attgctgcat aa                                                         192
```

<210> SEQ ID NO 134
<211> LENGTH: 91
<212> TYPE: PRT
<213> ORGANISM: Lactobacillus gasseri

<400> SEQUENCE: 134

```
Met Val Thr Lys Tyr Gly Arg Asn Leu Gly Leu Asn Lys Val Glu Leu
1               5                   10                  15

Phe Ala Ile Trp Ala Val Leu Val Val Ala Leu Leu Leu Thr Thr Ala
            20                  25                  30

Asn Ile Tyr Trp Ile Ala Asp Gln Phe Gly Ile His Leu Ala Thr Gly
        35                  40                  45

Thr Ala Arg Lys Leu Leu Asp Ala Met Ala Ser Gly Ala Ser Leu Gly
    50                  55                  60

Thr Ala Phe Ala Ala Ile Leu Gly Val Thr Leu Pro Ala Trp Ala Leu
65                  70                  75                  80

Ala Ala Ala Gly Ala Leu Gly Ala Thr Ala Ala
                85                  90
```

<210> SEQ ID NO 135
<211> LENGTH: 276
<212> TYPE: DNA
<213> ORGANISM: Lactobacillus gasseri

<400> SEQUENCE: 135

```
atggttacta agtacggacg taatttaggt ttgaacaagg tagagttgtt tgcaatttgg      60

gcggttttag tagttgctct tttattgacc acagcgaaca tttattggat tgctgatcaa     120

ttcgggattc atttagcgac tggaacagcc cgtaagttat tagatgcaat ggcttctggt     180

gcctcattgg gaactgcctt tgctgctatt ttgggcgtga cattacctgc atgggctttg     240

gcagctgcag gagcattggg agcgactgca gcctag                               276
```

<210> SEQ ID NO 136
<211> LENGTH: 75
<212> TYPE: PRT
<213> ORGANISM: Lactobacillus gasseri

<400> SEQUENCE: 136

Met Lys Asn Phe Asn Thr Leu Ser Phe Glu Thr Leu Ala Asn Ile Val
1 5 10 15

Gly Gly Arg Asn Asn Trp Ala Ala Asn Ile Gly Gly Val Gly Gly Ala
20 25 30

Thr Val Ala Gly Trp Ala Leu Gly Asn Ala Val Cys Gly Pro Ala Cys
35 40 45

Gly Phe Val Gly Ala His Tyr Val Pro Ile Ala Trp Ala Gly Val Thr
50 55 60

Ala Ala Thr Gly Gly Phe Gly Lys Ile Arg Lys
65 70 75

<210> SEQ ID NO 137
<211> LENGTH: 228
<212> TYPE: DNA
<213> ORGANISM: Lactobacillus gasseri

<400> SEQUENCE: 137
atgaaaaatt ttaatacatt atcatttgaa acattggcta acatagttgg tgggagaaat 60
aattgggctg ctaatatagg tggagtaggt ggagcgacag tcgctggatg ggctcttgga 120
aatgcagttt gcggtcctgc ttgtggcttt gttggagcac actatgttcc aatagcatgg 180
gctggcgtaa cggcagctac tggtggattc ggaaagataa gaaagtag 228

<210> SEQ ID NO 138
<211> LENGTH: 64
<212> TYPE: PRT
<213> ORGANISM: Lactobacillus plantarum

<400> SEQUENCE: 138

Met Ser Lys Leu Val Lys Thr Leu Thr Ile Ser Glu Ile Ser Lys Ala
1 5 10 15

Gln Asn Asn Gly Gly Lys Pro Ala Trp Cys Trp Tyr Thr Leu Ala Met
20 25 30

Cys Gly Ala Gly Tyr Asp Ser Gly Thr Cys Asp Tyr Met Tyr Ser His
35 40 45

Cys Phe Gly Ile Lys His His Ser Ser Gly Ser Ser Ser Tyr His Cys
50 55 60

<210> SEQ ID NO 139
<211> LENGTH: 195
<212> TYPE: DNA
<213> ORGANISM: Lactobacillus plantarum

<400> SEQUENCE: 139
atgagtaaat tggttaagac acttactata agtgaaattt ctaaggctca aaacaacggt 60
ggaaaacctg catggtgttg gtatacttta gcaatgtgtg gtgctggtta tgattcggga 120
acctgtgatt atatgtattc gcattgtttt ggtataaagc atcatagtag tggtagtagc 180
agttatcatt gttag 195

<210> SEQ ID NO 140
<211> LENGTH: 359

```
<212> TYPE: PRT
<213> ORGANISM: Haloferax mediterranei

<400> SEQUENCE: 140

Met Ser Lys Asp Arg Asp Gly Arg Arg Thr Ser Arg Arg Gly Thr Leu
1               5                   10                  15

Lys Lys Ile Gly Gly Phe Ser Leu Gly Ala Leu Ser Phe Gly Ala Val
            20                  25                  30

Gly Arg Thr Gln Ala Ala Thr Gly Ser Ser Val Thr Thr Ala Asp Ile
        35                  40                  45

Ala Pro Pro Gly Pro Asn Gly Asp Pro Lys Ser Val Gln Ile Asp Asp
    50                  55                  60

Lys Tyr Thr Gly Ala Glu Met Tyr Gly Glu Gly Asp Phe Arg Val Gly
65                  70                  75                  80

Leu Gly Thr Asp Leu Thr Met Tyr Pro Pro Val Tyr Arg Glu Ser Leu
                85                  90                  95

Gly Asn Gly Ser Gly Gly Trp Glu Phe Asp Phe Thr Val Cys Gly Ser
            100                 105                 110

Thr Ala Cys Arg Phe Val Asp Ser Asn Gly Asp Val Lys Glu Asp Asp
        115                 120                 125

Lys Ala Lys Glu Met Trp Trp Gln Glu Ile Asn Phe Asn Asp Ile Asn
    130                 135                 140

Gln Asp Leu Tyr Ser Arg Asn Asp Ser Asp Trp Val Gly Ser Thr Pro
145                 150                 155                 160

Ala Asp Thr Gln Pro Glu Phe Asp Tyr Thr Glu Phe Ala Leu Ala Arg
                165                 170                 175

Asp Gly Val Thr Leu Ala Leu Thr Ala Leu Asn Pro Ala Met Gly Ser
            180                 185                 190

Leu Ala Leu Gly Ala Thr Tyr Phe Leu Ser Asp Met Val Asn Trp Ile
        195                 200                 205

Ala Ser Gln His Glu Asp Asp Ser Ser Leu Lys Arg Lys Trp Asp Tyr
    210                 215                 220

Asp Gly Leu Ser Gly Pro Leu Tyr Ala Asp Ser Ser Thr Tyr Leu Leu
225                 230                 235                 240

Ala Arg Asp Glu Met Thr Ser Asn Ser Tyr Glu Ser Phe Thr Ile Asp
                245                 250                 255

Asn Ile Ala Val Ala Phe Pro Glu Phe Pro Val Arg Thr Lys Tyr Tyr
            260                 265                 270

Val Thr Phe Thr Ala Pro Asp Asp Pro Ser Thr Gln Ser Ile Ser Thr
        275                 280                 285

Leu Glu Glu Glu Gly Ile Tyr Arg Val Pro Ala Thr Glu Val Ala Ala
    290                 295                 300

Ala Arg Pro Pro Gly Ser Arg Arg Ser Lys Ser Ala Ala Asp Glu Met
305                 310                 315                 320

Val Tyr Val Ala Asp Pro Lys Lys Phe Ile Glu Val Glu Pro Val Lys
                325                 330                 335

Asn Pro Ser Ile Pro Asp Arg Ile Tyr Glu Glu Ile Glu Gln Lys Lys
            340                 345                 350

Lys Gln Arg Ser Arg Lys Gln
        355


<210> SEQ ID NO 141
<211> LENGTH: 1080
<212> TYPE: DNA
<213> ORGANISM: Haloferax mediterranei
```

<400> SEQUENCE: 141

```
atgtcgaaag acagagatgg gagaaggaca agtcggcgag gcacgttaaa gaaaatcggc     60
ggtttcagtc tcggagcgct tagtttcggg gcagtcggac gaactcaagc ggcgaccggc    120
tcatcggtta cgaccgctga tatcgcacct cccggaccga acggagaccc gaagagtgtt    180
cagatagatg ataaatacac cggagccgag atgtacggcg agggtgactt cagagtcggt    240
ctcggaactg acctgacgat gtatccgccc gtgtaccgtg agagtcttgg aaatggaagc    300
gggggttggg aattcgactt caccgtttgt gggtccactg cctgtcgatt tgtggacagt    360
aacggtgacg tcaaagagga cgacaaggcg aaagaaatgt ggtggcagga aattaacttc    420
aacgacataa atcaggattt atacagtcgg aacgattccg actgggtcgg gtcgacccct    480
gccgataccc aaccggagtt cgattacacc gactttgcgc tcgctcggga cggagtgacg    540
ctcgctctca cggcactcaa ccccgcaatg gggagtcttg cactcggtgc cacgtacttc    600
ctcagcgaca tggtgaactg gattgcgagc cagcacgaag acgacagttc gctcaagaga    660
aaatgggatt acgacgggct aagtgggccg ttgtacgccg attcgtcgac gtacctactg    720
gcacgcgacg agatgacttc gaactcgtac gaatcattca cgatcgataa catcgccgtt    780
gccttcccag agttccccgt ccggaccaag tactacgtca cattcactgc gccggatgac    840
ccgtcaacgc agtcgatatc tacgctcgaa gaggagggaa tctaccgagt gcccgctacg    900
gaagtggctg cggccagacc accggggtcc cgacgttcca aatcggcagc cgacgagatg    960
gtgtacgttg ccgatccgaa gaagttcata gaggtcgagc cggtgaagaa cccaagtatc   1020
ccggaccgaa tctacgagga gatagagcaa aaaaagaaac aacggagtag gaaacagtag   1080
```

<210> SEQ ID NO 142
<211> LENGTH: 311
<212> TYPE: PRT
<213> ORGANISM: Haloarchaeon S8a

<400> SEQUENCE: 142

```
Met Ser Asp Lys Asp Ser Ile Asn Arg Arg Asn Val Leu Arg Lys Ile
1               5                   10                  15

Gly Gly Ile Gly Val Ala Ser Ala Val Gly Phe Ser Gly Leu Ala Ser
            20                  25                  30

Gly Glu Ser Leu Ser Asp Asp Glu Lys Gln Asp Val Ile Asp Thr Ile
        35                  40                  45

Tyr Lys Ser Gln Arg Val Glu Gln Ile Lys Lys Lys Phe Gly Gly Val
    50                  55                  60

Asn Ile Glu Pro Lys Lys Val Gln Ser Val Thr Thr Asn Gln Ser Gly
65                  70                  75                  80

Asp Leu Val Thr Ala Lys Leu Ser Val Ser Asp Gly Asp Leu Val Tyr
                85                  90                  95

Ser Ser Val Lys Asp Thr Thr Val Ile Val Gln Phe Asp Arg Ser Ala
            100                 105                 110

Ser Glu Ile Gly Glu Ser Trp Pro Lys Asn Thr Glu Ala Phe Ile Lys
        115                 120                 125

Ser Thr Ser Ser Gly Val Asp Leu Leu Arg Thr Ala Thr Asp Glu Glu
    130                 135                 140

Ile Lys Asp Val Thr Glu Gly Val Asn Thr Ser Glu Ile Glu Ser Ala
145                 150                 155                 160

Asp Ala Val Asn Ile Phe Ile Asp Pro Glu Ser Gln Thr Tyr Tyr Met
                165                 170                 175
```

```
Glu Lys Tyr Asp Phe Asn Asn Lys Val Leu Glu Met Phe Glu Leu Ala
            180                 185                 190

Thr Gly Gly Thr Ser Ser Gly Lys Ile Ser Pro Thr Arg Glu Asp Gln
        195                 200                 205

Asn His Glu Tyr Asn Val Arg Glu His Lys Val Phe Asn Ser Glu Lys
    210                 215                 220

Gln Asn Ile Gln Leu Gln Ser Asp Cys Asn Ile Asn Ser Asn Thr Ala
225                 230                 235                 240

Ala Asp Val Ile Leu Cys Phe Asn Gln Val Gly Ser Cys Ala Leu Cys
                245                 250                 255

Ser Pro Thr Leu Val Gly Gly Pro Val Pro Thr Val Ala Cys Leu Leu
            260                 265                 270

Val Val Cys Phe Gly Thr Pro Asn Ala Val Ser Ala Ile Leu Glu Glu
        275                 280                 285

Val Asp Asn Ser Cys Phe Asn Leu Ile Lys Asp Val Ile Ser Cys Trp
    290                 295                 300

Asp Glu Trp Thr Ser Phe Trp
305                 310
```

<210> SEQ ID NO 143
<211> LENGTH: 936
<212> TYPE: DNA
<213> ORGANISM: Haloarchaeon S8a

<400> SEQUENCE: 143

```
atgtcggata aagacagcat taacagaaga aatgtattaa gaaaaattgg cggtatcggt     60

gtggcttcag ctgtcggatt ttctggtttg gcaagcgggg aaagtcttag cgatgatgag    120

aaacaagatg ttattgacac aatttacaaa tcacaaagag ttgaacagat aaagaaaaag    180

ttcggaggag tgaatattga gccgaaaaag gttcaatctg taacgaccaa tcagagcgga    240

gatcttgtta cggcgaagct gtcggttagt gatggggatt tggtatattc gagtgtcaaa    300

gatacaactg taatagttca gttcgataga tcggcttctg aaattggtga aagttggccc    360

aagaatactg aggcattcat caaatcgacg tcctctgggg tcgatcttct acgtacagca    420

actgatgaag aaataaagga cgttactgag ggagtcaaca catctgaaat tgaatctgcg    480

gatgctgtta acatatttat tgatcctgaa tcacagacat actatatgga gaaatatgac    540

tttaataata aggtacttga gatgtttgaa ttagcgacag gtgggacaag tagtggtaaa    600

atctccccca cacgtgaaga ccagaatcac gaatataatg ttagggaaca taaagtattt    660

aactcagaaa aacagaatat acaacttcag agtgactgta atataaacag taacaccgct    720

gctgatgtta ttctatgctt caaccaggtt ggttcttgtg cactctgctc cccgacttta    780

gtcggaggtc cagtccctac agttgcatgt ctcttagtcg tctgtttcgg cactccaaat    840

gctgtgtccg cgatacttga agaagtcgat aattcttgct ttaacttgat caaggatgta    900

atttcgtgtt gggatgaatg gactagcttc tggtga                               936
```

<210> SEQ ID NO 144
<211> LENGTH: 333
<212> TYPE: PRT
<213> ORGANISM: Lactobacillus helveticus

<400> SEQUENCE: 144

```
Met Lys His Leu Asn Glu Thr Thr Asn Val Arg Ile Leu Ser Gln Phe
1               5                   10                  15
```

```
Asp Met Asp Thr Gly Tyr Gln Ala Val Val Gln Lys Gly Asn Val Gly
            20                  25                  30

Ser Lys Tyr Val Tyr Gly Leu Gln Leu Arg Lys Gly Ala Thr Thr Ile
        35                  40                  45

Leu Arg Gly Tyr Arg Gly Ser Lys Ile Asn Asn Pro Ile Leu Glu Leu
    50                  55                  60

Ser Gly Gln Ala Gly Gly His Thr Gln Thr Trp Glu Phe Ala Gly Asp
65                  70                  75                  80

Arg Lys Asp Ile Asn Gly Glu Glu Arg Ala Gly Gln Trp Phe Ile Gly
                85                  90                  95

Val Lys Pro Ser Lys Ile Glu Gly Ser Lys Ile Ile Trp Ala Lys Gln
            100                 105                 110

Ile Ala Arg Val Asp Leu Arg Asn Gln Met Gly Pro His Tyr Ser Asn
        115                 120                 125

Thr Asp Phe Pro Arg Leu Ser Tyr Leu Asn Arg Ala Gly Ser Asn Pro
    130                 135                 140

Phe Ala Gly Asn Lys Met Thr His Ala Glu Ala Ala Val Ser Pro Asp
145                 150                 155                 160

Tyr Thr Lys Phe Leu Ile Ala Thr Val Glu Asn Asn Cys Ile Gly His
                165                 170                 175

Phe Thr Ile Tyr Asn Leu Asp Thr Ile Asn Glu Lys Leu Asp Glu Lys
            180                 185                 190

Gly Asn Ser Glu Asp Val Asn Leu Glu Thr Val Lys Tyr Glu Asp Ser
        195                 200                 205

Phe Ile Ile Asp Asn Leu Tyr Gly Asp Asp Asn Asn Ser Ile Val Asn
    210                 215                 220

Ser Ile Gln Gly Tyr Asp Leu Asp Asn Asp Gly Asn Ile Tyr Ile Ser
225                 230                 235                 240

Ser Gln Lys Ala Pro Asp Phe Asp Gly Ser Tyr Tyr Ala His His Lys
                245                 250                 255

Gln Ile Val Lys Ile Pro Tyr Tyr Ala Arg Ser Lys Glu Ser Glu Asp
            260                 265                 270

Gln Trp Arg Ala Val Asn Leu Ser Glu Phe Gly Gly Leu Asp Ile Pro
        275                 280                 285

Gly Lys His Ser Glu Val Glu Ser Ile Gln Ile Ile Gly Glu Asn His
    290                 295                 300

Cys Tyr Leu Thr Val Ala Tyr His Ser Lys Asn Lys Ala Gly Glu Asn
305                 310                 315                 320

Lys Thr Thr Leu Asn Glu Ile Tyr Glu Leu Ser Trp Asn
                325                 330
```

<210> SEQ ID NO 145
<211> LENGTH: 1002
<212> TYPE: DNA
<213> ORGANISM: Lactobacillus helveticus

<400> SEQUENCE: 145

```
atgaagcatt taaatgaaac aactaatgtt agaattttaa gtcaatttga tatggatact      60

ggctatcaag cagtagttca aaaaggcaat gtaggttcaa aatatgtata tggattacaa     120

cttcgcaaag gtgctactac tatcttgcgt ggttaccgtg gaagtaaaat taataaccct     180

attcttgaat tatctggtca agcaggtggt cacacacaga catgggaatt tgctggtgat     240

cgtaaagaca ttaatggtga agaaagagca ggtcaatggt ttataggtgt taaaccatcg     300

aaaattgaag gaagcaaaat tatttgggca aagcaaattg caagagttga tcttagaaat     360
```

caaatgggac ctcattattc aaatactgac tttcctcgat tatcctactt gaatcgcgcc 420
ggttctaatc catttgctgg taataagatg acgcatgccg aagccgcagt atcacctgat 480
tatactaagt ttttaattgc tactgttgaa aataactgta ttggtcattt tactatatac 540
aatttagata caattaatga aaaacttgat gaaaagggaa atagtgaaga tgttaatctc 600
gaaactgtta aatacgaaga tagttttatc attgataatt tatatggtga tgataataat 660
tctattgtaa attcaattca agggtatgat ttggataatg atggaaatat ttatatttcc 720
agtcaaaaag cgccagattt tgatggctct tattatgcac atcataagca gattgttaag 780
attccatatt atgctcggtc taaagaaagc gaagaccaat ggagagctgt aaatttaagc 840
gaattcggtg gcttggatat tccaggtaaa catagtgaag ttgaaagcat ccaaattatt 900
ggtgagaatc attgttactt aactgttgca tatcattcta aaaataaagc gggtgaaaat 960
aaaactactt tgaatgagat ttatgaatta tcttggaatt ag 1002

<210> SEQ ID NO 146
<211> LENGTH: 74
<212> TYPE: PRT
<213> ORGANISM: Enterococcus hirae

<400> SEQUENCE: 146

Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
            20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70

<210> SEQ ID NO 147
<211> LENGTH: 225
<212> TYPE: DNA
<213> ORGANISM: Enterococcus hirae

<400> SEQUENCE: 147
atgaaaaaga aagtattaaa acattgtgtt attctaggaa tattaggaac ttgtctagct 60
ggcatcggta caggaataaa agttgatgca gctacttact atggaaatgg tctttattgt 120
aacaaagaaa aatgttgggt agattggaat caagctaaag gagaaattgg aaaaattatt 180
gttaatggtt gggttaatca tggtccatgg gcacctagaa ggtag 225

<210> SEQ ID NO 148
<211> LENGTH: 75
<212> TYPE: PRT
<213> ORGANISM: Lactobacillus johnsonii

<400> SEQUENCE: 148

Met Lys Gln Phe Asn Tyr Leu Ser His Lys Asp Leu Ala Val Val Val
1               5                   10                  15

Gly Gly Arg Asn Asn Trp Gln Thr Asn Val Gly Gly Ala Val Gly Ser
            20                  25                  30

Ala Met Ile Gly Ala Thr Val Gly Gly Thr Ile Cys Gly Pro Ala Cys
        35                  40                  45

```
Ala Val Ala Gly Ala His Tyr Leu Pro Ile Leu Trp Thr Ala Val Thr
    50                  55                  60

Ala Ala Thr Gly Gly Phe Gly Lys Ile Arg Lys
65                  70                  75


<210> SEQ ID NO 149
<211> LENGTH: 228
<212> TYPE: DNA
<213> ORGANISM: Lactobacillus johnsonii

<400> SEQUENCE: 149

atgaaacaat ttaattattt atcacataaa gatttagcag tcgttgttgg tggaagaaat      60

aattggcaaa caaatgtggg aggagcagtg ggatcagcta tgattggggc tacagttggt     120

ggtacaattt gtggacctgc atgtgctgta gctggtgccc attatcttcc tattttatgg     180

acagcggtta cagctgcaac aggtggtttt ggcaagataa gaaagtag                  228


<210> SEQ ID NO 150
<211> LENGTH: 62
<212> TYPE: PRT
<213> ORGANISM: Lactobacillus johnsonii

<400> SEQUENCE: 150

Met Lys Leu Asn Asp Lys Glu Leu Ser Lys Ile Val Gly Gly Asn Arg
1               5                   10                  15

Trp Gly Asp Thr Val Leu Ser Ala Ala Ser Gly Ala Gly Thr Gly Ile
            20                  25                  30

Lys Ala Cys Lys Ser Phe Gly Pro Trp Gly Met Ala Ile Cys Gly Val
        35                  40                  45

Gly Gly Ala Ala Ile Gly Gly Tyr Phe Gly Tyr Thr His Asn
    50                  55                  60


<210> SEQ ID NO 151
<211> LENGTH: 189
<212> TYPE: DNA
<213> ORGANISM: Lactobacillus johnsonii

<400> SEQUENCE: 151

atgaaattaa atgacaaaga attatcaaag attgttggtg gaaatcgatg gggagatact      60

gttttatcag ctgctagtgg cgcaggaact ggtattaaag catgtaaaag ttttggccca     120

tggggaatgg caatttgtgg tgtaggaggt gcagcaatag gaggttattt tggctatact     180

cataattaa                                                              189


<210> SEQ ID NO 152
<211> LENGTH: 59
<212> TYPE: PRT
<213> ORGANISM: Lactococcus lactis subsp. lactis

<400> SEQUENCE: 152

Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala Cys Ser Thr
            20                  25                  30

Asn Thr Phe Ser Leu Ser Asp Tyr Trp Gly Asn Asn Gly Ala Trp Cys
        35                  40                  45

Thr Leu Thr His Glu Cys Met Ala Trp Cys Lys
    50                  55
```

<210> SEQ ID NO 153
<211> LENGTH: 180
<212> TYPE: DNA
<213> ORGANISM: Lactococcus lactis subsp. lactis

<400> SEQUENCE: 153
atgaacaaaa atgaaattga aacacaacca gttacatggt tggaagaagt atctgatcaa 60
aattttgatg aagatgtatt tggtgcgtgt agtactaaca cattctcgct cagtgattac 120
tggggaaata acggggcttg gtgtacactc actcatgaat gtatggcttg gtgtaaataa 180

<210> SEQ ID NO 154
<211> LENGTH: 65
<212> TYPE: PRT
<213> ORGANISM: Lactococcus lactis subsp. lactis

<400> SEQUENCE: 154

Met Lys Glu Lys Asn Met Lys Lys Asn Asp Thr Ile Glu Leu Gln Leu
1 5 10 15

Gly Lys Tyr Leu Glu Asp Asp Met Ile Glu Leu Ala Glu Gly Asp Glu
20 25 30

Ser His Gly Gly Thr Thr Pro Ala Thr Pro Ala Ile Ser Ile Leu Ser
35 40 45

Ala Tyr Ile Ser Thr Asn Thr Cys Pro Thr Thr Lys Cys Thr Arg Ala
50 55 60

Cys
65

<210> SEQ ID NO 155
<211> LENGTH: 198
<212> TYPE: DNA
<213> ORGANISM: Lactococcus lactis subsp. lactis

<400> SEQUENCE: 155
atgaaagaaa aaaatatgaa aaagaatgac actattgaat tacaattggg aaaatacctt 60
gaagatgata tgattgaatt agctgaaggg gatgagtctc atggaggaac aacaccagca 120
actcctgcaa tctctattct cagtgcatat attagtacca atacttgtcc aacaacaaaa 180
tgtacacgtg cttgttaa 198

<210> SEQ ID NO 156
<211> LENGTH: 51
<212> TYPE: PRT
<213> ORGANISM: Lactococcus lactis subsp. lactis

<400> SEQUENCE: 156

Met Lys Glu Gln Asn Ser Phe Asn Leu Leu Gln Glu Val Thr Glu Ser
1 5 10 15

Glu Leu Asp Leu Ile Leu Gly Ala Lys Gly Gly Ser Gly Val Ile His
20 25 30

Thr Ile Ser His Glu Cys Asn Met Asn Ser Trp Gln Phe Val Phe Thr
35 40 45

Cys Cys Ser
50

<210> SEQ ID NO 157
<211> LENGTH: 156
<212> TYPE: DNA
<213> ORGANISM: Lactococcus lactis subsp. lactis

```
<400> SEQUENCE: 157

atgaaagaac aaaactcttt taatcttctt caagaagtga cagaaagtga attggacctt     60

attttaggtg caaaaggcgg cagtggagtt attcatacaa tttctcatga atgtaatatg    120

aatagctggc aatttgtatt tacttgctgc tcttaa                              156


<210> SEQ ID NO 158
<211> LENGTH: 53
<212> TYPE: PRT
<213> ORGANISM: Lactococcus lactis

<400> SEQUENCE: 158

Met Ala Gly Phe Leu Lys Val Val Gln Leu Leu Ala Lys Tyr Gly Ser
1               5                   10                  15

Lys Ala Val Gln Trp Ala Trp Ala Asn Lys Gly Lys Ile Leu Asp Trp
            20                  25                  30

Leu Asn Ala Gly Gln Ala Ile Asp Trp Val Val Ser Lys Ile Lys Gln
        35                  40                  45

Ile Leu Gly Ile Lys
    50


<210> SEQ ID NO 159
<211> LENGTH: 162
<212> TYPE: DNA
<213> ORGANISM: Lactococcus lactis

<400> SEQUENCE: 159

atggcagggt ttttaaaagt agttcaatta ctagctaaat atggttctaa agctgtacaa     60

tgggcttggg caaacaaggg taagatttta gattggctta atgcaggtca ggctattgat    120

tgggtagttt cgaaaattaa gcaaatttta ggtattaagt aa                       162


<210> SEQ ID NO 160
<211> LENGTH: 53
<212> TYPE: PRT
<213> ORGANISM: Lactococcus lactis

<400> SEQUENCE: 160

Met Ala Gly Phe Leu Lys Val Val Gln Ile Leu Ala Lys Tyr Gly Ser
1               5                   10                  15

Lys Ala Val Gln Trp Ala Trp Ala Asn Lys Gly Lys Ile Leu Asp Trp
            20                  25                  30

Ile Asn Ala Gly Gln Ala Ile Asp Trp Val Val Glu Lys Ile Lys Gln
        35                  40                  45

Ile Leu Gly Ile Lys
    50


<210> SEQ ID NO 161
<211> LENGTH: 162
<212> TYPE: DNA
<213> ORGANISM: Lactococcus lactis

<400> SEQUENCE: 161

atggcagggt ttttaaaagt agtccaaatt ttggctaagt atggttctaa agccgtacaa     60

tgggcatggg caaataaagg aaaaatctta gattggatta atgcaggtca agctattgac    120

tgggtagttg aaaagattaa gcaaattttg ggtattaaat aa                       162


<210> SEQ ID NO 162
```

<211> LENGTH: 65
<212> TYPE: PRT
<213> ORGANISM: Lactobacillus amylovorus

<400> SEQUENCE: 162

```
Met Lys Gln Leu Asn Ser Glu Gln Leu Gln Asn Ile Ile Gly Gly Asn
1               5                   10                  15

Arg Trp Thr Asn Ala Tyr Ser Ala Ala Leu Gly Cys Ala Val Pro Gly
            20                  25                  30

Val Lys Tyr Gly Lys Lys Leu Gly Gly Val Trp Gly Ala Val Ile Gly
        35                  40                  45

Gly Val Gly Gly Ala Ala Val Cys Gly Leu Ala Gly Tyr Val Arg Lys
    50                  55                  60

Gly
65
```

<210> SEQ ID NO 163
<211> LENGTH: 198
<212> TYPE: DNA
<213> ORGANISM: Lactobacillus amylovorus

<400> SEQUENCE: 163

```
atgaaacaat tgaattcaga acaattacaa aatattatcg gtggaaatag atggactaat     60

gcatacagcg cagctttggg atgcgctgtc cctggagtta aatatggaaa aaaacttggt    120

ggcgtatggg gtgctgtaat tggtggcgta ggcggtgcag cagtctgtgg cttggcgggt    180

tatgttcgta aaggctaa                                                  198
```

<210> SEQ ID NO 164
<211> LENGTH: 68
<212> TYPE: PRT
<213> ORGANISM: Lactobacillus sakei L45

<400> SEQUENCE: 164

```
Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp Ser
            20                  25                  30

Thr Pro Val Leu Ala Ser Val Ala Val Ser Met Glu Leu Leu Pro Thr
        35                  40                  45

Ala Ser Val Leu Tyr Ser Asp Val Ala Gly Cys Phe Lys Tyr Ser Ala
    50                  55                  60

Lys His His Cys
65
```

<210> SEQ ID NO 165
<211> LENGTH: 207
<212> TYPE: DNA
<213> ORGANISM: Lactobacillus sakei L45

<400> SEQUENCE: 165

```
atgaaaacag aaaaaaaggt tttagatgaa ctgagcttac acgcttctgc aaaaatggga     60

gcacgtgatg ttgaatccag catgaatgca gactcaacac cagttttagc atcagtcgct    120

gtatccatgg aattattgcc aactgcgtct gttctttatt cggatgttgc aggttgcttc    180

aaatattctg caaaacatca ttgttag                                        207
```

<210> SEQ ID NO 166
<211> LENGTH: 91

```
<212> TYPE: PRT
<213> ORGANISM: Lactococcus lactis subsp. lactis

<400> SEQUENCE: 166

Met Lys Thr Lys Ser Leu Val Leu Ala Leu Ser Ala Val Thr Leu Phe
1               5                   10                  15

Ser Ala Gly Gly Ile Val Ala Gln Ala Glu Gly Thr Trp Gln His Gly
            20                  25                  30

Tyr Gly Val Ser Ser Ala Tyr Ser Asn Tyr His His Gly Ser Lys Thr
        35                  40                  45

His Ser Ala Thr Val Val Asn Asn Asn Thr Gly Arg Gln Gly Lys Asp
    50                  55                  60

Thr Gln Arg Ala Gly Val Trp Ala Lys Ala Thr Val Gly Arg Asn Leu
65                  70                  75                  80

Thr Glu Lys Ala Ser Phe Tyr Tyr Asn Phe Trp
                85                  90


<210> SEQ ID NO 167
<211> LENGTH: 276
<212> TYPE: DNA
<213> ORGANISM: Lactococcus lactis subsp. lactis

<400> SEQUENCE: 167

atgaaaacca agtctctcgt attggcatta tctgcggtta cgttattctc tgccggagga      60

attgtagctc aagctgaagg aacatggcaa catggatatg gtgttagttc ggcatattca     120

aattatcatc atggtagcaa aactcattca gccacagttg taaataataa tactggccga     180

caaggtaagg atacacaacg tgccggtgtt tgggcaaaag ctactgttgg acgtaactta     240

actgaaaaag cttcatttta ttataacttt tggtaa                               276


<210> SEQ ID NO 168
<211> LENGTH: 75
<212> TYPE: PRT
<213> ORGANISM: Lactococcus lactis subsp. cremoris

<400> SEQUENCE: 168

Met Lys Asn Gln Leu Asn Phe Asn Ile Val Ser Asp Glu Glu Leu Ser
1               5                   10                  15

Glu Ala Asn Gly Gly Lys Leu Thr Phe Ile Gln Ser Thr Ala Ala Gly
            20                  25                  30

Asp Leu Tyr Tyr Asn Thr Asn Thr His Lys Tyr Val Tyr Gln Gln Thr
        35                  40                  45

Gln Asn Ala Phe Gly Ala Ala Ala Asn Thr Ile Val Asn Gly Trp Met
    50                  55                  60

Gly Gly Ala Ala Gly Gly Phe Gly Leu His His
65                  70                  75


<210> SEQ ID NO 169
<211> LENGTH: 228
<212> TYPE: DNA
<213> ORGANISM: Lactococcus lactis subsp. cremoris

<400> SEQUENCE: 169

atgaaaaatc aattaaattt taatattgtt tcagatgaag aactttcaga agctaacgga      60

ggaaaattaa catttattca atcgacagcg gctggagatt tatattacaa tactaataca     120

cacaaatatg tttaccaaca aactcaaaac gcttttgggg ctgctgctaa taccattgtt     180

aatggatgga tgggtggcgc tgctggaggt ttcgggttgc accattga                  228
```

<210> SEQ ID NO 170
<211> LENGTH: 68
<212> TYPE: PRT
<213> ORGANISM: Lactococcus lactis subsp. cremoris

<400> SEQUENCE: 170

```
Met Lys Asn Gln Leu Asn Phe Asn Ile Val Ser Asp Glu Glu Leu Ala
1               5                   10                  15

Glu Val Asn Gly Gly Ser Leu Gln Tyr Val Met Ser Ala Gly Pro Tyr
            20                  25                  30

Thr Trp Tyr Lys Asp Thr Arg Thr Gly Lys Thr Ile Cys Lys Gln Thr
        35                  40                  45

Ile Asp Thr Ala Ser Tyr Thr Phe Gly Val Met Ala Glu Gly Trp Gly
    50                  55                  60

Lys Thr Phe His
65
```

<210> SEQ ID NO 171
<211> LENGTH: 207
<212> TYPE: DNA
<213> ORGANISM: Lactococcus lactis subsp. cremoris

<400> SEQUENCE: 171

```
atgaaaaatc aattaaattt taatattgtt tctgatgaag aacttgcaga agttaatgga      60

ggaagcttgc agtatgttat gagtgctgga ccatatactt ggtataaaga tactagaaca     120

ggaaaaacaa tatgtaaaca gacaattgac acagcaagtt atacatttgg tgtaatggca     180

gaaggatggg gaaaaacatt ccactaa                                         207
```

<210> SEQ ID NO 172
<211> LENGTH: 63
<212> TYPE: PRT
<213> ORGANISM: Lactococcus sp. QU 12

<400> SEQUENCE: 172

```
Met Lys Leu Ile Asp His Leu Gly Ala Pro Arg Trp Ala Val Asp Thr
1               5                   10                  15

Ile Leu Gly Ala Ile Ala Val Gly Asn Leu Ala Ser Trp Val Leu Ala
            20                  25                  30

Leu Val Pro Gly Pro Gly Trp Ala Val Lys Ala Gly Leu Ala Thr Ala
        35                  40                  45

Ala Ala Ile Val Lys His Gln Gly Lys Ala Ala Ala Ala Ala Trp
    50                  55                  60
```

<210> SEQ ID NO 173
<211> LENGTH: 192
<212> TYPE: DNA
<213> ORGANISM: Lactococcus sp. QU 12

<400> SEQUENCE: 173

```
atgaaattaa ttgatcattt aggtgctcca agatgggccg ttgatactat tttaggtgca      60

atcgcagttg ggaacttagc aagttgggtt ctagcgcttg tccctggtcc agggtgggca     120

gtaaaagctg gtttagcaac tgctgctgcc atcgttaaac atcaaggtaa agctgccgct     180

gctgcttggt aa                                                         192
```

<210> SEQ ID NO 174
<211> LENGTH: 50

<212> TYPE: PRT
<213> ORGANISM: Brevibacillus sp. GI-9

<400> SEQUENCE: 174

```
Met Ala Cys Gln Cys Pro Asp Ala Ile Ser Gly Trp Thr His Thr Asp
1               5                   10                  15

Tyr Gln Cys His Gly Leu Glu Asn Lys Met Tyr Arg His Val Tyr Ala
            20                  25                  30

Ile Cys Met Asn Gly Thr Gln Val Tyr Cys Arg Thr Glu Trp Gly Ser
        35                  40                  45

Ser Cys
    50
```

<210> SEQ ID NO 175
<211> LENGTH: 153
<212> TYPE: DNA
<213> ORGANISM: Brevibacillus sp. GI-9

<400> SEQUENCE: 175

```
atggcttgcc aatgtccaga tgcgatctca ggttggacgc atacagatta ccagtgtcac     60

ggtttggaga ataaaatgta tagacatgtt tatgcaattt gcatgaacgg tactcaagta    120

tattgcagaa cagagtgggg tagcagctgc tag                                 153
```

<210> SEQ ID NO 176
<211> LENGTH: 57
<212> TYPE: PRT
<213> ORGANISM: Leuconostoc pseudomesenteroides

<400> SEQUENCE: 176

```
Met Asn Lys Glu Tyr Asn Ser Ile Ser Asn Phe Lys Lys Ile Thr Asn
1               5                   10                  15

Lys Asp Leu Gln Asn Ile Asn Gly Gly Phe Ile Gly Arg Ala Ile Gly
            20                  25                  30

Asp Phe Val Tyr Phe Gly Ala Lys Gly Leu Arg Glu Ser Gly Lys Leu
        35                  40                  45

Leu Asn Tyr Tyr Tyr Lys His Lys His
    50                  55
```

<210> SEQ ID NO 177
<211> LENGTH: 174
<212> TYPE: DNA
<213> ORGANISM: Leuconostoc pseudomesenteroides

<400> SEQUENCE: 177

```
atgaataaag aatataatag cattagcaat tttaaaaaaa ttactaataa agacttgcaa     60

aacataaatg gtggatttat tggtagggca ataggtgact ttgtgtactt tggagcgaag    120

ggactaagag aatctggtaa actacttaat tattactata agcataagca ttga          174
```

<210> SEQ ID NO 178
<211> LENGTH: 53
<212> TYPE: PRT
<213> ORGANISM: Leuconostoc pseudomesenteroides

<400> SEQUENCE: 178

```
Met Lys Asn Gln Leu Met Ser Phe Glu Val Ile Ser Glu Lys Glu Leu
1               5                   10                  15

Ser Thr Val Gln Gly Gly Lys Gly Leu Gly Lys Leu Ile Gly Ile Asp
            20                  25                  30
```

```
Trp Leu Leu Gly Gln Ala Lys Asp Ala Val Lys Gln Tyr Lys Lys Asp
        35                  40                  45

Tyr Lys Arg Trp His
    50


<210> SEQ ID NO 179
<211> LENGTH: 162
<212> TYPE: DNA
<213> ORGANISM: Leuconostoc pseudomesenteroides

<400> SEQUENCE: 179

atgaaaaatc agttaatgtc tttcgaagtg atatcagaaa aagaattgtc cacggtacaa     60

ggtggcaaag gcttaggtaa actcatagga attgattggc ttttgggtca agctaaggac    120

gctgttaaac agtacaagaa ggattacaaa cgttggcact aa                       162


<210> SEQ ID NO 180
<211> LENGTH: 61
<212> TYPE: PRT
<213> ORGANISM: Leuconostoc gelidum

<400> SEQUENCE: 180

Met Met Asn Met Lys Pro Thr Glu Ser Tyr Glu Gln Leu Asp Asn Ser
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45

Gly Val His Arg Leu Ala Asn Gly Gly Asn Gly Phe Trp
    50                  55                  60


<210> SEQ ID NO 181
<211> LENGTH: 186
<212> TYPE: DNA
<213> ORGANISM: Leuconostoc gelidum

<400> SEQUENCE: 181

atgatgaaca tgaaacctac ggaaagctat gagcaattgg ataatagtgc tctcgaacaa     60

gtcgtaggag gtaagtatta tggtaacgga gttcattgca caaaaagtgg ttgttctgta    120

aactggggag aagccttttc agctggagta catcgtttag caaatggtgg aaatggtttc    180

tggtaa                                                               186


<210> SEQ ID NO 182
<211> LENGTH: 61
<212> TYPE: PRT
<213> ORGANISM: Leuconostoc carnosum

<400> SEQUENCE: 182

Met Asn Asn Met Lys Ser Ala Asp Asn Tyr Gln Gln Leu Asp Asn Asn
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45

Gly Val His Arg Leu Ala Asn Gly Gly Asn Gly Phe Trp
    50                  55                  60


<210> SEQ ID NO 183
<211> LENGTH: 186
```

<212> TYPE: DNA
<213> ORGANISM: Leuconostoc carnosum

<400> SEQUENCE: 183

```
atgaataaca tgaaatctgc ggataattat cagcaattgg ataataatgc tctcgaacaa     60

gtcgtaggag gtaagtatta tggtaacgga gttcattgca caaaaagtgg ttgttctgta    120

aactggggag aagccttttc agctggagta catcgtttag caaatggtgg aaatggtttc    180

tggtaa                                                               186
```

<210> SEQ ID NO 184
<211> LENGTH: 63
<212> TYPE: PRT
<213> ORGANISM: Leuconostoc mesenteroides

<400> SEQUENCE: 184

```
Met Phe Leu Val Asn Gln Leu Gly Ile Ser Lys Ser Leu Ala Asn Thr
1               5                   10                  15

Ile Leu Gly Ala Ile Ala Val Gly Asn Leu Ala Ser Trp Leu Leu Ala
            20                  25                  30

Leu Val Pro Gly Pro Gly Trp Ala Thr Lys Ala Ala Leu Ala Thr Ala
        35                  40                  45

Glu Thr Ile Val Lys His Glu Gly Lys Ala Ala Ala Ile Ala Trp
    50                  55                  60
```

<210> SEQ ID NO 185
<211> LENGTH: 192
<212> TYPE: DNA
<213> ORGANISM: Leuconostoc mesenteroides

<400> SEQUENCE: 185

```
atgttcttgg taaatcagtt agggatttca aaatcgttag ctaatactat tcttggtgca     60

attgctgttg gtaatttggc cagttggtta ttagctttgg ttcctggtcc gggttgggca    120

acaaaagcag cacttgcgac agctgaaaca attgtgaagc atgaaggaaa agcagctgct    180

attgcgtggt aa                                                        192
```

<210> SEQ ID NO 186
<211> LENGTH: 74
<212> TYPE: PRT
<213> ORGANISM: Bacillus licheniformis

<400> SEQUENCE: 186

```
Met Ser Lys Lys Glu Met Ile Leu Ser Trp Lys Asn Pro Met Tyr Arg
1               5                   10                  15

Thr Glu Ser Ser Tyr His Pro Ala Gly Asn Ile Leu Lys Glu Leu Gln
            20                  25                  30

Glu Glu Glu Gln His Ser Ile Ala Gly Gly Thr Ile Thr Leu Ser Thr
        35                  40                  45

Cys Ala Ile Leu Ser Lys Pro Leu Gly Asn Asn Gly Tyr Leu Cys Thr
    50                  55                  60

Val Thr Lys Glu Cys Met Pro Ser Cys Asn
65                  70
```

<210> SEQ ID NO 187
<211> LENGTH: 225
<212> TYPE: DNA
<213> ORGANISM: Bacillus licheniformis

<400> SEQUENCE: 187

```
atgtcaaaaa aggaaatgat tctttcatgg aaaaatccta tgtatcgcac tgaatcttct     60

tatcatccag cagggaacat ccttaaagaa ctccaggaag aggaacagca cagcatcgcc    120

ggaggcacaa tcacgctcag cacttgtgcc atcttgagca agccgttagg aaataacgga    180

tacctgtgta cagtgacaaa agaatgcatg ccaagctgta actaa                    225
```

<210> SEQ ID NO 188
<211> LENGTH: 266
<212> TYPE: PRT
<213> ORGANISM: Brevibacterium linens

<400> SEQUENCE: 188

```
Met Asn Asn Leu Tyr Arg Glu Leu Ala Pro Ile Pro Gly Pro Ala Trp
1               5                   10                  15

Ala Glu Ile Glu Glu Glu Ala Arg Arg Thr Phe Lys Arg Asn Ile Ala
            20                  25                  30

Gly Arg Arg Ile Val Asp Val Ala Gly Pro Thr Gly Phe Glu Thr Ser
        35                  40                  45

Ala Val Thr Thr Gly His Ile Arg Asp Val Gln Ser Glu Thr Ser Gly
    50                  55                  60

Leu Gln Val Lys Gln Arg Ile Val Gln Glu Tyr Ile Glu Leu Arg Thr
65                  70                  75                  80

Pro Phe Thr Val Thr Arg Gln Ala Ile Asp Asp Val Ala Arg Gly Ser
                85                  90                  95

Gly Asp Ser Asp Trp Gln Pro Val Lys Asp Ala Ala Thr Thr Ile Ala
            100                 105                 110

Met Ala Glu Asp Arg Ala Ile Leu His Gly Leu Asp Ala Ala Gly Ile
        115                 120                 125

Gly Gly Ile Val Pro Gly Ser Ser Asn Ala Ala Val Ala Ile Pro Asp
    130                 135                 140

Ala Val Glu Asp Phe Ala Asp Ala Val Ala Gln Ala Leu Ser Val Leu
145                 150                 155                 160

Arg Thr Val Gly Val Asp Gly Pro Tyr Ser Leu Leu Leu Ser Ser Ala
                165                 170                 175

Glu Tyr Thr Lys Val Ser Glu Ser Thr Asp His Gly Tyr Pro Ile Arg
            180                 185                 190

Glu His Leu Ser Arg Gln Leu Gly Ala Gly Glu Ile Ile Trp Ala Pro
        195                 200                 205

Ala Leu Glu Gly Ala Leu Leu Val Ser Thr Arg Gly Gly Asp Tyr Glu
    210                 215                 220

Leu His Leu Gly Gln Asp Leu Ser Ile Gly Tyr Tyr Ser His Asp Ser
225                 230                 235                 240

Glu Thr Val Glu Leu Tyr Leu Gln Glu Thr Phe Gly Phe Leu Ala Leu
                245                 250                 255

Thr Asp Glu Ser Ser Val Pro Leu Ser Leu
            260                 265
```

<210> SEQ ID NO 189
<211> LENGTH: 801
<212> TYPE: DNA
<213> ORGANISM: Brevibacterium linens

<400> SEQUENCE: 189

```
gtgaataacc tctatcgcga gcttgccccc atccccggcc cggcctgggc ggagatcgag     60

gaggaggctc gacggacatt caaacgcaat atcgccggcc gccggatcgt cgatgtcgca    120

gggcccacgg gcttcgagac ctccgcggtg accactggcc acatccgaga cgtccagtcg    180

gagacgagcg gactgcaggt taagcagcgc atcgtgcagg aatacatcga gctgcggacc    240

ccattcaccg tgactcggca ggccatcgat gacgtggccc gcgggtccgg tgactcggac    300

tggcagcccg tcaaggatgc ggccacgacg atcgcgatgg ctgaagatcg ggccattctc    360

cacgggctcg atgcggccgg gatcggcgga atcgttcccg gcagctcgaa tgccgcagtg    420

gccatccccg acgccgtcga ggacttcgcg gacgccgtcg cccaggcgct gagtgtgctg    480

cgcacggtgg gagtcgacgg gccctacagc ctgttgctct cctccgcgga gtacaccaag    540

gtctccgagt ccaccgacca cggctacccg atccgcgagc acctctcccg gcagctcggc    600

gccggagaga tcatctgggc gcccgcgctc gaaggggcgc tgctcgtctc cacgcgcggg    660

ggtgactacg agctccacct cggccaggac ctgtcgatcg gttactacag ccacgacagc    720

gagaccgtcg aactctatct gcaggagacc ttcggattcc tcgcgctgac cgacgaatcc    780

agtgtgcctt tgagcctctg a                                               801
```

<210> SEQ ID NO 190
<211> LENGTH: 71
<212> TYPE: PRT
<213> ORGANISM: Listeria innocua

<400> SEQUENCE: 190

```
Met Lys Lys Ala Ala Leu Lys Phe Ile Ile Val Ile Ala Ile Leu Gly
1               5                   10                  15

Phe Ser Phe Ser Phe Phe Ser Ile Gln Ser Glu Ala Lys Ser Tyr Gly
            20                  25                  30

Asn Gly Val Gln Cys Asn Lys Lys Lys Cys Trp Val Asp Trp Gly Ser
        35                  40                  45

Ala Ile Ser Thr Ile Gly Asn Asn Ser Ala Ala Asn Trp Ala Thr Gly
    50                  55                  60

Gly Ala Ala Gly Trp Lys Ser
65                  70
```

<210> SEQ ID NO 191
<211> LENGTH: 216
<212> TYPE: DNA
<213> ORGANISM: Listeria innocua

<400> SEQUENCE: 191

```
ttgaagaagg cagcgttaaa atttattatt gttattgcta ttctaggttt cagtttttct     60

ttctttagca tacaatctga agctaaatct tatggaaatg gagttcagtg taataagaaa    120

aaatgttggg tagattgggg tagtgctata agtactattg gaaataattc tgcagcgaat    180

tgggctacag gtggagcagc tggttggaaa agctga                              216
```

<210> SEQ ID NO 192
<211> LENGTH: 68
<212> TYPE: PRT
<213> ORGANISM: Bacillus sp.

<400> SEQUENCE: 192

```
Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
        35                  40                  45

Cys Thr Phe Thr Leu Pro Gly Gly Gly Gly Val Cys Thr Leu Thr Ser
    50                  55                  60

Glu Cys Ile Cys
65
```

<210> SEQ ID NO 193
<211> LENGTH: 207
<212> TYPE: DNA
<213> ORGANISM: Bacillus sp.

<400> SEQUENCE: 193

```
atgagtcaag aagctatcat tcgttcatgg aaagatcctt tttcccgtga aaattctaca      60

caaaatccag ctggtaaccc attcagtgag ctgaaagaag cacaaatgga taagttagta     120

ggtgcgggag acatggaagc agcatgtact tttacattgc ctggtggcgg cggtgtttgt     180

actctaactt ctgaatgtat ttgttaa                                         207
```

<210> SEQ ID NO 194
<211> LENGTH: 61
<212> TYPE: PRT
<213> ORGANISM: Leuconostoc mesenteroides

<400> SEQUENCE: 194

```
Met Thr Asn Met Lys Ser Val Glu Ala Tyr Gln Gln Leu Asp Asn Gln
1               5                   10                  15

Asn Leu Lys Lys Val Val Gly Gly Lys Tyr Tyr Gly Asn Gly Val His
            20                  25                  30

Cys Thr Lys Ser Gly Cys Ser Val Asn Trp Gly Glu Ala Ala Ser Ala
        35                  40                  45

Gly Ile His Arg Leu Ala Asn Gly Gly Asn Gly Phe Trp
    50                  55                  60
```

<210> SEQ ID NO 195
<211> LENGTH: 186
<212> TYPE: DNA
<213> ORGANISM: Leuconostoc mesenteroides

<400> SEQUENCE: 195

```
atgacgaata tgaagtctgt ggaagcatat cagcaattag ataaccagaa tctcaagaaa      60

gttgttggtg gaaagtatta tgggaatggt gttcactgta caaaaagtgg atgctctgtt     120

aactggggag aagctgcctc agctggcata catcgtttgg ccaatggtgg aaatggattt     180

tggtaa                                                                186
```

<210> SEQ ID NO 196
<211> LENGTH: 68
<212> TYPE: PRT
<213> ORGANISM: Clavibacter michiganensis subsp. michiganensis

<400> SEQUENCE: 196

Met Asn Asp Ile Leu Glu Thr Glu Thr Pro Val Met Val Ser Pro Arg
1 5 10 15

Trp Asp Met Leu Leu Asp Ala Gly Glu Asp Thr Ser Pro Ser Val Gln
20 25 30

Thr Gln Ile Asp Ala Glu Phe Arg Arg Val Val Ser Pro Tyr Met Ser
35 40 45

Ser Ser Gly Trp Leu Cys Thr Leu Thr Ile Glu Cys Gly Thr Ile Ile
50 55 60

Cys Ala Cys Arg
65

<210> SEQ ID NO 197
<211> LENGTH: 207
<212> TYPE: DNA
<213> ORGANISM: Clavibacter michiganensis subsp. michiganensis

<400> SEQUENCE: 197
atgaacgaca tcctcgagac ggagaccccc gtcatggtca gcccccggtg ggacatgctg 60
ctcgacgcgg gcgaggacac cagcccgtcc gtccagaccc agatcgacgc ggagttccgt 120
cgcgtcgtga gcccgtacat gtccagcagc ggctggctct gcacgctcac catcgaatgt 180
ggcaccatca tctgcgcgtg tcgctga 207

<210> SEQ ID NO 198
<211> LENGTH: 69
<212> TYPE: PRT
<213> ORGANISM: Escherichia coli

<400> SEQUENCE: 198

Met Glu Leu Lys Ala Ser Glu Phe Gly Val Val Leu Ser Val Asp Ala
1 5 10 15

Leu Lys Leu Ser Arg Gln Ser Pro Leu Gly Val Gly Ile Gly Gly Gly
20 25 30

Gly Gly Gly Gly Gly Gly Gly Ser Cys Gly Gly Gln Gly Gly Gly Cys
35 40 45

Gly Gly Cys Ser Asn Gly Cys Ser Gly Gly Asn Gly Gly Ser Gly Gly
50 55 60

Ser Gly Ser His Ile
65

<210> SEQ ID NO 199
<211> LENGTH: 207
<212> TYPE: DNA
<213> ORGANISM: Escherichia coli

<400> SEQUENCE: 199
atggaattaa aagcgagtga atttggtgta gttttgtccg ttgatgctct taaattatca 60
cgccagtctc cattaggtgt tggcattggt ggtggtggcg gcggcggcgg cggcggtagc 120
tgcggtggtc aaggtggcgg ttgtggtggt tgcagcaacg gttgtagtgg tggaaacggt 180
ggcagcggcg gaagtggttc acatatc 207

<210> SEQ ID NO 200
<211> LENGTH: 7
<212> TYPE: PRT
<213> ORGANISM: Escherichia coli

<400> SEQUENCE: 200

Met Arg Thr Gly Asn Ala Asn
1               5

<210> SEQ ID NO 201
<211> LENGTH: 24
<212> TYPE: DNA
<213> ORGANISM: Escherichia coli

<400> SEQUENCE: 201
atgcgtactg gtaatgcaaa ctaa 24

<210> SEQ ID NO 202
<211> LENGTH: 99
<212> TYPE: PRT
<213> ORGANISM: Klebsiella pneumoniae

<400> SEQUENCE: 202

Met Arg Glu Ile Ser Gln Lys Asp Leu Asn Leu Ala Phe Gly Ala Gly
1               5                   10                  15

Glu Thr Asp Pro Asn Thr Gln Leu Leu Asn Asp Leu Gly Asn Asn Met
            20                  25                  30

Ala Trp Gly Ala Ala Leu Gly Ala Pro Gly Gly Leu Gly Ser Ala Ala
        35                  40                  45

Leu Gly Ala Ala Gly Gly Ala Leu Gln Thr Val Gly Gln Gly Leu Ile
    50                  55                  60

Asp His Gly Pro Val Asn Val Pro Ile Pro Val Leu Ile Gly Pro Ser
65                  70                  75                  80

Trp Asn Gly Ser Gly Ser Gly Tyr Asn Ser Ala Thr Ser Ser Ser Gly
                85                  90                  95

Ser Gly Ser

<210> SEQ ID NO 203
<211> LENGTH: 300
<212> TYPE: DNA
<213> ORGANISM: Klebsiella pneumoniae

<400> SEQUENCE: 203
atgagagaaa ttagtcaaaa ggacttaaat cttgcttttg gtgcaggaga gaccgatcca 60
aatactcaac ttctaaacga ccttggaaat aatatggcat ggggtgctgc tcttggcgct 120
cctggcggat taggatcagc agctttgggg gccgcgggag gtgcattaca aactgtaggg 180
caaggattaa ttgaccatgg tcctgtaaat gtccccatcc ctgtactcat cgggccaagc 240
tggaatggta gcggtagtgg ttataacagc gcaacatcca gttccggtag tggtagttaa 300

<210> SEQ ID NO 204
<211> LENGTH: 75
<212> TYPE: PRT
<213> ORGANISM: Escherichia coli

<400> SEQUENCE: 204

Met Arg Glu Ile Thr Glu Ser Gln Leu Arg Tyr Ile Ser Gly Ala Gly
1               5                   10                  15

Gly Ala Pro Ala Thr Ser Ala Asn Ala Ala Gly Ala Ala Ala Ile Val
            20                  25                  30

Gly Ala Leu Ala Gly Ile Pro Gly Gly Pro Leu Gly Val Val Val Gly
        35                  40                  45

```
Ala Val Ser Ala Gly Leu Thr Thr Ala Ile Gly Ser Thr Val Gly Ser
    50                  55                  60

Gly Ser Ala Ser Ser Ser Ala Gly Gly Gly Ser
65                  70                  75


<210> SEQ ID NO 205
<211> LENGTH: 228
<212> TYPE: DNA
<213> ORGANISM: Escherichia coli

<400> SEQUENCE: 205

atgcgagaaa taacagaatc acagttaaga tatatttccg gggcgggagg tgcgccagcg     60

acttcagcta atgccgcagg tgctgcagct attgttggag ctctcgccgg aatacctggt    120

ggtccacttg ggttgtagt tggagccgta tctgccggtt tgacaacagc aattggctcg    180

accgtgggaa gtggtagtgc cagttcttct gctggtggcg gtagctaa                 228


<210> SEQ ID NO 206
<211> LENGTH: 58
<212> TYPE: PRT
<213> ORGANISM: Escherichia coli

<400> SEQUENCE: 206

Met Ile Lys His Phe His Phe Asn Lys Leu Ser Ser Gly Lys Lys Asn
1               5                   10                  15

Asn Val Pro Ser Pro Ala Lys Gly Val Ile Gln Ile Lys Lys Ser Ala
            20                  25                  30

Ser Gln Leu Thr Lys Gly Gly Ala Gly His Val Pro Glu Tyr Phe Val
        35                  40                  45

Gly Ile Gly Thr Pro Ile Ser Phe Tyr Gly
    50                  55


<210> SEQ ID NO 207
<211> LENGTH: 177
<212> TYPE: DNA
<213> ORGANISM: Escherichia coli

<400> SEQUENCE: 207

atgattaagc attttcattt taataaactg tcttctggta aaaaaaataa tgttccatct     60

cctgcaaagg gggttataca aataaaaaaa tcagcatcgc aactcacaaa aggtggtgca    120

ggacatgtgc ctgagtattt tgtggggatt ggtacaccta tatctttcta tggctga       177


<210> SEQ ID NO 208
<211> LENGTH: 90
<212> TYPE: PRT
<213> ORGANISM: Escherichia coli

<400> SEQUENCE: 208

Met Tyr Met Arg Glu Leu Asp Arg Glu Glu Leu Asn Cys Val Gly Gly
1               5                   10                  15

Ala Gly Asp Pro Leu Ala Asp Pro Asn Ser Gln Ile Val Arg Gln Ile
            20                  25                  30

Met Ser Asn Ala Ala Trp Gly Pro Pro Leu Val Pro Glu Arg Phe Arg
        35                  40                  45

Gly Met Ala Val Gly Ala Ala Gly Gly Val Thr Gln Thr Val Leu Gln
    50                  55                  60

Gly Ala Ala Ala His Met Pro Val Asn Val Pro Ile Pro Lys Val Pro
65                  70                  75                  80
```

```
Met Gly Pro Ser Trp Asn Gly Ser Lys Gly
                85                  90


<210> SEQ ID NO 209
<211> LENGTH: 273
<212> TYPE: DNA
<213> ORGANISM: Escherichia coli

<400> SEQUENCE: 209

atgtatatga gagagttaga tagagaggaa ttaaattgcg ttggtggggc tggagatccg     60

cttgcagatc ctaattccca aattgtaaga cagataatgt ctaatgcggc atggggcccg    120

cctttggtgc cagagcggtt taggggaatg gctgttggag ccgcaggtgg ggttacgcag    180

acagttcttc aaggagcagc agctcatatg ccggttaatg tccctatacc taaagttccg    240

atgggaccct catggaacgg aagtaaagga taa                                 273


<210> SEQ ID NO 210
<211> LENGTH: 50
<212> TYPE: PRT
<213> ORGANISM: Enterococcus mundtii

<400> SEQUENCE: 210

Met Ser Gln Val Val Gly Gly Lys Tyr Tyr Gly Asn Gly Val Ser Cys
1               5                   10                  15

Asn Lys Lys Gly Cys Ser Val Asp Trp Gly Lys Ala Ile Gly Ile Ile
            20                  25                  30

Gly Asn Asn Ser Ala Ala Asn Leu Ala Thr Gly Gly Ala Ala Gly Trp
        35                  40                  45

Lys Ser
    50


<210> SEQ ID NO 211
<211> LENGTH: 153
<212> TYPE: DNA
<213> ORGANISM: Enterococcus mundtii

<400> SEQUENCE: 211

atgtcacagg tagtaggtgg aaaatactac ggtaatggag tctcatgtaa taaaaaaggg     60

tgcagtgttg attggggaaa agcgattggc attattggaa ataattctgc tgcgaattta    120

gctactggtg gagcagctgg ttggaaaagt taa                                 153


<210> SEQ ID NO 212
<211> LENGTH: 58
<212> TYPE: PRT
<213> ORGANISM: Enterococcus mundtii

<400> SEQUENCE: 212

Met Lys Lys Leu Thr Ser Lys Glu Met Ala Gln Val Val Gly Gly Lys
1               5                   10                  15

Tyr Tyr Gly Asn Gly Leu Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55


<210> SEQ ID NO 213
<211> LENGTH: 177
```

<212> TYPE: DNA
<213> ORGANISM: Enterococcus mundtii

<400> SEQUENCE: 213
ttgaagaaat taacatcaaa agaaatggca caagtagtag gtgggaaata ctacggtaat 60
ggattatcat gtaataaaaa agggtgcagt gttgattggg gaaaagctat tggcattatt 120
ggaaataatt ctgctgcgaa tttagctact ggtggagcag ctggttggaa aagttaa 177

<210> SEQ ID NO 214
<211> LENGTH: 63
<212> TYPE: PRT
<213> ORGANISM: Streptococcus mutans

<400> SEQUENCE: 214

Met Ser Asn Thr Gln Leu Leu Glu Val Leu Gly Thr Glu Thr Phe Asp
1 5 10 15

Val Gln Glu Asp Leu Phe Ala Phe Asp Thr Thr Asp Thr Thr Ile Val
20 25 30

Ala Ser Asn Asp Asp Pro Asp Thr Arg Phe Lys Ser Trp Ser Leu Cys
35 40 45

Thr Pro Gly Cys Ala Arg Thr Gly Ser Phe Asn Ser Tyr Cys Cys
50 55 60

<210> SEQ ID NO 215
<211> LENGTH: 192
<212> TYPE: DNA
<213> ORGANISM: Streptococcus mutans

<400> SEQUENCE: 215
atgtcaaaca cacaattatt agaagtcctt ggtactgaaa cttttgatgt tcaagaagat 60
ctctttgctt ttgatacaac agatactact attgtggcaa gcaacgacga tccagatact 120
cgtttcaaaa gttggagcct ttgtacgcct ggttgtgcaa ggacaggtag tttcaatagt 180
tactgttgct ga 192

<210> SEQ ID NO 216
<211> LENGTH: 53
<212> TYPE: PRT
<213> ORGANISM: Streptococcus mutans

<400> SEQUENCE: 216

Met Asn Lys Leu Asn Ser Asn Ala Val Val Ser Leu Asn Glu Val Ser
1 5 10 15

Asp Ser Glu Leu Asp Thr Ile Leu Gly Gly Asn Arg Trp Trp Gln Gly
20 25 30

Val Val Pro Thr Val Ser Tyr Glu Cys Arg Met Asn Ser Trp Gln His
35 40 45

Val Phe Thr Cys Cys
50

<210> SEQ ID NO 217
<211> LENGTH: 162
<212> TYPE: DNA
<213> ORGANISM: Streptococcus mutans

<400> SEQUENCE: 217

```
atgaacaagt taaacagtaa cgcagtagtt tctttgaatg aagtttcaga ttctgaattg     60

gatactattt tgggtggtaa tcgttggtgg caaggtgttg tgccaacggt ctcatatgag    120

tgtcgcatga attcatggca acatgttttc acttgctgtt aa                       162
```

<210> SEQ ID NO 218
<211> LENGTH: 57
<212> TYPE: PRT
<213> ORGANISM: Lactococcus lactis subsp. lactis

<400> SEQUENCE: 218

```
Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55
```

<210> SEQ ID NO 219
<211> LENGTH: 174
<212> TYPE: DNA
<213> ORGANISM: Lactococcus lactis subsp. lactis

<400> SEQUENCE: 219

```
atgagtacaa aagattttaa cttggatttg gtatctgttt cgaagaaaga ttcaggtgca     60

tcaccacgca ttacaagtat ttcgctatgt acacccggtt gtaaaacagg agctctgatg    120

ggttgtaaca tgaaaacagc aacttgtcat tgtagtattc acgtaagcaa ataa          174
```

<210> SEQ ID NO 220
<211> LENGTH: 57
<212> TYPE: PRT
<213> ORGANISM: Lactococcus lactis

<400> SEQUENCE: 220

```
Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Val His Val Ser Lys
    50                  55
```

<210> SEQ ID NO 221
<211> LENGTH: 171
<212> TYPE: DNA
<213> ORGANISM: Lactococcus lactis

<400> SEQUENCE: 221

```
atgagtacaa aagatttcaa cttggatttg gtatctgttt cgaagaaaga ttcaggtgca     60

tcaccacgca ttacaagtat ttcgctatgt acacccggtt gtaaaacagg agctctgatg    120

ggttgtaaca tgaaaacagc aacttgtaat tgtagcgttc acgtaagcaa a             171
```

<210> SEQ ID NO 222

<211> LENGTH: 57
<212> TYPE: PRT
<213> ORGANISM: Lactococcus lactis

<400> SEQUENCE: 222

```
Met Ser Thr Lys Asp Phe Asn Leu Asp Leu Val Ser Val Ser Lys Thr
1               5                   10                  15

Asp Ser Gly Ala Ser Thr Arg Ile Thr Ser Ile Ser Leu Cys Thr Pro
            20                  25                  30

Gly Cys Lys Thr Gly Val Leu Met Gly Cys Asn Leu Lys Thr Ala Thr
        35                  40                  45

Cys Asn Cys Ser Val His Val Ser Lys
    50                  55
```

<210> SEQ ID NO 223
<211> LENGTH: 174
<212> TYPE: DNA
<213> ORGANISM: Lactococcus lactis

<400> SEQUENCE: 223

```
atgagtacaa aagatttcaa cttagatttg gtatctgttt caaaaacaga ttctggcgct     60

tcaacacgta ttaccagcat ttcgctttgt acaccaggtt gtaaaacagg tgttctgatg    120

ggatgtaacc tgaaaacagc aacttgtaat tgtagcgttc acgtaagcaa ataa          174
```

<210> SEQ ID NO 224
<211> LENGTH: 55
<212> TYPE: PRT
<213> ORGANISM: Streptococcus uberis

<400> SEQUENCE: 224

```
Met Asn Asn Glu Asp Phe Asn Leu Asp Leu Ile Lys Ile Ser Lys Glu
1               5                   10                  15

Asn Asn Ser Gly Ala Ser Pro Arg Ile Thr Ser Lys Ser Leu Cys Thr
            20                  25                  30

Pro Gly Cys Lys Thr Gly Ile Leu Met Thr Cys Pro Leu Lys Thr Ala
        35                  40                  45

Thr Cys Gly Cys His Phe Gly
    50                  55
```

<210> SEQ ID NO 225
<211> LENGTH: 168
<212> TYPE: DNA
<213> ORGANISM: Streptococcus uberis

<400> SEQUENCE: 225

```
atgaacaatg aagattttaa tttggatctc atcaaaatct caaaggaaaa caactcagga     60

gcttcacctc gaataactag taaatcatta tgtactcctg gatgtaagac gggtattttg    120

atgacttgtc cactaaaaac tgcaacctgt ggttgtcatt ttggataa                 168
```

<210> SEQ ID NO 226
<211> LENGTH: 57
<212> TYPE: PRT
<213> ORGANISM: Lactococcus lactis subsp. lactis

<400> SEQUENCE: 226

```
Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30
```

Gly Cys Lys Thr Gly Ala Leu Met Gly Cys Asn Met Lys Thr Ala Thr
35 40 45

Cys Asn Cys Ser Ile His Val Ser Lys
50 55

<210> SEQ ID NO 227
<211> LENGTH: 174
<212> TYPE: DNA
<213> ORGANISM: Lactococcus lactis subsp. lactis

<400> SEQUENCE: 227
atgagtacaa aagattttaa cttggatttg gtatctgttt cgaagaaaga ttcaggtgca 60
tcaccacgca ttacaagtat ttcgctatgt acacccggtt gtaaaacagg agctctgatg 120
ggttgtaaca tgaaaacagc aacttgtaat tgtagtattc acgtaagcaa ataa 174

<210> SEQ ID NO 228
<211> LENGTH: 57
<212> TYPE: PRT
<213> ORGANISM: Staphylococcus warneri

<400> SEQUENCE: 228

Met Glu Asn Ser Lys Val Met Lys Asp Ile Glu Val Ala Asn Leu Leu
1 5 10 15

Glu Glu Val Gln Glu Asp Glu Leu Asn Glu Val Leu Gly Ala Lys Lys
20 25 30

Lys Ser Gly Val Ile Pro Thr Val Ser His Asp Cys His Met Asn Ser
35 40 45

Phe Gln Phe Val Phe Thr Cys Cys Ser
50 55

<210> SEQ ID NO 229
<211> LENGTH: 174
<212> TYPE: DNA
<213> ORGANISM: Staphylococcus warneri

<400> SEQUENCE: 229
atggaaaatt ctaaagttat gaaggacatt gaagtagcaa atttattaga agaggttcaa 60
gaagatgaat tgaatgaagt cttaggagct aagaaaaagt caggagtaat cccaactgtg 120
tcacacgatt gccatatgaa ttctttccaa tttgtattta cttgttgttc ataa 174

<210> SEQ ID NO 230
<211> LENGTH: 58
<212> TYPE: PRT
<213> ORGANISM: Paenibacillus polymyxa

<400> SEQUENCE: 230

Met Ala Glu Asn Leu Phe Asp Leu Asp Ile Gln Val Asn Lys Ser Gln
1 5 10 15

Gly Ser Val Glu Pro Gln Val Leu Ser Ile Val Ala Cys Ser Ser Gly
20 25 30

Cys Gly Ser Gly Lys Thr Ala Ala Ser Cys Val Glu Thr Cys Gly Asn
35 40 45

Arg Cys Phe Thr Asn Val Gly Ser Leu Cys
50 55

<210> SEQ ID NO 231
<211> LENGTH: 177
<212> TYPE: DNA

<213> ORGANISM: Paenibacillus polymyxa

<400> SEQUENCE: 231

```
atggctgaaa acttatttga tctggacatt caagtaaaca aatctcaagg ttctgtagag      60

cctcaggttc tgagcattgt tgcatgttct agcggatgtg gtagcggtaa aacagctgcc     120

agttgtgttg aaacttgtgg caaccggtgc tttactaacg ttggttcact ctgctaa        177
```

<210> SEQ ID NO 232
<211> LENGTH: 62
<212> TYPE: PRT
<213> ORGANISM: Pediococcus acidilactici

<400> SEQUENCE: 232

```
Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Asn His Lys Cys
    50                  55                  60
```

<210> SEQ ID NO 233
<211> LENGTH: 189
<212> TYPE: DNA
<213> ORGANISM: Pediococcus acidilactici

<400> SEQUENCE: 233

```
atgaaaaaaa ttgaaaaatt aactgaaaaa gaaatggcca atatcattgg tggtaaatac      60

tacggtaatg gggttacttg tggcaaacat tcctgctctg ttgactgggg taaggctacc     120

acttgcataa tcaataatgg agctatggca tgggctactg gtggacatca aggtaatcat     180

aaatgctag                                                             189
```

<210> SEQ ID NO 234
<211> LENGTH: 60
<212> TYPE: PRT
<213> ORGANISM: Pediococcus pentosaceus

<400> SEQUENCE: 234

```
Met Thr Glu Ile Lys Val Leu Asn Asp Lys Glu Leu Lys Asn Val Val
1               5                   10                  15

Gly Gly Lys Tyr Tyr Gly Asn Gly Val His Cys Gly Lys Lys Thr Cys
            20                  25                  30

Tyr Val Asp Trp Gly Gln Ala Thr Ala Ser Ile Gly Lys Ile Ile Val
        35                  40                  45

Asn Gly Trp Thr Gln His Gly Pro Trp Ala His Arg
    50                  55                  60
```

<210> SEQ ID NO 235
<211> LENGTH: 183
<212> TYPE: DNA
<213> ORGANISM: Pediococcus pentosaceus

<400> SEQUENCE: 235

```
atgactgaaa ttaaagtact aaacgataag gaactaaaaa atgtcgtagg aggaaagtat     60
tacggtaacg gagtgcattg tggtaaaaag acttgctatg tggactgggg acaagctaca    120
gctagcattg gaaaaattat agtgaacgga tggacacaac acgggccttg ggcacataga    180
taa                                                                  183
```

<210> SEQ ID NO 236
<211> LENGTH: 60
<212> TYPE: PRT
<213> ORGANISM: Staphylococcus epidermidis

<400> SEQUENCE: 236

```
Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
    50                  55                  60
```

<210> SEQ ID NO 237
<211> LENGTH: 183
<212> TYPE: DNA
<213> ORGANISM: Staphylococcus epidermidis

<400> SEQUENCE: 237

```
atgaaaaata acaaaaattt atttgattta gaaattaaaa aagaaacaag tcaaaacact     60
gatgaacttg aacctcaaac tgctggacca gcgattagag cttctgtgaa acaatgtcag    120
aaaactttga aagctacgcg tttatttaca gtgtcttgca aaggaaaaaa cggatgtaaa    180
tag                                                                  183
```

<210> SEQ ID NO 238
<211> LENGTH: 62
<212> TYPE: PRT
<213> ORGANISM: Carnobacterium maltaromaticum

<400> SEQUENCE: 238

```
Met Lys Thr Val Lys Glu Leu Ser Val Lys Glu Met Gln Leu Thr Thr
1               5                   10                  15

Gly Gly Lys Tyr Tyr Gly Asn Gly Val Ser Cys Asn Lys Asn Gly Cys
            20                  25                  30

Thr Val Asp Trp Ser Lys Ala Ile Gly Ile Ile Gly Asn Asn Ala Ala
        35                  40                  45

Ala Asn Leu Thr Thr Gly Gly Ala Ala Gly Trp Asn Lys Gly
    50                  55                  60
```

<210> SEQ ID NO 239
<211> LENGTH: 189
<212> TYPE: DNA
<213> ORGANISM: Carnobacterium maltaromaticum

<400> SEQUENCE: 239

```
atgaaaactg ttaaagaact tagcgttaaa gaaatgcaac taactacagg aggtaagtat     60
tacggaaatg gcgtttcctg taataaaaat ggttgtactg tagattggag caaagctatt    120
```

```
gggattatag gaaacaatgc agcagcaaat ttgactacag gtggagccgc tggttggaac    180

aaaggataa                                                            189


<210> SEQ ID NO 240
<211> LENGTH: 69
<212> TYPE: PRT
<213> ORGANISM: Lactobacillus plantarum
<220> FEATURE:
<221> NAME/KEY: VARIANT
<222> LOCATION: 40
<223> OTHER INFORMATION: Xaa = any amino acid

<400> SEQUENCE: 240

Met Tyr Lys Glu Leu Thr Val Asp Glu Leu Ala Leu Ile Asp Gly Gly
1               5                   10                  15

Lys Lys Lys Lys Lys Lys Val Ala Cys Thr Trp Gly Asn Ala Ala Thr
            20                  25                  30

Ala Ala Ala Ser Gly Ala Val Xaa Gly Ile Leu Gly Gly Pro Thr Gly
        35                  40                  45

Ala Leu Ala Gly Ala Ile Trp Gly Val Ser Gln Cys Ala Ser Asn Asn
    50                  55                  60

Leu His Gly Met His
65


<210> SEQ ID NO 241
<211> LENGTH: 210
<212> TYPE: DNA
<213> ORGANISM: Lactobacillus plantarum
<220> FEATURE:
<221> NAME/KEY: misc_feature
<222> LOCATION: 119
<223> OTHER INFORMATION: n = a, c, t or g

<400> SEQUENCE: 241

atgtataaag aattaacagt tgatgaatta gcattgattg atggaggaaa aaagaagaag     60

aaaaaagtag cttgtacttg ggaaatgca gcaacagccg ctgcttctgg tgcagttang    120

ggtattcttg gtgggcctac tggtgcactg gctggagcta tctggggcgt ttcacaatgc    180

gcgtctaaca acttacacgg catgcactaa                                     210


<210> SEQ ID NO 242
<211> LENGTH: 56
<212> TYPE: PRT
<213> ORGANISM: Lactobacillus plantarum

<400> SEQUENCE: 242

Met Met Lys Lys Ile Glu Lys Leu Thr Glu Lys Glu Met Ala Asn Ile
1               5                   10                  15

Ile Gly Gly Lys Tyr Tyr Gly Asn Gly Val Thr Cys Gly Lys His Ser
            20                  25                  30

Cys Ser Val Asn Trp Gly Gln Ala Phe Ser Cys Ser Val Ser His Leu
        35                  40                  45

Ala Asn Phe Gly His Gly Lys Cys
    50                  55


<210> SEQ ID NO 243
<211> LENGTH: 171
<212> TYPE: DNA
<213> ORGANISM: Lactobacillus plantarum
```

<400> SEQUENCE: 243

```
atgatgaaaa aaattgaaaa attaactgaa aaagaaatgg ccaatatcat tggtggtaaa     60

tactatggta atggggttac ttgtggtaaa cattcctgct ctgttaactg ggccaagca    120

ttttcttgta gtgtgtcaca tttagctaac ttcggtcatg gaaagtgcta a            171
```

<210> SEQ ID NO 244
<211> LENGTH: 64
<212> TYPE: PRT
<213> ORGANISM: Lactobacillus plantarum

<400> SEQUENCE: 244

```
Met Ser Lys Leu Val Lys Thr Leu Thr Val Asp Glu Ile Ser Lys Ile
1               5                   10                  15

Gln Thr Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Val Lys His Ser Ser Gly Gly Gly Gly Ser Tyr His Cys
    50                  55                  60
```

<210> SEQ ID NO 245
<211> LENGTH: 195
<212> TYPE: DNA
<213> ORGANISM: Lactobacillus plantarum

<400> SEQUENCE: 245

```
atgagtaaac tagttaaaac attaactgtc gatgaaatct ctaagattca aaccaatggt     60

ggaaaacctg catggtgttg gtacacattg gcaatgtgcg gtgctggtta tgattcaggc    120

acttgtgatt atatgtattc acactgcttt ggtgtaaaac actctagcgg tggtggcggt    180

agctaccatt gttag                                                     195
```

<210> SEQ ID NO 246
<211> LENGTH: 56
<212> TYPE: PRT
<213> ORGANISM: Lactobacillus plantarum

<400> SEQUENCE: 246

```
Met Leu Gln Phe Glu Lys Leu Gln Tyr Ser Arg Leu Pro Gln Lys Lys
1               5                   10                  15

Leu Ala Lys Ile Ser Gly Gly Phe Asn Arg Gly Gly Tyr Asn Phe Gly
            20                  25                  30

Lys Ser Val Arg His Val Val Asp Ala Ile Gly Ser Val Ala Gly Ile
        35                  40                  45

Arg Gly Ile Leu Lys Ser Ile Arg
    50                  55
```

<210> SEQ ID NO 247
<211> LENGTH: 171
<212> TYPE: DNA
<213> ORGANISM: Lactobacillus plantarum

<400> SEQUENCE: 247

```
atgctacagt ttgagaaatt acaatattcc aggttgccgc aaaaaaagct tgccaaaata     60

tctggtggtt ttaatcgggg cggttataac tttggtaaaa gtgttcgaca tgttgttgat    120

gcaattggtt cagttgcagg cattcgtggt attttgaaaa gtattcgtta a            171
```

<210> SEQ ID NO 248
<211> LENGTH: 52
<212> TYPE: PRT
<213> ORGANISM: Lactobacillus plantarum

<400> SEQUENCE: 248

```
Met Lys Lys Phe Leu Val Leu Arg Asp Arg Glu Leu Asn Ala Ile Ser
1               5                   10                  15

Gly Gly Val Phe His Ala Tyr Ser Ala Arg Gly Val Arg Asn Asn Tyr
            20                  25                  30

Lys Ser Ala Val Gly Pro Ala Asp Trp Val Ile Ser Ala Val Arg Gly
        35                  40                  45

Phe Ile His Gly
    50
```

<210> SEQ ID NO 249
<211> LENGTH: 159
<212> TYPE: DNA
<213> ORGANISM: Lactobacillus plantarum

<400> SEQUENCE: 249

```
atgaaaaaat ttctagtttt gcgtgaccgt gaattaaatg ctatttcagg tggcgttttc     60

catgcctata gcgcgcgtgg cgttcggaat aattataaaa gtgctgttgg gcctgccgat    120

tgggtcatta gcgctgtccg aggattcatc cacggatag                           159
```

<210> SEQ ID NO 250
<211> LENGTH: 55
<212> TYPE: PRT
<213> ORGANISM: Lactobacillus plantarum

<400> SEQUENCE: 250

```
Met Thr Val Asn Lys Met Ile Lys Asp Leu Asp Val Val Asp Ala Phe
1               5                   10                  15

Ala Pro Ile Ser Asn Asn Lys Leu Asn Gly Val Val Gly Gly Gly Ala
            20                  25                  30

Trp Lys Asn Phe Trp Ser Ser Leu Arg Lys Gly Phe Tyr Asp Gly Glu
        35                  40                  45

Ala Gly Arg Ala Ile Arg Arg
    50                  55
```

<210> SEQ ID NO 251
<211> LENGTH: 168
<212> TYPE: DNA
<213> ORGANISM: Lactobacillus plantarum

<400> SEQUENCE: 251

```
atgactgtga acaaaatgat taaggatttg gatgtagtag atgcatttgc acctatttct     60

aataataagt tgaacggggt tgttggggga ggcgcttgga aaaatttctg gtctagttta    120

agaaaaggat tttatgatgg cgaagctggc agagcaatcc gtcgttaa                 168
```

<210> SEQ ID NO 252
<211> LENGTH: 57
<212> TYPE: PRT
<213> ORGANISM: Lactobacillus plantarum

<400> SEQUENCE: 252

```
Met Lys Ile Lys Leu Thr Val Leu Asn Glu Phe Glu Glu Leu Thr Ala
1               5                   10                  15
```

```
Asp Ala Glu Lys Asn Ile Ser Gly Gly Arg Arg Ser Arg Lys Asn Gly
            20                  25                  30

Ile Gly Tyr Ala Ile Gly Tyr Ala Phe Gly Ala Val Glu Arg Ala Val
        35                  40                  45

Leu Gly Gly Ser Arg Asp Tyr Asn Lys
    50                  55
```

<210> SEQ ID NO 253
<211> LENGTH: 174
<212> TYPE: DNA
<213> ORGANISM: Lactobacillus plantarum

<400> SEQUENCE: 253

```
atgaaaatta aattaactgt tttaaatgaa tttgaagaat taactgctga cgctgaaaag     60

aatatttctg gtggccgtcg gagtcgtaaa aatggaattg gatacgctat tggttatgcg    120

tttggcgcgg ttgaacgggc cgtgcttggt ggttcaaggg attataataa gtga          174
```

<210> SEQ ID NO 254
<211> LENGTH: 47
<212> TYPE: PRT
<213> ORGANISM: Lactobacillus plantarum

<400> SEQUENCE: 254

```
Met Asp Lys Phe Glu Lys Ile Ser Thr Ser Asn Leu Glu Lys Ile Ser
1               5                   10                  15

Gly Gly Asp Leu Thr Thr Lys Leu Trp Ser Ser Trp Gly Tyr Tyr Leu
            20                  25                  30

Gly Lys Lys Ala Arg Trp Asn Leu Lys His Pro Tyr Val Gln Phe
        35                  40                  45
```

<210> SEQ ID NO 255
<211> LENGTH: 141
<212> TYPE: DNA
<213> ORGANISM: Lactobacillus plantarum

<400> SEQUENCE: 255

```
atggataaat ttgaaaaaat tagtacatct aacctagaaa agatctctgg cggtgattta     60

acaaccaagt tatggagctc ttggggatat tatcttggca agaaagcacg ttggaattta    120

aagcacccat atgttcaatt t                                              141
```

<210> SEQ ID NO 256
<211> LENGTH: 55
<212> TYPE: PRT
<213> ORGANISM: Lactobacillus plantarum

<400> SEQUENCE: 256

```
Met Asn Asn Leu Asn Lys Phe Ser Thr Leu Gly Lys Ser Ser Leu Ser
1               5                   10                  15

Gln Ile Glu Gly Gly Ser Val Pro Thr Ser Val Tyr Thr Leu Gly Ile
            20                  25                  30

Lys Ile Leu Trp Ser Ala Tyr Lys His Arg Lys Thr Ile Glu Lys Ser
        35                  40                  45

Phe Asn Lys Gly Phe Tyr His
    50                  55
```

<210> SEQ ID NO 257
<211> LENGTH: 168
<212> TYPE: DNA
<213> ORGANISM: Lactobacillus plantarum

<400> SEQUENCE: 257
atgaataact tgaataaatt ttctactcta ggcaagagta gcttgtctca aattgagggc 60
ggatcagtcc caacttcagt atatacgctt ggaattaaaa ttctatggtc tgcgtataag 120
catcgcaaaa cgattgaaaa aagttttaat aaaggctttt atcattaa 168

<210> SEQ ID NO 258
<211> LENGTH: 55
<212> TYPE: PRT
<213> ORGANISM: Lactobacillus plantarum

<400> SEQUENCE: 258

Met Asn Asn Ala Leu Ser Phe Glu Gln Gln Phe Thr Asp Phe Ser Thr
1 5 10 15

Leu Ser Asp Ser Glu Leu Glu Ser Val Glu Gly Gly Arg Asn Lys Leu
20 25 30

Ala Tyr Asn Met Gly His Tyr Ala Gly Lys Ala Thr Ile Phe Gly Leu
35 40 45

Ala Ala Trp Ala Leu Leu Ala
50 55

<210> SEQ ID NO 259
<211> LENGTH: 168
<212> TYPE: DNA
<213> ORGANISM: Lactobacillus plantarum

<400> SEQUENCE: 259
atgaataacg cattaagttt tgaacaacaa tttacagact tcagcacctt atcggactct 60
gaattagaat ccgttgaggg tggccgaaat aagcttgcat ataatatggg gcattacgct 120
ggtaaggcaa ccatttttgg acttgcagca tgggcactcc ttgcatga 168

<210> SEQ ID NO 260
<211> LENGTH: 47
<212> TYPE: PRT
<213> ORGANISM: Lactobacillus plantarum

<400> SEQUENCE: 260

Met Asp Lys Ile Ile Lys Phe Gln Gly Ile Ser Asp Asp Gln Leu Asn
1 5 10 15

Ala Val Ile Gly Gly Lys Lys Lys Lys Gln Ser Trp Tyr Ala Ala Ala
20 25 30

Gly Asp Ala Ile Val Ser Phe Gly Glu Gly Phe Leu Asn Ala Trp
35 40 45

<210> SEQ ID NO 261
<211> LENGTH: 144
<212> TYPE: DNA
<213> ORGANISM: Lactobacillus plantarum

<400> SEQUENCE: 261
atggataaga ttattaagtt tcaagggatt tctgatgatc aattaaatgc tgttatcggt 60
gggaaaaaga aaaaacaatc ttggtacgca gcagctggtg atgcaatcgt tagttttggt 120
gaaggatttt taaatgcttg gtaa 144

<210> SEQ ID NO 262
<211> LENGTH: 59
<212> TYPE: PRT
<213> ORGANISM: Lactobacillus plantarum

<400> SEQUENCE: 262

```
Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala Lys Cys
            20                  25                  30

Lys Trp Trp Asn Ile Ser Cys Asp Leu Gly Asn Asn Gly His Val Cys
        35                  40                  45

Thr Leu Ser His Glu Cys Gln Val Ser Cys Asn
    50                  55
```

<210> SEQ ID NO 263
<211> LENGTH: 180
<212> TYPE: DNA
<213> ORGANISM: Lactobacillus plantarum

<400> SEQUENCE: 263

```
atgaaaattt ctaagattga agctcaggct cgtaaagatt tttttaaaaa aatcgatact      60

aactcgaact tattaaatgt aaatggtgcc aaatgcaagt ggtggaatat ttcgtgtgat     120

ttaggaaata atggccatgt ttgtaccttg tcacatgaat gccaagtatc ttgtaactaa     180
```

<210> SEQ ID NO 264
<211> LENGTH: 67
<212> TYPE: PRT
<213> ORGANISM: Lactobacillus plantarum

<400> SEQUENCE: 264

```
Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg Ser Gly Ile Pro Cys Thr Ile Gly Ala Ala Val Ala Ala
        35                  40                  45

Ser Ile Ala Val Cys Pro Thr Thr Lys Cys Ser Lys Arg Cys Gly Lys
    50                  55                  60

Arg Lys Lys
65
```

<210> SEQ ID NO 265
<211> LENGTH: 204
<212> TYPE: DNA
<213> ORGANISM: Lactobacillus plantarum

<400> SEQUENCE: 265

```
atgactaaaa ctagtcgtcg taagaatgct attgctaatt atttagaacc agtcgacgaa      60

aaaagtatta atgaatcttt tggggctggg gatccggaag caagatccgg aattccatgt     120

acaatcggcg cagctgtcgc agcatcaatt gcagtttgtc caactactaa gtgtagtaaa     180

cgttgtggca agcgtaagaa ataa                                            204
```

<210> SEQ ID NO 266
<211> LENGTH: 48
<212> TYPE: PRT
<213> ORGANISM: Lactobacillus plantarum

<400> SEQUENCE: 266

```
Met Lys Ile Gln Ile Lys Gly Met Lys Gln Leu Ser Asn Lys Glu Met
1               5                   10                  15
```

```
Gln Lys Ile Val Gly Gly Lys Ser Ser Ala Tyr Ser Leu Gln Met Gly
            20                  25                  30

Ala Thr Ala Ile Lys Gln Val Lys Lys Leu Phe Lys Lys Trp Gly Trp
        35                  40                  45


<210> SEQ ID NO 267
<211> LENGTH: 147
<212> TYPE: DNA
<213> ORGANISM: Lactobacillus plantarum

<400> SEQUENCE: 267

atgaaaattc aaattaaagg tatgaagcaa cttagtaata aggaaatgca aaaaatagta      60

ggtggaaaga gtagtgcgta ttctttgcag atgggggcaa ctgcaattaa acaggtaaag     120

aaactgttta aaaaatgggg atggtaa                                         147


<210> SEQ ID NO 268
<211> LENGTH: 207
<212> TYPE: PRT
<213> ORGANISM: Propionibacterium jensenii

<400> SEQUENCE: 268

Met Asn Lys Thr His Lys Met Ala Thr Leu Val Ile Ala Ala Ile Leu
1               5                   10                  15

Ala Ala Gly Met Thr Ala Pro Thr Ala Tyr Ala Asp Ser Pro Gly Asn
            20                  25                  30

Thr Arg Ile Thr Ala Ser Glu Gln Ser Val Leu Thr Gln Ile Leu Gly
        35                  40                  45

His Lys Pro Thr Gln Thr Glu Tyr Asn Arg Tyr Val Glu Thr Tyr Gly
    50                  55                  60

Ser Val Pro Thr Glu Ala Asp Ile Asn Ala Tyr Ile Glu Ala Ser Glu
65                  70                  75                  80

Ser Glu Gly Ser Ser Ser Gln Thr Ala Ala His Asp Asp Ser Thr Ser
                85                  90                  95

Pro Gly Thr Ser Thr Glu Ile Tyr Thr Gln Ala Ala Pro Ala Arg Phe
            100                 105                 110

Ser Met Phe Phe Leu Ser Gly Thr Trp Ile Thr Arg Ser Gly Val Val
        115                 120                 125

Ser Leu Ser Leu Lys Pro Arg Lys Gly Gly Ile Gly Asn Glu Gly Asp
    130                 135                 140

Glu Arg Thr Trp Lys Thr Val Tyr Asp Lys Phe His Asn Ala Gly Gln
145                 150                 155                 160

Trp Thr Arg Tyr Lys Asn Asn Gly Val Asp Ala Ser Met Lys Lys Gln
                165                 170                 175

Tyr Met Cys His Phe Lys Tyr Gly Met Val Lys Thr Pro Trp Asn Leu
            180                 185                 190

Glu Pro His Lys Lys Ala Ala Asp Val Ser Pro Val Lys Cys Asn
        195                 200                 205


<210> SEQ ID NO 269
<211> LENGTH: 624
<212> TYPE: DNA
<213> ORGANISM: Propionibacterium jensenii

<400> SEQUENCE: 269

atgaacaaaa cacacaaaat ggcgacgctg gtaattgccg cgatcttggc cgccggaatg      60

accgcaccaa ctgcctatgc agattctcct ggaaacacca gaattacagc cagcgagcaa     120
```

agcgtcctta cccagatact cggccacaaa cctacacaaa ctgaatataa ccgatacgtt 180
gagacttacg gaagcgtacc gaccgaagca gacatcaacg catatataga agcgtctgaa 240
tctgagggat catcaagtca aacggctgct cacgatgact cgacatcacc cggcacgagt 300
accgaaatct acacgcaggc agcccctgcc aggttctcaa tgtttttcct gtccggaact 360
tggatcacta ggagtggtgt agtatcgctc tccttgaagc caaggaaggg tggtattggc 420
aacgaggggg acgagcgtac ctggaagact gtatacgaca aattccataa cgctgggcaa 480
tggacacgat acaagaacaa cggcgtagac gccagcatga aaaagcagta catgtgccac 540
ttcaagtacg ggatggtgaa gacgccatgg aatctggagc cccacaagaa ggctgcagac 600
gtcagtccag tcaagtgcaa ctag 624

<210> SEQ ID NO 270
<211> LENGTH: 96
<212> TYPE: PRT
<213> ORGANISM: Propionibacterium thoenii

<400> SEQUENCE: 270

Met Lys Lys Thr Leu Leu Arg Ser Gly Thr Ile Ala Leu Ala Thr Ala
1 5 10 15

Ala Ala Phe Gly Ala Ser Leu Ala Ala Ala Pro Ser Ala Met Ala Val
20 25 30

Pro Gly Gly Cys Thr Tyr Thr Arg Ser Asn Arg Asp Val Ile Gly Thr
35 40 45

Cys Lys Thr Gly Ser Gly Gln Phe Arg Ile Arg Leu Asp Cys Asn Asn
50 55 60

Ala Pro Asp Lys Thr Ser Val Trp Ala Lys Pro Lys Val Met Val Ser
65 70 75 80

Val His Cys Leu Val Gly Gln Pro Arg Ser Ile Ser Phe Glu Thr Lys
85 90 95

<210> SEQ ID NO 271
<211> LENGTH: 291
<212> TYPE: DNA
<213> ORGANISM: Propionibacterium thoenii

<400> SEQUENCE: 271
atgaagaaga ccctcctgcg aagtggaacg atcgcactgg cgaccgcggc tgcatttggc 60
gcatcattgg cagccgcccc atctgccatg gccgttcctg gtggttgcac gtacacaaga 120
agcaatcgcg acgtcatcgg tacctgcaag actggaagcg gccagttccg aatccgactt 180
gactgcaaca acgctccaga caaaacttca gtctgggcca agcccaaggt aatggtgtcg 240
gttcactgtc ttgttggtca accgaggtcc atctcgttcg agaccaagtg a 291

<210> SEQ ID NO 272
<211> LENGTH: 255
<212> TYPE: PRT
<213> ORGANISM: Propionibacterium freudenreichii subsp freudenreii

<400> SEQUENCE: 272

Met Asn Thr Lys Ala Val Asn Leu Lys Ser Glu Asn Thr Thr Lys Leu
1 5 10 15

Val Ser Tyr Leu Thr Glu Asn Gln Leu Asp Glu Phe Ile Arg Arg Ile
20 25 30

Arg Ile Asp Gly Ala Leu Val Glu Glu Val Ser Gln Asn Ala Lys Gln
35 40 45

```
Ala Leu Asp Asn Thr Gly Leu Asn Gly Trp Ile Asn Thr Asp Cys Asp
    50                  55                  60

Glu Gly Leu Leu Ser Asp Phe Ile Ser Lys Ile Ala Ser Ala Arg Trp
65                  70                  75                  80

Ile Pro Leu Ala Glu Ser Ile Arg Pro Ala Val Thr Asp Arg Asp Lys
                85                  90                  95

Tyr Arg Val Ser Cys Trp Phe Tyr Gln Gly Met Asn Ile Ala Ile Tyr
            100                 105                 110

Ala Asn Ile Gly Gly Val Ala Asn Ile Ile Gly Tyr Thr Glu Ala Ala
        115                 120                 125

Val Ala Thr Leu Leu Gly Ala Val Val Ala Val Ala Pro Val Val Pro
    130                 135                 140

Gly Thr Pro Thr Pro Pro Lys Asp Lys Ser Ser Gln Tyr Lys Glu Val
145                 150                 155                 160

Pro Leu Ala Val Arg Leu Ser Glu Thr Tyr His Glu Glu Gly Val Arg
                165                 170                 175

Gly Leu Phe Asp Glu Leu Asn Tyr Ser Glu Ser Arg Met Ile Ser Thr
            180                 185                 190

Leu Arg Arg Ala Ser Thr Asp Gly Val Leu Ile Asn Ser Trp Asn Asp
        195                 200                 205

Gly Gln Asp Thr Ile Leu Leu Lys Lys Tyr Asn Phe Gln Asp Leu Gln
    210                 215                 220

Leu Thr Val Arg Ser Arg Ile Val Gly Asn Gln Thr Ile Ile Glu Glu
225                 230                 235                 240

Cys Lys Ile Thr Asp Gly Arg Lys Thr Leu Ser Asp Glu Thr Val
                245                 250                 255
```

<210> SEQ ID NO 273
<211> LENGTH: 768
<212> TYPE: DNA
<213> ORGANISM: Propionibacterium freudenreichii subsp freudenreii

<400> SEQUENCE: 273

```
atgaatacca aagctgtaaa tctgaagtca gaaaacacga ctaagttggt gagctacctt      60

acggaaaatc aattggatga gtttattaga aggattcgca ttgatggcgc tcttgtggaa     120

gaggtcagtc aaaatgctaa gcaggcctta gataatactg ggctcaatgg ctggataaat     180

actgattgcg atgaaggcct tctctctgat ttcatttcaa agatagcaag tgctagatgg     240

attccattag ctgagtcaat tcgacctgcg gtgactgaca gggataagta tcgagtaagt     300

tgctggttct accaggggat gaatatagca atttacgcaa atatcggtgg cgtggccaat     360

attatcggct atacggaggc cgcagtcgca acactccttg gtgcagttgt ggcggtagct     420

cctgtggtcc ctggaactcc aacccctcca aaggacaaga gttcgcaata taaggaggtt     480

ccccttgccg ttcgtctttc cgaaacatac cacgaagagg gagtacgagg tctattcgac     540

gagctgaact actccgagag ccgtatgatc tctactctaa ggcgagcatc aaccgatgga     600

gtcctaatta attcttggaa cgatgggcag gatacaattc tgcttaagaa gtacaatttc     660

caagacttgc aactgactgt caggagccgc attgttggga atcaaacaat aattgaagaa     720

tgcaaaatca ctgatggtag aaaaactctt tcagacgaga ctgtgtag                  768
```

<210> SEQ ID NO 274
<211> LENGTH: 618
<212> TYPE: PRT
<213> ORGANISM: Pseudomonas aeruginosa

<400> SEQUENCE: 274

```
Met Ala Arg Pro Ile Ala Asp Leu Ile His Phe Asn Ser Thr Thr Val
1               5                   10                  15

Thr Ala Ser Gly Asp Val Tyr Tyr Gly Pro Gly Gly Gly Thr Gly Ile
            20                  25                  30

Gly Pro Ile Ala Arg Pro Ile Glu His Gly Leu Asp Ser Ser Thr Glu
        35                  40                  45

Asn Gly Trp Gln Glu Phe Glu Ser Tyr Ala Asp Val Gly Val Asp Pro
    50                  55                  60

Arg Arg Tyr Val Pro Leu Gln Val Lys Glu Lys Arg Arg Glu Ile Glu
65                  70                  75                  80

Leu Gln Phe Arg Asp Ala Glu Lys Lys Leu Glu Ala Ser Val Gln Ala
                85                  90                  95

Glu Leu Asp Lys Ala Asp Ala Ala Leu Gly Pro Ala Lys Asn Leu Ala
            100                 105                 110

Pro Leu Asp Val Ile Asn Arg Ser Leu Thr Ile Val Gly Asn Ala Leu
        115                 120                 125

Gln Gln Lys Asn Gln Lys Leu Leu Leu Asn Gln Lys Lys Ile Thr Ser
    130                 135                 140

Leu Gly Ala Lys Asn Phe Leu Thr Arg Thr Ala Glu Glu Ile Gly Glu
145                 150                 155                 160

Gln Ala Val Arg Glu Gly Asn Ile Asn Gly Pro Glu Ala Tyr Met Arg
                165                 170                 175

Phe Leu Asp Arg Glu Met Glu Gly Leu Thr Ala Ala Tyr Asn Val Lys
            180                 185                 190

Leu Phe Thr Glu Ala Ile Ser Ser Leu Gln Ile Arg Met Asn Thr Leu
        195                 200                 205

Thr Ala Ala Lys Ala Ser Ile Glu Ala Ala Ala Ala Asn Lys Ala Arg
    210                 215                 220

Glu Gln Ala Ala Ala Glu Ala Lys Arg Lys Ala Glu Glu Gln Ala Arg
225                 230                 235                 240

Gln Gln Ala Ala Ile Arg Ala Ala Asn Thr Tyr Ala Met Pro Ala Asn
                245                 250                 255

Gly Ser Val Val Ala Thr Ala Ala Gly Arg Gly Leu Ile Gln Val Ala
            260                 265                 270

Gln Gly Ala Ala Ser Leu Ala Gln Ala Ile Ser Asp Ala Ile Ala Val
        275                 280                 285

Leu Gly Arg Val Leu Ala Ser Ala Pro Ser Val Met Ala Val Gly Phe
    290                 295                 300

Ala Ser Leu Thr Tyr Ser Ser Arg Thr Ala Glu Gln Trp Gln Asp Gln
305                 310                 315                 320

Thr Pro Asp Ser Val Arg Tyr Ala Leu Gly Met Asp Ala Ala Lys Leu
                325                 330                 335

Gly Leu Pro Pro Ser Val Asn Leu Asn Ala Val Ala Lys Ala Ser Gly
            340                 345                 350

Thr Val Asp Leu Pro Met Arg Leu Thr Asn Glu Ala Arg Gly Asn Thr
        355                 360                 365

Thr Thr Leu Ser Val Val Ser Thr Asp Gly Val Ser Val Pro Lys Ala
    370                 375                 380

Val Pro Val Arg Met Ala Ala Tyr Asn Ala Thr Thr Gly Leu Tyr Glu
385                 390                 395                 400

Val Thr Val Pro Ser Thr Thr Ala Glu Ala Pro Pro Leu Ile Leu Thr
                405                 410                 415
```

```
Trp Thr Pro Ala Ser Pro Pro Gly Asn Gln Asn Pro Ser Ser Thr Thr
            420                 425                 430

Pro Val Val Pro Lys Pro Val Pro Val Tyr Glu Gly Ala Thr Leu Thr
        435                 440                 445

Pro Val Lys Ala Thr Pro Glu Thr Tyr Pro Gly Val Ile Thr Leu Pro
    450                 455                 460

Glu Asp Leu Ile Ile Gly Phe Pro Ala Asp Ser Gly Ile Lys Pro Ile
465                 470                 475                 480

Tyr Val Met Phe Arg Asp Pro Arg Asp Val Pro Gly Ala Ala Thr Gly
                485                 490                 495

Lys Gly Gln Pro Val Ser Gly Asn Trp Leu Gly Ala Ala Ser Gln Gly
            500                 505                 510

Glu Gly Ala Pro Ile Pro Ser Gln Ile Ala Asp Lys Leu Arg Gly Lys
        515                 520                 525

Thr Phe Lys Asn Trp Arg Asp Phe Arg Glu Gln Phe Trp Ile Ala Val
    530                 535                 540

Ala Asn Asp Pro Glu Leu Ser Lys Gln Phe Asn Pro Gly Ser Leu Ala
545                 550                 555                 560

Val Met Arg Asp Gly Gly Ala Pro Tyr Val Arg Glu Ser Glu Gln Ala
                565                 570                 575

Gly Gly Arg Ile Lys Ile Glu Ile His His Lys Val Arg Val Ala Asp
            580                 585                 590

Gly Gly Gly Val Tyr Asn Met Gly Asn Leu Val Ala Val Thr Pro Lys
        595                 600                 605

Arg His Ile Glu Ile His Lys Gly Gly Lys
    610                 615
```

<210> SEQ ID NO 275
<211> LENGTH: 1857
<212> TYPE: DNA
<213> ORGANISM: Pseudomonas aeruginosa

<400> SEQUENCE: 275

```
atggcacgac ccattgctga ccttatccac ttcaactcta caactgtcac ggcaagcgga     60

gacgtttatt acggccctgg gggaggtacc ggcattggcc ccattgccag acctatagag    120

cacggcttgg attcgtccac tgaaaatggc tggcaagagt ttgaaagtta tgctgatgtg    180

ggcgttgacc ccagacgcta tgttcctctt caggttaaag aaaaacgcag ggagatcgag    240

cttcagttcc gagatgccga gaaaaaactt gaggcgtcgg tacaagccga gctggataag    300

gctgatgccg ctcttggtcc ggcaaagaat cttgcaccat tggacgtcat caaccgcagt    360

ctgaccatcg ttggaaacgc cctccagcaa aagaatcaaa aactactgct gaatcagaag    420

aagattacca gcctgggtgc aaagaatttc cttacccgta cggcggaaga gatcggtgaa    480

caagcggtgc gagaaggcaa tattaacggg cctgaagcct atatgcgctt cctcgacagg    540

gaaatggaag gtctcacggc agcttataac gtaaaactct tcaccgaagc gatcagtagt    600

ctccagatcc gcatgaatac gttgaccgcc gccaaagcaa gtattgaggc ggccgcagca    660

aacaaggcgc gtgaacaagc agcggctgag gccaaacgca aagccgaaga gcaggcccgc    720

cagcaagcgg cgataagagc tgccaatacc tatgccatgc cggccaatgg cagcgttgtc    780

gccaccgccg caggccgggg tctgatccag gtcgcacaag gcgccgcatc ccttgctcaa    840

gcgatctccg atgcgattgc cgtcctgggc cgggtcctgg cttcagcacc ctcggtgatg    900

gccgtgggct ttgccagtct gacctactcc tcccggactg ccgagcaatg gcaggaccaa    960
```

```
acgcccgata gcgttcgtta cgccctgggc atggatgccg ctaaattggg gcttccccca   1020

agcgtaaacc tgaacgcggt tgcaaaagcc agcggtaccg tcgatctgcc gatgcgcctg   1080

accaacgagg cacgaggcaa cacgacgacc ctttcggtgg tcagcaccga tggtgtgagc   1140

gttccgaaag ccgttccggt ccggatggcg gcctacaatg ccacgacagg cctgtacgag   1200

gttacggttc cctctacgac cgcagaagcg ccgccactga tcctgacctg gacgccggcg   1260

agtcctccag gaaaccagaa cccttcgagt accactccgg tcgtaccgaa gccggtgccg   1320

gtatatgagg gagcgaccct tacaccggtg aaggctaccc cggaaaccta tcctggggtg   1380

attacactac cggaagacct gatcatcggc ttcccggccg actcggggat caagccgatc   1440

tatgtgatgt tcagggatcc gcgggatgta cctggtgctg cgactggcaa gggacagccc   1500

gtcagcggta attggctcgg cgccgcctct caaggtgagg gggctccaat tccaagccag   1560

attgcggata aactacgtgg taagacattc aaaaactggc gggactttcg ggaacaattc   1620

tggatagctg tggctaatga tcctgagtta agtaaacagt ttaatcctgg tagtttagct   1680

gtaatgagag atggaggggc tccttatgtc agagagtcag aacaggctgg cgggagaata   1740

aagatcgaaa tccaccacaa ggttcgagta gcagatggag gcggcgttta caatatgggg   1800

aaccttgttg cagtaacgcc aaaacgtcat atagaaatcc acaagggagg gaagtga      1857
```

```
<210> SEQ ID NO 276
<211> LENGTH: 689
<212> TYPE: PRT
<213> ORGANISM: Pseudomonas aeruginosa

<400> SEQUENCE: 276

Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
        195                 200                 205
```

```
Lys Ala Arg Lys Ala Asn Val Glu Lys Lys Val Gln Ser Glu Leu Asp
    210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
                245                 250                 255

Lys Lys Leu Gln Thr Ala Asn Asn Ala Leu Ile Ala Lys Ala Pro Asn
            260                 265                 270

Ala Leu Glu Lys Gln Lys Ala Thr Tyr Asn Ala Asp Leu Leu Val Asp
        275                 280                 285

Glu Ile Ala Ser Leu Gln Ala Arg Leu Asp Lys Leu Asn Ala Glu Thr
    290                 295                 300

Ala Arg Arg Lys Glu Ile Ala Arg Gln Ala Ala Ile Arg Ala Ala Asn
305                 310                 315                 320

Thr Tyr Ala Met Pro Ala Asn Gly Ser Val Val Ala Thr Ala Ala Gly
                325                 330                 335

Arg Gly Leu Ile Gln Val Ala Gln Gly Ala Ala Ser Leu Ala Gln Ala
            340                 345                 350

Ile Ser Asp Ala Ile Ala Val Leu Gly Arg Val Leu Ala Ser Ala Pro
        355                 360                 365

Ser Val Met Ala Val Gly Phe Ala Ser Leu Thr Tyr Ser Ser Arg Thr
    370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
            420                 425                 430

Asn Glu Ala Arg Gly Asn Thr Thr Thr Leu Ser Val Val Ser Thr Asp
        435                 440                 445

Gly Val Ser Val Pro Lys Ala Val Pro Val Arg Met Ala Ala Tyr Asn
    450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Pro Gly Asn
                485                 490                 495

Gln Asn Pro Ser Ser Thr Thr Pro Val Val Pro Lys Pro Val Pro Val
            500                 505                 510

Tyr Glu Gly Ala Thr Leu Thr Pro Val Lys Ala Thr Pro Glu Thr Tyr
        515                 520                 525

Pro Gly Val Ile Thr Leu Pro Glu Asp Leu Ile Ile Gly Phe Pro Ala
    530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
            580                 585                 590

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
    610                 615                 620
```

```
Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
                645                 650                 655

His Lys Val Arg Ile Ala Asp Gly Gly Gly Val Tyr Asn Met Gly Asn
            660                 665                 670

Leu Val Ala Val Thr Pro Lys Arg His Ile Glu Ile His Lys Gly Gly
        675                 680                 685

Lys


<210> SEQ ID NO 277
<211> LENGTH: 2070
<212> TYPE: DNA
<213> ORGANISM: Pseudomonas aeruginosa

<400> SEQUENCE: 277

atggctgtca atgattacga acctggttcg atggttatta cacatgtgca gggtggtggg     60

cgtgacataa tccagtatat tcctgctcga tcaagctacg gtactccacc atttgtccca    120

ccaggaccaa gtccgtatgt cggtactgga atgcaggagt acaggaagct aagaagtacg    180

cttgataagt cccattcaga actcaagaaa aacctgaaaa atgaaaccct gaaggaggtt    240

gatgaactca agagtgaagc ggggttgcca ggtaaagcgg tcagtgccaa tgacatccgc    300

gatgaaaaga gtatcgttga tgcactcatg gatgccaaag caaaatcgct aaaggccatt    360

gaggatcgcc cggccaatct ttatacggct tcagactttc ctcagaagtc agagtcgatg    420

taccagagtc agttgctggc cagccgaaaa ttctatggag agttcctgga tcgccatatg    480

agtgagctgg ccaaagcgta cagcgccgat atctataagg cgcaaatcgc tatcttgaaa    540

caaacgtctc aagagctgga gaataaagcc cggtcattgg aagcagaagc ccagcgagcc    600

gctgctgagg tggaggcgga ctacaaggcc aggaaggcaa atgtcgagaa aaaagtgcag    660

tccgagcttg accaggctgg gaatgctttg cctcaactga ccaatccaac gccagagcag    720

tggcttgaac gcgctactca actggttacg caggcgatcg ccaataagaa gaaattgcag    780

actgcaaaca atgccttgat tgccaaggca cccaatgcac tggagaaaca aaaggcaacc    840

tacaacgccg atctcctagt ggatgaaatc gccagcctgc aagcacggct ggacaagctg    900

aacgccgaaa cggcaaggcg caaggaaatc gctcgtcaag cggcgatcag ggctgccaat    960

acttatgcca tgccagccaa tggcagcgtt gtcgccaccg ccgcaggccg ggtctgatc    1020

caggtcgcac aaggcgccgc atcccttgct caagcgatct ccgatgcgat tgccgtcctg   1080

ggccgggtcc tggcttcagc accctcggtg atggccgtgg gctttgccag tctgacctac   1140

tcctcccgga ctgccgagca atggcaggac caaacgcccg atagcgttcg ttacgccctg   1200

ggcatggatg ccgctaaatt ggggcttccc ccaagcgtaa acctgaacgc ggttgcaaaa   1260

gccagcggta ccgtcgatct gccgatgcgc ctgaccaacg aggcacgagg caacacgacg   1320

acccttcgg tggtcagcac cgatggtgtg agcgttccga aagccgttcc ggtccggatg    1380

gcggcctaca atgccacgac aggcctgtac gaggttacgg ttccctctac gaccgcagaa   1440

gcgccgccac tgatcctgac ctggacgccg gcgagtcctc caggaaacca gaacccttcg   1500

agtaccactc cggtcgtacc gaagccggtg ccggtatatg agggagcgac ccttacaccg   1560

gtgaaggcta ccccggaaac ctatcctggg gtgattacac taccggaaga cctgatcatc   1620

ggcttcccgg ccgactcggg gatcaagccg atctatgtga tgttcaggga tccgcgggat   1680

gtacctggtg ctgcgactgg caagggacag cccgtcagcg gtaattggct cggcgccgcc   1740
```

```
tctcaaggtg agggggctcc aattccaagc cagattgcgg ataaactacg tggtaagaca   1800

ttcaaaaact ggcgggactt tcgggaacaa ttctggatag ctgtggctaa tgatcctgag   1860

ttaagtaaac agtttaatcc tggtagttta gctgtaatga gagatggagg ggctccttat   1920

gtcagagagt cagaacaggc tggcgggaga ataaagatcg aaatccacca caaggttcga   1980

atagcagatg gaggcggcgt ttacaatatg gggaaccttg ttgcagtaac gccaaaacgt   2040

catatagaaa tccacaaggg agggaagtga                                    2070


<210> SEQ ID NO 278
<211> LENGTH: 47
<212> TYPE: PRT
<213> ORGANISM: Ruminococcus gnavus

<400> SEQUENCE: 278

Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
            20                  25                  30

His Glu Cys Asn Met Asn Thr Trp Gln Phe Leu Phe Thr Cys Cys
        35                  40                  45


<210> SEQ ID NO 279
<211> LENGTH: 144
<212> TYPE: DNA
<213> ORGANISM: Ruminococcus gnavus

<400> SEQUENCE: 279

atgagaaatg acgtattaac attaacaaac ccaatggaag agaacgaact ggagcagatc     60

ttaggtggtg gcaatggtgt gttaaaaacg attagccacg aatgcaatat gaacacatgg    120

cagttcctgt ttacttgttg ctaa                                           144


<210> SEQ ID NO 280
<211> LENGTH: 55
<212> TYPE: PRT
<213> ORGANISM: Lactobacillus sakei

<400> SEQUENCE: 280

Met Lys Asn Ala Lys Ser Leu Thr Ile Gln Glu Met Lys Ser Ile Thr
1               5                   10                  15

Gly Gly Lys Tyr Tyr Gly Asn Gly Val Ser Cys Asn Ser His Gly Cys
            20                  25                  30

Ser Val Asn Trp Gly Gln Ala Trp Thr Cys Gly Val Asn His Leu Ala
        35                  40                  45

Asn Gly Gly His Gly Val Cys
    50                  55


<210> SEQ ID NO 281
<211> LENGTH: 168
<212> TYPE: DNA
<213> ORGANISM: Lactobacillus sakei

<400> SEQUENCE: 281

atgaaaaacg caaaaagcct aacaattcaa gaaatgaaat ctattacagg tggtaaatac     60

tatggtaatg gcgttagctg taactctcac ggctgttcag taaattgggg gcaagcatgg    120

acttgtggag taaaccatct agctaatggc ggtcatggag tttgttaa                 168
```

<210> SEQ ID NO 282
<211> LENGTH: 59
<212> TYPE: PRT
<213> ORGANISM: Lactobacillus sakei

<400> SEQUENCE: 282

```
Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55
```

<210> SEQ ID NO 283
<211> LENGTH: 180
<212> TYPE: DNA
<213> ORGANISM: Lactobacillus sakei

<400> SEQUENCE: 283

```
atgaataatg taaaagaatt aagtatgaca gaattacaaa caattaccgg cggtgctaga      60

tcatatggca acggtgttta ctgtaataat aaaaaatgtt gggtaaatcg ggtgaagca     120

acgcaaagta ttattggtgg tatgattagc ggctgggcta gtggtttagc tggaatgtaa    180
```

<210> SEQ ID NO 284
<211> LENGTH: 61
<212> TYPE: PRT
<213> ORGANISM: Lactobacillus sakei

<400> SEQUENCE: 284

```
Met Glu Lys Phe Ile Glu Leu Ser Leu Lys Glu Val Thr Ala Ile Thr
1               5                   10                  15

Gly Gly Lys Tyr Tyr Gly Asn Gly Val His Cys Gly Lys His Ser Cys
            20                  25                  30

Thr Val Asp Trp Gly Thr Ala Ile Gly Asn Ile Gly Asn Asn Ala Ala
        35                  40                  45

Ala Asn Trp Ala Thr Gly Gly Asn Ala Gly Trp Asn Lys
    50                  55                  60
```

<210> SEQ ID NO 285
<211> LENGTH: 186
<212> TYPE: DNA
<213> ORGANISM: Lactobacillus sakei

<400> SEQUENCE: 285

```
atggaaaagt ttattgaatt atctttaaaa gaagtaacag caattacagg tggaaaatat      60

tatggtaacg gtgtacactg tggaaaacat tcatgtaccg tagactgggg aacagctatt     120

ggaaatatcg gaaataatgc agctgcaaac tgggccacag gcggaaacgc tggctggaat     180

aaataa                                                                186
```

<210> SEQ ID NO 286
<211> LENGTH: 56
<212> TYPE: PRT
<213> ORGANISM: Streptococcus salivarius

<400> SEQUENCE: 286

```
Met Lys Ser Thr Asn Asn Gln Ser Ile Ala Glu Ile Ala Ala Val Asn
1               5                   10                  15
```

Ser Leu Gln Glu Val Ser Met Glu Glu Leu Asp Gln Ile Ile Gly Ala
20 25 30

Gly Asn Gly Val Val Leu Thr Leu Thr His Glu Cys Asn Leu Ala Thr
35 40 45

Trp Thr Lys Lys Leu Lys Cys Cys
50 55

<210> SEQ ID NO 287
<211> LENGTH: 171
<212> TYPE: DNA
<213> ORGANISM: Streptococcus salivarius

<400> SEQUENCE: 287
atgaaatcaa caaataatca aagtatcgca gaaattgcag cagtaaactc actacaagaa 60
gtaagtatgg aggaactaga ccaaattatt ggtgccggaa acggagtggt tcttactctt 120
actcatgaat gtaacctagc aacttggaca aaaaaactaa aatgttgcta a 171

<210> SEQ ID NO 288
<211> LENGTH: 51
<212> TYPE: PRT
<213> ORGANISM: Streptococcus pyogenes serotype M28

<400> SEQUENCE: 288

Met Ser Phe Met Lys Asn Ser Lys Asp Ile Leu Thr Asn Ala Ile Glu
1 5 10 15

Glu Val Ser Glu Lys Glu Leu Met Glu Val Ala Gly Gly Lys Lys Gly
20 25 30

Ser Gly Trp Phe Ala Thr Ile Thr Asp Asp Cys Pro Asn Ser Val Phe
35 40 45

Val Cys Cys
50

<210> SEQ ID NO 289
<211> LENGTH: 156
<212> TYPE: DNA
<213> ORGANISM: Streptococcus pyogenes serotype M28

<400> SEQUENCE: 289
atgagtttta tgaaaaattc aaaggatatt ttgactaatg ctatcgaaga agtttctgaa 60
aaagaactta tggaagtagc tggtggtaaa aaaggttccg gttggtttgc aactattact 120
gatgactgtc cgaactcagt attcgtttgt tgttaa 156

<210> SEQ ID NO 290
<211> LENGTH: 48
<212> TYPE: PRT
<213> ORGANISM: Streptococcus salivarius

<400> SEQUENCE: 290

Met Lys Asn Ser Lys Asp Val Leu Asn Asn Ala Ile Glu Glu Val Ser
1 5 10 15

Glu Lys Glu Leu Met Glu Val Ala Gly Gly Lys Lys Gly Pro Gly Trp
20 25 30

Ile Ala Thr Ile Thr Asp Asp Cys Pro Asn Ser Ile Phe Val Cys Cys
35 40 45

<210> SEQ ID NO 291
<211> LENGTH: 147
<212> TYPE: DNA

<213> ORGANISM: Streptococcus salivarius

<400> SEQUENCE: 291

```
atgaaaaact caaaagatgt tttgaacaat gctatcgaag aggtttctga aaaagaactt     60

atggaagtag ctggtggtaa aaaaggtcca ggttggattg caactattac tgatgactgt    120

ccaaactcaa tattcgtttg ttgttaa                                        147
```

<210> SEQ ID NO 292
<211> LENGTH: 48
<212> TYPE: PRT
<213> ORGANISM: Streptococcus salivarius

<400> SEQUENCE: 292

```
Met Lys Asn Ser Lys Asp Ile Leu Asn Asn Ala Ile Glu Glu Val Ser
1               5                   10                  15

Glu Lys Glu Leu Met Glu Val Ala Gly Gly Lys Arg Gly Ser Gly Trp
            20                  25                  30

Ile Ala Thr Ile Thr Asp Asp Cys Pro Asn Ser Val Phe Val Cys Cys
        35                  40                  45
```

<210> SEQ ID NO 293
<211> LENGTH: 147
<212> TYPE: DNA
<213> ORGANISM: Streptococcus salivarius

<400> SEQUENCE: 293

```
atgaaaaact caaaagatat tttgaacaat gctatcgaag aagtttctga aaaagaactt     60

atggaagtag ctggtggtaa aagaggttca ggttggattg caactattac tgatgactgt    120

ccaaactcag tattcgtttg ttgttaa                                        147
```

<210> SEQ ID NO 294
<211> LENGTH: 62
<212> TYPE: PRT
<213> ORGANISM: Staphylococcus aureus

<400> SEQUENCE: 294

```
Met Lys Ser Ser Phe Leu Glu Lys Asp Ile Glu Glu Gln Val Thr Trp
1               5                   10                  15

Phe Glu Glu Val Ser Glu Gln Glu Phe Asp Asp Asp Ile Phe Gly Ala
            20                  25                  30

Cys Ser Thr Asn Thr Phe Ser Leu Ser Asp Tyr Trp Gly Asn Lys Gly
        35                  40                  45

Asn Trp Cys Thr Ala Thr His Glu Cys Met Ser Trp Cys Lys
    50                  55                  60
```

<210> SEQ ID NO 295
<211> LENGTH: 189
<212> TYPE: DNA
<213> ORGANISM: Staphylococcus aureus

<400> SEQUENCE: 295

```
atgaaaagtt ctttttttaga aaaagatata gaagaacaag tgacatggtt cgaggaagtt     60

tcagaacaag aatttgacga tgatattttt ggagcttgta gtacaaacac tttttctttg    120

agtgactatt ggggtaataa aggaaattgg tgtactgcta ctcacgaatg tatgtcttgg    180

tgtaaataa                                                            189
```

<210> SEQ ID NO 296

```
<211> LENGTH: 67
<212> TYPE: PRT
<213> ORGANISM: Staphylococcus aureus

<400> SEQUENCE: 296

Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
            20                  25                  30

Tyr Ala Ala Gly Thr Pro Leu Ala Leu Leu Gly Gly Ala Ala Thr Gly
        35                  40                  45

Val Ile Gly Tyr Ile Ser Asn Gln Thr Cys Pro Thr Thr Ala Cys Thr
    50                  55                  60

Arg Ala Cys
65


<210> SEQ ID NO 297
<211> LENGTH: 204
<212> TYPE: DNA
<213> ORGANISM: Staphylococcus aureus

<400> SEQUENCE: 297

atgaaaaatg aattaggtaa gtttttagaa gaaaacgaat tagagttagg taaattttca     60

gaatcagaca tgctagaaat tactgatgat gaagtatatg cagctggaac acctttagcc    120

ttattgggtg gagctgccac cggggtgata ggttatattt ctaaccaaac atgtccaaca    180

actgcttgta cacgcgcttg ctag                                           204


<210> SEQ ID NO 298
<211> LENGTH: 46
<212> TYPE: PRT
<213> ORGANISM: Streptococcus pyogenes

<400> SEQUENCE: 298

Met Asn Asn Thr Ile Lys Asp Phe Asp Leu Asp Leu Lys Thr Asn Lys
1               5                   10                  15

Lys Asp Thr Ala Thr Pro Tyr Val Gly Ser Arg Tyr Leu Cys Thr Pro
            20                  25                  30

Gly Ser Cys Trp Lys Leu Val Cys Phe Thr Thr Thr Val Lys
        35                  40                  45


<210> SEQ ID NO 299
<211> LENGTH: 141
<212> TYPE: DNA
<213> ORGANISM: Streptococcus pyogenes

<400> SEQUENCE: 299

atgaataaca caattaaaga ctttgatctc gatttgaaaa caaataaaaa agacactgct     60

acaccttatg ttggtagccg ttacctatgt acccctggtt cttgttggaa attagtttgc    120

tttacaacaa ctgttaaata a                                              141


<210> SEQ ID NO 300
<211> LENGTH: 51
<212> TYPE: PRT
<213> ORGANISM: Streptococcus pyogenes

<400> SEQUENCE: 300

Met Glu Lys Asn Asn Glu Val Ile Asn Ser Ile Gln Glu Val Ser Leu
1               5                   10                  15
```

```
Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50


<210> SEQ ID NO 301
<211> LENGTH: 156
<212> TYPE: DNA
<213> ORGANISM: Streptococcus pyogenes

<400> SEQUENCE: 301

atggaaaaaa ataatgaagt aatcaactct attcaagaag ttagtcttga agaactcgat     60

caaattatcg gtgctggaaa aaatggtgtg tttaaaacaa tttctcatga gtgtcatttg    120

aatacatggg cattccttgc tacttgttgt tcataa                             156


<210> SEQ ID NO 302
<211> LENGTH: 51
<212> TYPE: PRT
<213> ORGANISM: Streptococcus pyogenes serotype M49

<400> SEQUENCE: 302

Met Thr Lys Glu His Glu Ile Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50


<210> SEQ ID NO 303
<211> LENGTH: 156
<212> TYPE: DNA
<213> ORGANISM: Streptococcus pyogenes serotype M49

<400> SEQUENCE: 303

atggaaaaaa ataatgaagt aatcaactct attcaagaag ttagtcttga agaactcgat     60

caaattatcg gtgctggaaa aaatggtgtg tttaaaacaa tttctcatga gtgtcatttg    120

aatacatggg cattccttgc tacttgttgc tcataa                             156


<210> SEQ ID NO 304
<211> LENGTH: 56
<212> TYPE: PRT
<213> ORGANISM: Bacillus subtilis

<400> SEQUENCE: 304

Met Glu Lys Leu Phe Lys Glu Val Lys Leu Glu Glu Leu Glu Asn Gln
1               5                   10                  15

Lys Gly Ser Gly Leu Gly Lys Ala Gln Cys Ala Ala Leu Trp Leu Gln
            20                  25                  30

Cys Ala Ser Gly Gly Thr Ile Gly Cys Gly Gly Gly Ala Val Ala Cys
        35                  40                  45

Gln Asn Tyr Arg Gln Phe Cys Arg
    50                  55


<210> SEQ ID NO 305
```

<211> LENGTH: 171
<212> TYPE: DNA
<213> ORGANISM: Bacillus subtilis

<400> SEQUENCE: 305
atggaaaagc tatttaaaga agttaaacta gaggaactcg aaaaccaaaa aggtagtgga 60
ttaggaaaag ctcagtgtgc tgcgttgtgg ctacaatgtg ctagtggcgg tacaattggt 120
tgtggtggcg gagctgttgc ttgtcaaaac tatcgtcaat tctgcagata a 171

<210> SEQ ID NO 306
<211> LENGTH: 56
<212> TYPE: PRT
<213> ORGANISM: Bacillus subtilis

<400> SEQUENCE: 306

Met Ser Lys Phe Asp Asp Phe Asp Leu Asp Val Val Lys Val Ser Lys
1 5 10 15

Gln Asp Ser Lys Ile Thr Pro Gln Trp Lys Ser Glu Ser Leu Cys Thr
20 25 30

Pro Gly Cys Val Thr Gly Ala Leu Gln Thr Cys Phe Leu Gln Thr Leu
35 40 45

Thr Cys Asn Cys Lys Ile Ser Lys
50 55

<210> SEQ ID NO 307
<211> LENGTH: 171
<212> TYPE: DNA
<213> ORGANISM: Bacillus subtilis

<400> SEQUENCE: 307
atgtcaaagt tcgatgattt cgatttggat gttgtgaaag tctctaaaca agactcaaaa 60
atcactccgc aatggaaaag tgaatcactt tgtacaccag gatgtgtaac tggtgcattg 120
caaacttgct tccttcaaac actaacttgt aactgcaaaa tctctaaata a 171

<210> SEQ ID NO 308
<211> LENGTH: 50
<212> TYPE: PRT
<213> ORGANISM: Bacillus subtilis

<400> SEQUENCE: 308

Met Lys Leu Pro Val Gln Gln Val Tyr Ser Val Tyr Gly Gly Lys Asp
1 5 10 15

Leu Pro Lys Gly His Ser His Ser Thr Met Pro Phe Leu Ser Lys Leu
20 25 30

Gln Phe Leu Thr Lys Ile Tyr Leu Leu Asp Ile His Thr Gln Pro Phe
35 40 45

Phe Ile
50

<210> SEQ ID NO 309
<211> LENGTH: 153
<212> TYPE: DNA
<213> ORGANISM: Bacillus subtilis

<400> SEQUENCE: 309
ttgaaattgc cggtgcaaca ggtctattcg gtctatgggg gtaaggatct cccaaaaggg 60
catagtcatt ctactatgcc ctttttaagt aaattacaat ttttaactaa aatctacctc 120
ttggatatac atacacaacc gtttttcatt tga 153

<210> SEQ ID NO 310
<211> LENGTH: 43
<212> TYPE: PRT
<213> ORGANISM: Bacillus subtilis

<400> SEQUENCE: 310

Met Lys Lys Ala Val Ile Val Glu Asn Lys Gly Cys Ala Thr Cys Ser
1               5                   10                  15

Ile Gly Ala Ala Cys Leu Val Asp Gly Pro Ile Pro Asp Phe Glu Ile
            20                  25                  30

Ala Gly Ala Thr Gly Leu Phe Gly Leu Trp Gly
        35                  40

<210> SEQ ID NO 311
<211> LENGTH: 132
<212> TYPE: DNA
<213> ORGANISM: Bacillus subtilis

<400> SEQUENCE: 311
atgaaaaaag ctgtcattgt agaaaacaaa ggttgtgcaa catgctcgat cggagccgct     60
tgtctagtgg acggtcctat ccctgatttt gaaattgccg gtgcaacagg tctattcggt    120
ctatgggggt aa                                                        132

<210> SEQ ID NO 312
<211> LENGTH: 58
<212> TYPE: PRT
<213> ORGANISM: Streptococcus thermophilus

<400> SEQUENCE: 312

Met Met Asn Ala Thr Glu Asn Gln Ile Phe Val Glu Thr Val Ser Asp
1               5                   10                  15

Gln Glu Leu Glu Met Leu Ile Gly Gly Ala Asp Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55

<210> SEQ ID NO 313
<211> LENGTH: 177
<212> TYPE: DNA
<213> ORGANISM: Streptococcus thermophilus

<400> SEQUENCE: 313
atgatgaatg ctactgaaaa ccaaattttt gttgagactg tgagtgacca agaattagaa     60
atgttaattg gtggtgcaga tcgtggatgg attaagactt taacaaaaga ttgtccaaat    120
gtaatttctt caatttgtgc aggtacaatt attacagcct gtaaaaattg tgcttaa       177

<210> SEQ ID NO 314
<211> LENGTH: 64
<212> TYPE: PRT
<213> ORGANISM: Streptococcus thermophilus

<400> SEQUENCE: 314

Met Lys Gln Tyr Asn Gly Phe Glu Val Leu His Glu Leu Asp Leu Ala
1               5                   10                  15

Asn Val Thr Gly Gly Gln Ile Asn Trp Gly Ser Val Val Gly His Cys
            20                  25                  30

```
Ile Gly Gly Ala Ile Ile Gly Gly Ala Phe Ser Gly Gly Ala Ala Ala
        35                  40                  45

Gly Val Gly Cys Leu Val Gly Ser Gly Lys Ala Ile Ile Asn Gly Leu
    50                  55                  60


<210> SEQ ID NO 315
<211> LENGTH: 195
<212> TYPE: DNA
<213> ORGANISM: Streptococcus thermophilus

<400> SEQUENCE: 315

atgaagcagt ataatggttt tgaggttcta catgaacttg acttagcaaa tgtaactggc      60

ggtcaaatta attggggatc agttgtagga cactgtatag gtggagctat tatcggaggt     120

gcattttcag gaggtgcagc ggctggagta ggatgccttg ttgggagcgg aaaggcaatc     180

ataaatggat tataa                                                      195


<210> SEQ ID NO 316
<211> LENGTH: 85
<212> TYPE: PRT
<213> ORGANISM: Streptococcus thermophilus

<400> SEQUENCE: 316

Met Asn Thr Ile Thr Ile Cys Lys Phe Asp Val Leu Asp Ala Glu Leu
1               5                   10                  15

Leu Ser Thr Val Glu Gly Gly Tyr Ser Gly Lys Asp Cys Leu Lys Asp
            20                  25                  30

Met Gly Gly Tyr Ala Leu Ala Gly Ala Gly Ser Gly Ala Leu Trp Gly
        35                  40                  45

Ala Pro Ala Gly Gly Val Gly Ala Leu Pro Gly Ala Phe Val Gly Ala
    50                  55                  60

His Val Gly Ala Ile Ala Gly Gly Phe Ala Cys Met Gly Gly Met Ile
65                  70                  75                  80

Gly Asn Lys Phe Asn
                85


<210> SEQ ID NO 317
<211> LENGTH: 258
<212> TYPE: DNA
<213> ORGANISM: Streptococcus thermophilus

<400> SEQUENCE: 317

atgaatacaa taactatttg taaatttgat gttttagatg ctgaacttct ttcgacagtt      60

gagggtggat actctggtaa ggattgttta aaagacatgg gaggatatgc attggcagga     120

gctggaagtg gagctctgtg gggagctcca gcaggaggtg ttggagcact tccaggtgca     180

tttgtcggag ctcatgttgg ggcaattgca ggaggctttg catgtatggg tggaatgatt     240

ggtaataagt ttaactaa                                                   258


<210> SEQ ID NO 318
<211> LENGTH: 52
<212> TYPE: PRT
<213> ORGANISM: Bacillus cereus

<400> SEQUENCE: 318

Met Ser Glu Ile Lys Lys Ala Leu Asn Thr Leu Glu Ile Glu Asp Phe
1               5                   10                  15
```

```
Asp Ala Ile Glu Met Val Asp Val Asp Ala Met Pro Glu Asn Glu Ala
            20                  25                  30

Leu Glu Ile Met Gly Ala Ser Cys Thr Thr Cys Val Cys Thr Cys Ser
        35                  40                  45

Cys Cys Thr Thr
    50


<210> SEQ ID NO 319
<211> LENGTH: 159
<212> TYPE: DNA
<213> ORGANISM: Bacillus cereus

<400> SEQUENCE: 319

atgagtgaaa ttaaaaaagc attaaatacg cttgaaattg aagattttga tgcaattgaa      60

atggttgatg ttgatgctat gccagaaaac gaagcgcttg aaattatggg agcgtcatgt     120

acgacatgcg tatgtacatg cagttgttgt acaacttga                            159


<210> SEQ ID NO 320
<211> LENGTH: 47
<212> TYPE: PRT
<213> ORGANISM: Bacillus cereus

<400> SEQUENCE: 320

Met Glu Val Met Asn Asn Ala Leu Ile Thr Lys Val Asp Glu Glu Ile
1               5                   10                  15

Gly Gly Asn Ala Ala Cys Val Ile Gly Cys Ile Gly Ser Cys Val Ile
            20                  25                  30

Ser Glu Gly Ile Gly Ser Leu Val Gly Thr Ala Phe Thr Leu Gly
        35                  40                  45


<210> SEQ ID NO 321
<211> LENGTH: 144
<212> TYPE: DNA
<213> ORGANISM: Bacillus cereus

<400> SEQUENCE: 321

atggaagtta tgaacaatgc tttaattaca aaagtagatg aggagattgg aggaaacgct      60

gcttgtgtaa ttggttgtat tggcagttgc gtaattagtg aaggaattgg ttcacttgta     120

ggaacagcat ttactttagg ttaa                                            144


<210> SEQ ID NO 322
<211> LENGTH: 49
<212> TYPE: PRT
<213> ORGANISM: Bacillus cereus

<400> SEQUENCE: 322

Met Glu Val Leu Asn Lys Gln Asn Val Asn Ile Ile Pro Glu Ser Glu
1               5                   10                  15

Glu Val Gly Gly Trp Val Ala Cys Val Gly Ala Cys Gly Thr Val Cys
            20                  25                  30

Leu Ala Ser Gly Gly Val Gly Thr Glu Phe Ala Ala Ala Ser Tyr Phe
        35                  40                  45

Leu


<210> SEQ ID NO 323
<211> LENGTH: 150
<212> TYPE: DNA
<213> ORGANISM: Bacillus cereus
```

<400> SEQUENCE: 323
atggaagttt taaacaaaca aaatgtaaat attattccag aatctgaaga agtaggtgga 60
tgggtagcat gtgttggagc atgtggtaca gtatgtcttg ctagtggtgg tgttggaaca 120
gagtttgcag ctgcatctta tttcctataa 150

<210> SEQ ID NO 324
<211> LENGTH: 40
<212> TYPE: PRT
<213> ORGANISM: Bacillus thuringiensis

<400> SEQUENCE: 324

Met Glu Thr Pro Val Val Gln Pro Arg Asp Trp Thr Cys Trp Ser Cys
1 5 10 15

Leu Val Cys Ala Ala Cys Ser Val Glu Leu Leu Asn Leu Val Thr Ala
20 25 30

Ala Thr Gly Ala Ser Thr Ala Ser
35 40

<210> SEQ ID NO 325
<211> LENGTH: 123
<212> TYPE: DNA
<213> ORGANISM: Bacillus thuringiensis

<400> SEQUENCE: 325
atggaaacac cagtagtaca accaagggat tggacttgtt ggagttgctt agtatgtgca 60
gcatgttctg tggaattatt aaatttagtt actgcggcaa caggggctag tactgcaagc 120
taa 123

<210> SEQ ID NO 326
<211> LENGTH: 42
<212> TYPE: PRT
<213> ORGANISM: Rhizobium leguminosarum bv. trifolii

<400> SEQUENCE: 326

Met Asp Asn Lys Val Ala Lys Asn Val Glu Val Lys Lys Gly Ser Ile
1 5 10 15

Lys Ala Thr Phe Lys Ala Ala Val Leu Lys Ser Lys Thr Lys Val Asp
20 25 30

Ile Gly Gly Ser Arg Gln Gly Cys Val Ala
35 40

<210> SEQ ID NO 327
<211> LENGTH: 129
<212> TYPE: DNA
<213> ORGANISM: Rhizobium leguminosarum bv. trifolii

<400> SEQUENCE: 327
atggataaca aggttgcgaa gaatgtcgaa gtgaagaagg gctccatcaa ggcgaccttc 60
aaggctgctg ttctgaagtc gaagacgaag gtcgacatcg gaggtagccg tcagggctgc 120
gtcgcttaa 129

<210> SEQ ID NO 328
<211> LENGTH: 70
<212> TYPE: PRT
<213> ORGANISM: Streptococcus uberis

<400> SEQUENCE: 328

Met Asn Thr Ile Glu Lys Phe Glu Asn Ile Lys Leu Phe Ser Leu Lys
1 5 10 15

Lys Ile Ile Gly Gly Lys Thr Val Asn Tyr Gly Asn Gly Leu Tyr Cys
20 25 30

Asn Gln Lys Lys Cys Trp Val Asn Trp Ser Glu Thr Ala Thr Thr Ile
35 40 45

Val Asn Asn Ser Ile Met Asn Gly Leu Thr Gly Gly Asn Ala Gly Trp
50 55 60

His Ser Gly Gly Arg Ala
65 70

<210> SEQ ID NO 329
<211> LENGTH: 213
<212> TYPE: DNA
<213> ORGANISM: Streptococcus uberis

<400> SEQUENCE: 329
atgaatacaa ttgaaaaatt tgaaaatatt aaactttttt cactaaagaa aattatcggt 60
ggcaaaactg taaattatgg taatggcctt tattgtaacc aaaaaaaatg ctgggtaaac 120
tggtcagaaa ctgctacaac aatagtaaat aattccatca tgaacgggct cacaggtggt 180
aatgcgggtt ggcactcagg cgggagagca taa 213

<210> SEQ ID NO 330
<211> LENGTH: 76
<212> TYPE: PRT
<213> ORGANISM: Streptococcus uberis

<400> SEQUENCE: 330

Met Asp Ile Leu Leu Glu Leu Ala Gly Tyr Thr Gly Ile Ala Ser Gly
1 5 10 15

Thr Ala Lys Lys Val Val Asp Ala Ile Asp Lys Gly Ala Ala Ala Phe
20 25 30

Val Ile Ile Ser Ile Ile Ser Thr Val Ile Ser Ala Gly Ala Leu Gly
35 40 45

Ala Val Ser Ala Ser Ala Asp Phe Ile Ile Leu Thr Val Lys Asn Tyr
50 55 60

Ile Ser Arg Asn Leu Lys Ala Gln Ala Val Ile Trp
65 70 75

<210> SEQ ID NO 331
<211> LENGTH: 231
<212> TYPE: DNA
<213> ORGANISM: Streptococcus uberis

<400> SEQUENCE: 331
atggacattt tattagaact cgcaggatat actgggatag cctcaggtac tgcaaaaaaa 60
gttgttgatg ccattgataa aggagctgca gcctttgtta ttatttcaat tatctcaaca 120
gtaattagtg cgggagcatt gggagcagtt tcagcctcag ctgattttat tattttaact 180
gtaaaaaatt acattagtag aaatttaaaa gcacaagctg tcatttggta a 231

<210> SEQ ID NO 332
<211> LENGTH: 64
<212> TYPE: PRT
<213> ORGANISM: Clostridium perfringens

<400> SEQUENCE: 332

```
Met Asp Ser Glu Leu Phe Lys Leu Met Ala Thr Gln Gly Ala Phe Ala
1               5                   10                  15

Ile Leu Phe Ser Tyr Leu Leu Phe Tyr Val Leu Lys Glu Asn Ser Lys
            20                  25                  30

Arg Glu Asp Lys Tyr Gln Asn Ile Ile Glu Glu Leu Thr Glu Leu Leu
        35                  40                  45

Pro Lys Ile Lys Glu Asp Val Glu Asp Ile Lys Glu Lys Leu Asn Lys
    50                  55                  60
```

<210> SEQ ID NO 333
<211> LENGTH: 195
<212> TYPE: DNA
<213> ORGANISM: Clostridium perfringens

<400> SEQUENCE: 333

```
atggatagtg aattatttaa gttaatggca acacaaggag cctttgcaat attattttcg     60

tatttattgt tttatgtttt aaaagagaat agtaaaagag aagataagta tcaaaatata    120

atagaggagc ttacagaatt attgccaaaa ataaaagaag atgtagaaga tataaaagaa    180

aaacttaata aatag                                                     195
```

<210> SEQ ID NO 334
<211> LENGTH: 47
<212> TYPE: PRT
<213> ORGANISM: Micrococcus varians

<400> SEQUENCE: 334

```
Met Thr Asn Ala Phe Gln Ala Leu Asp Glu Val Thr Asp Ala Glu Leu
1               5                   10                  15

Asp Ala Ile Leu Gly Gly Gly Ser Gly Val Ile Pro Thr Ile Ser His
            20                  25                  30

Glu Cys His Met Asn Ser Phe Gln Phe Val Phe Thr Cys Cys Ser
        35                  40                  45
```

<210> SEQ ID NO 335
<211> LENGTH: 144
<212> TYPE: DNA
<213> ORGANISM: Micrococcus varians

<400> SEQUENCE: 335

```
atgacgaacg catttcaggc actggacgaa gtcacggacg ccgagctcga cgccatcctt     60

ggcgggggca gtggtgttat tcccacgatc agccacgagt gccacatgaa ctccttccag    120

ttcgtgttca cctgctgctc ctga                                           144
```

<210> SEQ ID NO 336
<211> LENGTH: 285
<212> TYPE: PRT
<213> ORGANISM: Streptococcus equi subsp. zooepidemicus

<400> SEQUENCE: 336

```
Met Lys Arg Ile Phe Phe Ala Phe Leu Ser Leu Cys Leu Phe Ile Phe
1               5                   10                  15

Gly Thr Gln Thr Val Ser Ala Ala Thr Tyr Thr Arg Pro Leu Asp Thr
            20                  25                  30

Gly Asn Ile Thr Thr Gly Phe Asn Gly Tyr Pro Gly His Val Gly Val
        35                  40                  45
```

```
Asp Tyr Ala Val Pro Val Gly Thr Pro Val Arg Ala Val Ala Asn Gly
    50                  55                  60

Thr Val Lys Phe Ala Gly Asn Gly Ala Asn His Pro Trp Met Leu Trp
65                  70                  75                  80

Met Ala Gly Asn Cys Val Leu Ile Gln His Ala Asp Gly Met His Thr
                85                  90                  95

Gly Tyr Ala His Leu Ser Lys Ile Ser Val Ser Thr Asp Ser Thr Val
            100                 105                 110

Lys Gln Gly Gln Ile Ile Gly Tyr Thr Gly Ala Thr Gly Gln Val Thr
        115                 120                 125

Gly Pro His Leu His Phe Glu Met Leu Pro Ala Asn Pro Asn Trp Gln
    130                 135                 140

Asn Gly Phe Ser Gly Arg Ile Asp Pro Thr Gly Tyr Ile Ala Asn Ala
145                 150                 155                 160

Pro Val Phe Asn Gly Thr Thr Pro Thr Glu Pro Thr Thr Pro Thr Thr
                165                 170                 175

Asn Leu Lys Ile Tyr Lys Val Asp Asp Leu Gln Lys Ile Asn Gly Ile
            180                 185                 190

Trp Gln Val Arg Asn Asn Ile Leu Val Pro Thr Asp Phe Thr Trp Val
        195                 200                 205

Asp Asn Gly Ile Ala Ala Asp Asp Val Ile Glu Val Thr Ser Asn Gly
    210                 215                 220

Thr Arg Thr Ser Asp Gln Val Leu Gln Lys Gly Gly Tyr Phe Val Ile
225                 230                 235                 240

Asn Pro Asn Asn Val Lys Ser Val Gly Thr Pro Met Lys Gly Ser Gly
                245                 250                 255

Gly Leu Ser Trp Ala Gln Val Asn Phe Thr Thr Gly Gly Asn Val Trp
            260                 265                 270

Leu Asn Thr Thr Ser Lys Asp Asn Leu Leu Tyr Gly Lys
        275                 280                 285
```

<210> SEQ ID NO 337
<211> LENGTH: 858
<212> TYPE: DNA
<213> ORGANISM: Streptococcus equi subsp. zooepidemicus

<400> SEQUENCE: 337

```
atgaaacgta tattttttgc tttcttaagt ttatgcttat ttatattcgg aacacaaacg      60

gtatctgcag ctacttatac tcggccatta gatacgggaa atatcactac agggtttaac     120

ggataccctg gtcatgttgg agtcgattat gcagtacccg ttggaactcc ggttagagca     180

gttgcaaatg gtacagtcaa atttgcaggt aatggggcta atcacccatg gatgctttgg     240

atggctggaa actgtgttct aattcaacat gctgacggga tgcatactgg atatgcacac     300

ttatcaaaaa tttcagttag cacagatagt acagttaaac aaggacaaat cataggttat     360

actggtgcca ccggccaagt taccggtcca catttgcatt ttgaaatgtt gccagcaaat     420

cctaactggc aaaatggttt ttctggaaga atagatccaa ccggatacat cgctaatgcc     480

cctgtattta atggaacaac acctacagaa cctactactc ctacaacaaa tttaaaaatc     540

tataaagttg atgatttaca aaaaattaat ggtatttggc aagtaagaaa taacatactt     600

gtaccaactg atttcacatg ggttgataat ggaattgcag cagatgatgt aattgaagta     660

actagcaatg gaacaagaac ctctgaccaa gttcttcaaa aggtggtta ttttgtcatc     720

aatcctaata atgttaaaag tgttggaact ccgatgaaag gtagtggtgg tctatcttgg     780
```

gctcaagtaa actttacaac aggtggaaat gtctggttaa atactactag caaagacaac 840
ttactttacg gaaaataa 858

<210> SEQ ID NO 338
<211> LENGTH: 45
<212> TYPE: PRT
<213> ORGANISM: Myxococcus fulvus

<400> SEQUENCE: 338

Ala Asn Cys Ser Cys Ser Thr Ala Ser Asp Tyr Cys Pro Ile Leu Thr
1 5 10 15

Phe Cys Thr Thr Gly Thr Ala Cys Ser Tyr Thr Pro Thr Gly Cys Gly
20 25 30

Thr Gly Trp Val Tyr Cys Ala Cys Asn Gly Asn Phe Tyr
35 40 45

<210> SEQ ID NO 339
<211> LENGTH: 135
<212> TYPE: DNA
<213> ORGANISM: Artificial Sequence
<220> FEATURE:
<223> OTHER INFORMATION: Polynucleotide encoding the polypeptide of SEQ ID NO: 338

<400> SEQUENCE: 339
gcgaactgca gctgcagcac cgcgagcgat tattgcccga ttctgacctt ttgcaccacc 60
ggcaccgcgt gcagctatac cccgaccggc tgcggcaccg gctgggtgta ttgcgcgtgc 120
aacggcaact tttat 135

<210> SEQ ID NO 340
<211> LENGTH: 19
<212> TYPE: PRT
<213> ORGANISM: Streptomyces griseoluteus

<400> SEQUENCE: 340

Cys Ala Asn Ser Cys Ser Tyr Gly Pro Leu Thr Trp Ser Cys Asp Gly
1 5 10 15

Asn Thr Lys

<210> SEQ ID NO 341
<211> LENGTH: 57
<212> TYPE: DNA
<213> ORGANISM: Artificial Sequence
<220> FEATURE:
<223> OTHER INFORMATION: Polynucleotide encoding the polypeptide of SEQ ID NO: 340

<400> SEQUENCE: 341
tgcgcgaaca gctgcagcta tggcccgctg acctggagct gcgatggcaa caccaaa 57

<210> SEQ ID NO 342
<211> LENGTH: 19
<212> TYPE: PRT
<213> ORGANISM: Streptoverticillium griseoverticillatum

<400> SEQUENCE: 342

Cys Lys Gln Ser Cys Ser Phe Gly Pro Phe Thr Phe Val Cys Asp Gly
1 5 10 15

Asn Thr Lys

<210> SEQ ID NO 343
<211> LENGTH: 57
<212> TYPE: DNA
<213> ORGANISM: Artificial Sequence
<220> FEATURE:
<223> OTHER INFORMATION: Polynucleotide encoding the polypeptide of SEQ ID NO: 342

<400> SEQUENCE: 343
tgcaaacaga gctgcagctt tggcccgttt acctttgtgt gcgatggcaa caccaaa 57

<210> SEQ ID NO 344
<211> LENGTH: 7
<212> TYPE: PRT
<213> ORGANISM: Carnobacterium sp.

<400> SEQUENCE: 344

Gly Ser Glu Ile Gln Pro Arg
1 5

<210> SEQ ID NO 345
<211> LENGTH: 21
<212> TYPE: DNA
<213> ORGANISM: Artificial Sequence
<220> FEATURE:
<223> OTHER INFORMATION: Polynucleotide encoding the polypeptide of SEQ ID NO: 344

<400> SEQUENCE: 345
ggcagcgaaa ttcagccgcg c 21

<210> SEQ ID NO 346
<211> LENGTH: 39
<212> TYPE: PRT
<213> ORGANISM: Lactococcus lactis subsp. lactis

<400> SEQUENCE: 346

Gly Thr Trp Asp Asp Ile Gly Gln Gly Ile Gly Arg Val Ala Tyr Trp
1 5 10 15

Val Gly Lys Ala Met Gly Asn Met Ser Asp Val Asn Gln Ala Ser Arg
20 25 30

Ile Asn Arg Lys Lys Lys His
35

<210> SEQ ID NO 347
<211> LENGTH: 117
<212> TYPE: DNA
<213> ORGANISM: Artificial Sequence
<220> FEATURE:
<223> OTHER INFORMATION: Polynucleotide encoding the polypeptide of SEQ ID NO: 346

<400> SEQUENCE: 347
ggcacctggg atgatattgg ccagggcatt ggccgcgtgg cgtattgggt gggcaaagcg 60
atgggcaaca tgagcgatgt gaaccaggcg agccgcatta accgcaaaaa aaaacat 117

<210> SEQ ID NO 348
<211> LENGTH: 35
<212> TYPE: PRT
<213> ORGANISM: Lactococcus lactis subsp. lactis

<400> SEQUENCE: 348

Lys Lys Trp Gly Trp Leu Ala Trp Val Asp Pro Ala Tyr Glu Phe Ile
1 5 10 15

Lys Gly Phe Gly Lys Gly Ala Ile Lys Glu Gly Asn Lys Asp Lys Trp
20 25 30

Lys Asn Ile
35

<210> SEQ ID NO 349
<211> LENGTH: 105
<212> TYPE: DNA
<213> ORGANISM: Artificial Sequence
<220> FEATURE:
<223> OTHER INFORMATION: Polynucleotide encoding the polypeptide of SEQ ID NO: 348

<400> SEQUENCE: 349
aaaaaatggg gctggctggc gtgggtggat ccggcgtatg aatttattaa aggctttggc 60
aaaggcgcga ttaaagaagg caacaaagat aaatggaaaa acatt 105

<210> SEQ ID NO 350
<211> LENGTH: 19
<212> TYPE: PRT
<213> ORGANISM: Streptomyces sp.

<400> SEQUENCE: 350

Cys Val Gln Ser Cys Ser Phe Gly Pro Leu Thr Trp Ser Cys Asp Gly
1 5 10 15

Asn Thr Lys

<210> SEQ ID NO 351
<211> LENGTH: 57
<212> TYPE: DNA
<213> ORGANISM: Artificial Sequence
<220> FEATURE:
<223> OTHER INFORMATION: Polynucleotide encoding the polypeptide of SEQ ID NO: 350

<400> SEQUENCE: 351
tgcgtgcaga gctgcagctt tggcccgctg acctggagct gcgatggcaa caccaaa 57

<210> SEQ ID NO 352
<211> LENGTH: 19
<212> TYPE: PRT
<213> ORGANISM: Actinoplanes liguriae

<400> SEQUENCE: 352

Ser Ser Gly Trp Val Cys Thr Leu Thr Ile Glu Cys Gly Thr Val Ile
1 5 10 15

Cys Ala Cys

<210> SEQ ID NO 353
<211> LENGTH: 57
<212> TYPE: DNA
<213> ORGANISM: Artificial Sequence
<220> FEATURE:
<223> OTHER INFORMATION: Polynucleotide encoding the polypeptide of SEQ ID NO: 352

<400> SEQUENCE: 353
agcagcggct gggtgtgcac cctgaccatt gaatgcggca ccgtgatttg cgcgtgc 57

<210> SEQ ID NO 354
<211> LENGTH: 38
<212> TYPE: PRT
<213> ORGANISM: Lactobacillus curvatus
<220> FEATURE:

```
<221> NAME/KEY: VARIANT
<222> LOCATION: 34
<223> OTHER INFORMATION: Xaa = any amino acid
<220> FEATURE:
<221> NAME/KEY: VARIANT
<222> LOCATION: 37
<223> OTHER INFORMATION: Xaa = any amino acid

<400> SEQUENCE: 354

Tyr Thr Ala Lys Gln Cys Leu Gln Ala Ile Gly Ser Cys Gly Ile Ala
1               5                   10                  15

Gly Thr Gly Ala Gly Ala Ala Gly Gly Pro Ala Gly Ala Phe Val Gly
            20                  25                  30

Ala Xaa Val Val Xaa Ile
        35


<210> SEQ ID NO 355
<211> LENGTH: 114
<212> TYPE: DNA
<213> ORGANISM: Artificial Sequence
<220> FEATURE:
<223> OTHER INFORMATION: Polynucleotide encoding the polypeptide of SEQ
      ID NO: 354
<220> FEATURE:
<221> NAME/KEY: misc_feature
<222> LOCATION: 100, 101, 102, 109, 110, 111
<223> OTHER INFORMATION: n = A,T,C or G
<220> FEATURE:
<221> NAME/KEY: misc_feature
<222> LOCATION: (100)...(102)
<223> OTHER INFORMATION: nnn = a codon other than a stop codon
<220> FEATURE:
<221> NAME/KEY: misc_feature
<222> LOCATION: (109)...(111)
<223> OTHER INFORMATION: nnn = a codon other than a stop codon

<400> SEQUENCE: 355

tataccgcga aacagtgcct gcaggcgatt ggcagctgcg gcattgcggg caccggcgcg     60

ggcgcggcgg gcggcccggc gggcgcgttt gtgggcgcgn nngtggtgnn natt          114


<210> SEQ ID NO 356
<211> LENGTH: 42
<212> TYPE: PRT
<213> ORGANISM: Lactobacillus sakei
<220> FEATURE:
<221> NAME/KEY: VARIANT
<222> LOCATION: 32
<223> OTHER INFORMATION: Xaa = any amino acid

<400> SEQUENCE: 356

Thr Lys Tyr Tyr Gly Asn Gly Val Tyr Cys Asn Ser Lys Lys Cys Trp
1               5                   10                  15

Val Asp Trp Gly Gln Ala Ala Gly Gly Ile Gly Gln Thr Val Val Xaa
            20                  25                  30

Gly Trp Leu Gly Gly Ala Ile Pro Gly Lys
        35                  40


<210> SEQ ID NO 357
<211> LENGTH: 126
<212> TYPE: DNA
<213> ORGANISM: Artificial Sequence
<220> FEATURE:
<223> OTHER INFORMATION: Polynucleotide encoding the polypeptide of SEQ
      ID NO: 356
<220> FEATURE:
<221> NAME/KEY: misc_feature
<222> LOCATION: (94)...(96)
<223> OTHER INFORMATION: nnn = any amino acid-coding triplet
```

<400> SEQUENCE: 357
accaaatatt atggcaacgg cgtgtattgc aacagcaaaa aatgctgggt ggattggggc 60
caggcggcgg gcggcattgg ccagaccgtg gtgnnnggct ggctgggcgg cgcgattccg 120
ggcaaa 126

<210> SEQ ID NO 358
<211> LENGTH: 22
<212> TYPE: PRT
<213> ORGANISM: Streptococcus mutans

<400> SEQUENCE: 358

Phe Lys Ser Trp Ser Phe Cys Thr Pro Gly Cys Ala Lys Thr Gly Ser
1 5 10 15

Phe Asn Ser Tyr Cys Cys
20

<210> SEQ ID NO 359
<211> LENGTH: 132
<212> TYPE: DNA
<213> ORGANISM: Artificial Sequence
<220> FEATURE:
<223> OTHER INFORMATION: Polynucleotide encoding the polypeptide of SEQ ID NO: 358

<400> SEQUENCE: 359
tttaaaagct ggagcttttg caccccgggc tgcgcgaaaa ccggcagctt taacagctat 60
tgctgcttta aaagctggag cttttgcacc ccgggctgcg cgaaaaccgg cagctttaac 120
agctattgct gc 132

<210> SEQ ID NO 360
<211> LENGTH: 43
<212> TYPE: PRT
<213> ORGANISM: Enterococcus mundtii

<400> SEQUENCE: 360

Lys Tyr Tyr Gly Asn Gly Val Ser Cys Asn Lys Lys Gly Cys Ser Val
1 5 10 15

Asp Trp Gly Lys Ala Ile Gly Ile Ile Gly Asn Asn Ser Ala Ala Asn
20 25 30

Leu Ala Thr Gly Gly Ala Ala Gly Trp Ser Lys
35 40

<210> SEQ ID NO 361
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 360

<400> SEQUENCE: 361
aaatattatg gcaacggcgt gagctgcaac aaaaaaggct gcagcgtgga ttggggcaaa 60
gcgattggca ttattggcaa caacagcgcg gcgaacctgg cgaccggcgg cgcggcgggc 120
tggagcaaa 129

<210> SEQ ID NO 362
<211> LENGTH: 41
<212> TYPE: PRT
<213> ORGANISM: Lactobacillus sakei
<220> FEATURE:
<221> NAME/KEY: VARIANT
<222> LOCATION: 9, 14, 33, 37
<223> OTHER INFORMATION: Xaa = any amino acid

<400> SEQUENCE: 362

```
Lys Tyr Tyr Gly Asn Gly Val His Xaa Gly Lys His Ser Xaa Thr Val
1               5                   10                  15

Asp Trp Gly Thr Ala Ile Gly Asn Ile Gly Asn Asn Ala Ala Ala Asn
            20                  25                  30

Xaa Ala Thr Gly Xaa Asn Ala Gly Gly
        35                  40
```

<210> SEQ ID NO 363
<211> LENGTH: 123
<212> TYPE: DNA
<213> ORGANISM: Artificial Sequence
<220> FEATURE:
<223> OTHER INFORMATION: Polynucleotide encoding the polypeptide of SEQ ID NO: 362
<220> FEATURE:
<221> NAME/KEY: misc_feature
<222> LOCATION: (25)...(27)
<223> OTHER INFORMATION: nnn = any amino acid-coding triplet
<220> FEATURE:
<221> NAME/KEY: misc_feature
<222> LOCATION: (40)...(42)
<223> OTHER INFORMATION: nnn = any amino acid-coding triplet
<220> FEATURE:
<221> NAME/KEY: misc_feature
<222> LOCATION: (97)...(99)
<223> OTHER INFORMATION: nnn = any amino acid-coding triplet
<220> FEATURE:
<221> NAME/KEY: misc_feature
<222> LOCATION: (109)...(111)
<223> OTHER INFORMATION: nnn = any amino acid-coding triplet

<400> SEQUENCE: 363

```
aaatattatg gcaacggcgt gcatnnnggc aaacatagcn nnaccgtgga ttggggcacc     60

gcgattggca acattggcaa caacgcggcg gcgaacnnng cgaccggcnn naacgcgggc    120

ggc                                                                  123
```

<210> SEQ ID NO 364
<211> LENGTH: 31
<212> TYPE: PRT
<213> ORGANISM: Lactobacillus paracasei

<400> SEQUENCE: 364

```
Gly Met Ser Gly Tyr Ile Gln Gly Ile Pro Asp Phe Leu Lys Gly Tyr
1               5                   10                  15

Leu His Gly Ile Ser Ala Ala Asn Lys His Lys Lys Gly Arg Leu
            20                  25                  30
```

<210> SEQ ID NO 365
<211> LENGTH: 93
<212> TYPE: DNA
<213> ORGANISM: Artificial Sequence
<220> FEATURE:
<223> OTHER INFORMATION: Polynucleotide encoding the polypeptide of SEQ ID NO: 364

<400> SEQUENCE: 365

```
ggcatgagcg gctatattca gggcattccg gattttctga aaggctatct gcatggcatt     60

agcgcggcga acaaacataa aaaaggccgc ctg                                 93
```

<210> SEQ ID NO 366
<211> LENGTH: 31
<212> TYPE: PRT
<213> ORGANISM: Leuconostoc mesenteroides

<400> SEQUENCE: 366

```
Lys Gly Lys Gly Phe Trp Ser Trp Ala Ser Lys Ala Thr Ser Trp Leu
1               5                   10                  15

Thr Gly Pro Gln Gln Pro Gly Ser Pro Leu Leu Lys Lys His Arg
            20                  25                  30
```

<210> SEQ ID NO 367
<211> LENGTH: 93
<212> TYPE: DNA
<213> ORGANISM: Artificial Sequence
<220> FEATURE:
<223> OTHER INFORMATION: Polynucleotide encoding the polypeptide of SEQ ID NO: 366

<400> SEQUENCE: 367

```
aaaggcaaag gcttttggag ctgggcgagc aaagcgacca gctggctgac cggcccgcag     60

cagccgggca gcccgctgct gaaaaaacat cgc                                  93
```

<210> SEQ ID NO 368
<211> LENGTH: 43
<212> TYPE: PRT
<213> ORGANISM: Leuconostoc mesenteroides

<400> SEQUENCE: 368

```
Lys Asn Tyr Gly Asn Gly Val His Cys Thr Lys Lys Gly Cys Ser Val
1               5                   10                  15

Asp Trp Gly Tyr Ala Trp Thr Asn Ile Ala Asn Asn Ser Val Met Asn
            20                  25                  30

Gly Leu Thr Gly Gly Asn Ala Gly Trp His Asn
        35                  40
```

<210> SEQ ID NO 369
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 368

<400> SEQUENCE: 369

```
aaaaactatg gcaacggcgt gcattgcacc aaaaaaggct gcagcgtgga ttggggctat     60

gcgtggacca acattgcgaa caacagcgtg atgaacggcc tgaccggcgg caacgcgggc    120

tggcataac                                                            129
```

<210> SEQ ID NO 370
<211> LENGTH: 47
<212> TYPE: PRT
<213> ORGANISM: Bacillus subtilis

<400> SEQUENCE: 370

```
Ala Ile Lys Leu Val Gln Ser Pro Asn Gly Asn Phe Ala Ala Ser Phe
1               5                   10                  15

Val Leu Asp Gly Thr Lys Trp Ile Phe Lys Ser Lys Tyr Tyr Asp Ser
            20                  25                  30

Ser Lys Gly Tyr Trp Val Gly Ile Tyr Glu Val Trp Asp Arg Lys
        35                  40                  45
```

<210> SEQ ID NO 371
<211> LENGTH: 141
<212> TYPE: DNA
<213> ORGANISM: Artificial Sequence
<220> FEATURE:
<223> OTHER INFORMATION: Polynucleotide encoding the polypeptide of SEQ ID NO: 370

<400> SEQUENCE: 371
gcgattaaac tggtgcagag cccgaacggc aactttgcgg cgagctttgt gctggatggc 60
accaaatgga tttttaaaag caaatattat gatagcagca aaggctattg ggtgggcatt 120
tatgaagtgt gggatcgcaa a 141

<210> SEQ ID NO 372
<211> LENGTH: 12
<212> TYPE: PRT
<213> ORGANISM: Bacillus licheniformis
<220> FEATURE:
<221> NAME/KEY: VARIANT
<222> LOCATION: 7
<223> OTHER INFORMATION: Xaa = any amino acid

<400> SEQUENCE: 372

Ile Ser Leu Glu Ile Cys Xaa Ile Phe His Asp Asn
1 5 10

<210> SEQ ID NO 373
<211> LENGTH: 36
<212> TYPE: DNA
<213> ORGANISM: Artificial Sequence
<220> FEATURE:
<223> OTHER INFORMATION: Polynucleotide encoding the polypeptide of SEQ ID NO: 372
<220> FEATURE:
<221> NAME/KEY: misc_feature
<222> LOCATION: (19)...(21)
<223> OTHER INFORMATION: nnn = any amino acid-coding triplet

<400> SEQUENCE: 373
attagcctgg aaatttgcnn nattttttcat gataac 36

<210> SEQ ID NO 374
<211> LENGTH: 37
<212> TYPE: PRT
<213> ORGANISM: Lactococcus lactis subsp. lactis

<400> SEQUENCE: 374

Thr Ser Tyr Gly Asn Gly Val His Cys Asn Lys Ser Lys Cys Trp Ile
1 5 10 15

Asp Val Ser Glu Leu Glu Thr Tyr Lys Ala Gly Thr Val Ser Asn Pro
20 25 30

Lys Asp Ile Leu Trp
35

<210> SEQ ID NO 375
<211> LENGTH: 111
<212> TYPE: DNA
<213> ORGANISM: Artificial Sequence
<220> FEATURE:
<223> OTHER INFORMATION: Polynucleotide encoding the polypeptide of SEQ ID NO: 374

<400> SEQUENCE: 375

```
accagctatg gcaacggcgt gcattgcaac aaaagcaaat gctggattga tgtgagcgaa     60

ctggaaacct ataaagcggg caccgtgagc aacccgaaag atattctgtg g             111
```

<210> SEQ ID NO 376
<211> LENGTH: 9
<212> TYPE: PRT
<213> ORGANISM: Serratia plymuthica

<400> SEQUENCE: 376

```
Asp Tyr His His Gly Val Arg Val Leu
1               5
```

<210> SEQ ID NO 377
<211> LENGTH: 27
<212> TYPE: DNA
<213> ORGANISM: Artificial Sequence
<220> FEATURE:
<223> OTHER INFORMATION: Polynucleotide encoding the polypeptide of SEQ ID NO: 376

<400> SEQUENCE: 377

```
gattatcatc atggcgtgcg cgtgctg                                         27
```

<210> SEQ ID NO 378
<211> LENGTH: 15
<212> TYPE: PRT
<213> ORGANISM: Halobacterium sp.

<400> SEQUENCE: 378

```
Asp Ile Asp Ile Thr Gly Cys Ser Ala Cys Lys Tyr Ala Ala Gly
1               5                   10                  15
```

<210> SEQ ID NO 379
<211> LENGTH: 45
<212> TYPE: DNA
<213> ORGANISM: Artificial Sequence
<220> FEATURE:
<223> OTHER INFORMATION: Polynucleotide encoding the polypeptide of SEQ ID NO: 378

<400> SEQUENCE: 379

```
gatattgata ttaccggctg cagcgcgtgc aaatatgcgg cgggc                     45
```

<210> SEQ ID NO 380
<211> LENGTH: 12
<212> TYPE: PRT
<213> ORGANISM: Bacillus subtilis
<220> FEATURE:
<221> NAME/KEY: VARIANT
<222> LOCATION: 1, 2, 6
<223> OTHER INFORMATION: Xaa = any amino acid

<400> SEQUENCE: 380

```
Xaa Xaa Lys Glu Ile Xaa His Ile Phe His Asp Asn
1               5                   10
```

<210> SEQ ID NO 381
<211> LENGTH: 36
<212> TYPE: DNA
<213> ORGANISM: Artificial Sequence
<220> FEATURE:
<223> OTHER INFORMATION: Polynucleotide encoding the polypeptide of SEQ ID NO: 380
<220> FEATURE:

<221> NAME/KEY: misc_feature
<222> LOCATION: (1)...(3)
<223> OTHER INFORMATION: nnn = any amino acid-coding triplet
<220> FEATURE:
<221> NAME/KEY: misc_feature
<222> LOCATION: (4)...(6)
<223> OTHER INFORMATION: nnn = any amino acid-coding triplet
<220> FEATURE:
<221> NAME/KEY: misc_feature
<222> LOCATION: (16)...(18)
<223> OTHER INFORMATION: nnn = any amino acid-coding triplet

<400> SEQUENCE: 381
nnnnnnaaag aaattnnnca tatttttcat gataac 36

<210> SEQ ID NO 382
<211> LENGTH: 12
<212> TYPE: PRT
<213> ORGANISM: Lactobacillus curvatus

<400> SEQUENCE: 382

Thr Pro Val Val Asn Pro Pro Phe Leu Gln Gln Thr
1 5 10

<210> SEQ ID NO 383
<211> LENGTH: 36
<212> TYPE: DNA
<213> ORGANISM: Artificial Sequence
<220> FEATURE:
<223> OTHER INFORMATION: Polynucleotide encoding the polypeptide of SEQ ID NO: 382

<400> SEQUENCE: 383
accccggtgg tgaacccgcc gtttctgcag cagacc 36

<210> SEQ ID NO 384
<211> LENGTH: 10
<212> TYPE: PRT
<213> ORGANISM: Lactobacillus curvatus
<220> FEATURE:
<221> NAME/KEY: VARIANT
<222> LOCATION: 10
<223> OTHER INFORMATION: Xaa = any amino acid

<400> SEQUENCE: 384

Val Ala Pro Phe Pro Glu Gln Phe Leu Xaa
1 5 10

<210> SEQ ID NO 385
<211> LENGTH: 30
<212> TYPE: DNA
<213> ORGANISM: Artificial Sequence
<220> FEATURE:
<223> OTHER INFORMATION: Polynucleotide encoding the polypeptide of SEQ ID NO: 384
<220> FEATURE:
<221> NAME/KEY: misc_feature
<222> LOCATION: (28)...(30)
<223> OTHER INFORMATION: nnn = any amino acid-coding triplet

<400> SEQUENCE: 385
gtggcgccgt ttccggaaca gtttctgnnn 30

<210> SEQ ID NO 386
<211> LENGTH: 9
<212> TYPE: PRT
<213> ORGANISM: Lactobacillus curvatus

<400> SEQUENCE: 386

Asn Ile Pro Gln Leu Thr Pro Thr Pro
1 5

<210> SEQ ID NO 387
<211> LENGTH: 27
<212> TYPE: DNA
<213> ORGANISM: Artificial Sequence
<220> FEATURE:
<223> OTHER INFORMATION: Polynucleotide encoding the polypeptide of SEQ ID NO: 386

<400> SEQUENCE: 387
aacattccgc agctgacccc gaccccg 27

<210> SEQ ID NO 388
<211> LENGTH: 18
<212> TYPE: PRT
<213> ORGANISM: Bacillus thuringiensis subsp. entomocidus
<220> FEATURE:
<221> NAME/KEY: VARIANT
<222> LOCATION: 4, 7, 10
<223> OTHER INFORMATION: Xaa = any amino acid

<400> SEQUENCE: 388

Asp Trp Thr Xaa Trp Ser Xaa Leu Val Xaa Ala Ala Cys Ser Val Glu
1 5 10 15

Leu Leu

<210> SEQ ID NO 389
<211> LENGTH: 54
<212> TYPE: DNA
<213> ORGANISM: Artificial Sequence
<220> FEATURE:
<223> OTHER INFORMATION: Polynucleotide encoding the polypeptide of SEQ ID NO: 388
<220> FEATURE:
<221> NAME/KEY: misc_feature
<222> LOCATION: (10)...(12)
<223> OTHER INFORMATION: nnn = any amino acid-coding triplet
<220> FEATURE:
<221> NAME/KEY: misc_feature
<222> LOCATION: (19)...(21)
<223> OTHER INFORMATION: nnn = any amino acid-coding triplet
<220> FEATURE:
<221> NAME/KEY: misc_feature
<222> LOCATION: (28)...(30)
<223> OTHER INFORMATION: nnn = any amino acid-coding triplet

<400> SEQUENCE: 389
gattggaccn nntggagcnn nctggtgnnn gcggcgtgca gcgtggaact gctg 54

<210> SEQ ID NO 390
<211> LENGTH: 30
<212> TYPE: PRT
<213> ORGANISM: Lactobacillus curvatus

<400> SEQUENCE: 390

Ala Tyr Pro Gly Asn Gly Val His Cys Gly Lys Tyr Ser Cys Thr Val
1 5 10 15

Asp Lys Gln Thr Ala Ile Gly Asn Ile Gly Asn Asn Ala Ala
20 25 30

<210> SEQ ID NO 391
<211> LENGTH: 90
<212> TYPE: DNA

<213> ORGANISM: Artificial Sequence
<220> FEATURE:
<223> OTHER INFORMATION: Polynucleotide encoding the polypeptide of SEQ ID NO: 390

<400> SEQUENCE: 391
gcgtatccgg gcaacggcgt gcattgcggc aaatatagct gcaccgtgga taaacagacc 60
gcgattggca acattggcaa caacgcggcg 90

<210> SEQ ID NO 392
<211> LENGTH: 43
<212> TYPE: PRT
<213> ORGANISM: Carnobacterium divergens

<400> SEQUENCE: 392

Thr Lys Tyr Tyr Gly Asn Gly Val Tyr Cys Asn Ser Lys Lys Cys Trp
1 5 10 15

Val Asp Trp Gly Thr Ala Gln Gly Cys Ile Asp Val Val Ile Gly Gln
20 25 30

Leu Gly Gly Gly Ile Pro Gly Lys Gly Lys Cys
35 40

<210> SEQ ID NO 393
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 392

<400> SEQUENCE: 393
accaaatatt atggcaacgg cgtgtattgc aacagcaaaa aatgctgggt ggattggggc 60
accgcgcagg gctgcattga tgtggtgatt ggccagctgg gcggcggcat tccgggcaaa 120
ggcaaatgc 129

<210> SEQ ID NO 394
<211> LENGTH: 62
<212> TYPE: PRT
<213> ORGANISM: Enterococcus sp.

<400> SEQUENCE: 394

Asn Arg Trp Tyr Cys Asn Ser Ala Ala Gly Gly Val Gly Gly Ala Ala
1 5 10 15

Val Cys Gly Leu Ala Gly Tyr Val Gly Glu Ala Lys Glu Asn Ile Ala
20 25 30

Gly Glu Val Arg Lys Gly Trp Gly Met Ala Gly Gly Phe Thr His Asn
35 40 45

Lys Ala Cys Lys Ser Phe Pro Gly Ser Gly Trp Ala Ser Gly
50 55 60

<210> SEQ ID NO 395
<211> LENGTH: 186
<212> TYPE: DNA
<213> ORGANISM: Artificial Sequence
<220> FEATURE:
<223> OTHER INFORMATION: Polynucleotide encoding the polypeptide of SEQ ID NO: 394

<400> SEQUENCE: 395
aaccgctggt attgcaacag cgcggcgggc ggcgtgggcg gcgcggcggt gtgcggcctg 60
gcgggctatg tgggcgaagc gaaagaaaac attgcgggcg aagtgcgcaa aggctggggc 120
atggcgggcg gctttaccca taacaaagcg tgcaaaagct ttccgggcag cggctgggcg 180
agcggc 186

<210> SEQ ID NO 396
<211> LENGTH: 39
<212> TYPE: PRT
<213> ORGANISM: Enterococcus faecium

<400> SEQUENCE: 396

Thr Thr Lys Asn Tyr Gly Asn Gly Val Cys Asn Ser Val Asn Trp Cys
1 5 10 15

Gln Cys Gly Asn Val Trp Ala Ser Cys Asn Leu Ala Thr Gly Cys Ala
20 25 30

Ala Trp Leu Cys Lys Leu Ala
35

<210> SEQ ID NO 397
<211> LENGTH: 117
<212> TYPE: DNA
<213> ORGANISM: Artificial Sequence
<220> FEATURE:
<223> OTHER INFORMATION: Polynucleotide encoding the polypeptide of SEQ ID NO: 396

<400> SEQUENCE: 397
accaccaaaa actatggcaa cggcgtgtgc aacagcgtga actggtgcca gtgcggcaac 60
gtgtgggcga gctgcaacct ggcgaccggc tgcgcggcgt ggctgtgcaa actggcg 117

<210> SEQ ID NO 398
<211> LENGTH: 30
<212> TYPE: PRT
<213> ORGANISM: Paenibacillus polymyxa

<400> SEQUENCE: 398

Ala Ser Ile Ile Lys Thr Thr Ile Lys Val Ser Lys Ala Val Cys Lys
1 5 10 15

Thr Leu Thr Cys Ile Cys Thr Gly Ser Cys Ser Asn Cys Lys
20 25 30

<210> SEQ ID NO 399
<211> LENGTH: 90
<212> TYPE: DNA
<213> ORGANISM: Artificial Sequence
<220> FEATURE:
<223> OTHER INFORMATION: Polynucleotide encoding the polypeptide of SEQ ID NO: 398

<400> SEQUENCE: 399
gcgagcatta ttaaaaccac cattaaagtg agcaaagcgg tgtgcaaaac cctgacctgc 60
atttgcaccg gcagctgcag caactgcaaa 90

<210> SEQ ID NO 400
<211> LENGTH: 31
<212> TYPE: PRT
<213> ORGANISM: Staphylococcus epidermidis

<400> SEQUENCE: 400

Ser Ala Ser Ile Val Lys Thr Thr Ile Lys Ala Ser Lys Lys Leu Cys
1 5 10 15

Arg Gly Phe Thr Leu Thr Cys Gly Cys His Phe Thr Gly Lys Lys
20 25 30

<210> SEQ ID NO 401
<211> LENGTH: 93
<212> TYPE: DNA
<213> ORGANISM: Artificial Sequence
<220> FEATURE:
<223> OTHER INFORMATION: Polynucleotide encoding the polypeptide of SEQ ID NO: 400

<400> SEQUENCE: 401
agcgcgagca ttgtgaaaac caccattaaa gcgagcaaaa aactgtgccg cggctttacc 60
ctgacctgcg gctgccattt taccggcaaa aaa 93

<210> SEQ ID NO 402
<211> LENGTH: 43
<212> TYPE: PRT
<213> ORGANISM: Enterococcus faecium

<400> SEQUENCE: 402

Lys Tyr Tyr Gly Asn Gly Val Ser Cys Asn Lys Lys Gly Cys Ser Val
1 5 10 15

Asp Trp Gly Lys Ala Ile Gly Ile Ile Gly Asn Asn Ala Ala Ala Asn
20 25 30

Leu Thr Thr Gly Gly Lys Ala Ala Trp Ala Cys
35 40

<210> SEQ ID NO 403
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 402

<400> SEQUENCE: 403
aaatattatg gcaacggcgt gagctgcaac aaaaaaggct gcagcgtgga ttggggcaaa 60
gcgattggca ttattggcaa caacgcggcg gcgaacctga ccaccggcgg caaagcggcg 120
tgggcgtgc 129

<210> SEQ ID NO 404
<211> LENGTH: 39
<212> TYPE: PRT
<213> ORGANISM: Paenibacillus polymyxa

<400> SEQUENCE: 404

Ala Thr Tyr Tyr Gly Asn Gly Leu Tyr Cys Asn Lys Gln Lys His Tyr
1 5 10 15

Thr Trp Val Asp Trp Asn Lys Ala Ser Arg Glu Ile Gly Lys Ile Thr
20 25 30

Val Asn Gly Trp Val Gln His
35

<210> SEQ ID NO 405
<211> LENGTH: 117
<212> TYPE: DNA
<213> ORGANISM: Artificial Sequence
<220> FEATURE:
<223> OTHER INFORMATION: Polynucleotide encoding the polypeptide of SEQ ID NO: 404

<400> SEQUENCE: 405
gcgacctatt atggcaacgg cctgtattgc aacaaacaga aacattatac ctgggtggat 60
tggaacaaag cgagccgcga aattggcaaa attaccgtga acggctgggt gcagcat 117

<210> SEQ ID NO 406
<211> LENGTH: 35
<212> TYPE: PRT
<213> ORGANISM: Bacillus circulans

<400> SEQUENCE: 406

Val Asn Tyr Gly Asn Gly Val Ser Cys Ser Lys Thr Lys Cys Ser Val
1 5 10 15

Asn Trp Gly Ile Ile Thr His Gln Ala Phe Arg Val Thr Ser Gly Val
20 25 30

Ala Ser Gly
35

<210> SEQ ID NO 407
<211> LENGTH: 105
<212> TYPE: DNA
<213> ORGANISM: Artificial Sequence
<220> FEATURE:
<223> OTHER INFORMATION: Polynucleotide encoding the polypeptide of SEQ ID NO: 406

<400> SEQUENCE: 407
gtgaactatg gcaacggcgt gagctgcagc aaaaccaaat gcagcgtgaa ctggggcatt 60
attacccatc aggcgtttcg cgtgaccagc ggcgtggcga gcggc 105

<210> SEQ ID NO 408
<211> LENGTH: 30
<212> TYPE: PRT
<213> ORGANISM: Paenibacillus polymyxa

<400> SEQUENCE: 408

Phe Val Tyr Gly Asn Gly Val Thr Ser Ile Leu Val Gln Ala Gln Phe
1 5 10 15

Leu Val Asn Gly Gln Arg Arg Phe Phe Tyr Thr Pro Asp Lys
20 25 30

<210> SEQ ID NO 409
<211> LENGTH: 90
<212> TYPE: DNA
<213> ORGANISM: Artificial Sequence
<220> FEATURE:
<223> OTHER INFORMATION: Polynucleotide encoding the polypeptide of SEQ ID NO: 408

<400> SEQUENCE: 409
tttgtgtatg gcaacggcgt gaccagcatt ctggtgcagg cgcagtttct ggtgaacggc 60
cagcgccgct ttttttatac cccggataaa 90

<210> SEQ ID NO 410
<211> LENGTH: 13
<212> TYPE: PRT
<213> ORGANISM: Lactobacillus rhamnosus

<400> SEQUENCE: 410

Ala Val Pro Ala Val Arg Lys Thr Asn Glu Thr Leu Asp
1 5 10

```
<210> SEQ ID NO 411
<211> LENGTH: 39
<212> TYPE: DNA
<213> ORGANISM: Artificial Sequence
<220> FEATURE:
<223> OTHER INFORMATION: Polynucleotide encoding the polypeptide of SEQ
      ID NO: 410

<400> SEQUENCE: 411

gcggtgccgg cggtgcgcaa aaccaacgaa accctggat                           39


<210> SEQ ID NO 412
<211> LENGTH: 69
<212> TYPE: PRT
<213> ORGANISM: Bacillus licheniformis

<400> SEQUENCE: 412

Met Lys Asn Ser Ala Ala Arg Glu Ala Phe Lys Gly Ala Asn His Pro
1               5                   10                  15

Ala Gly Met Val Ser Glu Glu Glu Leu Lys Ala Leu Val Gly Gly Asn
            20                  25                  30

Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys Pro Thr Thr Lys
    50                  55                  60

Cys Thr Ser Arg Cys
65


<210> SEQ ID NO 413
<211> LENGTH: 207
<212> TYPE: DNA
<213> ORGANISM: Artificial Sequence
<220> FEATURE:
<223> OTHER INFORMATION: Polynucleotide encoding the polypeptide of SEQ
      ID NO: 412

<400> SEQUENCE: 413

atgaaaaaca gcgcggcgcg cgaagcgttt aaaggcgcga accatccggc gggcatggtg     60

agcgaagaag aactgaaagc gctggtgggc ggcaacgatg tgaacccgga aaccaccccg    120

gcgaccacca gcagctggac ctgcattacc gcgggcgtga ccgtgagcgc gagcctgtgc    180

ccgaccacca aatgcaccag ccgctgc                                        207


<210> SEQ ID NO 414
<211> LENGTH: 36
<212> TYPE: PRT
<213> ORGANISM: Lactobacillus plantarum

<400> SEQUENCE: 414

Lys Tyr Tyr Gly Asn Gly Leu Ser Cys Ser Lys Lys Gly Cys Thr Val
1               5                   10                  15

Asn Trp Gly Gln Ala Phe Ser Cys Gly Val Asn Arg Val Ala Thr Ala
            20                  25                  30

Gly His Gly Lys
        35


<210> SEQ ID NO 415
<211> LENGTH: 108
<212> TYPE: DNA
<213> ORGANISM: Artificial Sequence
```

<220> FEATURE:
<223> OTHER INFORMATION: Polynucleotide encoding the polypeptide of SEQ ID NO: 414

<400> SEQUENCE: 415
aaatattatg gcaacggcct gagctgcagc aaaaaaggct gcaccgtgaa ctggggccag 60
gcgtttagct gcggcgtgaa ccgcgtggcg accgcgggcc atggcaaa 108

<210> SEQ ID NO 416
<211> LENGTH: 24
<212> TYPE: PRT
<213> ORGANISM: Lactobacillus acidophilus

<400> SEQUENCE: 416

Gly Asn Pro Lys Val Ala His Cys Ala Ser Gln Ile Gly Arg Ser Thr
1 5 10 15

Ala Trp Gly Ala Val Ser Gly Ala
20

<210> SEQ ID NO 417
<211> LENGTH: 72
<212> TYPE: DNA
<213> ORGANISM: Artificial Sequence
<220> FEATURE:
<223> OTHER INFORMATION: Polynucleotide encoding the polypeptide of SEQ ID NO: 416

<400> SEQUENCE: 417
ggcaacccga aagtggcgca ttgcgcgagc cagattggcc gcagcaccgc gtggggcgcg 60
gtgagcggcg cg 72

<210> SEQ ID NO 418
<211> LENGTH: 40
<212> TYPE: PRT
<213> ORGANISM: Enterococcus faecalis

<400> SEQUENCE: 418

Trp Leu Pro Pro Ala Gly Leu Leu Gly Arg Cys Gly Arg Trp Phe Arg
1 5 10 15

Pro Trp Leu Leu Trp Leu Gln Ser Gly Ala Gln Tyr Lys Trp Leu Gly
20 25 30

Asn Leu Phe Gly Leu Gly Pro Lys
35 40

<210> SEQ ID NO 419
<211> LENGTH: 120
<212> TYPE: DNA
<213> ORGANISM: Artificial Sequence
<220> FEATURE:
<223> OTHER INFORMATION: Polynucleotide encoding the polypeptide of SEQ ID NO: 418

<400> SEQUENCE: 419
tggctgccgc cggcgggcct gctgggccgc tgcggccgct ggtttcgccc gtggctgctg 60
tggctgcaga gcggcgcgca gtataaatgg ctgggcaacc tgtttggcct gggcccgaaa 120

<210> SEQ ID NO 420
<211> LENGTH: 40
<212> TYPE: PRT
<213> ORGANISM: Anabaena variabilis

<400> SEQUENCE: 420

Asn Leu Asp Gln Trp Leu Thr Glu Gln Val His Glu Phe Gln Asp Met
1 5 10 15

Tyr Leu Glu Pro Gln Ala Ile Ser Asn Gln Asp Ile Thr Phe Lys Leu
20 25 30

Ser Asp Leu Asp Phe Ile His Asn
35 40

<210> SEQ ID NO 421
<211> LENGTH: 124
<212> TYPE: DNA
<213> ORGANISM: Anabaena variabilis

<400> SEQUENCE: 421
taatttagat cagtggttaa cagaacaagt tcatgagttt caagatatgt acttggaacc 60
acaagcaata tccaatcaag acattacctt caaactatct gacctagatt ttattcataa 120
ttga 124

<210> SEQ ID NO 422
<211> LENGTH: 40
<212> TYPE: PRT
<213> ORGANISM: Nostoc sp

<400> SEQUENCE: 422

Asn Leu Asp Gln Trp Leu Thr Glu Gln Val His Glu Phe Gln Asp Met
1 5 10 15

Tyr Leu Glu Pro Gln Ala Ile Ser Asn Gln Asp Ile Thr Phe Lys Leu
20 25 30

Ser Asp Leu Asp Phe Ile His Asn
35 40

<210> SEQ ID NO 423
<211> LENGTH: 123
<212> TYPE: DNA
<213> ORGANISM: Nostoc sp

<400> SEQUENCE: 423
aatttagatc aatggttaac agaacaagtt catgagtttc aagatatgta cttggaacca 60
caagcaatat ccaatcaaga cattaccttc aaactgtcag acctagattt tattcataat 120
tga 123

<210> SEQ ID NO 424
<211> LENGTH: 7
<212> TYPE: PRT
<213> ORGANISM: Nostoc azollae

<400> SEQUENCE: 424

His Arg Glu Lys Lys Ser Ala
1 5

<210> SEQ ID NO 425
<211> LENGTH: 24
<212> TYPE: DNA
<213> ORGANISM: Nostoc azollae

<400> SEQUENCE: 425
cacagagaga aaaaatcagc atag 24

<210> SEQ ID NO 426
<211> LENGTH: 23
<212> TYPE: PRT
<213> ORGANISM: Acaryochloris marina

<400> SEQUENCE: 426

Thr Ser Asn Asn Trp Leu Ala Lys Asn Tyr Leu Ser Met Trp Asn Lys
1 5 10 15

Lys Ser Ser Asn Pro Asn Leu
20

<210> SEQ ID NO 427
<211> LENGTH: 72
<212> TYPE: DNA
<213> ORGANISM: Acaryochloris marina

<400> SEQUENCE: 427
acaagcaata actggctagc caaaaactat ctttctatgt ggaataaaaa gagcagtaat 60
ccaaaccttt ag 72

<210> SEQ ID NO 428
<211> LENGTH: 6
<212> TYPE: PRT
<213> ORGANISM: Cyanothece

<400> SEQUENCE: 428

Phe Arg Tyr Phe Trp Trp
1 5

<210> SEQ ID NO 429
<211> LENGTH: 21
<212> TYPE: DNA
<213> ORGANISM: Cyanothece

<400> SEQUENCE: 429
tttagatatt tttggtggta a 21

<210> SEQ ID NO 430
<211> LENGTH: 6
<212> TYPE: PRT
<213> ORGANISM: Cyanothece

<400> SEQUENCE: 430

Phe Arg Tyr Phe Trp Trp
1 5

<210> SEQ ID NO 431
<211> LENGTH: 21
<212> TYPE: DNA
<213> ORGANISM: Cyanothece

<400> SEQUENCE: 431
tttagatatt tttggtggta a 21

<210> SEQ ID NO 432
<211> LENGTH: 9
<212> TYPE: PRT
<213> ORGANISM: Cyanothece

<400> SEQUENCE: 432

Cys Gly Glu Lys Trp Arg Ile Phe Ser
1 5

<210> SEQ ID NO 433
<211> LENGTH: 27
<212> TYPE: DNA
<213> ORGANISM: Cyanothece

<400> SEQUENCE: 433
tgtggagaaa aatggagaat ttttagc 27

<210> SEQ ID NO 434
<211> LENGTH: 8
<212> TYPE: PRT
<213> ORGANISM: Cyanothece

<400> SEQUENCE: 434

Phe Arg Leu Gln Leu Trp Gln Phe
1 5

<210> SEQ ID NO 435
<211> LENGTH: 24
<212> TYPE: DNA
<213> ORGANISM: Cyanothece

<400> SEQUENCE: 435
tttcgcttac aactgtggca attt 24

<210> SEQ ID NO 436
<211> LENGTH: 16
<212> TYPE: PRT
<213> ORGANISM: Cyanothece

<400> SEQUENCE: 436

Leu Gly Cys Asn Gln Ser Ser Ile Trp Ser Ile Phe Phe Trp Asn His
1 5 10 15

<210> SEQ ID NO 437
<211> LENGTH: 51
<212> TYPE: DNA
<213> ORGANISM: Cyanothece

<400> SEQUENCE: 437
ctaggatgta accagagcag tatctggtca atttttttct ggaatcatta a 51

<210> SEQ ID NO 438
<211> LENGTH: 40
<212> TYPE: PRT
<213> ORGANISM: Microcoleus chthonoplastes

<400> SEQUENCE: 438

Tyr Asn Leu Gln Gly Leu Pro Ala Ile Glu Ser Glu Asp Cys Ile Pro
1 5 10 15

Asp Ser Val Ala Pro Ser Asp Asp Trp Phe Ser Gly Val Ser Ser Leu
20 25 30

Phe Asn Arg Leu Thr Gly Leu Gly
35 40

<210> SEQ ID NO 439
<211> LENGTH: 123
<212> TYPE: DNA
<213> ORGANISM: Microcoleus chthonoplastes

<400> SEQUENCE: 439
tataacctac aggggttgcc agcaattgag tcagaagact gtatcccaga ttctgtagcg 60
ccttcggatg attggttttc aggcgtatcg tctctgttta accgcttgac tgggttgggt 120
tag 123

<210> SEQ ID NO 440
<211> LENGTH: 37
<212> TYPE: PRT
<213> ORGANISM: Nostoc sp

<400> SEQUENCE: 440

Trp Met Ala Ile Arg Arg Ile Leu Arg Cys His Pro Phe His Pro Gly
1 5 10 15

Gly Tyr Asp Pro Val Pro Glu Leu Gly Glu His Cys Cys His His Asp
20 25 30

Ser Gly Asn Lys Gly
35

<210> SEQ ID NO 441
<211> LENGTH: 114
<212> TYPE: DNA
<213> ORGANISM: Nostoc sp

<400> SEQUENCE: 441
tggatggcga ttcgccgcat tttgcgttgt catccattcc acccaggggg ttatgatcct 60
gtaccagagt tgggtgagca ttgttgtcat catgatagcg ggaataaggg gtga 114

<210> SEQ ID NO 442
<211> LENGTH: 35
<212> TYPE: PRT
<213> ORGANISM: Anabaena variabilis

<400> SEQUENCE: 442

Trp Met Gly Ile Arg Arg Ile Leu Arg Cys His Pro Phe His Pro Gly
1 5 10 15

Gly Tyr Asp Pro Val Pro Glu Val Gly Glu His Cys Cys His His Asp
20 25 30

Ser Gly Lys
35

<210> SEQ ID NO 443
<211> LENGTH: 108
<212> TYPE: DNA
<213> ORGANISM: Anabaena variabilis

<400> SEQUENCE: 443
tggatgggga ttcgccgcat tttgcgttgt catccattcc acccaggcgg ttatgatcct 60
gtaccagagg tgggtgagca ttgttgtcat catgatagcg ggaagtag 108

<210> SEQ ID NO 444
<211> LENGTH: 48
<212> TYPE: PRT
<213> ORGANISM: Nodularia spumigena

<400> SEQUENCE: 444

Trp Met Ala Thr Arg Arg Ile Leu Arg Cys His Pro Phe His Pro Gly
1 5 10 15

```
Gly Tyr Asp Pro Val Pro Glu Val Lys His Asn Cys Cys Asp Gln His
            20                  25                  30

Leu Ser Asp Ser Gly Lys Gln Thr Thr Glu Asp His His Lys Gly Ser
        35                  40                  45


<210> SEQ ID NO 445
<211> LENGTH: 147
<212> TYPE: DNA
<213> ORGANISM: Nodularia spumigena

<400> SEQUENCE: 445

tggatggcga ctcggcggat tttgcgttgt catcccttcc atcctggtgg atatgatcca     60

gttccagagg taaaacacaa ttgctgcgat cagcatctgt ccgattctgg gaaacagacc    120

acagaagacc atcacaaagg ctcgtag                                        147


<210> SEQ ID NO 446
<211> LENGTH: 34
<212> TYPE: PRT
<213> ORGANISM: Nostoc azollae

<400> SEQUENCE: 446

Trp Met Ala Thr Leu Arg Ile Leu Arg Cys His Pro Phe His Pro Gly
1               5                   10                  15

Gly Tyr Asp Pro Val Pro Gly Leu Ala Glu Lys Ser Cys Cys Asp His
            20                  25                  30

His Asp


<210> SEQ ID NO 447
<211> LENGTH: 105
<212> TYPE: DNA
<213> ORGANISM: Nostoc azollae

<400> SEQUENCE: 447

tggatggcaa ctttgcggat tttacgctgt catcctttcc atcctggtgg ttatgatcct     60

gtaccaggac tagcggaaaa atcctgttgt gaccatcatg attga                    105


<210> SEQ ID NO 448
<211> LENGTH: 28
<212> TYPE: PRT
<213> ORGANISM: Synechococcus

<400> SEQUENCE: 448

Trp Leu Thr Ala Lys Arg Phe Cys Arg Cys His Pro Leu His Pro Gly
1               5                   10                  15

Gly Tyr Asp Pro Val Pro Glu Lys Lys Ser Val Leu
            20                  25


<210> SEQ ID NO 449
<211> LENGTH: 87
<212> TYPE: DNA
<213> ORGANISM: Synechococcus

<400> SEQUENCE: 449

tggctaacag ccaagcgctt ttgtcgctgt catccgcttc atcctggcgg gtatgatccg     60

gtaccggaga agaaatcggt actctaa                                         87


<210> SEQ ID NO 450
<211> LENGTH: 23
<212> TYPE: PRT
```

<213> ORGANISM: Prochlorococcus marinus

<400> SEQUENCE: 450

Trp Leu Thr Leu Arg Arg Leu Ser Arg Cys His Pro Phe Thr Pro Cys
1 5 10 15

Gly Cys Asp Pro Val Pro Asp
20

<210> SEQ ID NO 451
<211> LENGTH: 72
<212> TYPE: DNA
<213> ORGANISM: Prochlorococcus marinus

<400> SEQUENCE: 451
tggctcaccc tgcggcgcct gtctcgttgc catcctttta ccccctgtgg ttgcgacccg 60
gtgcctgatt aa 72

<210> SEQ ID NO 452
<211> LENGTH: 69
<212> TYPE: PRT
<213> ORGANISM: Escherichia coli

<400> SEQUENCE: 452

Met Ser Tyr Lys Lys Leu Tyr Gln Leu Thr Ala Ile Phe Ser Leu Pro
1 5 10 15

Leu Thr Ile Leu Leu Val Ser Leu Ser Ser Leu Arg Ile Val Gly Glu
20 25 30

Gly Asn Ser Tyr Val Asp Val Phe Leu Ser Phe Ile Ile Phe Leu Gly
35 40 45

Phe Ile Glu Leu Ile His Gly Ile Arg Lys Ile Leu Val Trp Ser Gly
50 55 60

Trp Lys Asn Gly Ser
65

<210> SEQ ID NO 453
<211> LENGTH: 210
<212> TYPE: DNA
<213> ORGANISM: Escherichia coli

<400> SEQUENCE: 453
atgagttata aaaaactgta ccaattgacg gctatattta gtttacctct tactatctta 60
ttggtttcac tttcatccct tcggattgtt ggcgaaggga attcttatgt tgacgttttt 120
ctaagcttta taatatttct tggttttatt gagctgattc atgggattcg aaagattttg 180
gtctggtcag gctggaaaaa cggaagttaa 210

<210> SEQ ID NO 454
<211> LENGTH: 85
<212> TYPE: PRT
<213> ORGANISM: Escherichia coli

<400> SEQUENCE: 454

Met Gly Leu Lys Leu Asp Leu Thr Trp Phe Asp Lys Ser Thr Glu Asp
1 5 10 15

Phe Lys Gly Glu Glu Tyr Ser Lys Asp Phe Gly Asp Asp Gly Ser Val
20 25 30

Met Glu Ser Leu Gly Val Pro Phe Lys Asp Asn Val Asn Asn Gly Cys
35 40 45

```
Phe Asp Val Ile Ala Glu Trp Val Pro Leu Leu Gln Pro Tyr Phe Asn
    50                  55                  60

His Gln Ile Asp Ile Ser Asp Asn Glu Tyr Phe Val Ser Phe Asp Tyr
65                  70                  75                  80

Arg Asp Gly Asp Trp
                85


<210> SEQ ID NO 455
<211> LENGTH: 258
<212> TYPE: DNA
<213> ORGANISM: Escherichia coli

<400> SEQUENCE: 455

atgggactta aattggattt aacttggttt gataaaagta cagaagattt taagggtgag      60

gagtattcaa aagattttgg agatgacggt tcagttatgg aaagtctagg tgtgcctttt     120

aaggataatg ttaataacgg ttgctttgat gttatagctg aatgggtacc tttgctacaa     180

ccatacttta atcatcaaat tgatatttcc gataatgagt attttgtttc gtttgattat     240

cgtgatggtg attggtga                                                   258


<210> SEQ ID NO 456
<211> LENGTH: 113
<212> TYPE: PRT
<213> ORGANISM: Escherichia coli

<400> SEQUENCE: 456

Met Ser Leu Arg Tyr Tyr Ile Lys Asn Ile Leu Phe Gly Leu Tyr Cys
1               5                   10                  15

Thr Leu Ile Tyr Ile Tyr Leu Ile Thr Lys Asn Ser Glu Gly Tyr Tyr
            20                  25                  30

Phe Leu Val Ser Asp Lys Met Leu Tyr Ala Ile Val Ile Ser Thr Ile
        35                  40                  45

Leu Cys Pro Tyr Ser Lys Tyr Ala Ile Glu Tyr Ile Ala Phe Asn Phe
    50                  55                  60

Ile Lys Lys Asp Phe Phe Glu Arg Arg Lys Asn Leu Asn Asn Ala Pro
65                  70                  75                  80

Val Ala Lys Leu Asn Leu Phe Met Leu Tyr Asn Leu Leu Cys Leu Val
                85                  90                  95

Leu Ala Ile Pro Phe Gly Leu Leu Gly Leu Phe Ile Ser Ile Lys Asn
            100                 105                 110

Asn


<210> SEQ ID NO 457
<211> LENGTH: 342
<212> TYPE: DNA
<213> ORGANISM: Escherichia coli

<400> SEQUENCE: 457

atgagcttaa gatactacat aaaaaatatt ttatttggcc tgtactgcac acttatatat      60

atatacctta taacaaaaaa cagcgaaggg tattatttcc ttgtgtcaga taagatgcta     120

tatgcaatag tgataagcac tattctatgt ccatattcaa aatatgctat tgaatacata     180

gcttttaact tcataaagaa agattttttc gaaagaagaa aaaacctaaa taacgccccc     240

gtagcaaaat taaacctatt tatgctatat aatctacttt gtttggtcct agcaatccca     300

tttggattgc taggactttt tatatcaata aagaataatt aa                        342
```

<210> SEQ ID NO 458
<211> LENGTH: 85
<212> TYPE: PRT
<213> ORGANISM: Escherichia coli

<400> SEQUENCE: 458

Met Gly Leu Lys Leu His Ile His Trp Phe Asp Lys Lys Thr Glu Glu
1 5 10 15

Phe Lys Gly Gly Glu Tyr Ser Lys Asp Phe Gly Asp Asp Gly Ser Val
20 25 30

Ile Glu Ser Leu Gly Met Pro Leu Lys Asp Asn Ile Asn Asn Gly Trp
35 40 45

Phe Asp Val Glu Lys Pro Trp Val Ser Ile Leu Gln Pro His Phe Lys
50 55 60

Asn Val Ile Asp Ile Ser Lys Phe Asp Tyr Phe Val Ser Phe Val Tyr
65 70 75 80

Arg Asp Gly Asn Trp
85

<210> SEQ ID NO 459
<211> LENGTH: 258
<212> TYPE: DNA
<213> ORGANISM: Escherichia coli

<400> SEQUENCE: 459
atggggctta aattacatat tcattggttt gataagaaaa ccgaagagtt taaaggcggt 60
gaatactcaa aagacttcgg tgatgatggt tctgtcattg aaagtctggg gatgccttta 120
aaggataata ttaataatgg ttggtttgat gttgaaaaac catgggtttc gatattacag 180
ccacacttta aaaatgtaat cgatattagt aaatttgatt actttgtatc ctttgtttac 240
cgggatggta actggtaa 258

<210> SEQ ID NO 460
<211> LENGTH: 86
<212> TYPE: PRT
<213> ORGANISM: Escherichia coli

<400> SEQUENCE: 460

Met Glu Leu Lys His Ser Ile Ser Asp Tyr Thr Glu Ala Glu Phe Leu
1 5 10 15

Glu Phe Val Lys Lys Ile Cys Arg Ala Glu Gly Ala Thr Glu Glu Asp
20 25 30

Asp Asn Lys Leu Val Arg Glu Phe Glu Arg Leu Thr Glu His Pro Asp
35 40 45

Gly Ser Asp Leu Ile Tyr Tyr Pro Arg Asp Asp Arg Glu Asp Ser Pro
50 55 60

Glu Gly Ile Val Lys Glu Ile Lys Glu Trp Arg Ala Ala Asn Gly Lys
65 70 75 80

Ser Gly Phe Lys Gln Gly
85

<210> SEQ ID NO 461
<211> LENGTH: 261
<212> TYPE: DNA
<213> ORGANISM: Escherichia coli

<400> SEQUENCE: 461

```
atggaactga aacatagtat tagtgattat accgaggctg aatttctgga gtttgtaaaa     60
aaaatatgta gagctgaagg tgctactgaa gaggatgaca ataaattagt gagagagttt    120
gagcgattaa ctgagcaccc agatggttca gatctgattt attatcctcg cgatgacagg    180
gaagatagtc ctgaagggat tgtcaaggaa attaaagaat ggcgagctgc taacggtaag    240
tcaggattta aacagggctg a                                              261
```

<210> SEQ ID NO 462
<211> LENGTH: 178
<212> TYPE: PRT
<213> ORGANISM: Citrobacter freundii

<400> SEQUENCE: 462

```
Met Met Asn Glu His Ser Ile Asp Thr Asp Asn Arg Lys Ala Asn Asn
1               5                   10                  15

Ala Leu Tyr Leu Phe Ile Ile Ile Gly Leu Ile Pro Leu Leu Cys Ile
            20                  25                  30

Phe Val Val Tyr Tyr Lys Thr Pro Asp Ala Leu Leu Leu Arg Lys Ile
        35                  40                  45

Ala Thr Ser Thr Glu Asn Leu Pro Ser Ile Thr Ser Ser Tyr Asn Pro
    50                  55                  60

Leu Met Thr Lys Val Met Asp Ile Tyr Cys Lys Thr Ala Pro Phe Leu
65                  70                  75                  80

Ala Leu Ile Leu Tyr Ile Leu Thr Phe Lys Ile Arg Lys Leu Ile Asn
                85                  90                  95

Asn Thr Asp Arg Asn Thr Val Leu Arg Ser Cys Leu Leu Ser Pro Leu
            100                 105                 110

Val Tyr Ala Ala Ile Val Tyr Leu Phe Cys Phe Arg Asn Phe Glu Leu
        115                 120                 125

Thr Thr Ala Gly Arg Pro Val Arg Leu Met Ala Thr Asn Asp Ala Thr
    130                 135                 140

Leu Leu Leu Phe Tyr Ile Gly Leu Tyr Ser Ile Ile Phe Phe Thr Thr
145                 150                 155                 160

Tyr Ile Thr Leu Phe Thr Pro Val Thr Ala Phe Lys Leu Leu Lys Lys
                165                 170                 175

Arg Gln
```

<210> SEQ ID NO 463
<211> LENGTH: 537
<212> TYPE: DNA
<213> ORGANISM: Citrobacter freundii

<400> SEQUENCE: 463

```
atgatgaatg aacactcaat agatacggac aacagaaagg ccaataacgc attgtattta     60
tttataataa tcggattaat accattattg tgcatttttg ttgtttacta caaaacgcca    120
gacgctttac ttttacgtaa aattgctaca agcactgaga atctcccgtc aataacatcc    180
tcctacaacc cattaatgac aaaggttatg gatatttatt gtaaaacagc gcctttcctt    240
gccttaatac tatacatcct aacctttaaa atcagaaaat taatcaacaa caccgacagg    300
aacactgtac ttagatcttg tttattaagt ccattggtct atgcagcaat tgtttatcta    360
ttctgcttcc gaaattttga gttaacaaca gccggaaggc ctgtcagatt aatggccacc    420
```

```
aatgacgcaa cactattgtt attttatatt ggtctgtact caataatttt ctttacaacc    480

tatatcacgc tattcacacc agtcactgca tttaaattat taaaaaaaag gcagtaa       537


<210> SEQ ID NO 464
<211> LENGTH: 111
<212> TYPE: PRT
<213> ORGANISM: Escherichia coli

<400> SEQUENCE: 464

Met Asn Arg Lys Tyr Tyr Phe Asn Asn Met Trp Trp Gly Trp Val Thr
1               5                   10                  15

Gly Gly Tyr Met Leu Tyr Met Ser Trp Asp Tyr Glu Phe Lys Tyr Arg
            20                  25                  30

Leu Leu Phe Trp Cys Ile Ser Leu Cys Gly Met Val Leu Tyr Pro Val
        35                  40                  45

Ala Lys Trp Tyr Ile Glu Asp Thr Ala Leu Lys Phe Thr Arg Pro Asp
    50                  55                  60

Phe Trp Asn Ser Gly Phe Phe Ala Asp Thr Pro Gly Lys Met Gly Leu
65                  70                  75                  80

Leu Ala Val Tyr Thr Gly Thr Val Phe Ile Leu Ser Leu Pro Leu Ser
                85                  90                  95

Met Ile Tyr Ile Leu Ser Val Ile Ile Lys Arg Leu Ser Val Arg
            100                 105                 110


<210> SEQ ID NO 465
<211> LENGTH: 336
<212> TYPE: DNA
<213> ORGANISM: Escherichia coli

<400> SEQUENCE: 465

atgaacagaa aatattattt taataaatatg tggtggggat gggtgacggg gggatatatg     60

ctgtatatgt catgggatta tgagtttaaa tacagattac tgttctggtg tatttctctc    120

tgcggaatgg ttttgtatcc ggttgcaaaa tggtatattg aagatacagc tctaaaattt    180

acccggcctg atttctggaa cagcggtttt tttgctgata cacctggaaa aatggggttg    240

cttgcggttt atacgggtac tgttttcata ttatctcttc cgttaagtat gatatatatt    300

ctttctgtta ttataaaaag gctgtctgta agatag                              336


<210> SEQ ID NO 466
<211> LENGTH: 115
<212> TYPE: PRT
<213> ORGANISM: Escherichia coli

<400> SEQUENCE: 466

Met Lys Leu Asp Ile Ser Val Lys Tyr Leu Leu Lys Ser Leu Ile Pro
1               5                   10                  15

Ile Leu Ile Ile Leu Thr Val Phe Tyr Leu Gly Trp Lys Asp Asn Gln
            20                  25                  30

Glu Asn Ala Arg Met Phe Tyr Ala Phe Ile Gly Cys Ile Ile Ser Ala
        35                  40                  45

Ile Thr Phe Pro Phe Ser Met Arg Ile Ile Gln Lys Met Val Ile Arg
    50                  55                  60

Phe Thr Gly Lys Glu Phe Trp Gln Lys Asp Phe Phe Thr Asn Pro Val
65                  70                  75                  80

Gly Gly Ser Leu Thr Ala Ile Phe Glu Leu Phe Cys Phe Val Ile Ser
                85                  90                  95
```

```
Val Pro Val Val Ala Ile Tyr Leu Ile Phe Ile Leu Cys Lys Ala Leu
            100                 105                 110

Ser Gly Lys
        115


<210> SEQ ID NO 467
<211> LENGTH: 348
<212> TYPE: DNA
<213> ORGANISM: Escherichia coli

<400> SEQUENCE: 467

atgaaactgg atatatctgt aaagtattta ctgaaaagcc tgataccaat cctcattatt      60

cttacagttt tttatctggg atggaaagat aaccaggaaa atgcaagaat gttttatgcg     120

ttcatcggat gcattatcag tgccattact tttccttttt caatgaggat aatacagaaa     180

atggtaataa ggtttacagg gaaagaattc tggcaaaaag acttctttac aaatccagtt     240

ggcggaagct taactgcaat atttgaatta ttctgtttcg ttatatcagt tcctgtggtt     300

gccatttact taatttttat actctgcaaa gccctttcag gaaaatga                 348


<210> SEQ ID NO 468
<211> LENGTH: 131
<212> TYPE: PRT
<213> ORGANISM: Escherichia coli

<400> SEQUENCE: 468

Met His Asn Thr Leu Leu Glu Lys Ile Ile Ala Tyr Leu Ser Leu Pro
1               5                   10                  15

Gly Phe His Ser Leu Asn Asn Pro Pro Leu Ser Glu Ala Phe Asn Leu
            20                  25                  30

Tyr Val His Thr Ala Pro Leu Ala Ala Thr Ser Leu Phe Ile Phe Thr
        35                  40                  45

His Lys Glu Leu Glu Leu Lys Pro Lys Ser Ser Pro Leu Arg Ala Leu
    50                  55                  60

Lys Ile Leu Thr Pro Phe Thr Ile Leu Tyr Ile Ser Met Ile Tyr Cys
65                  70                  75                  80

Phe Leu Leu Thr Asp Thr Glu Leu Thr Leu Ser Ser Lys Thr Phe Val
                85                  90                  95

Leu Ile Val Lys Lys Arg Ser Val Phe Val Phe Phe Leu Tyr Asn Thr
            100                 105                 110

Ile Tyr Trp Asp Ile Tyr Ile His Ile Phe Val Leu Leu Val Pro Tyr
        115                 120                 125

Arg Asn Ile
    130


<210> SEQ ID NO 469
<211> LENGTH: 396
<212> TYPE: DNA
<213> ORGANISM: Escherichia coli

<400> SEQUENCE: 469

atgcacaata cactcctcga aaaaatcatc gcatacctat ccctaccagg atttcattca      60

ttaaacaacc cgcccctaag cgaagcattc aatctctatg ttcatacagc ccctttagct     120

gcaaccagct tattcatatt cacacacaaa gaattagagt taaaaccaaa gtcgtcacct     180

ctgcgggcac taaagatatt aactcctttc actattcttt atatatccat gatatactgt     240

ttcttgctaa ctgacacaga actaaccttg tcatcaaaaa catttgtatt aatagtcaaa     300
```

```
aaacgatctg tttttgtctt ttttctatat aacactatat attgggatat atatattcac    360

atatttgtac ttttggttcc ttataggaac atataa                              396


<210> SEQ ID NO 470
<211> LENGTH: 85
<212> TYPE: PRT
<213> ORGANISM: Escherichia coli

<400> SEQUENCE: 470

Met Glu Leu Lys Asn Ser Ile Ser Asp Tyr Thr Glu Thr Glu Phe Lys
1               5                   10                  15

Lys Ile Ile Glu Asp Ile Ile Asn Cys Glu Gly Asp Glu Lys Lys Gln
            20                  25                  30

Asp Asp Asn Leu Glu His Phe Ile Ser Val Thr Glu His Pro Ser Gly
        35                  40                  45

Ser Asp Leu Ile Tyr Tyr Pro Glu Gly Asn Asn Asp Gly Ser Pro Glu
    50                  55                  60

Ala Val Ile Lys Glu Ile Lys Glu Trp Arg Ala Ala Asn Gly Lys Ser
65                  70                  75                  80

Gly Phe Lys Gln Gly
                85


<210> SEQ ID NO 471
<211> LENGTH: 258
<212> TYPE: DNA
<213> ORGANISM: Escherichia coli

<400> SEQUENCE: 471

atggaactga aaaacagcat tagtgattac actgaaactg aattcaaaaa aattattgaa     60

gacatcatca attgtgaagg tgatgaaaaa aaacaggatg ataacctcga gcattttata    120

agtgttactg agcatcctag tggttctgat ctgatttatt acccagaagg taataatgat    180

ggtagccctg aagctgttat taaagagatt aaagaatggc gagctgctaa cggtaagtca    240

ggatttaaac agggctga                                                  258


<210> SEQ ID NO 472
<211> LENGTH: 98
<212> TYPE: PRT
<213> ORGANISM: Lactococcus lactis subsp. lactis

<400> SEQUENCE: 472

Met Lys Lys Lys Gln Ile Glu Phe Glu Asn Glu Leu Arg Ser Met Leu
1               5                   10                  15

Ala Thr Ala Leu Glu Lys Asp Ile Ser Gln Glu Glu Arg Asn Ala Leu
            20                  25                  30

Asn Ile Ala Glu Lys Ala Leu Asp Asn Ser Glu Tyr Leu Pro Lys Ile
        35                  40                  45

Ile Leu Asn Leu Arg Lys Ala Leu Thr Pro Leu Ala Ile Asn Arg Thr
    50                  55                  60

Leu Asn His Asp Leu Ser Glu Leu Tyr Lys Phe Ile Thr Ser Ser Lys
65                  70                  75                  80

Ala Ser Asn Lys Asn Leu Gly Gly Gly Leu Ile Met Ser Trp Gly Arg
                85                  90                  95

Leu Phe


<210> SEQ ID NO 473
```

<211> LENGTH: 297
<212> TYPE: DNA
<213> ORGANISM: Lactococcus lactis subsp. lactis

<400> SEQUENCE: 473

```
atgaaaaaaa aacaaataga atttgaaaac gagctaagaa gtatgttggc taccgccctt     60

gaaaaagaca ttagtcaaga ggaaagaaat gctctgaata ttgcagaaaa ggcgcttgac    120

aattctgaat atttaccaaa aattatttta aacctcagaa aagccctaac tccattagct    180

ataaatcgaa cacttaacca tgatttatct gaactgtata aattcattac aagttccaaa    240

gcatcaaaca aaaatttagg tggtggttta attatgtcgt ggggacgact attctaa       297
```

<210> SEQ ID NO 474
<211> LENGTH: 98
<212> TYPE: PRT
<213> ORGANISM: Lactococcus lactis subsp. cremoris

<400> SEQUENCE: 474

```
Met Lys Lys Lys Gln Ile Glu Phe Glu Asn Glu Leu Arg Ser Met Leu
1               5                   10                  15

Ala Thr Ala Leu Glu Lys Asp Ile Ser Gln Glu Glu Arg Asn Ala Leu
            20                  25                  30

Asn Ile Ala Glu Lys Ala Leu Asp Asn Ser Glu Tyr Leu Pro Lys Ile
        35                  40                  45

Ile Leu Asn Leu Arg Lys Ala Leu Thr Pro Leu Ala Ile Asn Arg Thr
    50                  55                  60

Leu Asn His Asp Leu Ser Glu Leu Tyr Lys Phe Ile Thr Ser Ser Lys
65                  70                  75                  80

Ala Ser Asn Lys Asn Leu Gly Gly Gly Leu Ile Met Ser Trp Gly Arg
                85                  90                  95

Leu Phe
```

<210> SEQ ID NO 475
<211> LENGTH: 297
<212> TYPE: DNA
<213> ORGANISM: Lactococcus lactis subsp. cremoris

<400> SEQUENCE: 475

```
atgaaaaaaa aacaaataga atttgaaaac gagctaagaa gtatgttggc taccgccctt     60

gaaaaagaca ttagtcaaga ggaaagaaat gctctgaata ttgcagaaaa ggcgcttgac    120

aattctgaat atttaccaaa aattatttta aacctcagaa aagccctaac tccattagct    180

ataaatcgaa cacttaacca tgatttatct gaactgtata aattcattac aagttccaaa    240

gcatcaaaca aaaatttagg tggtggttta attatgtcgt ggggacgact attctaa       297
```

<210> SEQ ID NO 476
<211> LENGTH: 87
<212> TYPE: PRT
<213> ORGANISM: Escherichia coli

<400> SEQUENCE: 476

```
Met Asn Lys Met Ala Met Ile Asp Leu Ala Lys Leu Phe Leu Ala Ser
1               5                   10                  15

Lys Ile Thr Ala Ile Glu Phe Ser Glu Arg Ile Cys Val Glu Arg Arg
            20                  25                  30

Arg Leu Tyr Gly Val Lys Asp Leu Ser Pro Asn Ile Leu Asn Cys Gly
        35                  40                  45
```

```
Glu Glu Leu Phe Met Ala Ala Glu Arg Phe Glu Pro Asp Ala Asp Arg
    50                  55                  60

Ala Asn Tyr Glu Ile Asp Asp Asn Gly Leu Lys Val Glu Val Arg Ser
65                  70                  75                  80

Ile Leu Glu Lys Phe Lys Leu
                85
```

<210> SEQ ID NO 477
<211> LENGTH: 249
<212> TYPE: DNA
<213> ORGANISM: Escherichia coli

<400> SEQUENCE: 477

```
atgatcgatt tggcgaaatt atttttagct tcgaaaatta cagtgattga gttttcagag     60

cgaatttgtg ttgaacggag aagattgtat ggtgttaagg atttgtctcc gaatatatta    120

aattgtgggg aagagttgtc tatggctgct gagcgatttg agcctgatgc agatagggct    180

aattatgaaa ttgatgataa tggacttaag gtcgaggtcc gatctatctt ggaaaaactt    240

aaatcataa                                                            249
```

<210> SEQ ID NO 478
<211> LENGTH: 83
<212> TYPE: PRT
<213> ORGANISM: Escherichia coli

<400> SEQUENCE: 478

```
Met Lys Leu Ser Pro Lys Ala Ala Ile Glu Val Cys Asn Glu Ala Ala
1               5                   10                  15

Lys Lys Gly Leu Trp Ile Leu Gly Ile Asp Gly Gly His Trp Leu Asn
            20                  25                  30

Pro Gly Phe Arg Ile Asp Ser Ser Ala Ser Trp Thr Tyr Asp Met Pro
        35                  40                  45

Glu Glu Tyr Lys Ser Lys Ile Pro Glu Asn Asn Arg Leu Ala Ile Glu
    50                  55                  60

Asn Ile Lys Asp Asp Ile Glu Asn Gly Tyr Thr Ala Phe Ile Ile Thr
65                  70                  75                  80

Leu Lys Met
```

<210> SEQ ID NO 479
<211> LENGTH: 243
<212> TYPE: DNA
<213> ORGANISM: Escherichia coli

<400> SEQUENCE: 479

```
atgaagttat caccaaaagc tgcaatagaa gtttgtaatg aagcagcgaa aaaaggctta     60

tggattttgg gcattgatgg tgggcattgg ctgaatcctg gattcaggat agatagttca    120

gcatcatgga catatgatat gccggagaat acaaatcaaa aatccctgaa aataatagat    180

tggctattga aaatattaaa gatgatattg agaatggata cactgctttc attatcacgt    240

taa                                                                  243
```

<210> SEQ ID NO 480
<211> LENGTH: 85
<212> TYPE: PRT
<213> ORGANISM: Escherichia coli

<400> SEQUENCE: 480

Met Gly Leu Lys Leu His Ile Asn Trp Phe Asp Lys Arg Thr Glu Glu
1 5 10 15

Phe Lys Gly Gly Glu Tyr Ser Lys Asp Phe Gly Asp Asp Gly Ser Val
20 25 30

Ile Glu Arg Leu Gly Met Pro Phe Lys Asp Asn Ile Asn Asn Gly Trp
35 40 45

Phe Asp Val Ile Ala Glu Trp Val Pro Leu Leu Gln Pro Tyr Phe Asn
50 55 60

His Gln Ile Asp Ile Ser Asp Asn Glu Tyr Phe Val Ser Phe Asp Tyr
65 70 75 80

Arg Asp Gly Asp Trp
85

<210> SEQ ID NO 481
<211> LENGTH: 258
<212> TYPE: DNA
<213> ORGANISM: Escherichia coli

<400> SEQUENCE: 481
atggggctta aattacatat taattggttt gataagacga ccgaggaatt taaaggtggt 60
gagtattcaa aagattttgg agatgatggc tcggtcattg aacgtcttgg aatgccttta 120
aaagataata tcaataatgg ttggtttgat gttatagctg aatgggtacc tttgctacaa 180
ccatacttta atcatcaaat tgatatttcc gataatgagt attttgtttc gtttgattat 240
cgtgatggtg attggtga 258

<210> SEQ ID NO 482
<211> LENGTH: 85
<212> TYPE: PRT
<213> ORGANISM: Escherichia coli

<400> SEQUENCE: 482

Met Glu Leu Lys Lys Ser Ile Gly Asp Tyr Thr Glu Thr Glu Phe Lys
1 5 10 15

Lys Ile Ile Glu Asn Ile Ile Asn Cys Glu Gly Asp Glu Lys Lys Gln
20 25 30

Asp Asp Asn Leu Glu His Phe Ile Ser Val Thr Glu His Pro Ser Gly
35 40 45

Ser Asp Leu Ile Tyr Tyr Pro Glu Gly Asn Asn Asp Gly Ser Pro Glu
50 55 60

Ala Val Ile Lys Glu Ile Lys Glu Trp Arg Ala Ala Asn Gly Lys Ser
65 70 75 80

Gly Phe Lys Gln Gly
85

<210> SEQ ID NO 483
<211> LENGTH: 258
<212> TYPE: DNA
<213> ORGANISM: Escherichia coli

<400> SEQUENCE: 483
gtggagctaa agaaaagtat tggtgattac actgaaaccg aattcaaaaa aattattgaa 60
aacatcatca attgtgaagg tgatgaaaaa aaacaggatg ataacctcga gcattttata 120
agtgttactg agcatcctag tggttctgat ctgatttatt acccagaagg taataatgat 180

```
ggtagccctg aagctgttat taaagagatt aaagaatggc gagctgctaa cggtaagtca    240

ggatttaaac agggctga                                                  258


<210> SEQ ID NO 484
<211> LENGTH: 86
<212> TYPE: PRT
<213> ORGANISM: Escherichia coli

<400> SEQUENCE: 484

Met Glu Leu Lys His Ser Ile Ser Asp Tyr Thr Glu Ala Glu Phe Leu
1               5                   10                  15

Gln Leu Val Thr Thr Ile Cys Asn Ala Asp Thr Ser Ser Glu Glu Glu
            20                  25                  30

Leu Val Lys Leu Val Thr His Phe Glu Glu Met Thr Glu His Pro Ser
        35                  40                  45

Gly Ser Asp Leu Ile Tyr Tyr Pro Lys Glu Gly Asp Asp Ser Pro
    50                  55                  60

Ser Gly Ile Val Asn Thr Val Lys Gln Trp Arg Ala Ala Asn Gly Lys
65                  70                  75                  80

Ser Gly Phe Lys Gln Gly
                85


<210> SEQ ID NO 485
<211> LENGTH: 261
<212> TYPE: DNA
<213> ORGANISM: Escherichia coli

<400> SEQUENCE: 485

atggaactga agcatagcat tagtgattat acagaagctg aatttttaca acttgtaaca     60

acaatttgta atgcgaacac ttccagtgaa gaagaactgg ttaaattggt tacacacttt    120

gaggaaatga ctgagcaccc tagtggtagt gatttaatat attacccaaa agaaggtgat    180

gatgactcac cttcaggtat tgtaaacaca gtaaaacaat ggcgagccgc taacggtaag    240

tcaggattta aacagggcta a                                              261


<210> SEQ ID NO 486
<211> LENGTH: 141
<212> TYPE: PRT
<213> ORGANISM: Escherichia coli

<400> SEQUENCE: 486

Met Leu Thr Leu Tyr Gly Tyr Ile Arg Asn Val Phe Leu Tyr Arg Met
1               5                   10                  15

Asn Asp Arg Ser Cys Gly Asp Phe Met Lys Val Ile Ser Met Lys Phe
            20                  25                  30

Ile Phe Ile Leu Thr Ile Ile Ala Leu Ala Ala Val Phe Phe Trp Ser
        35                  40                  45

Glu Asp Lys Gly Pro Ala Cys Tyr Gln Val Ser Asp Glu Gln Ala Arg
    50                  55                  60

Thr Phe Val Lys Asn Asp Tyr Leu Gln Arg Met Lys Arg Trp Asp Asn
65                  70                  75                  80

Asp Val Gln Leu Leu Gly Thr Glu Ile Pro Lys Ile Thr Trp Glu Lys
                85                  90                  95

Ile Glu Arg Ser Leu Thr Asp Val Glu Asp Glu Lys Thr Leu Leu Val
            100                 105                 110

Pro Phe Lys Ala Glu Gly Pro Asp Gly Lys Arg Met Tyr Tyr Gly Met
        115                 120                 125
```

```
Tyr His Cys Glu Glu Gly Tyr Val Glu Tyr Ala Asn Asp
    130                 135                 140


<210> SEQ ID NO 487
<211> LENGTH: 354
<212> TYPE: DNA
<213> ORGANISM: Escherichia coli

<400> SEQUENCE: 487

atgaaagtaa ttagcatgaa atttattttt attttaacga ttattgctct tgctgctgtt      60

tttttctggt ctgaagataa aggtccggca tgctatcagg tcagcgatga acaggccaga     120

acgtttgtaa aaaatgatta cctgcaaaga atgaaacgct gggacaacga tgtacaactt     180

cttggtacag aaatcccgaa aattacatgg gaaaagattg agagaagttt aacagatgtt     240

gaagatgaaa aaacacttct tgtcccattt aaagctgaag gcccggacgg taagagaatg     300

tattatggca tgtaccattg tgaggaggga tatgttgaat atgcgaatga ctaa           354


<210> SEQ ID NO 488
<211> LENGTH: 175
<212> TYPE: PRT
<213> ORGANISM: Escherichia coli

<400> SEQUENCE: 488

Met Thr Ser Asn Lys Asp Lys Asn Lys Lys Ala Asn Glu Ile Leu Tyr
1               5                   10                  15

Ala Phe Ser Ile Ile Gly Ile Ile Pro Leu Met Ala Ile Leu Ile Leu
            20                  25                  30

Arg Ile Asn Asp Pro Tyr Ser Gln Val Leu Tyr Tyr Leu Tyr Asn Lys
        35                  40                  45

Val Ala Phe Leu Pro Ser Ile Thr Ser Leu His Asp Pro Val Met Thr
    50                  55                  60

Thr Leu Met Ser Asn Tyr Asn Lys Thr Ala Pro Val Met Gly Ile Leu
65                  70                  75                  80

Val Phe Leu Cys Thr Tyr Lys Thr Arg Glu Ile Ile Lys Pro Val Thr
                85                  90                  95

Arg Lys Leu Val Val Gln Ser Cys Phe Trp Gly Pro Val Phe Tyr Ala
            100                 105                 110

Ile Leu Ile Tyr Ile Thr Leu Phe Tyr Asn Leu Glu Leu Thr Thr Ala
        115                 120                 125

Gly Gly Phe Phe Lys Leu Leu Ser His Asn Val Ile Thr Leu Phe Ile
    130                 135                 140

Leu Tyr Cys Ser Ile Tyr Phe Thr Val Leu Thr Met Thr Tyr Ala Ile
145                 150                 155                 160

Leu Leu Met Pro Leu Leu Val Ile Lys Tyr Phe Lys Gly Arg Gln
                165                 170                 175


<210> SEQ ID NO 489
<211> LENGTH: 528
<212> TYPE: DNA
<213> ORGANISM: Escherichia coli

<400> SEQUENCE: 489

atgaccagca ataaagataa gaacaagaaa gcaaacgaaa tattatatgc attttccata      60

atcgggatta ttccattaat ggctatatta atacttcgaa taaatgatcc atattctcaa     120

gtgctgtact acttatataa taaggtggca tttctccctt ctattacatc attgcatgat     180
```

```
cccgtcatga caacacttat gtcaaactac aacaagacag cgccagttat gggtattctc    240

gtttttcttt gcacatataa gacaagagaa atcataaagc cagtaacaag aaaacttgtt    300

gtgcaatcct gtttctgggg gcccgttttt tatgccattc tgatttatat cacactgttc    360

tataatctgg aactaacaac agcaggtggt ttttttaaat tattatctca taatgtcatc    420

actctgttta ttttatattg ctccatttac tttactgttt taaccatgac atatgcgatt    480

ttactgatgc cattacttgt cattaaatat tttaaaggga ggcagtaa                 528


<210> SEQ ID NO 490
<211> LENGTH: 78
<212> TYPE: PRT
<213> ORGANISM: Escherichia coli

<400> SEQUENCE: 490

Met Asp Arg Lys Arg Thr Lys Leu Glu Leu Leu Phe Ala Phe Ile Ile
1               5                   10                  15

Asn Ala Thr Ala Ile Tyr Ile Ala Leu Ala Ile Tyr Asp Cys Val Phe
            20                  25                  30

Arg Gly Lys Asp Phe Leu Ser Met His Thr Phe Cys Phe Ser Ala Leu
        35                  40                  45

Met Ser Ala Ile Cys Tyr Phe Val Gly Asp Asn Tyr Tyr Ser Ile Ser
    50                  55                  60

Asp Lys Ile Lys Arg Arg Ser Tyr Glu Asn Ser Asp Ser Lys
65                  70                  75


<210> SEQ ID NO 491
<211> LENGTH: 237
<212> TYPE: DNA
<213> ORGANISM: Escherichia coli

<400> SEQUENCE: 491

atggatagaa aaagaacaaa attagagttg ttatttgcat ttataataaa tgccaccgca     60

atatatattg cattagctat atatgattgt gtttttagag gaaaggactt tttatccatg    120

catacatttt gcttctctgc attaatgtct gcaatatgtt actttgttgg tgataattat    180

tattcaatat ccgataagat aaaaaggaga tcatatgaga actctgactc taaatga       237


<210> SEQ ID NO 492
<211> LENGTH: 113
<212> TYPE: PRT
<213> ORGANISM: Shigella sonnei

<400> SEQUENCE: 492

Met Ser Leu Arg Tyr Tyr Ile Lys Asn Ile Leu Phe Gly Leu Tyr Cys
1               5                   10                  15

Ala Leu Ile Tyr Ile Tyr Leu Ile Thr Lys Asn Asn Glu Gly Tyr Tyr
            20                  25                  30

Phe Leu Ala Ser Asp Lys Met Leu Tyr Ala Ile Val Ile Ser Thr Ile
        35                  40                  45

Leu Cys Pro Tyr Ser Lys Tyr Ala Ile Glu His Ile Phe Phe Lys Phe
    50                  55                  60

Ile Lys Lys Asp Phe Phe Arg Lys Arg Lys Asn Leu Asn Lys Cys Pro
65                  70                  75                  80

Arg Gly Lys Ile Lys Pro Tyr Leu Cys Val Tyr Asn Leu Leu Cys Leu
                85                  90                  95
```

```
Val Leu Ala Ile Pro Phe Gly Leu Leu Gly Leu Val Tyr Ile Asn Lys
            100                 105                 110

Glu


<210> SEQ ID NO 493
<211> LENGTH: 342
<212> TYPE: DNA
<213> ORGANISM: Shigella sonnei

<400> SEQUENCE: 493

atgagtttaa gatactacat aaaaaatatt ttgtttggcc tatactgcgc acttatatat     60

atatacctta taacaaaaaa caacgaaggg tattatttcc tagcgtcaga taagatgcta    120

tacgcaatag tgataagcac tattctatgc ccatattcaa aatatgctat tgaacacata    180

tttttaagt tcataaagaa agattttttc agaaaaagaa aaaacctaaa taaatgcccc    240

cgtggcaaaa ttaaaccgta tttatgcgta tacaatctac tttgtttggt cctagcaatc    300

ccatttggat tgctaggact tgtttatatc aataaagaat aa                       342


<210> SEQ ID NO 494
<211> LENGTH: 113
<212> TYPE: PRT
<213> ORGANISM: Escherichia coli

<400> SEQUENCE: 494

Met Ser Leu Arg Tyr Tyr Ile Lys Asn Ile Leu Phe Gly Leu Tyr Cys
1               5                   10                  15

Thr Leu Ile Tyr Ile Tyr Leu Ile Thr Lys Asn Ser Glu Glu Tyr Tyr
            20                  25                  30

Phe Leu Val Thr Asp Lys Met Leu Tyr Ala Ile Val Ile Ser Thr Ile
        35                  40                  45

Leu Cys Pro Tyr Ser Lys Tyr Ala Ile Glu His Ile Ala Phe Asn Phe
    50                  55                  60

Ile Lys Lys His Phe Phe Glu Arg Arg Lys Asn Leu Asn Asn Ala Pro
65                  70                  75                  80

Val Ala Lys Leu Asn Leu Phe Met Leu Tyr Asn Leu Leu Cys Leu Val
                85                  90                  95

Leu Ala Ile Pro Phe Gly Leu Leu Gly Leu Phe Ile Ser Ile Lys Asn
            100                 105                 110

Asn


<210> SEQ ID NO 495
<211> LENGTH: 342
<212> TYPE: DNA
<213> ORGANISM: Escherichia coli

<400> SEQUENCE: 495

atgagcttaa gatactacat aaaaaatatt ttatttggcc tgtactgcac acttatatat     60

atatacctta taacaaaaaa cagcgaagag tattatttcc ttgtgacaga taagatgcta    120

tatgcaatag tgataagcac tattctatgt ccatattcaa aatatgctat tgaacacata    180

gcttttaact tcataaagaa acattttttc gaaagaagaa aaaacctaaa taacgccccc    240

gtagcaaaat taaacctatt tatgctatat aatctacttt gtttggtcct agcaatccca    300

tttggattgc taggactttt tatatcaata aagaataatt aa                       342


<210> SEQ ID NO 496
```

```
<211> LENGTH: 113
<212> TYPE: PRT
<213> ORGANISM: Leuconostoc gelidum

<400> SEQUENCE: 496

Met Arg Lys Asn Asn Ile Leu Leu Asp Asp Ala Lys Ile Tyr Thr Asn
1               5                   10                  15

Lys Leu Tyr Leu Leu Leu Ile Asp Arg Lys Asp Asp Ala Gly Tyr Gly
            20                  25                  30

Asp Ile Cys Asp Val Leu Phe Gln Val Ser Lys Lys Leu Asp Ser Thr
        35                  40                  45

Lys Asn Val Glu Ala Leu Ile Asn Arg Leu Val Asn Tyr Ile Arg Ile
    50                  55                  60

Thr Ala Ser Thr Asn Arg Ile Lys Phe Ser Lys Asp Glu Glu Ala Val
65                  70                  75                  80

Ile Ile Glu Leu Gly Val Ile Gly Gln Lys Ala Gly Leu Asn Gly Gln
                85                  90                  95

Tyr Met Ala Asp Phe Ser Asp Lys Ser Gln Phe Tyr Ser Ile Phe Glu
            100                 105                 110

Arg


<210> SEQ ID NO 497
<211> LENGTH: 342
<212> TYPE: DNA
<213> ORGANISM: Leuconostoc gelidum

<400> SEQUENCE: 497

ttgagaaaaa ataacatttt attggacgat gctaaaatat acacgaacaa actctatttg     60

ctattaatcg atagaaaaga tgacgctggg tatggagata tttgtgatgt tttgtttcag    120

gtatccaaaa aattagatag cacaaaaaat gtagaagcat tgattaaccg attggtcaat    180

tatatacgaa ttaccgcttc aacaaacaga attaagtttt caaaagatga agaggctgta    240

attatagaac ttggtgtaat tggtcagaag gctggattaa acggccaata catggctgat    300

ttttctgaca aatctcagtt ttatagtatc tttgaaagat aa                       342


<210> SEQ ID NO 498
<211> LENGTH: 91
<212> TYPE: PRT
<213> ORGANISM: Lactococcus lactis subsp. cremoris

<400> SEQUENCE: 498

Met Lys Lys Lys Val Asp Thr Glu Lys Gln Ile Thr Ser Trp Ala Ser
1               5                   10                  15

Asp Leu Ala Ser Lys Asn Glu Thr Lys Val Gln Glu Lys Leu Ile Leu
            20                  25                  30

Ser Ser Tyr Ile Gln Asp Ile Glu Asn His Val Tyr Phe Pro Lys Ala
        35                  40                  45

Met Ile Ser Leu Glu Lys Lys Leu Arg Asp Gln Asn Asn Ile Cys Ala
    50                  55                  60

Leu Ser Lys Glu Val Asn Gln Phe Tyr Phe Lys Val Val Glu Val Asn
65                  70                  75                  80

Gln Arg Lys Ser Trp Met Val Gly Leu Ile Val
                85                  90


<210> SEQ ID NO 499
<211> LENGTH: 276
<212> TYPE: DNA
```

<213> ORGANISM: Lactococcus lactis subsp. cremoris

<400> SEQUENCE: 499

```
atgaaaaaaa aagttgatac agaaaaacaa attacttctt gggcatctga cttagcttcc     60

aaaaatgaaa caaaggttca agaaaaatta atactgtctt cttatattca ggacatcgaa    120

aaccatgttt actttccaaa agcaatgatt tctttagaaa aaaaattacg agaccaaaat    180

aatatttgcg ctttatcaaa agaagtcaat cagttttatt ttaaagttgt tgaagtaaat    240

caaagaaaat cctggatggt aggtttgata gtttaa                              276
```

<210> SEQ ID NO 500
<211> LENGTH: 112
<212> TYPE: PRT
<213> ORGANISM: Pediococcus acidilactici

<400> SEQUENCE: 500

```
Met Asn Lys Thr Lys Ser Glu His Ile Lys Gln Gln Ala Leu Asp Leu
1               5                   10                  15

Phe Thr Arg Leu Gln Phe Leu Leu Gln Lys His Asp Thr Ile Glu Pro
            20                  25                  30

Tyr Gln Tyr Val Leu Asp Ile Leu Glu Thr Gly Ile Ser Lys Thr Lys
        35                  40                  45

His Asn Gln Gln Thr Pro Glu Arg Gln Ala Arg Val Val Tyr Asn Lys
    50                  55                  60

Ile Ala Ser Gln Ala Leu Val Asp Lys Leu His Phe Thr Ala Glu Glu
65                  70                  75                  80

Asn Lys Val Leu Ala Ala Ile Asn Glu Leu Ala His Ser Gln Lys Gly
                85                  90                  95

Trp Gly Glu Phe Asn Met Leu Asp Thr Thr Asn Thr Trp Pro Ser Gln
            100                 105                 110
```

<210> SEQ ID NO 501
<211> LENGTH: 339
<212> TYPE: DNA
<213> ORGANISM: Pediococcus acidilactici

<400> SEQUENCE: 501

```
atgaataaga ctaagtcgga acatattaaa caacaagctt tggacttatt tactaggcta     60

cagtttttac tacagaagca cgatactatc gaaccttacc agtacgtttt agatattctg    120

gagactggta tcagtaaaac taaacataac cagcaaacgc ctgaacgaca agctcgtgta    180

gtctacaaca agattgccag ccaagcgtta gtagataagt tacattttac tgccgaagaa    240

aacaaagttc tagcagccat caatgaattg gcgcattctc aaaaagggtg gggcgagttt    300

aacatgctag atactaccaa tacgtggcct agccaatag                           339
```

<210> SEQ ID NO 502
<211> LENGTH: 88
<212> TYPE: PRT
<213> ORGANISM: Carnobacterium maltaromaticum

<400> SEQUENCE: 502

```
Met Ile Lys Asp Glu Lys Ile Asn Lys Ile Tyr Ala Leu Val Lys Ser
1               5                   10                  15

Ala Leu Asp Asn Thr Asp Val Lys Asn Asp Lys Lys Leu Ser Leu Leu
            20                  25                  30

Leu Met Arg Ile Gln Glu Thr Ser Ile Asn Gly Glu Leu Phe Tyr Asp
        35                  40                  45
```

```
Tyr Lys Lys Glu Leu Gln Pro Ala Ile Ser Met Tyr Ser Ile Gln His
    50                  55                  60

Asn Phe Arg Val Pro Asp Asp Leu Val Lys Leu Leu Ala Leu Val Gln
65                  70                  75                  80

Thr Pro Lys Ala Trp Ser Gly Phe
                85
```

<210> SEQ ID NO 503
<211> LENGTH: 267
<212> TYPE: DNA
<213> ORGANISM: Carnobacterium maltaromaticum

<400> SEQUENCE: 503

```
atgataaaag atgaaaaaat aaataaaatc tatgctttag ttaagagcgc acttgataat     60

acggatgtta agaatgataa aaaactttct ttacttctta tgagaataca agaaacatca    120

attaatggag aactatttta cgattataaa aaagaattac agccagctat tagtatgtac    180

tctattcaac ataactttcg ggttcctgac gatctagtaa aactgttagc attagttcaa    240

acacctaaag cttggtcagg gttttaa                                        267
```

<210> SEQ ID NO 504
<211> LENGTH: 111
<212> TYPE: PRT
<213> ORGANISM: Carnobacterium maltaromaticum

<400> SEQUENCE: 504

```
Met Asp Ile Lys Ser Gln Thr Leu Tyr Leu Asn Leu Ser Glu Ala Tyr
1               5                   10                  15

Lys Asp Pro Glu Val Lys Ala Asn Glu Phe Leu Ser Lys Leu Val Val
            20                  25                  30

Gln Cys Ala Gly Lys Leu Thr Ala Ser Asn Ser Glu Asn Ser Tyr Ile
        35                  40                  45

Glu Val Ile Ser Leu Leu Ser Arg Gly Ile Ser Ser Tyr Tyr Leu Ser
    50                  55                  60

His Lys Arg Ile Ile Pro Ser Ser Met Leu Thr Ile Tyr Thr Gln Ile
65                  70                  75                  80

Gln Lys Asp Ile Lys Asn Gly Asn Ile Asp Thr Glu Lys Leu Arg Lys
                85                  90                  95

Tyr Glu Ile Ala Lys Gly Leu Met Ser Val Pro Tyr Ile Tyr Phe
            100                 105                 110
```

<210> SEQ ID NO 505
<211> LENGTH: 336
<212> TYPE: DNA
<213> ORGANISM: Carnobacterium maltaromaticum

<400> SEQUENCE: 505

```
atggatataa agtctcaaac attatatttg aatctaagcg aggcatataa agaccctgaa     60

gtaaaagcta atgaattctt atcaaaatta gttgtacaat gtgctgggaa attaacagct    120

tcaaacagtg agaacagtta tattgaagta atatcattgc tatctagggg tatttctagt    180

tattatttat cccataaacg tataattcct tcaagtatgt taactatata tactcaaata    240

caaaaggata taaaaaacgg gaatattgac accgaaaaat taaggaaata tgagatagca    300

aaaggattaa tgtccgttcc ttatatatat ttctaa                              336
```

<210> SEQ ID NO 506

<211> LENGTH: 245
<212> TYPE: PRT
<213> ORGANISM: Lactococcus lactis subsp. lactis

<400> SEQUENCE: 506

```
Met Arg Arg Tyr Leu Ile Leu Ile Val Ala Leu Ile Gly Ile Thr Gly
1               5                   10                  15

Leu Ser Gly Cys Tyr Gln Thr Ser His Lys Lys Val Arg Phe Asp Glu
            20                  25                  30

Gly Ser Tyr Thr Asn Phe Ile Tyr Asp Asn Lys Ser Tyr Phe Val Thr
        35                  40                  45

Asp Lys Glu Ile Pro Gln Glu Asn Val Asn Asn Ser Lys Val Lys Phe
    50                  55                  60

Tyr Lys Leu Leu Ile Val Asp Met Lys Ser Glu Lys Leu Leu Ser Ser
65                  70                  75                  80

Ser Asn Lys Asn Ser Val Thr Leu Val Leu Asn Asn Ile Tyr Glu Ala
                85                  90                  95

Ser Asp Lys Ser Leu Cys Met Gly Ile Asn Asp Arg Tyr Tyr Lys Ile
            100                 105                 110

Leu Pro Glu Ser Asp Lys Gly Ala Val Lys Ala Leu Arg Leu Gln Asn
        115                 120                 125

Phe Asp Val Thr Ser Asp Ile Ser Asp Asp Asn Phe Val Ile Asp Lys
    130                 135                 140

Asn Asp Ser Arg Lys Ile Asp Tyr Met Gly Asn Ile Tyr Ser Ile Ser
145                 150                 155                 160

Asp Thr Thr Val Ser Asp Glu Glu Leu Gly Glu Tyr Gln Asp Val Leu
                165                 170                 175

Ala Glu Val Arg Val Phe Asp Ser Val Ser Gly Lys Ser Ile Pro Arg
            180                 185                 190

Ser Glu Trp Gly Arg Ile Asp Lys Asp Gly Ser Asn Ser Lys Gln Ser
        195                 200                 205

Arg Thr Glu Trp Asp Tyr Gly Glu Ile His Ser Ile Arg Gly Lys Ser
    210                 215                 220

Leu Thr Glu Ala Phe Ala Val Glu Ile Asn Asp Asp Phe Lys Leu Ala
225                 230                 235                 240

Thr Lys Val Gly Asn
                245
```

<210> SEQ ID NO 507
<211> LENGTH: 738
<212> TYPE: DNA
<213> ORGANISM: Lactococcus lactis subsp. lactis

<400> SEQUENCE: 507

```
atgagaagat atttaatact tattgtggcc ttaataggga taacaggttt atcagggtgt     60

tatcaaacaa gtcataaaaa ggtgaggttt gacgaaggaa gttatactaa ttttatttat    120

gataataaat cgtatttcgt aactgataag gagattcctc aggagaacgt taacaattcc    180

aaagtaaaat tttataagct gttgattgtt gacatgaaaa gtgagaaact tttatcaagt    240

agcaacaaaa atagtgtgac tttggtctta aataatattt atgaggcttc tgacaagtcg    300

ctatgtatgg gtattaacga cagatactat aagatacttc cagaaagtga taagggggcg    360

gtcaaagctt tgagattaca aaactttgat gtgacaagcg atatttctga tgataatttt    420

gttattgata aaaatgattc acgaaaaatt gactatatgg gaaatattta cagtatatcg    480

gacaccaccg tatctgatga agaattggga gaatatcagg atgttttagc tgaagtacgt    540
```

```
gtgtttgatt cagttagtgg caaaagtatc ccgaggtctg aatgggggag aattgataag    600

gatggttcaa attccaaaca gagtaggacg gaatgggatt atggcgaaat ccattctatt    660

agaggaaaat ctcttactga agcatttgcc gttgagataa atgatgattt taagcttgca    720

acgaaggtag gaaactag                                                  738
```

<210> SEQ ID NO 508
<211> LENGTH: 261
<212> TYPE: PRT
<213> ORGANISM: Rhizobium leguminosarum bv. trifolii

<400> SEQUENCE: 508

```
Met Asn Asp Glu Ile Cys Leu Thr Gly Gly Gly Arg Thr Thr Val Thr
1               5                   10                  15

Arg Arg Gly Gly Val Val Tyr Arg Glu Gly Gly Pro Trp Ser Ser Thr
            20                  25                  30

Val Ile Ser Leu Leu Arg His Leu Glu Ala Ser Gly Phe Ala Glu Ala
        35                  40                  45

Pro Ser Val Val Gly Thr Gly Phe Asp Glu Arg Gly Arg Glu Thr Leu
    50                  55                  60

Ser Phe Ile Glu Gly Glu Phe Val His Pro Gly Pro Trp Ser Glu Glu
65                  70                  75                  80

Ala Phe Pro Gln Phe Gly Met Met Leu Arg Arg Leu His Asp Ala Thr
                85                  90                  95

Ala Ser Phe Lys Pro Pro Glu Asn Ser Met Trp Arg Asp Trp Phe Gly
            100                 105                 110

Arg Asn Leu Gly Glu Gly Gln His Val Ile Gly His Cys Asp Thr Gly
        115                 120                 125

Pro Trp Asn Ile Val Cys Arg Ser Gly Leu Pro Val Gly Leu Ile Asp
    130                 135                 140

Trp Glu Val Ala Gly Pro Val Arg Ala Asp Ile Glu Leu Ala Gln Ala
145                 150                 155                 160

Cys Trp Leu Asn Ala Gln Leu Tyr Asp Asp Asp Ile Ala Glu Arg Val
                165                 170                 175

Gly Leu Gly Ser Val Thr Met Arg Ala His Gln Val Arg Leu Leu Leu
            180                 185                 190

Asp Gly Tyr Gly Leu Ser Arg Lys Gln Arg Gly Gly Phe Val Asp Lys
        195                 200                 205

Leu Ile Thr Phe Ala Val His Asp Ala Ala Glu Gln Ala Lys Glu Ala
    210                 215                 220

Ala Val Thr Pro Glu Ser Asn Asp Ala Glu Pro Leu Trp Ala Ile Ala
225                 230                 235                 240

Trp Arg Thr Arg Ser Ala Ser Trp Met Leu His His Arg Gln Thr Leu
                245                 250                 255

Glu Ala Ala Leu Ala
            260
```

<210> SEQ ID NO 509
<211> LENGTH: 786
<212> TYPE: DNA
<213> ORGANISM: Rhizobium leguminosarum bv. trifolii

<400> SEQUENCE: 509

```
atgaatgatg agatttgcct gacaggtggc ggacgaacga ctgtcacgcg gcgcggcgga     60

gtcgtgtatc gcgaaggcgg cccgtggtca tcaaccgtca tttcgctcct gcggcatctg    120
```

```
gaagcctctg gcttcgctga agctccttcc gttgtcggca ccggtttcga tgagcgcggc    180

cgggagacat tatcgtttat cgagggtgag tttgttcacc caggcccttg gtcggaggag    240

gcttttccgc aatttggaat gatgttgcgg cgactgcacg atgccaccgc ctcgttcaaa    300

cctcccgaaa actcgatgtg gcgcgattgg ttcgggcgta acctcggtga gggtcaacac    360

gtaataggac actgcgacac aggcccatgg aacattgttt gccggtcagg attgcctgtc    420

gggttgatag attgggaggt ggctgggcct gtcagggcgg atatcgaatt ggcccaggct    480

tgttggctga atgcccagct ctacgatgac gacattgcgg agagggtcgg attaggctct    540

gtgaccatga gagcgcatca agttcgcctg ctgcttgacg gctatggtct gtctcggaag    600

caacgcggcg gcttcgtcga caagctaatc acgttcgcag ttcacgatgc ggccgagcag    660

gcgaaagagg cggctgtcac gccagagtcg aacgatgcgg aaccgctatg ggcaattgcc    720

tggcgcacta gaagtgcctc ctggatgctc catcatcggc aaacactgga agcagcgctg    780

gcatag                                                               786
```

<210> SEQ ID NO 510
<211> LENGTH: 436
<212> TYPE: PRT
<213> ORGANISM: Bacillus subtilis

<400> SEQUENCE: 510

```
Met Asn Asn Ile Ile Pro Ile Met Ser Leu Leu Phe Lys Gln Leu Tyr
1               5                   10                  15

Ser Arg Gln Gly Lys Lys Asp Ala Ile Arg Ile Ala Ala Gly Leu Val
            20                  25                  30

Ile Leu Ala Val Phe Glu Ile Gly Leu Ile Arg Gln Ala Gly Ile Asp
        35                  40                  45

Glu Ser Val Leu Arg Lys Thr Tyr Ile Ile Leu Ala Leu Leu Leu Met
    50                  55                  60

Asn Thr Tyr Met Val Phe Leu Ser Val Thr Ser Gln Trp Lys Glu Ser
65                  70                  75                  80

Tyr Met Lys Leu Ser Cys Leu Leu Pro Ile Ser Ser Arg Ser Phe Trp
                85                  90                  95

Leu Ala Gln Ser Val Val Leu Phe Val Asp Thr Cys Leu Arg Arg Thr
            100                 105                 110

Leu Phe Phe Phe Ile Leu Pro Leu Phe Leu Phe Gly Asn Gly Thr Leu
        115                 120                 125

Ser Gly Ala Gln Thr Leu Phe Trp Leu Gly Arg Phe Ser Phe Phe Thr
    130                 135                 140

Val Tyr Ser Ile Ile Phe Gly Val Val Leu Ser Asn His Phe Val Lys
145                 150                 155                 160

Lys Lys Asn Leu Met Phe Leu Leu His Ala Ala Ile Phe Ala Cys Val
                165                 170                 175

Cys Ile Ser Ala Ala Leu Met Pro Ala Ala Thr Ile Pro Leu Cys Ala
            180                 185                 190

Val His Ile Leu Trp Ala Val Val Ile Asp Phe Pro Val Phe Leu Gln
        195                 200                 205

Ala Pro Pro Gln Gln Gly Lys Met His Ser Phe Met Arg Arg Ser Glu
    210                 215                 220

Phe Ser Phe Tyr Lys Arg Glu Trp Asn Arg Phe Ile Ser Ser Lys Ala
225                 230                 235                 240
```

```
Met Leu Leu Asn Tyr Ala Val Met Ala Val Phe Ser Gly Phe Phe Ser
                245                 250                 255

Phe Gln Met Met Asn Thr Gly Ile Phe Asn Gln Gln Val Ile Tyr Ile
            260                 265                 270

Val Ile Ser Ala Leu Leu Leu Ile Cys Ser Pro Ile Ala Leu Leu Tyr
        275                 280                 285

Ser Ile Glu Lys Asn Asp Arg Met Leu Leu Ile Thr Leu Pro Ile Lys
    290                 295                 300

Arg Lys Thr Met Phe Trp Ala Lys Tyr Arg Phe Tyr Ser Gly Leu Leu
305                 310                 315                 320

Ala Gly Gly Phe Leu Leu Val Val Met Ile Val Gly Phe Ile Ser Gly
                325                 330                 335

Arg Ser Ile Ser Val Leu Thr Phe Leu Gln Cys Ile Glu Leu Leu Leu
            340                 345                 350

Ala Gly Ala Tyr Ile Arg Leu Thr Ala Asp Glu Lys Arg Pro Ser Phe
        355                 360                 365

Ser Trp Gln Thr Glu Gln Gln Leu Trp Ser Gly Phe Ser Lys Tyr Arg
    370                 375                 380

Ser Tyr Leu Phe Cys Leu Pro Leu Phe Leu Ala Ile Leu Ala Gly Thr
385                 390                 395                 400

Ala Val Ser Leu Ala Val Ile Pro Ile Ala Gly Leu Val Ile Val Tyr
                405                 410                 415

Tyr Leu Gln Lys Gln Asp Gly Gly Phe Phe Asp Thr Ser Lys Arg Glu
            420                 425                 430

Arg Leu Gly Ser
        435
```

<210> SEQ ID NO 511
<211> LENGTH: 1000
<212> TYPE: DNA
<213> ORGANISM: Bacillus subtilis

<400> SEQUENCE: 511

```
atgaataaca taatccctat catgtctttg ctgttcaaac agctttacag ccggcaaggg     60

aaaaaggacg ccatccgcat tgccgcaggc cttgtcattc tggccgtgtt tgaaatcggg    120

ctgatccgcc aggccggcat tgatgaatcg gtgttgcgca aaacgtatat catactcgcg    180

cttcttttga tgaacacata tatggtgttt ctttccgtga catcacaatg gaaggaatct    240

tatatgaagc tgagctgcct gctgccgatt tcttcacgga gcttttggct cgcccagagt    300

gtcgttttgt ttgtcgatac ctgtttgaga agaactttat tctttttat tttaccgctg     360

ttcttatttg gaaacggaac gctgtcaggg gcgcaaacat tgttttggct cggcaggttt    420

tcgtttttta ccgtttactc cattattttc ggagttgtgc taagcaacca cttcgtcaaa    480

aagaagaact tgatgtttct gctgcatgcg gcgatattcg cctgtgtatg tatcagcgcc    540

gctttgatgc cggccgccac gattccgctt tgcgcggttc atatcctgtg ggcggtggtc    600

attgactttc ctgtctttct gcaggcgcct ccgcagcagg gcaagatgca ttcatttatg    660

cggcgatctg aattttcgtt ttacaaaaga gaatggaacc gatttatctc ttctaaagcg    720

atgctgttaa attacgcggt aatggcggta ttcagcggct tcttttcgtt ccagatgatg    780

aacaccggca tcttcaatca gcaagtgatt tatatcgtga tttccgcgct tttgctcatc    840

tgctcgccga tcgccctttt gtattcgatt gaaaaaaatg accggatgct gctcatcacg    900
```

```
cttccgatca agcgaaaaac gatgttttgg gcgaaatatc gcttttattc aggcctattg    960

gcaggcggat ttctccttgt cgtgatgatt gtgggtttca                          1000


<210> SEQ ID NO 512
<211> LENGTH: 239
<212> TYPE: PRT
<213> ORGANISM: Bacillus subtilis

<400> SEQUENCE: 512

Met Ser Ile Leu Asp Ile His Asp Val Ser Val Trp Tyr Glu Arg Asp
1               5                   10                  15

Asn Val Ile Leu Glu Gln Val Asp Leu His Leu Glu Lys Gly Ala Val
            20                  25                  30

Tyr Gly Leu Leu Gly Val Asn Gly Ala Gly Lys Thr Thr Leu Ile Asn
        35                  40                  45

Thr Leu Thr Gly Val Asn Arg Asn Phe Ser Gly Arg Phe Thr Leu Cys
    50                  55                  60

Gly Ile Glu Ala Glu Ala Gly Met Pro Gln Lys Thr Ser Asp Gln Leu
65                  70                  75                  80

Lys Thr His Arg Tyr Phe Ala Ala Asp Tyr Pro Leu Leu Phe Thr Glu
                85                  90                  95

Ile Thr Ala Lys Asp Tyr Val Ser Phe Val His Ser Leu Tyr Gln Lys
            100                 105                 110

Asp Phe Ser Glu Gln Gln Phe Ala Ser Leu Ala Glu Ala Phe His Phe
        115                 120                 125

Ser Lys Tyr Ile Asn Arg Arg Ile Ser Glu Leu Ser Leu Gly Asn Arg
    130                 135                 140

Gln Lys Val Val Leu Met Thr Gly Leu Leu Leu Arg Ala Pro Leu Phe
145                 150                 155                 160

Ile Leu Asp Glu Pro Leu Val Gly Leu Asp Val Glu Ser Ile Glu Val
                165                 170                 175

Phe Tyr Gln Lys Met Arg Glu Tyr Cys Glu Ala Gly Gly Thr Ile Leu
            180                 185                 190

Phe Ser Ser His Leu Leu Asp Val Val Gln Arg Phe Cys Asp Tyr Ala
        195                 200                 205

Ala Ile Leu His Asn Lys Gln Ile Gln Lys Val Ile Pro Ile Gly Glu
    210                 215                 220

Glu Thr Asp Leu Arg Arg Glu Phe Phe Glu Val Ile Gly His Glu
225                 230                 235


<210> SEQ ID NO 513
<211> LENGTH: 716
<212> TYPE: DNA
<213> ORGANISM: Bacillus subtilis

<400> SEQUENCE: 513

gcattttgga tatacacgat gtatccgttt ggtatgaacg ggacaacgtc atcttagagc     60

acgtggactt acacttagaa aaaggcgccg tttacggatt gcttggggta aacggtgccg    120

gcaaaacaac actgatcaat acgctgacag gagtgaaccg caattacagc gggggcttta    180

cgctgtgcgg cattgaagct gaggccggca tgccgcagaa aacatcagat caactgaaga    240

ttcaccgtta cttcgccgct gattatccgc tgctgtttac agaaattacg gcgaaggact    300

atgtgtcttt cgtccattcg ctttatcaaa aggatttttc agagcgacag tttgccagtt    360

tggctgaggc ctttcatttt tcaaaataca tcaacaggag aatctcggag ctgtccttgg    420
```

```
ggaacaggca aaaggttgtg ttgatgacag gattattgct gcgggctccc ctgtttattt    480

tggatgagcc gctcgtcggt ttggatgtgg aatcaataga ggtcttttat cagaaaatgc    540

gggagtactg tgaggaaggc ggaaccattt tgttttcttc ccatctgctc gatgtcgtgc    600

agagattttg tgattttgcg gccattctgc acaacaaaca gatccaaaag gtcattccga    660

ttggggagga gaccgatctg cggcgggaat tttttgaggt tatcggccat gaataa        716


<210> SEQ ID NO 514
<211> LENGTH: 53
<212> TYPE: PRT
<213> ORGANISM: Bacillus subtilis

<400> SEQUENCE: 514

Met Ser Pro Ala Gln Arg Arg Ile Leu Leu Tyr Ile Leu Ser Phe Ile
1               5                   10                  15

Phe Val Ile Gly Ala Val Val Tyr Phe Val Lys Ser Asp Tyr Leu Phe
            20                  25                  30

Thr Leu Ile Phe Ile Ala Ile Ala Ile Leu Phe Gly Met Arg Ala Arg
        35                  40                  45

Lys Ala Asp Ser Arg
    50


<210> SEQ ID NO 515
<211> LENGTH: 162
<212> TYPE: DNA
<213> ORGANISM: Bacillus subtilis

<400> SEQUENCE: 515

ttgtcaccag cacaaagaag aattttactg tatatccttt catttatctt tgtcatcggc     60

gcagtcgtct attttgtcaa aagcgattat ctgtttacgc tgattttcat tgccattgcc    120

attctgttcg ggatgcgcgc gcggaaggct gactcgcgat ga                       162


<210> SEQ ID NO 516
<211> LENGTH: 87
<212> TYPE: PRT
<213> ORGANISM: Escherichia coli

<400> SEQUENCE: 516

Met Glu Leu Lys Asn Ser Ile Ser Asp Tyr Thr Glu Ala Glu Phe Val
1               5                   10                  15

Gln Leu Leu Lys Glu Ile Glu Lys Glu Asn Val Ala Ala Thr Asp Asp
            20                  25                  30

Val Leu Asp Val Leu Leu Glu His Phe Val Lys Ile Thr Glu His Pro
        35                  40                  45

Asp Gly Thr Asp Leu Ile Tyr Tyr Pro Ser Asp Asn Arg Asp Asp Ser
    50                  55                  60

Pro Glu Gly Ile Val Lys Glu Ile Lys Glu Trp Arg Ala Ala Asn Gly
65                  70                  75                  80

Lys Pro Gly Phe Lys Gln Gly
                85


<210> SEQ ID NO 517
<211> LENGTH: 264
<212> TYPE: DNA
<213> ORGANISM: Escherichia coli
```

<400> SEQUENCE: 517
atggaactga aaaatagtat tagtgattac acagaggctg agtttgttca acttcttaag 60
gaaattgaaa aagagaatgt tgctgcaact gatgatgtgt tagatgtgtt actcgaacac 120
tttgtaaaaa ttactgagca tccagatgga acggatctga tttattatcc tagtgataat 180
agagacgata gccccgaagg gattgtcaag gaaattaaag aatggcgagc tgctaacggt 240
aagccaggat ttaaacaggg ctga 264

<210> SEQ ID NO 518
<211> LENGTH: 87
<212> TYPE: PRT
<213> ORGANISM: Pseudomonas aeruginosa

<400> SEQUENCE: 518

Met Lys Ser Lys Ile Ser Glu Tyr Thr Glu Lys Glu Phe Leu Glu Phe
1               5                   10                  15

Val Glu Asp Ile Tyr Thr Asn Asn Lys Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

Leu Pro Gly Phe Lys Ala Gly
                85

<210> SEQ ID NO 519
<211> LENGTH: 264
<212> TYPE: DNA
<213> ORGANISM: Pseudomonas aeruginosa

<400> SEQUENCE: 519
atgaagtcca agatttccga atatacggaa aaagagtttc ttgagtttgt tgaagacata 60
tacacaaaca ataagaaaaa gttccctacc gaggagtctc atattcaagc cgtgcttgaa 120
tttaaaaaac taacggaaca cccaagcggc tcagaccttc tttactaccc caacgaaaat 180
agagaagata gcccagctgg agttgtaaag gaagttaaag aatggcgtgc ttccaagggg 240
cttcctggct ttaaggccgg ttag 264

<210> SEQ ID NO 520
<211> LENGTH: 87
<212> TYPE: PRT
<213> ORGANISM: Pseudomonas aeruginosa

<400> SEQUENCE: 520

Met Lys Ser Lys Ile Ser Glu Tyr Thr Glu Lys Glu Phe Leu Glu Phe
1               5                   10                  15

Val Lys Asp Ile Tyr Thr Asn Asn Lys Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

```
Leu Pro Gly Phe Lys Ala Gly
                85


<210> SEQ ID NO 521
<211> LENGTH: 264
<212> TYPE: DNA
<213> ORGANISM: Pseudomonas aeruginosa

<400> SEQUENCE: 521

atgaagtcca agatttccga atatacggaa aaagagtttc ttgagtttgt taaagacata     60

tacacaaaca ataagaaaaa gttccctacc gaggagtctc atattcaagc cgtgcttgaa    120

tttaaaaaac taacggaaca cccaagcggc tcagaccttc tttactaccc caacgaaaat    180

agagaagata gcccagctgg agttgtaaag gaagttaaag aatggcgtgc ttccaagggg    240

cttcctggct ttaaggccgg ttag                                           264


<210> SEQ ID NO 522
<211> LENGTH: 95
<212> TYPE: PRT
<213> ORGANISM: Enterococcus hirae

<400> SEQUENCE: 522

Met Asp Phe Thr Lys Glu Glu Lys Leu Leu Asn Ala Ile Ser Lys Val
1               5                   10                  15

Tyr Asn Glu Ala Thr Ile Asp Asp Tyr Pro Asp Leu Lys Glu Lys Leu
            20                  25                  30

Phe Leu Tyr Ser Lys Glu Ile Ser Glu Gly Lys Ser Val Gly Glu Val
        35                  40                  45

Ser Met Lys Leu Ser Ser Phe Leu Gly Arg Tyr Ile Leu Lys His Lys
    50                  55                  60

Phe Gly Leu Pro Lys Ser Leu Ile Glu Leu Gln Glu Ile Val Ser Lys
65                  70                  75                  80

Glu Ser Gln Val Tyr Arg Gly Trp Ala Ser Ile Gly Ile Trp Ser
                85                  90                  95


<210> SEQ ID NO 523
<211> LENGTH: 288
<212> TYPE: DNA
<213> ORGANISM: Enterococcus hirae

<400> SEQUENCE: 523

atggatttta ctaaagaaga aaaactttta aatgcaatta gtaaagtata caatgaagca     60

actatagatg actatcctga cttaaaagaa aagctctttc tttattctaa agaaatcagt    120

gagggaaaaa gtgttggtga agttagtatg aaattaagta gttttcttgg aagatatatt    180

ttaaaacata aatttggatt acctaaatct ttaatagaat tacaagaaat tgttagtaag    240

gaatctcaag tatatagagg atgggcttct attggtattt ggagttaa                 288


<210> SEQ ID NO 524
<211> LENGTH: 113
<212> TYPE: PRT
<213> ORGANISM: Leuconostoc mesenteroides

<400> SEQUENCE: 524

Met Lys Lys Lys Tyr Arg Tyr Leu Glu Asp Ser Lys Asn Tyr Thr Ser
1               5                   10                  15

Thr Leu Tyr Ser Leu Leu Val Asp Asn Val Asp Lys Pro Gly Tyr Ser
            20                  25                  30
```

```
Asp Ile Cys Asp Val Leu Leu Gln Val Ser Lys Lys Leu Asp Asn Thr
        35                  40                  45

Gln Ser Val Glu Ala Leu Ile Asn Arg Leu Val Asn Tyr Ile Arg Ile
    50                  55                  60

Thr Ala Ser Thr Tyr Lys Ile Ile Phe Ser Lys Lys Glu Glu Glu Leu
65                  70                  75                  80

Ile Ile Lys Leu Gly Val Ile Gly Gln Lys Ala Gly Leu Asn Gly Gln
                85                  90                  95

Tyr Met Ala Asp Phe Ser Asp Lys Ser Gln Phe Tyr Ser Val Phe Asp
            100                 105                 110

Gln


<210> SEQ ID NO 525
<211> LENGTH: 342
<212> TYPE: DNA
<213> ORGANISM: Leuconostoc mesenteroides

<400> SEQUENCE: 525

ttgaaaaaaa agtatcggta tttagaagat agcaaaaatt acactagtac actctattct     60

ctgttagttg ataatgttga caaacctgga tactcagata tttgcgatgt tttgcttcaa    120

gtttctaaga agttggataa tactcaaagt gttgaagcgc taattaatcg attggttaat    180

tatattcgta ttactgcttc aacatacaaa attatttttt caaaaaaaga agaggaattg    240

attataaaac ttggtgttat tggacaaaaa gctggactta atggtcagta tatggctgat    300

ttttcagaca agtctcagtt ttacagcgtt ttcgatcagt aa                       342


<210> SEQ ID NO 526
<211> LENGTH: 93
<212> TYPE: PRT
<213> ORGANISM: Escherichia coli

<400> SEQUENCE: 526

Met Ser Phe Leu Asn Phe Ala Phe Ser Pro Val Phe Phe Ser Ile Met
1               5                   10                  15

Ala Cys Tyr Phe Ile Val Trp Arg Asn Lys Arg Asn Glu Phe Val Cys
            20                  25                  30

Asn Arg Leu Leu Ser Ile Ile Ile Ile Ser Phe Leu Ile Cys Phe Ile
        35                  40                  45

Tyr Pro Trp Leu Asn Tyr Lys Ile Glu Val Lys Tyr Tyr Ile Phe Glu
    50                  55                  60

Gln Phe Tyr Leu Phe Cys Phe Leu Ser Ser Leu Val Ala Val Val Ile
65                  70                  75                  80

Asn Leu Ile Val Tyr Phe Ile Leu Tyr Arg Arg Cys Ile
                85                  90


<210> SEQ ID NO 527
<211> LENGTH: 282
<212> TYPE: DNA
<213> ORGANISM: Escherichia coli

<400> SEQUENCE: 527

atgagttttc ttaattttgc attttctcct gtattcttct ccattatggc gtgttatttc     60

attgtatgga gaaataaacg aaacgaattt gtctgcaata gattgctatc aattataata    120

atatcttttt tgatatgctt catatatcca tggctaaatt acaaaatcga agttaaatat    180
```

```
tatatatttg aacagtttta tcttttttgt tttttatcgt cactcgtggc tgttgtaata    240

aacctaattg tatactttat attatacagg agatgtatat ga                       282


<210> SEQ ID NO 528
<211> LENGTH: 96
<212> TYPE: PRT
<213> ORGANISM: Escherichia coli

<400> SEQUENCE: 528

Met His Leu Lys Tyr Tyr Leu His Asn Leu Pro Glu Ser Leu Ile Pro
1               5                   10                  15

Trp Ile Leu Ile Leu Ile Phe Asn Asp Asn Asp Asn Thr Pro Leu Leu
            20                  25                  30

Phe Ile Phe Ile Ser Ser Ile His Val Leu Leu Tyr Pro Tyr Ser Lys
        35                  40                  45

Leu Thr Ile Ser Arg Tyr Ile Lys Glu Asn Thr Lys Leu Lys Lys Glu
    50                  55                  60

Pro Trp Tyr Leu Cys Lys Leu Ser Ala Leu Phe Tyr Leu Leu Met Ala
65                  70                  75                  80

Ile Pro Val Gly Leu Pro Ser Phe Ile Tyr Tyr Thr Leu Lys Arg Asn
                85                  90                  95


<210> SEQ ID NO 529
<211> LENGTH: 291
<212> TYPE: DNA
<213> ORGANISM: Escherichia coli

<400> SEQUENCE: 529

atgcatttaa aatactacct acataattta cctgaatcac ttataccatg gattcttatt     60

ttaatattta acgacaatga taacactcct ttgttattta tatttatatc atcaatacat    120

gtattgctat atccatactc taaattaacc atatctagat atatcaaaga aaatacaaag    180

ttaaaaaaag aaccctggta cttatgcaag ttatctgcat tgttttattt attaatggca    240

atcccagtag gattgccaag tttcatatat tacactctaa agagaaatta a             291


<210> SEQ ID NO 530
<211> LENGTH: 344
<212> TYPE: PRT
<213> ORGANISM: Escherichia coli

<400> SEQUENCE: 530

Met Met Ile Gln Ser His Pro Leu Leu Ala Ala Pro Leu Ala Val Gly
1               5                   10                  15

Asp Thr Ile Gly Phe Phe Ser Ser Ser Ala Pro Ala Thr Val Thr Ala
            20                  25                  30

Lys Asn Arg Phe Phe Arg Gly Val Glu Phe Leu Gln Arg Lys Gly Phe
        35                  40                  45

Lys Leu Val Ser Gly Lys Leu Thr Gly Lys Thr Asp Phe Tyr Arg Ser
    50                  55                  60

Gly Thr Ile Lys Glu Arg Ala Gln Glu Phe Asn Glu Leu Val Tyr Asn
65                  70                  75                  80

Pro Asp Ile Thr Cys Ile Met Ser Thr Ile Gly Gly Asp Asn Ser Asn
                85                  90                  95

Ser Leu Leu Pro Phe Leu Asp Tyr Asp Ala Ile Ile Ala Asn Pro Lys
            100                 105                 110
```

```
Ile Ile Ile Gly Tyr Ser Asp Thr Thr Ala Leu Leu Ala Gly Ile Tyr
        115                 120                 125

Ala Lys Thr Gly Leu Ile Thr Phe Tyr Gly Pro Ala Leu Ile Pro Ser
    130                 135                 140

Phe Gly Glu His Pro Pro Leu Val Asp Ile Thr Tyr Glu Ser Phe Ile
145                 150                 155                 160

Lys Ile Leu Thr Arg Lys Gln Ser Gly Ile Tyr Thr Tyr Thr Leu Pro
                165                 170                 175

Glu Lys Trp Ser Asp Glu Ser Ile Asn Trp Asn Glu Asn Lys Ile Leu
            180                 185                 190

Arg Pro Lys Lys Leu Tyr Lys Asn Asn Cys Ala Phe Tyr Gly Ser Gly
        195                 200                 205

Lys Val Glu Gly Arg Val Ile Gly Gly Asn Leu Asn Thr Leu Thr Gly
    210                 215                 220

Ile Trp Gly Ser Glu Trp Met Pro Glu Ile Leu Asn Gly Asp Ile Leu
225                 230                 235                 240

Phe Ile Glu Asp Ser Arg Lys Ser Ile Ala Thr Ile Glu Arg Leu Phe
                245                 250                 255

Ser Met Leu Lys Leu Asn Arg Val Phe Asp Lys Val Ser Ala Ile Ile
            260                 265                 270

Leu Gly Lys His Glu Leu Phe Asp Cys Ala Gly Ser Lys Arg Arg Pro
        275                 280                 285

Tyr Glu Val Leu Thr Glu Val Leu Asp Gly Lys Gln Ile Pro Val Leu
    290                 295                 300

Asp Gly Phe Asp Cys Ser His Thr His Pro Met Leu Thr Leu Pro Leu
305                 310                 315                 320

Gly Val Lys Leu Ala Ile Asp Phe Asp Asn Lys Asn Ile Ser Ile Thr
                325                 330                 335

Glu Gln Tyr Leu Ser Thr Glu Lys
            340
```

<210> SEQ ID NO 531
<211> LENGTH: 1000
<212> TYPE: DNA
<213> ORGANISM: Escherichia coli

<400> SEQUENCE: 531

```
atgatgatac aatctcatcc actactggcc gctcccctgg cagtaggaga tacaattggt      60

ttcttttcat catctgctcc ggcaacagtt actgcaaaaa atcgtttttt tcggggagtt     120

gagtttcttc agagaaaggg atttaagctg gtatcaggga agcttaccgg taaaacagat     180

ttttatcgtt caggtactat taaagaaaga gctcaagaat ttaatgagtt agtctacaat     240

cctgatatta cctgtataat gtcaacgatc ggtggagata acagtaattc actactaccg     300

tttctggact atgatgctat cattgcaaac cccaaaatta tcataggtta ctcagataca     360

actgctttat tagcaggaat atatgcaaaa acagggttaa taacattcta tggaccagct     420

cttattcctt cgtttggtga acatccacct cttgtggata taacatatga atcatttatt     480

aaaatactaa caagaaaaca atcaggaata tatacctaca cattacctga aaagtggagt     540

gatgagagca taaactggaa tgaaaacaag atattaaggc ctaagaagct atataaaaac     600

aactgtgcct tttatggttc cggaaaagtt gaggggcgtg taattggagg aaatctaaat     660

actttgacag gtatatgggg gagtgaatgg atgcctgaaa ttcttaatgg agatatattg     720

tttattgagg acagtcggaa aagcattgca acaattgaac gattattctc tatgctaaag     780
```

```
cttaatcgcg tgtttgataa agttagtgca ataatactcg ggaaacatga gctttttgat     840

tgtgcaggaa gtaaacgcag accatatgaa gtattaacag aggtattaga tgggaaacag     900

attcctgtac tggatggatt tgattgttca catacacatc caatgctaac tcttccactt     960

ggtgtaaaat tagctattga ctttgacaac aaaaatatat                          1000


<210> SEQ ID NO 532
<211> LENGTH: 90
<212> TYPE: PRT
<213> ORGANISM: Lactobacillus sakei

<400> SEQUENCE: 532

Met Lys Ala Asp Tyr Lys Lys Ile Asn Ser Ile Leu Thr Tyr Thr Ser
1               5                   10                  15

Thr Ala Leu Lys Asn Pro Lys Ile Ile Lys Asp Lys Asp Leu Val Val
            20                  25                  30

Leu Leu Thr Ile Ile Gln Glu Glu Ala Lys Gln Asn Arg Ile Phe Tyr
        35                  40                  45

Asp Tyr Lys Arg Lys Phe Arg Pro Ala Val Thr Arg Phe Thr Ile Asp
    50                  55                  60

Asn Asn Phe Glu Ile Pro Asp Cys Leu Val Lys Leu Leu Ser Ala Val
65                  70                  75                  80

Glu Thr Pro Lys Ala Trp Ser Gly Phe Ser
                85                  90


<210> SEQ ID NO 533
<211> LENGTH: 268
<212> TYPE: DNA
<213> ORGANISM: Lactobacillus sakei

<400> SEQUENCE: 533

ggcagattat aaaaaaataa attcaatact aacttacaca tctactgctt taaaaaaccc      60

taaaattata aaagataaag atttagtagt ccttctaact attattcaag aagaagccaa     120

acaaaataga atcttttatg attataaaag aaaatttcgt ccagcggtta ctcgctttac     180

aattgataat aattttgaga ttcctgattg tttggttaaa ctactgtcag ctgttgaaac     240

acctaaggcg tggtctggat ttagttag                                        268


<210> SEQ ID NO 534
<211> LENGTH: 83
<212> TYPE: PRT
<213> ORGANISM: Escherichia coli

<400> SEQUENCE: 534

Met Lys Leu Ser Pro Lys Ala Ala Ile Glu Val Cys Asn Glu Ala Ala
1               5                   10                  15

Lys Lys Gly Leu Trp Ile Leu Gly Ile Asp Gly Gly His Trp Leu Asn
            20                  25                  30

Pro Gly Phe Arg Ile Asp Ser Ser Ala Ser Trp Thr Tyr Asp Met Pro
        35                  40                  45

Glu Glu Tyr Lys Ser Lys Thr Pro Glu Asn Asn Arg Leu Ala Ile Glu
    50                  55                  60

Asn Ile Lys Asp Asp Ile Glu Asn Gly Tyr Thr Ala Phe Ile Ile Thr
65                  70                  75                  80

Leu Lys Met
```

<210> SEQ ID NO 535
<211> LENGTH: 251
<212> TYPE: DNA
<213> ORGANISM: Escherichia coli

<400> SEQUENCE: 535

```
tgaagttatc accaaaagct gcaatagaag tttgtaatga agcagcgaaa aaaggcttat     60

ggattttggg cattgatggt gggcattggc tgaatcctgg attcaggata gatagttcag    120

catcatggac atatgatatg ccggaggaat acaaatcaaa aacccctgaa aataatagat    180

tggctattga aaatattaaa gatgatattg agaatggata cactgctttc attatcacgt    240

taaagatgta a                                                         251
```

<210> SEQ ID NO 536
<211> LENGTH: 436
<212> TYPE: PRT
<213> ORGANISM: Bacillus subtilis

<400> SEQUENCE: 536

```
Met Asn Asn Ile Phe Pro Ile Met Ser Leu Leu Phe Lys Gln Leu Tyr
1               5                   10                  15

Ser Arg Gln Gly Lys Lys Asp Ala Ile Arg Ile Ala Ala Gly Leu Val
            20                  25                  30

Ile Leu Ala Val Phe Glu Ile Gly Leu Ile Arg Gln Ala Gly Ile Asp
        35                  40                  45

Glu Ser Val Leu Gly Lys Thr Tyr Ile Ile Leu Ala Leu Leu Leu Met
    50                  55                  60

Asn Thr Tyr Met Val Phe Leu Ser Val Thr Ser Gln Trp Lys Glu Ser
65                  70                  75                  80

Tyr Met Lys Leu Ser Cys Leu Leu Pro Ile Ser Ser Arg Ser Phe Trp
                85                  90                  95

Leu Ala Gln Ser Val Val Leu Phe Val Asp Thr Cys Leu Arg Arg Thr
            100                 105                 110

Leu Phe Phe Phe Ile Leu Pro Leu Phe Leu Phe Gly Asn Gly Thr Leu
        115                 120                 125

Ser Gly Ala Gln Thr Leu Phe Trp Leu Gly Arg Phe Ser Phe Phe Thr
    130                 135                 140

Val Tyr Ser Ile Leu Phe Gly Val Met Leu Ser Asn His Phe Val Lys
145                 150                 155                 160

Lys Lys Asn Ser Met Phe Leu Leu His Ala Ala Val Phe Ala Phe Val
                165                 170                 175

Cys Leu Ser Ala Ala Phe Met Pro Ala Val Thr Ile Pro Leu Cys Ala
            180                 185                 190

Val His Met Leu Trp Ala Val Ile Ile Asp Phe Pro Val Phe Leu Gln
        195                 200                 205

Ala Pro Pro His Gln Ser Lys Met His Phe Phe Met Arg Arg Ser Glu
    210                 215                 220

Phe Ser Phe Tyr Lys Arg Glu Trp Asn Arg Phe Ile Ser Ser Lys Ala
225                 230                 235                 240

Met Leu Leu Asn Tyr Val Val Met Ala Ala Phe Ser Gly Phe Phe Ser
                245                 250                 255

Phe Gln Met Met Asn Thr Gly Ile Phe Asn Gln Gln Val Ile Tyr Ile
            260                 265                 270

Val Ile Ser Ala Leu Leu Leu Ile Cys Ser Pro Ile Ala Leu Leu Tyr
        275                 280                 285
```

```
Ser Ile Glu Lys Asn Asp Arg Met Leu Leu Ile Thr Leu Pro Ile Lys
    290                 295                 300

Arg Arg Thr Met Phe Trp Ala Lys Tyr Arg Phe Tyr Ser Gly Leu Leu
305                 310                 315                 320

Ala Gly Gly Phe Leu Leu Val Ala Ile Ile Val Gly Phe Ile Ser Gly
                325                 330                 335

Arg Pro Ile Ser Ala Leu Thr Phe Val Gln Cys Met Glu Leu Leu Leu
            340                 345                 350

Ala Gly Ala Phe Ile Arg Leu Thr Ala Asp Glu Lys Arg Pro Ser Phe
        355                 360                 365

Gly Trp Gln Thr Glu Gln Gln Leu Trp Ser Gly Phe Ser Lys Tyr Arg
    370                 375                 380

Ser Tyr Leu Phe Cys Leu Pro Leu Phe Leu Ala Thr Leu Ala Gly Thr
385                 390                 395                 400

Ala Val Ser Leu Ala Val Ile Pro Ile Ala Ala Leu Ile Ile Val Tyr
                405                 410                 415

Tyr Leu Gln Lys Gln Asp Gly Gly Phe Phe Asp Thr Ser Lys Arg Glu
            420                 425                 430

Arg Ile Gly Ser
        435
```

<210> SEQ ID NO 537
<211> LENGTH: 1000
<212> TYPE: DNA
<213> ORGANISM: Bacillus subtilis

<400> SEQUENCE: 537

```
ttggggagga gaccgatctg cggcgggaat tttttgaggt tatcggccat gaataacata     60

ttccccatca tgtcgttgct gttcaaacag ctgtacagcc ggcaagggaa aaaggacgct    120

atccgcattg ctgcagggct tgtgattctc gccgtgtttg aaatcgggct gatccgacaa    180

gccggcattg acgaatcggt gttgggaaaa acgtatatca tattggcgct tctcttaatg    240

aacacgtata tggtgtttct ttccgtgaca tcacaatgga aggaatctta tatgaagctg    300

agctgtctgc tgccgatttc atcacggagc ttttggctcg cccagagtgt cgttctgttt    360

gtcgatacct gtttgagaag aacgttattc ttttttattt taccgctgtt cttatttgga    420

aacggaacgc tgtcaggggc gcaaacattg ttttggcttg gcagattttc gttttttacc    480

gtttactcga ttctattcgg agttatgcta agcaaccatt tcgtcaaaaa gaagaactcg    540

atgtttctgc tgcatgcggc ggtattcgcc tttgtatgcc tcagtgccgc ttttatgccg    600

gccgtcacga tcccgctatg cgcggttcac atgctatggg cggtgatcat tgactttccg    660

gtctttctgc aggcgcctcc gcatcagagc aagatgcatt tttttatgcg gcgatctgaa    720

ttttcgtttt acaaaagaga atggaaccga tttatttctt ctaaagcgat gctgttaaat    780

tacgtggtga tggcggcgtt cagcggattc ttttcgttcc agatgatgaa cactggcatc    840

ttcaatcagc aagtgattta tattgtgatt tccgctctat tgctgatttg ctcgccgatc    900

gccctttgt actctattga aaaaaacgat cgcatgctgc tcatcacgct tccaattaaa    960

agaagaacga tgttttgggc gaaatatcgc ttttattcag                          1000
```

<210> SEQ ID NO 538
<211> LENGTH: 580
<212> TYPE: PRT
<213> ORGANISM: Escherichia coli

<400> SEQUENCE: 538

```
Met Glu Arg Lys Gln Lys Asn Ser Leu Phe Asn Tyr Ile Tyr Ser Leu
1               5                   10                  15

Met Asp Val Arg Gly Lys Phe Leu Phe Phe Ser Met Leu Phe Ile Thr
            20                  25                  30

Ser Leu Ser Ser Ile Ile Ile Ser Ile Ser Pro Leu Ile Leu Ala Lys
        35                  40                  45

Ile Thr Asp Leu Leu Ser Gly Ser Leu Ser Asn Phe Ser Tyr Glu Tyr
    50                  55                  60

Leu Val Leu Leu Ala Cys Leu Tyr Met Phe Cys Val Ile Ser Asn Lys
65                  70                  75                  80

Ala Ser Val Phe Leu Phe Met Ile Leu Gln Ser Ser Leu Arg Ile Asn
                85                  90                  95

Met Gln Lys Lys Met Ser Leu Lys Tyr Leu Arg Glu Leu Tyr Asn Glu
            100                 105                 110

Asn Ile Thr Asn Leu Ser Lys Asn Asn Ala Gly Tyr Thr Thr Gln Ser
        115                 120                 125

Leu Asn Gln Ala Ser Asn Asp Ile Tyr Ile Leu Val Arg Asn Val Ser
    130                 135                 140

Gln Asn Ile Leu Ser Pro Val Ile Gln Leu Ile Ser Thr Ile Val Val
145                 150                 155                 160

Val Leu Ser Thr Lys Asp Trp Phe Ser Ala Gly Val Phe Phe Leu Tyr
                165                 170                 175

Ile Leu Val Phe Val Ile Phe Asn Thr Arg Leu Thr Gly Ser Leu Ala
            180                 185                 190

Ser Leu Arg Lys His Ser Met Asp Ile Thr Leu Asn Ser Tyr Ser Leu
        195                 200                 205

Leu Ser Asp Thr Val Asp Asn Met Ile Ala Ala Lys Lys Asn Asn Ala
    210                 215                 220

Leu Arg Leu Ile Ser Glu Arg Tyr Glu Asp Ala Leu Thr Gln Glu Asn
225                 230                 235                 240

Asn Ala Gln Lys Lys Tyr Trp Leu Leu Ser Ser Lys Val Leu Leu Leu
                245                 250                 255

Asn Ser Leu Leu Ala Val Ile Leu Phe Gly Ser Val Phe Ile Tyr Asn
            260                 265                 270

Ile Leu Gly Val Leu Asn Gly Val Val Ser Ile Gly His Phe Ile Met
        275                 280                 285

Ile Thr Ser Tyr Ile Ile Leu Leu Ser Thr Pro Val Glu Asn Ile Gly
    290                 295                 300

Ala Leu Leu Ser Glu Ile Arg Gln Ser Met Ser Ser Leu Ala Gly Phe
305                 310                 315                 320

Ile Gln Arg His Ala Glu Asn Lys Ala Thr Ser Pro Ser Ile Pro Phe
                325                 330                 335

Leu Asn Met Glu Arg Lys Leu Asn Leu Ser Ile Arg Glu Leu Ser Phe
            340                 345                 350

Ser Tyr Ser Asp Asp Lys Lys Ile Leu Asn Ser Val Ser Leu Asp Leu
        355                 360                 365

Phe Thr Gly Lys Met Tyr Ser Leu Thr Gly Pro Ser Gly Ser Gly Lys
    370                 375                 380

Ser Thr Leu Val Lys Ile Ile Ser Gly Tyr Tyr Lys Asn Tyr Phe Gly
385                 390                 395                 400
```

```
Asp Ile Tyr Leu Asn Asp Ile Ser Leu Arg Asn Ile Ser Asp Glu Asp
                405                 410                 415

Leu Asn Asp Ala Ile Tyr Tyr Leu Thr Gln Asp Asp Tyr Ile Phe Met
            420                 425                 430

Asp Thr Leu Arg Phe Asn Leu Arg Leu Ala Asn Tyr Asp Ala Ser Glu
        435                 440                 445

Asn Glu Ile Phe Lys Val Leu Lys Leu Ala Asn Leu Ser Val Val Asn
    450                 455                 460

Asn Glu Pro Val Ser Leu Asp Thr His Leu Ile Asn Arg Gly Asn Asn
465                 470                 475                 480

Tyr Ser Gly Gly Gln Lys Gln Arg Ile Ser Leu Ala Arg Leu Phe Leu
                485                 490                 495

Arg Lys Pro Ala Ile Ile Ile Ile Asp Glu Ala Thr Ser Ala Leu Asp
            500                 505                 510

Tyr Ile Asn Glu Ser Glu Ile Leu Ser Ser Ile Arg Thr His Phe Pro
        515                 520                 525

Asp Ala Leu Ile Ile Asn Ile Ser His Arg Ile Asn Leu Leu Glu Cys
    530                 535                 540

Ser Asp Cys Val Tyr Val Leu Asn Glu Gly Asn Ile Val Ala Ser Gly
545                 550                 555                 560

His Phe Arg Asp Leu Met Val Ser Asn Glu Tyr Ile Ser Gly Leu Ala
                565                 570                 575

Ser Val Thr Glu
            580


<210> SEQ ID NO 539
<211> LENGTH: 1000
<212> TYPE: DNA
<213> ORGANISM: Escherichia coli

<400> SEQUENCE: 539

atggaaagaa aacagaaaaa ctcattattt aattatattt attcattaat ggatgtaaga      60

ggtaaatttt tattcttttc catgttattc attacatcat tatcatcgat aatcatatct     120

atttcaccat tgattcttgc aaagattaca gatttactgt ctggctcatt gtcaaatttt     180

agttatgaat atctggtttt acttgcctgt ttatacatgt tttgcgttat atctaataaa     240

gcaagtgttt ttttatttat gatactgcaa agtagtctac gtattaacat gcagaaaaaa     300

atgtcgctaa agtatttgag agaattgtat aacgaaaata taactaactt gagtaaaaat     360

aatgctggat atacaacgca aagtcttaac caggcttcaa atgacattta tattcttgtg     420

agaaatgttt cccagaatat cctgtcacct gttatacaac ttatttccac tattgttgtt     480

gttttatcta cgaaggactg gttttctgcc ggtgtgtttt ttctctatat tctggtattt     540

gtaattttta ataccagact gactggcagt ttagcgtctc tcagaaaaca cagcatggat     600

atcactctta actcttatag tctgttatct gatactgttg ataacatgat agcagctaaa     660

aagaataatg cattaagact tatttctgaa cgttatgaag atgctctcac tcaggaaaac     720

aatgctcaga aaaaatactg gttactcagt tctaaagttc ttttattgaa ctctttactt     780

gctgtaatat tatttggttc tgtattcata tataatattt taggtgtgct gaatggtgta     840

gttagtatcg gccacttcat tatgattaca tcatatatca ttcttctttc aacgccagtg     900

gaaaatatag ggcattgct aagtgagatc aggcagtcaa tgtctagcct ggcaggtttt     960

attcaacgtc atgccgagaa taaagccaca tctccttcaa                          1000
```

<210> SEQ ID NO 540
<211> LENGTH: 95
<212> TYPE: PRT
<213> ORGANISM: Klebsiella pneumoniae

<400> SEQUENCE: 540

```
Met Thr Leu Leu Ser Phe Gly Phe Ser Pro Val Phe Phe Ser Val Met
1               5                   10                  15

Ala Phe Cys Ile Ile Ser Arg Ser Lys Phe Tyr Pro Gln Arg Thr Arg
            20                  25                  30

Asn Lys Val Ile Val Leu Ile Leu Leu Thr Phe Phe Ile Cys Phe Leu
        35                  40                  45

Tyr Pro Leu Thr Lys Val Tyr Leu Val Gly Ser Tyr Gly Ile Phe Asp
    50                  55                  60

Lys Phe Tyr Leu Phe Cys Phe Ile Ser Thr Leu Ile Ala Ile Ala Ile
65                  70                  75                  80

Asn Val Val Ile Leu Thr Ile Asn Gly Ala Lys Asn Glu Arg Asn
                85                  90                  95
```

<210> SEQ ID NO 541
<211> LENGTH: 288
<212> TYPE: DNA
<213> ORGANISM: Klebsiella pneumoniae

<400> SEQUENCE: 541

```
atgacattac tttcatttgg attttctcct gttttctttt cagtcatggc gttctgtatc     60

atttcacgta gtaaattcta tccgcagaga acgcgaaaca aagttattgt tctgatttta    120

ctaacttttt ttatttgttt tttatatcca ttaacaaaag tgtatctggt gggaagttac    180

ggtatatttg acaaattcta cctcttttgc tttatttcta cgttaattgc aatagcaatt    240

aacgtagtga tacttacaat aaatggagct aagaatgaga gaaattag                 288
```

<210> SEQ ID NO 542
<211> LENGTH: 13
<212> TYPE: RNA
<213> ORGANISM: Artificial Sequence
<220> FEATURE:
<223> OTHER INFORMATION: Kozak sequence

<400> SEQUENCE: 542

```
gccgccrcca ugg                                                        13
```

<210> SEQ ID NO 543
<211> LENGTH: 6
<212> TYPE: RNA
<213> ORGANISM: Artificial Sequence
<220> FEATURE:
<223> OTHER INFORMATION: Shine-Delgarno sequence

<400> SEQUENCE: 543

```
ggaggu                                                                 6
```

<210> SEQ ID NO 544
<211> LENGTH: 30
<212> TYPE: DNA
<213> ORGANISM: Artificial Sequence
<220> FEATURE:
<223> OTHER INFORMATION: Lead promoter

<400> SEQUENCE: 544

```
gaaaaccttg tcaatgaaga gcgatctatg                                      30
```

<210> SEQ ID NO 545
<211> LENGTH: 30
<212> TYPE: DNA
<213> ORGANISM: Artificial Sequence
<220> FEATURE:
<223> OTHER INFORMATION: FecA promoter

<400> SEQUENCE: 545
ttctcgttcg actcatagct gaacacaaca 30

<210> SEQ ID NO 546
<211> LENGTH: 16
<212> TYPE: DNA
<213> ORGANISM: Artificial Sequence
<220> FEATURE:
<223> OTHER INFORMATION: Cu-sensitive promoter

<400> SEQUENCE: 546
atgacaaaat tgtcat 16

<210> SEQ ID NO 547
<211> LENGTH: 30
<212> TYPE: DNA
<213> ORGANISM: Artificial Sequence
<220> FEATURE:
<223> OTHER INFORMATION: Fe promoter

<400> SEQUENCE: 547
accaatgctg ggaacggcca gggcacctaa 30

<210> SEQ ID NO 548
<211> LENGTH: 30
<212> TYPE: DNA
<213> ORGANISM: Artificial Sequence
<220> FEATURE:
<223> OTHER INFORMATION: Fe and UV promoters

<400> SEQUENCE: 548
ctgaaagcgc ataccgctat ggagggggtt 30

<210> SEQ ID NO 549
<211> LENGTH: 30
<212> TYPE: DNA
<213> ORGANISM: Artificial Sequence
<220> FEATURE:
<223> OTHER INFORMATION: PrFe (PI + PII rus operon)

<400> SEQUENCE: 549
tagatatgcc tgaaagcgca taccgctatg 30

<210> SEQ ID NO 550
<211> LENGTH: 30
<212> TYPE: DNA
<213> ORGANISM: Artificial Sequence
<220> FEATURE:
<223> OTHER INFORMATION: Lux cassette right promoter

<400> SEQUENCE: 550
tgttatagtc gaatacctct ggcggtgata 30

<210> SEQ ID NO 551
<211> LENGTH: 30
<212> TYPE: DNA
<213> ORGANISM: Artificial Sequence
<220> FEATURE:

<223> OTHER INFORMATION: P(Las) TetO

<400> SEQUENCE: 551
ttttggtaca ctccctatca gtgatagaga 30

<210> SEQ ID NO 552
<211> LENGTH: 30
<212> TYPE: DNA
<213> ORGANISM: Artificial Sequence
<220> FEATURE:
<223> OTHER INFORMATION: P(Las) CIO

<400> SEQUENCE: 552
ctttttggta cactacctct ggcggtgata 30

<210> SEQ ID NO 553
<211> LENGTH: 30
<212> TYPE: DNA
<213> ORGANISM: Artificial Sequence
<220> FEATURE:
<223> OTHER INFORMATION: P(Rhl)

<400> SEQUENCE: 553
tacgcaagaa aatggtttgt tatagtcgaa 30

<210> SEQ ID NO 554
<211> LENGTH: 30
<212> TYPE: DNA
<213> ORGANISM: Artificial Sequence
<220> FEATURE:
<223> OTHER INFORMATION: Double Promoter (LuxR/HSL, positive / cI, negative)

<400> SEQUENCE: 554
cgtgcgtgtt gataacaccg tgcgtgttga 30

<210> SEQ ID NO 555
<211> LENGTH: 30
<212> TYPE: DNA
<213> ORGANISM: Artificial Sequence
<220> FEATURE:
<223> OTHER INFORMATION: P2 promoter in agr operon from S. aureus

<400> SEQUENCE: 555
agattgtact aaatcgtata atgacagtga 30

<210> SEQ ID NO 556
<211> LENGTH: 30
<212> TYPE: DNA
<213> ORGANISM: Artificial Sequence
<220> FEATURE:
<223> OTHER INFORMATION: plux-cI hybrid promoter

<400> SEQUENCE: 556
gtgttgatgc ttttatcacc gccagtggta 30

<210> SEQ ID NO 557
<211> LENGTH: 30
<212> TYPE: DNA
<213> ORGANISM: Artificial Sequence
<220> FEATURE:
<223> OTHER INFORMATION: plux-lac hybrid promoter

<400> SEQUENCE: 557
agtgtgtgga attgtgagcg gataacaatt 30

<210> SEQ ID NO 558
<211> LENGTH: 30
<212> TYPE: DNA
<213> ORGANISM: Artificial Sequence
<220> FEATURE:
<223> OTHER INFORMATION: CinR, CinL and glucose controlled promotor

<400> SEQUENCE: 558
acatcttaaa agttttagta tcatattcgt 30

<210> SEQ ID NO 559
<211> LENGTH: 30
<212> TYPE: DNA
<213> ORGANISM: Artificial Sequence
<220> FEATURE:
<223> OTHER INFORMATION: RhIR promoter repressible by CI

<400> SEQUENCE: 559
tacgcaagaa aatggtttgt tatagtcgaa 30

<210> SEQ ID NO 560
<211> LENGTH: 30
<212> TYPE: DNA
<213> ORGANISM: Artificial Sequence
<220> FEATURE:
<223> OTHER INFORMATION: Reverse Lux Promoter

<400> SEQUENCE: 560
tcttgcgtaa acctgtacga tcctacaggt 30

<210> SEQ ID NO 561
<211> LENGTH: 30
<212> TYPE: DNA
<213> ORGANISM: Artificial Sequence
<220> FEATURE:
<223> OTHER INFORMATION: rhlI promoter

<400> SEQUENCE: 561
atcctccttt agtcttcccc ctcatgtgtg 30

<210> SEQ ID NO 562
<211> LENGTH: 30
<212> TYPE: DNA
<213> ORGANISM: Artificial Sequence
<220> FEATURE:
<223> OTHER INFORMATION: lasI promoter

<400> SEQUENCE: 562
taaaattatg aaatttgcat aaattcttca 30

<210> SEQ ID NO 563
<211> LENGTH: 30
<212> TYPE: DNA
<213> ORGANISM: Artificial Sequence
<220> FEATURE:
<223> OTHER INFORMATION: LuxR+3OC6HSL independent R0065

<400> SEQUENCE: 563
gtgttgacta ttttacctct ggcggtgata 30

<210> SEQ ID NO 564
<211> LENGTH: 30
<212> TYPE: DNA
<213> ORGANISM: Artificial Sequence
<220> FEATURE:

<223> OTHER INFORMATION: LasR/LasI Inducible & RHLR/RHLI repressible Promoter

<400> SEQUENCE: 564
gaaatctggc agtttttggt acacgaaagc 30

<210> SEQ ID NO 565
<211> LENGTH: 30
<212> TYPE: DNA
<213> ORGANISM: Artificial Sequence
<220> FEATURE:
<223> OTHER INFORMATION: pLux/cI Hybrid Promoter

<400> SEQUENCE: 565
acaccgtgcg tgttgatata gtcgaataaa 30

<210> SEQ ID NO 566
<211> LENGTH: 30
<212> TYPE: DNA
<213> ORGANISM: Artificial Sequence
<220> FEATURE:
<223> OTHER INFORMATION: pLas promoter

<400> SEQUENCE: 566
aaaattatga aatttgtata aattcttcag 30

<210> SEQ ID NO 567
<211> LENGTH: 30
<212> TYPE: DNA
<213> ORGANISM: Artificial Sequence
<220> FEATURE:
<223> OTHER INFORMATION: pLas/cI Hybrid Promoter

<400> SEQUENCE: 567
ggttcttttt ggtacctctg gcggtgataa 30

<210> SEQ ID NO 568
<211> LENGTH: 30
<212> TYPE: DNA
<213> ORGANISM: Artificial Sequence
<220> FEATURE:
<223> OTHER INFORMATION: pLas/Lux Hybrid Promoter

<400> SEQUENCE: 568
tgtaggatcg tacaggtata aattcttcag 30

<210> SEQ ID NO 569
<211> LENGTH: 30
<212> TYPE: DNA
<213> ORGANISM: Artificial Sequence
<220> FEATURE:
<223> OTHER INFORMATION: pLux

<400> SEQUENCE: 569
caagaaaatg gtttgttata gtcgaataaa 30

<210> SEQ ID NO 570
<211> LENGTH: 30
<212> TYPE: DNA
<213> ORGANISM: Artificial Sequence
<220> FEATURE:
<223> OTHER INFORMATION: pLux/Las Hybrid Promoter

<400> SEQUENCE: 570
ctatctcatt tgctagtata gtcgaataaa 30

<210> SEQ ID NO 571
<211> LENGTH: 30
<212> TYPE: DNA
<213> ORGANISM: Artificial Sequence
<220> FEATURE:
<223> OTHER INFORMATION: Hybrid promoter: HSL-LuxR activated, P22 C2 repressed

<400> SEQUENCE: 571
tagtttataa tttaagtgtt ctttaatttc 30

<210> SEQ ID NO 572
<211> LENGTH: 30
<212> TYPE: DNA
<213> ORGANISM: Artificial Sequence
<220> FEATURE:
<223> OTHER INFORMATION: PAI+LasR -> LuxI (AI)

<400> SEQUENCE: 572
caccttcggg tgggcctttc tgcgtttata 30

<210> SEQ ID NO 573
<211> LENGTH: 30
<212> TYPE: DNA
<213> ORGANISM: Artificial Sequence
<220> FEATURE:
<223> OTHER INFORMATION: PAI+LasR -> LasI & AI+LuxR --[\m]LasI

<400> SEQUENCE: 573
aataactctg atagtgctag tgtagatctc 30

<210> SEQ ID NO 574
<211> LENGTH: 30
<212> TYPE: DNA
<213> ORGANISM: Artificial Sequence
<220> FEATURE:
<223> OTHER INFORMATION: PAI+LasR -> LasI+GFP & AI+LuxR --[\m]LasI+GFP

<400> SEQUENCE: 574
caccttcggg tgggcctttc tgcgtttata 30

<210> SEQ ID NO 575
<211> LENGTH: 30
<212> TYPE: DNA
<213> ORGANISM: Artificial Sequence
<220> FEATURE:
<223> OTHER INFORMATION: Complex QS -> LuxI & LasI circuit

<400> SEQUENCE: 575
caccttcggg tgggcctttc tgcgtttata 30

<210> SEQ ID NO 576
<211> LENGTH: 30
<212> TYPE: DNA
<213> ORGANISM: Artificial Sequence
<220> FEATURE:
<223> OTHER INFORMATION: position 3 mutated promoter lux pR-3 (luxR & HSL regulated)

<400> SEQUENCE: 576
caagaaaatg gtttgttata gtcgaataaa 30

<210> SEQ ID NO 577
<211> LENGTH: 30
<212> TYPE: DNA
<213> ORGANISM: Artificial Sequence
<220> FEATURE:

<223> OTHER INFORMATION: position 5 mutated promoter lux pR-5 (luxR & HSL regulated)

<400> SEQUENCE: 577
caagaaaatg gtttgttata gtcgaataaa 30

<210> SEQ ID NO 578
<211> LENGTH: 30
<212> TYPE: DNA
<213> ORGANISM: Artificial Sequence
<220> FEATURE:
<223> OTHER INFORMATION: position 3&5 mutated promoter lux pR-3/5 (luxR & HSL regulated)

<400> SEQUENCE: 578
caagaaaatg gtttgttata gtcgaataaa 30

<210> SEQ ID NO 579
<211> LENGTH: 30
<212> TYPE: DNA
<213> ORGANISM: Artificial Sequence
<220> FEATURE:
<223> OTHER INFORMATION: Promoter (HSL-mediated luxR repressor)

<400> SEQUENCE: 579
ttgacacctg taggatcgta caggtataat 30

<210> SEQ ID NO 580
<211> LENGTH: 30
<212> TYPE: DNA
<213> ORGANISM: Artificial Sequence
<220> FEATURE:
<223> OTHER INFORMATION: Promoter (luxR & HSL regulated -- lux pR)

<400> SEQUENCE: 580
caagaaaatg gtttgttata gtcgaataaa 30

<210> SEQ ID NO 581
<211> LENGTH: 30
<212> TYPE: DNA
<213> ORGANISM: Artificial Sequence
<220> FEATURE:
<223> OTHER INFORMATION: Promoter (luxR & HSL regulated -- lux pL)

<400> SEQUENCE: 581
cacgcaaaac ttgcgacaaa caataggtaa 30

<210> SEQ ID NO 582
<211> LENGTH: 30
<212> TYPE: DNA
<213> ORGANISM: Artificial Sequence
<220> FEATURE:
<223> OTHER INFORMATION: Promoter (RhlR & C4-HSL regulated)

<400> SEQUENCE: 582
gttagctttc gaattggcta aaaagtgttc 30

<210> SEQ ID NO 583
<211> LENGTH: 30
<212> TYPE: DNA
<213> ORGANISM: Artificial Sequence
<220> FEATURE:
<223> OTHER INFORMATION: Promoter (cinR and HSL regulated)

<400> SEQUENCE: 583
ccattctgct ttccacgaac ttgaaaacgc 30

<210> SEQ ID NO 584
<211> LENGTH: 30
<212> TYPE: DNA
<213> ORGANISM: Artificial Sequence
<220> FEATURE:
<223> OTHER INFORMATION: Promoter (LasR & PAI regulated)

<400> SEQUENCE: 584
ggccgcgggt tctttttggt acacgaaagc 30

<210> SEQ ID NO 585
<211> LENGTH: 30
<212> TYPE: DNA
<213> ORGANISM: Artificial Sequence
<220> FEATURE:
<223> OTHER INFORMATION: Promoter, Standard (luxR and HSL regulated -- lux pR)

<400> SEQUENCE: 585
aagaaaatgg tttgttgata ctcgaataaa 30

<210> SEQ ID NO 586
<211> LENGTH: 30
<212> TYPE: DNA
<213> ORGANISM: Artificial Sequence
<220> FEATURE:
<223> OTHER INFORMATION: P(Bla)

<400> SEQUENCE: 586
gtttatacat aggcgagtac tctgttatgg 30

<210> SEQ ID NO 587
<211> LENGTH: 30
<212> TYPE: DNA
<213> ORGANISM: Artificial Sequence
<220> FEATURE:
<223> OTHER INFORMATION: P(Cat)

<400> SEQUENCE: 587
agaggttcca actttcacca taatgaaaca 30

<210> SEQ ID NO 588
<211> LENGTH: 30
<212> TYPE: DNA
<213> ORGANISM: Artificial Sequence
<220> FEATURE:
<223> OTHER INFORMATION: P(Kat)

<400> SEQUENCE: 588
taaacaacta acggacaatt ctacctaaca 30

<210> SEQ ID NO 589
<211> LENGTH: 30
<212> TYPE: DNA
<213> ORGANISM: Artificial Sequence
<220> FEATURE:
<223> OTHER INFORMATION: Template for Building Primer Family Member

<400> SEQUENCE: 589
acatcaagcc aaattaaaca ggattaacac 30

<210> SEQ ID NO 590
<211> LENGTH: 30
<212> TYPE: DNA
<213> ORGANISM: Artificial Sequence
<220> FEATURE:
<223> OTHER INFORMATION: Reverse lambda cI-regulated promoter

<400> SEQUENCE: 590
gaggtaaaat agtcaacacg cacggtgtta 30

<210> SEQ ID NO 591
<211> LENGTH: 30
<212> TYPE: DNA
<213> ORGANISM: Artificial Sequence
<220> FEATURE:
<223> OTHER INFORMATION: Key Promoter absorbs 3

<400> SEQUENCE: 591
caggccggaa taactcccta taatgcgcca 30

<210> SEQ ID NO 592
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 592
ggctagctca gtcctaggta cagtgctagc 30

<210> SEQ ID NO 593
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 593
agctagctca gtcctaggta ttatgctagc 30

<210> SEQ ID NO 594
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 594
agctagctca gtcctaggta ctgtgctagc 30

<210> SEQ ID NO 595
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 595
agctagctca gtcctaggga ttatgctagc 30

<210> SEQ ID NO 596
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 596
agctagctca gtcctaggta ttgtgctagc 30

<210> SEQ ID NO 597
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 597
ggctagctca gtcctaggta ctatgctagc 30

<210> SEQ ID NO 598
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 598
ggctagctca gtcctaggta tagtgctagc 30

<210> SEQ ID NO 599
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 599
ggctagctca gccctaggta ttatgctagc 30

<210> SEQ ID NO 600
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 600
agctagctca gtcctaggta taatgctagc 30

<210> SEQ ID NO 601
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 601
agctagctca gtcctaggga ctgtgctagc 30

<210> SEQ ID NO 602
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 602
ggctagctca gtcctaggta caatgctagc 30

<210> SEQ ID NO 603
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 603
ggctagctca gtcctaggta tagtgctagc 30

<210> SEQ ID NO 604
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 604
agctagctca gtcctaggga ttatgctagc 30

<210> SEQ ID NO 605
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 605
ggctagctca gtcctaggga ttatgctagc 30

<210> SEQ ID NO 606
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 606
ggctagctca gtcctaggta caatgctagc 30

<210> SEQ ID NO 607
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 607
agctagctca gcccttggta caatgctagc 30

<210> SEQ ID NO 608
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 608
agctagctca gtcctaggga ctatgctagc 30

<210> SEQ ID NO 609
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 609
agctagctca gtcctaggga ttgtgctagc 30

<210> SEQ ID NO 610

<211> LENGTH: 30
<212> TYPE: DNA
<213> ORGANISM: Artificial Sequence
<220> FEATURE:
<223> OTHER INFORMATION: constitutive promoter family member

<400> SEQUENCE: 610
ggctagctca gtcctaggta ttgtgctagc 30

<210> SEQ ID NO 611
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 611
agctagctca gtcctaggta taatgctagc 30

<210> SEQ ID NO 612
<211> LENGTH: 30
<212> TYPE: DNA
<213> ORGANISM: Artificial Sequence
<220> FEATURE:
<223> OTHER INFORMATION: 1bp mutant from J23107

<400> SEQUENCE: 612
ggctagctca gtcctaggta ttatgctagc 30

<210> SEQ ID NO 613
<211> LENGTH: 30
<212> TYPE: DNA
<213> ORGANISM: Artificial Sequence
<220> FEATURE:
<223> OTHER INFORMATION: 1bp mutant from J23114

<400> SEQUENCE: 613
ggctagctca gtcctaggta caatgctagc 30

<210> SEQ ID NO 614
<211> LENGTH: 30
<212> TYPE: DNA
<213> ORGANISM: Artificial Sequence
<220> FEATURE:
<223> OTHER INFORMATION: pBAD reverse

<400> SEQUENCE: 614
aaagtgtgac gccgtgcaaa taatcaatgt 30

<210> SEQ ID NO 615
<211> LENGTH: 30
<212> TYPE: DNA
<213> ORGANISM: Artificial Sequence
<220> FEATURE:
<223> OTHER INFORMATION: NikR promoter, a protein of the ribbon helix-
helix family of trancription factors that repress expre

<400> SEQUENCE: 615
gacgaatact taaaatcgtc atacttattt 30

<210> SEQ ID NO 616
<211> LENGTH: 30
<212> TYPE: DNA
<213> ORGANISM: Artificial Sequence
<220> FEATURE:
<223> OTHER INFORMATION: lacq_Promoter

<400> SEQUENCE: 616
aaacctttcg cggtatggca tgatagcgcc 30

<210> SEQ ID NO 617
<211> LENGTH: 30
<212> TYPE: DNA
<213> ORGANISM: Artificial Sequence
<220> FEATURE:
<223> OTHER INFORMATION: lacIQ - promoter sequence

<400> SEQUENCE: 617
tgatagcgcc cggaagagag tcaattcagg 30

<210> SEQ ID NO 618
<211> LENGTH: 30
<212> TYPE: DNA
<213> ORGANISM: Artificial Sequence
<220> FEATURE:
<223> OTHER INFORMATION: E. Coli CreABCD phosphate sensing operon promoter

<400> SEQUENCE: 618
ttatttaccg tgacgaacta attgctcgtg 30

<210> SEQ ID NO 619
<211> LENGTH: 30
<212> TYPE: DNA
<213> ORGANISM: Artificial Sequence
<220> FEATURE:
<223> OTHER INFORMATION: GlnRS promoter

<400> SEQUENCE: 619
catacgccgt tatacgttgt ttacgctttg 30

<210> SEQ ID NO 620
<211> LENGTH: 30
<212> TYPE: DNA
<213> ORGANISM: Artificial Sequence
<220> FEATURE:
<223> OTHER INFORMATION: Constitutive weak promoter of lacZ

<400> SEQUENCE: 620
ttatgcttcc ggctcgtatg ttgtgtggac 30

<210> SEQ ID NO 621
<211> LENGTH: 30
<212> TYPE: DNA
<213> ORGANISM: Artificial Sequence
<220> FEATURE:
<223> OTHER INFORMATION: Mutated LacZ promoter

<400> SEQUENCE: 621
ttatgcttcc ggctcgtatg gtgtgtggac 30

<210> SEQ ID NO 622
<211> LENGTH: 30
<212> TYPE: DNA
<213> ORGANISM: Artificial Sequence
<220> FEATURE:
<223> OTHER INFORMATION: constitutive promoter with (TA)10 between -10 and -35 elements

<400> SEQUENCE: 622
atatatatat atatataatg gaagcgtttt 30

<210> SEQ ID NO 623
<211> LENGTH: 30
<212> TYPE: DNA
<213> ORGANISM: Artificial Sequence
<220> FEATURE:
<223> OTHER INFORMATION: constitutive promoter with (TA)9 between -10 and -35 elements

<400> SEQUENCE: 623
atatatatat atatataatg gaagcgtttt 30

<210> SEQ ID NO 624
<211> LENGTH: 30
<212> TYPE: DNA
<213> ORGANISM: Artificial Sequence
<220> FEATURE:
<223> OTHER INFORMATION: constitutive promoter with (C)10 between -10 and -35 elements

<400> SEQUENCE: 624
ccccgaaagc ttaagaatat aattgtaagc 30

<210> SEQ ID NO 625
<211> LENGTH: 30
<212> TYPE: DNA
<213> ORGANISM: Artificial Sequence
<220> FEATURE:
<223> OTHER INFORMATION: constitutive promoter with (C)12 between -10 and -35 elements

<400> SEQUENCE: 625
ccccgaaagc ttaagaatat aattgtaagc 30

<210> SEQ ID NO 626
<211> LENGTH: 30
<212> TYPE: DNA
<213> ORGANISM: Artificial Sequence
<220> FEATURE:
<223> OTHER INFORMATION: optimized (TA) repeat constitutive promoter with 13 bp between -10 and -35 elements

<400> SEQUENCE: 626
tgacaatata tatatatata taatgctagc 30

<210> SEQ ID NO 627
<211> LENGTH: 30
<212> TYPE: DNA
<213> ORGANISM: Artificial Sequence
<220> FEATURE:
<223> OTHER INFORMATION: optimized (TA) repeat constitutive promoter with 15 bp between -10 and -35 elements

<400> SEQUENCE: 627
acaatatata tatatatata taatgctagc 30

<210> SEQ ID NO 628
<211> LENGTH: 30
<212> TYPE: DNA
<213> ORGANISM: Artificial Sequence
<220> FEATURE:
<223> OTHER INFORMATION: optimized (TA) repeat constitutive promoter with 17 bp between -10 and -35 elements

<400> SEQUENCE: 628
aatatatata tatatatata taatgctagc 30

<210> SEQ ID NO 629

<211> LENGTH: 30
<212> TYPE: DNA
<213> ORGANISM: Artificial Sequence
<220> FEATURE:
<223> OTHER INFORMATION: optimized (TA) repeat constitutive promoter with 19 bp between -10 and -35 elements

<400> SEQUENCE: 629
tatatatata tatatatata taatgctagc 30

<210> SEQ ID NO 630
<211> LENGTH: 30
<212> TYPE: DNA
<213> ORGANISM: Artificial Sequence
<220> FEATURE:
<223> OTHER INFORMATION: optimized (TA) repeat constitutive promoter with 21 bp between -10 and -35 elements

<400> SEQUENCE: 630
tatatatata tatatatata taatgctagc 30

<210> SEQ ID NO 631
<211> LENGTH: 30
<212> TYPE: DNA
<213> ORGANISM: Artificial Sequence
<220> FEATURE:
<223> OTHER INFORMATION: optimized (A) repeat constitutive promoter with 17 bp between -10 and -35 elements

<400> SEQUENCE: 631
aaaaaaaaaa aaaaaaaata taatgctagc 30

<210> SEQ ID NO 632
<211> LENGTH: 30
<212> TYPE: DNA
<213> ORGANISM: Artificial Sequence
<220> FEATURE:
<223> OTHER INFORMATION: optimized (A) repeat constitutive promoter with 18 bp between -10 and -35 elements

<400> SEQUENCE: 632
aaaaaaaaaa aaaaaaaata taatgctagc 30

<210> SEQ ID NO 633
<211> LENGTH: 30
<212> TYPE: DNA
<213> ORGANISM: Artificial Sequence
<220> FEATURE:
<223> OTHER INFORMATION: J23101:GFP

<400> SEQUENCE: 633
caccttcggg tgggcctttc tgcgtttata 30

<210> SEQ ID NO 634
<211> LENGTH: 30
<212> TYPE: DNA
<213> ORGANISM: Artificial Sequence
<220> FEATURE:
<223> OTHER INFORMATION: J23119:IFP

<400> SEQUENCE: 634
caccttcggg tgggcctttc tgcgtttata 30

<210> SEQ ID NO 635
<211> LENGTH: 30
<212> TYPE: DNA
<213> ORGANISM: Artificial Sequence

<220> FEATURE:
<223> OTHER INFORMATION: J23119:H01

<400> SEQUENCE: 635
caccttcggg tgggcctttc tgcgtttata 30

<210> SEQ ID NO 636
<211> LENGTH: 30
<212> TYPE: DNA
<213> ORGANISM: Artificial Sequence
<220> FEATURE:
<223> OTHER INFORMATION: Infrared signal reporter (J23119:IFP:J23119:H01)

<400> SEQUENCE: 636
caccttcggg tgggcctttc tgcgtttata 30

<210> SEQ ID NO 637
<211> LENGTH: 30
<212> TYPE: DNA
<213> ORGANISM: Artificial Sequence
<220> FEATURE:
<223> OTHER INFORMATION: Double terminator + constitutive promoter

<400> SEQUENCE: 637
ggctagctca gtcctaggta cagtgctagc 30

<210> SEQ ID NO 638
<211> LENGTH: 30
<212> TYPE: DNA
<213> ORGANISM: Artificial Sequence
<220> FEATURE:
<223> OTHER INFORMATION: Double terminator + Constitutive promoter + Strong RBS

<400> SEQUENCE: 638
tgctagctac tagagattaa agaggagaaa 30

<210> SEQ ID NO 639
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 639
ttgtgagcgg ataacaagat actgagcaca 30

<210> SEQ ID NO 640
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 640
ttgtgagcgg ataacaagat actgagcaca 30

<210> SEQ ID NO 641
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 641
ttgtgagcgg ataacaagat actgagcaca 30

<210> SEQ ID NO 642
<211> LENGTH: 30
<212> TYPE: DNA
<213> ORGANISM: Artificial Sequence
<220> FEATURE:
<223> OTHER INFORMATION: M13K07 gene I promoter

<400> SEQUENCE: 642
cctgttttta tgttattctc tctgtaaagg 30

<210> SEQ ID NO 643
<211> LENGTH: 30
<212> TYPE: DNA
<213> ORGANISM: Artificial Sequence
<220> FEATURE:
<223> OTHER INFORMATION: M13K07 gene II promoter

<400> SEQUENCE: 643
aaatatttgc ttatacaatc ttcctgtttt 30

<210> SEQ ID NO 644
<211> LENGTH: 30
<212> TYPE: DNA
<213> ORGANISM: Artificial Sequence
<220> FEATURE:
<223> OTHER INFORMATION: M13K07 gene III promoter

<400> SEQUENCE: 644
gctgataaac cgatacaatt aaaggctcct 30

<210> SEQ ID NO 645
<211> LENGTH: 30
<212> TYPE: DNA
<213> ORGANISM: Artificial Sequence
<220> FEATURE:
<223> OTHER INFORMATION: M13K07 gene IV promoter

<400> SEQUENCE: 645
ctcttctcag cgtcttaatc taagctatcg 30

<210> SEQ ID NO 646
<211> LENGTH: 30
<212> TYPE: DNA
<213> ORGANISM: Artificial Sequence
<220> FEATURE:
<223> OTHER INFORMATION: M13K07 gene V promoter

<400> SEQUENCE: 646
atgagccagt tcttaaaatc gcataaggta 30

<210> SEQ ID NO 647
<211> LENGTH: 30
<212> TYPE: DNA
<213> ORGANISM: Artificial Sequence
<220> FEATURE:
<223> OTHER INFORMATION: M13K07 gene VI promoter

<400> SEQUENCE: 647
ctattgattg tgacaaaata aacttattcc 30

<210> SEQ ID NO 648

<211> LENGTH: 30
<212> TYPE: DNA
<213> ORGANISM: Artificial Sequence
<220> FEATURE:
<223> OTHER INFORMATION: M13K07 gene VIII promoter

<400> SEQUENCE: 648
gtttcgcgct tggtataatc gctgggggtc 30

<210> SEQ ID NO 649
<211> LENGTH: 30
<212> TYPE: DNA
<213> ORGANISM: Artificial Sequence
<220> FEATURE:
<223> OTHER INFORMATION: M13110

<400> SEQUENCE: 649
ctttgcttct gactataata gtcagggtaa 30

<210> SEQ ID NO 650
<211> LENGTH: 30
<212> TYPE: DNA
<213> ORGANISM: Artificial Sequence
<220> FEATURE:
<223> OTHER INFORMATION: Modified promoter sequence of g3.

<400> SEQUENCE: 650
aaaccgatac aattaaaggc tcctgctagc 30

<210> SEQ ID NO 651
<211> LENGTH: 30
<212> TYPE: DNA
<213> ORGANISM: Artificial Sequence
<220> FEATURE:
<223> OTHER INFORMATION: Constitutive Promoter I

<400> SEQUENCE: 651
caccacactg atagtgctag tgtagatcac 30

<210> SEQ ID NO 652
<211> LENGTH: 30
<212> TYPE: DNA
<213> ORGANISM: Artificial Sequence
<220> FEATURE:
<223> OTHER INFORMATION: Constitutive Promoter II

<400> SEQUENCE: 652
gccggaataa ctccctataa tgcgccacca 30

<210> SEQ ID NO 653
<211> LENGTH: 30
<212> TYPE: DNA
<213> ORGANISM: Artificial Sequence
<220> FEATURE:
<223> OTHER INFORMATION: --Specify Parts List--

<400> SEQUENCE: 653
ttgacaagct tttcctcagc tccgtaaact 30

<210> SEQ ID NO 654
<211> LENGTH: 30
<212> TYPE: DNA
<213> ORGANISM: Artificial Sequence
<220> FEATURE:
<223> OTHER INFORMATION: Full-length stationary phase osmY promoter

<400> SEQUENCE: 654
ggtttcaaaa ttgtgatcta tatttaacaa 30

<210> SEQ ID NO 655
<211> LENGTH: 30
<212> TYPE: DNA
<213> ORGANISM: Artificial Sequence
<220> FEATURE:
<223> OTHER INFORMATION: Minimal stationary phase osmY promoter

<400> SEQUENCE: 655
ggtttcaaaa ttgtgatcta tatttaacaa 30

<210> SEQ ID NO 656
<211> LENGTH: 30
<212> TYPE: DNA
<213> ORGANISM: Artificial Sequence
<220> FEATURE:
<223> OTHER INFORMATION: htpG Heat Shock Promoter

<400> SEQUENCE: 656
tctattccaa taaagaaatc ttcctgcgtg 30

<210> SEQ ID NO 657
<211> LENGTH: 30
<212> TYPE: DNA
<213> ORGANISM: Artificial Sequence
<220> FEATURE:
<223> OTHER INFORMATION: Promoter veg a constitutive promoter for B. subtilis

<400> SEQUENCE: 657
aaaaatgggc tcgtgttgta caataaatgt 30

<210> SEQ ID NO 658
<211> LENGTH: 30
<212> TYPE: DNA
<213> ORGANISM: Artificial Sequence
<220> FEATURE:
<223> OTHER INFORMATION: Promoter 43 a constitutive promoter for B. subtilis

<400> SEQUENCE: 658
aaaaaaagcg cgcgattatg taaaatataa 30

<210> SEQ ID NO 659
<211> LENGTH: 30
<212> TYPE: DNA
<213> ORGANISM: Artificial Sequence
<220> FEATURE:
<223> OTHER INFORMATION: Strong constitutive promoter for Bacillus subtilis

<400> SEQUENCE: 659
aattgcagta ggcatgacaa aatggactca 30

<210> SEQ ID NO 660
<211> LENGTH: 30
<212> TYPE: DNA
<213> ORGANISM: Artificial Sequence
<220> FEATURE:
<223> OTHER INFORMATION: PliaG

<400> SEQUENCE: 660
caagcttttc ctttataata gaatgaatga 30

<210> SEQ ID NO 661
<211> LENGTH: 30
<212> TYPE: DNA
<213> ORGANISM: Artificial Sequence
<220> FEATURE:
<223> OTHER INFORMATION: PlepA

<400> SEQUENCE: 661
tctaagctag tgtattttgc gtttaatagt 30

<210> SEQ ID NO 662
<211> LENGTH: 30
<212> TYPE: DNA
<213> ORGANISM: Artificial Sequence
<220> FEATURE:
<223> OTHER INFORMATION: Pveg

<400> SEQUENCE: 662
aatgggctcg tgttgtacaa taaatgtagt 30

<210> SEQ ID NO 663
<211> LENGTH: 30
<212> TYPE: DNA
<213> ORGANISM: Artificial Sequence
<220> FEATURE:
<223> OTHER INFORMATION: Promoter ctc for B. subtilis

<400> SEQUENCE: 663
atccttatcg ttatgggtat tgtttgtaat 30

<210> SEQ ID NO 664
<211> LENGTH: 30
<212> TYPE: DNA
<213> ORGANISM: Artificial Sequence
<220> FEATURE:
<223> OTHER INFORMATION: Promoter gsiB for B. subtilis

<400> SEQUENCE: 664
taaaagaatt gtgagcggga atacaacaac 30

<210> SEQ ID NO 665
<211> LENGTH: 30
<212> TYPE: DNA
<213> ORGANISM: Artificial Sequence
<220> FEATURE:
<223> OTHER INFORMATION: Promoter 43 a constitutive promoter for B.
subtilis

<400> SEQUENCE: 665
aaaaaaagcg cgcgattatg taaaatataa 30

<210> SEQ ID NO 666
<211> LENGTH: 30
<212> TYPE: DNA
<213> ORGANISM: Artificial Sequence
<220> FEATURE:
<223> OTHER INFORMATION: Pspv2 from Salmonella

<400> SEQUENCE: 666
tacaaaataa ttcccctgca aacattatca 30

<210> SEQ ID NO 667
<211> LENGTH: 30
<212> TYPE: DNA
<213> ORGANISM: Artificial Sequence
<220> FEATURE:
<223> OTHER INFORMATION: Pspv from Salmonella

<400> SEQUENCE: 667
tacaaaataa ttcccctgca aacattatcg 30

<210> SEQ ID NO 668
<211> LENGTH: 30
<212> TYPE: DNA
<213> ORGANISM: Artificial Sequence
<220> FEATURE:
<223> OTHER INFORMATION: T7 promoter (strong promoter from T7 bacteriophage)

<400> SEQUENCE: 668
agggaataca agctacttgt tctttttgca 30

<210> SEQ ID NO 669
<211> LENGTH: 23
<212> TYPE: DNA
<213> ORGANISM: Artificial Sequence
<220> FEATURE:
<223> OTHER INFORMATION: T7 Promoter

<400> SEQUENCE: 669
taatacgact cactataggg aga 23

<210> SEQ ID NO 670
<211> LENGTH: 28
<212> TYPE: DNA
<213> ORGANISM: Artificial Sequence
<220> FEATURE:
<223> OTHER INFORMATION: T7 Promoter

<400> SEQUENCE: 670
gaatttaata cgactcacta tagggaga 28

<210> SEQ ID NO 671
<211> LENGTH: 19
<212> TYPE: DNA
<213> ORGANISM: Artificial Sequence
<220> FEATURE:
<223> OTHER INFORMATION: T7 consensus -10 and rest

<400> SEQUENCE: 671
taatacgact cactatagg 19

<210> SEQ ID NO 672
<211> LENGTH: 30
<212> TYPE: DNA
<213> ORGANISM: Artificial Sequence
<220> FEATURE:
<223> OTHER INFORMATION: overlapping T7 promoter

<400> SEQUENCE: 672
gagtcgtatt aatacgactc actatagggg 30

<210> SEQ ID NO 673
<211> LENGTH: 30
<212> TYPE: DNA
<213> ORGANISM: Artificial Sequence
<220> FEATURE:
<223> OTHER INFORMATION: more overlapping T7 promoter

<400> SEQUENCE: 673
agtgagtcgt actacgactc actatagggg 30

<210> SEQ ID NO 674
<211> LENGTH: 30
<212> TYPE: DNA
<213> ORGANISM: Artificial Sequence
<220> FEATURE:
<223> OTHER INFORMATION: weaken overlapping T7 promoter

<400> SEQUENCE: 674
gagtcgtatt aatacgactc tctatagggg 30

<210> SEQ ID NO 675
<211> LENGTH: 23
<212> TYPE: DNA
<213> ORGANISM: Artificial Sequence
<220> FEATURE:
<223> OTHER INFORMATION: T7 Consensus Promoter Sequence

<400> SEQUENCE: 675
taatacgact cactataggg aga 23

<210> SEQ ID NO 676
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 676
ttatacgact cactataggg aga 23

<210> SEQ ID NO 677
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 677
gaatacgact cactataggg aga 23

<210> SEQ ID NO 678
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 678
taatacgtct cactataggg aga 23

<210> SEQ ID NO 679
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 679
tcatacgact cactataggg aga 23

<210> SEQ ID NO 680
<211> LENGTH: 30
<212> TYPE: DNA
<213> ORGANISM: Artificial Sequence
<220> FEATURE:

<223> OTHER INFORMATION: T7 strong promoter

<400> SEQUENCE: 680
taatacgact cactataggg agaccacaac 30

<210> SEQ ID NO 681
<211> LENGTH: 30
<212> TYPE: DNA
<213> ORGANISM: Artificial Sequence
<220> FEATURE:
<223> OTHER INFORMATION: T7 weak binding and processivity

<400> SEQUENCE: 681
taattgaact cactaaaggg agaccacagc 30

<210> SEQ ID NO 682
<211> LENGTH: 30
<212> TYPE: DNA
<213> ORGANISM: Artificial Sequence
<220> FEATURE:
<223> OTHER INFORMATION: T7 weak binding promoter

<400> SEQUENCE: 682
cgaagtaata cgactcacta ttagggaaga 30

<210> SEQ ID NO 683
<211> LENGTH: 30
<212> TYPE: DNA
<213> ORGANISM: Artificial Sequence
<220> FEATURE:
<223> OTHER INFORMATION: pCyc (Medium) Promoter

<400> SEQUENCE: 683
acaaacacaa atacacacac taaattaata 30

<210> SEQ ID NO 684
<211> LENGTH: 30
<212> TYPE: DNA
<213> ORGANISM: Artificial Sequence
<220> FEATURE:
<223> OTHER INFORMATION: pAdh (Strong) Promoter

<400> SEQUENCE: 684
ccaagcatac aatcaactat ctcatataca 30

<210> SEQ ID NO 685
<211> LENGTH: 30
<212> TYPE: DNA
<213> ORGANISM: Artificial Sequence
<220> FEATURE:
<223> OTHER INFORMATION: pSte5 (Weak) Promoter

<400> SEQUENCE: 685
gatacaggat acagcggaaa caacttttaa 30

<210> SEQ ID NO 686
<211> LENGTH: 30
<212> TYPE: DNA
<213> ORGANISM: Artificial Sequence
<220> FEATURE:
<223> OTHER INFORMATION: yeast ADH1 promoter

<400> SEQUENCE: 686
tttcaagcta taccaagcat acaatcaact 30

<210> SEQ ID NO 687
<211> LENGTH: 30
<212> TYPE: DNA
<213> ORGANISM: Artificial Sequence
<220> FEATURE:
<223> OTHER INFORMATION: cyc100 minimal promoter

<400> SEQUENCE: 687
cctttgcagc ataaattact atacttctat 30

<210> SEQ ID NO 688
<211> LENGTH: 30
<212> TYPE: DNA
<213> ORGANISM: Artificial Sequence
<220> FEATURE:
<223> OTHER INFORMATION: cyc70 minimal promoter

<400> SEQUENCE: 688
cctttgcagc ataaattact atacttctat 30

<210> SEQ ID NO 689
<211> LENGTH: 30
<212> TYPE: DNA
<213> ORGANISM: Artificial Sequence
<220> FEATURE:
<223> OTHER INFORMATION: cyc43 minimal promoter

<400> SEQUENCE: 689
cctttgcagc ataaattact atacttctat 30

<210> SEQ ID NO 690
<211> LENGTH: 30
<212> TYPE: DNA
<213> ORGANISM: Artificial Sequence
<220> FEATURE:
<223> OTHER INFORMATION: cyc28 minimal promoter

<400> SEQUENCE: 690
cctttgcagc ataaattact atacttctat 30

<210> SEQ ID NO 691
<211> LENGTH: 30
<212> TYPE: DNA
<213> ORGANISM: Artificial Sequence
<220> FEATURE:
<223> OTHER INFORMATION: cyc16 minimal promoter

<400> SEQUENCE: 691
cctttgcagc ataaattact atacttctat 30

<210> SEQ ID NO 692
<211> LENGTH: 30
<212> TYPE: DNA
<213> ORGANISM: Artificial Sequence
<220> FEATURE:
<223> OTHER INFORMATION: pPGK1

<400> SEQUENCE: 692
ttatctactt tttacaacaa atataaaaca 30

<210> SEQ ID NO 693
<211> LENGTH: 30
<212> TYPE: DNA
<213> ORGANISM: Artificial Sequence
<220> FEATURE:
<223> OTHER INFORMATION: pCYC Yeast Promoter

<400> SEQUENCE: 693
acaaacacaa atacacacac taaattaata 30

<210> SEQ ID NO 694
<211> LENGTH: 30
<212> TYPE: DNA
<213> ORGANISM: Artificial Sequence
<220> FEATURE:
<223> OTHER INFORMATION: Yeast GPD (TDH3) Promoter

<400> SEQUENCE: 694
gtttcgaata aacacacata aacaaacaaa 30

<210> SEQ ID NO 695
<211> LENGTH: 30
<212> TYPE: DNA
<213> ORGANISM: Artificial Sequence
<220> FEATURE:
<223> OTHER INFORMATION: yeast mid-length ADH1 promoter

<400> SEQUENCE: 695
ccaagcatac aatcaactat ctcatataca 30

<210> SEQ ID NO 696
<211> LENGTH: 30
<212> TYPE: DNA
<213> ORGANISM: Artificial Sequence
<220> FEATURE:
<223> OTHER INFORMATION: Yeast CLB1 promoter region, G2/M cell cycle specific

<400> SEQUENCE: 696
accatcaaag gaagctttaa tcttctcata 30

<210> SEQ ID NO 697
<211> LENGTH: 30
<212> TYPE: DNA
<213> ORGANISM: Artificial Sequence
<220> FEATURE:
<223> OTHER INFORMATION: CMV promoter

<400> SEQUENCE: 697
agaacccact gcttactggc ttatcgaaat 30

<210> SEQ ID NO 698
<211> LENGTH: 30
<212> TYPE: DNA
<213> ORGANISM: Artificial Sequence
<220> FEATURE:
<223> OTHER INFORMATION: Ubc Promoter

<400> SEQUENCE: 698
ggccgttttt ggctttttg ttagacgaag 30

<210> SEQ ID NO 699
<211> LENGTH: 9
<212> TYPE: PRT
<213> ORGANISM: Lactobacillus curvatus

<400> SEQUENCE: 699

Asn Ile Pro Gln Leu Thr Pro Thr Pro
1 5

<210> SEQ ID NO 700
<211> LENGTH: 27

<212> TYPE: DNA
<213> ORGANISM: Lactobacillus curvatus

<400> SEQUENCE: 700
aacattccgc agctgacccc gaccccg 27

<210> SEQ ID NO 701
<211> LENGTH: 18
<212> TYPE: PRT
<213> ORGANISM: Bacillus thuringiensis
<220> FEATURE:
<221> NAME/KEY: VARIANT
<222> LOCATION: 4, 7, 10
<223> OTHER INFORMATION: Xaa = any amino acid

<400> SEQUENCE: 701

Asp Trp Thr Xaa Trp Ser Xaa Leu Val Xaa Ala Ala Cys Ser Val Glu
1 5 10 15

Leu Leu

<210> SEQ ID NO 702
<211> LENGTH: 54
<212> TYPE: DNA
<213> ORGANISM: Bacillus thuringiensis
<220> FEATURE:
<221> NAME/KEY: misc_feature
<222> LOCATION: 10, 11, 12, 19, 20, 21, 28, 29, 30
<223> OTHER INFORMATION: n = A,T,C or G

<400> SEQUENCE: 702
gattggaccn nntggagcnn nctggtgnnn gcggcgtgca gcgtggaact gctg 54

<210> SEQ ID NO 703
<211> LENGTH: 30
<212> TYPE: PRT
<213> ORGANISM: Lactobacillus curvatus L442

<400> SEQUENCE: 703

Ala Tyr Pro Gly Asn Gly Val His Cys Gly Lys Tyr Ser Cys Thr Val
1 5 10 15

Asp Lys Gln Thr Ala Ile Gly Asn Ile Gly Asn Asn Ala Ala
20 25 30

<210> SEQ ID NO 704
<211> LENGTH: 90
<212> TYPE: DNA
<213> ORGANISM: Lactobacillus curvatus L442

<400> SEQUENCE: 704
gcgtatccgg gcaacggcgt gcattgcggc aaatatagct gcaccgtgga taaacagacc 60
gcgattggca acattggcaa caacgcggcg 90

<210> SEQ ID NO 705
<211> LENGTH: 43
<212> TYPE: PRT
<213> ORGANISM: Carnobacterium divergens

<400> SEQUENCE: 705

Thr Lys Tyr Tyr Gly Asn Gly Val Tyr Cys Asn Ser Lys Lys Cys Trp
1 5 10 15

```
Val Asp Trp Gly Thr Ala Gln Gly Cys Ile Asp Val Val Ile Gly Gln
            20                  25                  30

Leu Gly Gly Gly Ile Pro Gly Lys Gly Lys Cys
        35                  40


<210> SEQ ID NO 706
<211> LENGTH: 129
<212> TYPE: DNA
<213> ORGANISM: Carnobacterium divergens

<400> SEQUENCE: 706

accaaatatt atggcaacgg cgtgtattgc aacagcaaaa aatgctgggt ggattggggc      60

accgcgcagg gctgcattga tgtggtgatt ggccagctgg gcggcggcat tccgggcaaa     120

ggcaaatgc                                                             129


<210> SEQ ID NO 707
<211> LENGTH: 24
<212> TYPE: PRT
<213> ORGANISM: Microbispora sp. (strain 107891)

<400> SEQUENCE: 707

Val Thr Ser Trp Ser Leu Cys Thr Pro Gly Cys Thr Ser Pro Gly Gly
1               5                   10                  15

Gly Ser Asn Cys Ser Phe Cys Cys
            20


<210> SEQ ID NO 708
<211> LENGTH: 72
<212> TYPE: DNA
<213> ORGANISM: Microbispora sp. (strain 107891)

<400> SEQUENCE: 708

gtgaccagct ggagcctgtg caccccgggc tgcaccagcc cgggcggcgg cagcaactgc      60

agcttttgct gc                                                          72


<210> SEQ ID NO 709
<211> LENGTH: 62
<212> TYPE: PRT
<213> ORGANISM: Enterococcus sp.

<400> SEQUENCE: 709

Asn Arg Trp Tyr Cys Asn Ser Ala Ala Gly Gly Val Gly Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
        35                  40                  45

Lys Ala Cys Lys Ser Phe Pro Gly Ser Gly Trp Ala Ser Gly
    50                  55                  60


<210> SEQ ID NO 710
<211> LENGTH: 186
<212> TYPE: DNA
<213> ORGANISM: Enterococcus sp.

<400> SEQUENCE: 710

aaccgctggt attgcaacag cgcggcgggc ggcgtgggcg gcgcggcggt gtgcggcctg      60

gcgggctatg tgggcgaagc gaaagaaaac attgcgggcg aagtgcgcaa aggctggggc     120
```

```
atggcgggcg gctttaccca taacaaagcg tgcaaaagct ttccgggcag cggctgggcg    180

agcggc                                                               186


<210> SEQ ID NO 711
<211> LENGTH: 39
<212> TYPE: PRT
<213> ORGANISM: Enterococcus faecium

<400> SEQUENCE: 711

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
        35


<210> SEQ ID NO 712
<211> LENGTH: 117
<212> TYPE: DNA
<213> ORGANISM: Enterococcus faecium

<400> SEQUENCE: 712

accaccaaaa actatggcaa cggcgtgtgc aacagcgtga actggtgcca gtgcggcaac     60

gtgtgggcga gctgcaacct ggcgaccggc tgcgcggcgt ggctgtgcaa actggcg       117


<210> SEQ ID NO 713
<211> LENGTH: 30
<212> TYPE: PRT
<213> ORGANISM: Paenibacillus polymyxa

<400> SEQUENCE: 713

Ala Ser Ile Ile Lys Thr Thr Ile Lys Val Ser Lys Ala Val Cys Lys
1               5                   10                  15

Thr Leu Thr Cys Ile Cys Thr Gly Ser Cys Ser Asn Cys Lys
            20                  25                  30


<210> SEQ ID NO 714
<211> LENGTH: 90
<212> TYPE: DNA
<213> ORGANISM: Paenibacillus polymyxa

<400> SEQUENCE: 714

gcgagcatta ttaaaaccac cattaaagtg agcaaagcgg tgtgcaaaac cctgacctgc     60

atttgcaccg gcagctgcag caactgcaaa                                      90


<210> SEQ ID NO 715
<211> LENGTH: 31
<212> TYPE: PRT
<213> ORGANISM: Staphylococcus epidermidis

<400> SEQUENCE: 715

Ser Ala Ser Ile Val Lys Thr Thr Ile Lys Ala Ser Lys Lys Leu Cys
1               5                   10                  15

Arg Gly Phe Thr Leu Thr Cys Gly Cys His Phe Thr Gly Lys Lys
            20                  25                  30


<210> SEQ ID NO 716
<211> LENGTH: 93
<212> TYPE: DNA
<213> ORGANISM: Staphylococcus epidermidis
```

<400> SEQUENCE: 716
agcgcgagca ttgtgaaaac caccattaaa gcgagcaaaa aactgtgccg cggctttacc 60
ctgacctgcg gctgccattt taccggcaaa aaa 93

<210> SEQ ID NO 717
<211> LENGTH: 58
<212> TYPE: PRT
<213> ORGANISM: Enterococcus faecium

<400> SEQUENCE: 717

Met Glu Lys Leu Thr Val Lys Glu Met Ser Gln Val Val Gly Gly Lys
1 5 10 15

Tyr Tyr Gly Asn Gly Val Ser Cys Asn Lys Lys Gly Cys Ser Val Asp
20 25 30

Trp Gly Lys Ala Ile Gly Ile Ile Gly Asn Asn Ala Ala Ala Asn Leu
35 40 45

Thr Thr Gly Gly Lys Ala Gly Trp Lys Gly
50 55

<210> SEQ ID NO 718
<211> LENGTH: 178
<212> TYPE: DNA
<213> ORGANISM: Enterococcus faecium

<400> SEQUENCE: 718
atggaaaaat taactgtgaa agaaatgtcg caagtagttg gcggaaagta ctatggtaac 60
ggagtatcat gtaataaaaa gggatgtagt gttgattggg gaaaagctat tggtattatt 120
ggaaataatg ctgctgctaa tttaactact ggcggaaaag cagggtggaa aggttaac 178

<210> SEQ ID NO 719
<211> LENGTH: 39
<212> TYPE: PRT
<213> ORGANISM: Paenibacillus polymyxa

<400> SEQUENCE: 719

Ala Thr Tyr Tyr Gly Asn Gly Leu Tyr Cys Asn Lys Gln Lys His Tyr
1 5 10 15

Thr Trp Val Asp Trp Asn Lys Ala Ser Arg Glu Ile Gly Lys Ile Thr
20 25 30

Val Asn Gly Trp Val Gln His
35

<210> SEQ ID NO 720
<211> LENGTH: 93
<212> TYPE: DNA
<213> ORGANISM: Paenibacillus polymyxa

<400> SEQUENCE: 720
agcgcgagca ttgtgaaaac caccattaaa gcgagcaaaa aactgtgccg cggctttacc 60
ctgacctgcg gctgccattt taccggcaaa aaa 93

<210> SEQ ID NO 721
<211> LENGTH: 35
<212> TYPE: PRT
<213> ORGANISM: Bacillus circulans

<400> SEQUENCE: 721

Val Asn Tyr Gly Asn Gly Val Ser Cys Ser Lys Thr Lys Cys Ser Val
1 5 10 15

```
Asn Trp Gly Ile Ile Thr His Gln Ala Phe Arg Val Thr Ser Gly Val
            20                  25                  30

Ala Ser Gly
        35


<210> SEQ ID NO 722
<211> LENGTH: 105
<212> TYPE: DNA
<213> ORGANISM: Bacillus circulans

<400> SEQUENCE: 722

gtgaactatg gcaacggcgt gagctgcagc aaaaccaaat gcagcgtgaa ctggggcatt     60

attacccatc aggcgtttcg cgtgaccagc ggcgtggcga gcggc                    105


<210> SEQ ID NO 723
<211> LENGTH: 30
<212> TYPE: PRT
<213> ORGANISM: Paenibacillus polymyxa

<400> SEQUENCE: 723

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30


<210> SEQ ID NO 724
<211> LENGTH: 90
<212> TYPE: DNA
<213> ORGANISM: Paenibacillus polymyxa

<400> SEQUENCE: 724

tttgtgtatg gcaacggcgt gaccagcatt ctggtgcagg cgcagtttct ggtgaacggc     60

cagcgccgct ttttttatac cccggataaa                                      90


<210> SEQ ID NO 725
<211> LENGTH: 13
<212> TYPE: PRT
<213> ORGANISM: Lactobacillus rhamnosus

<400> SEQUENCE: 725

Ala Val Pro Ala Val Arg Lys Thr Asn Glu Thr Leu Asp
1               5                   10


<210> SEQ ID NO 726
<211> LENGTH: 39
<212> TYPE: DNA
<213> ORGANISM: Lactobacillus rhamnosus

<400> SEQUENCE: 726

gcggtgccgg cggtgcgcaa aaccaacgaa accctggat                            39


<210> SEQ ID NO 727
<211> LENGTH: 60
<212> TYPE: PRT
<213> ORGANISM: Bacillus licheniformis

<400> SEQUENCE: 727

Met Lys Asn Ser Ala Ala Arg Glu Ala Phe Lys Gly Ala Asn His Pro
1               5                   10                  15

Ala Gly Met Val Ser Glu Glu Glu Leu Lys Ala Leu Val Gly Gly Asn
            20                  25                  30
```

```
Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys
    50                  55                  60


<210> SEQ ID NO 728
<211> LENGTH: 180
<212> TYPE: DNA
<213> ORGANISM: Bacillus licheniformis

<400> SEQUENCE: 728

atgaaaaaca gcgcggcgcg cgaagcgttt aaaggcgcga accatccggc gggcatggtg      60

agcgaagaag aactgaaagc gctggtgggc ggcaacgatg tgaacccgga aaccaccccg     120

gcgaccacca gcagctggac ctgcattacc gcgggcgtga ccgtgagcgc gagcctgtgc     180


<210> SEQ ID NO 729
<211> LENGTH: 689
<212> TYPE: PRT
<213> ORGANISM: Pseudomonas aeruginosa

<400> SEQUENCE: 729

Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
        195                 200                 205

Lys Ala Arg Lys Ala Asn Val Glu Lys Lys Val Gln Ser Glu Leu Asp
    210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
                245                 250                 255

Lys Lys Leu Gln Thr Ala Asn Asn Ala Leu Ile Ala Lys Ala Pro Asn
            260                 265                 270
```

```
Ala Leu Glu Lys Gln Lys Ala Thr Tyr Asn Ala Asp Leu Leu Val Asp
        275                 280                 285

Glu Ile Ala Ser Leu Gln Ala Arg Leu Asp Lys Leu Asn Ala Glu Thr
    290                 295                 300

Ala Arg Arg Lys Glu Ile Ala Arg Gln Ala Ala Ile Arg Ala Ala Asn
305                 310                 315                 320

Thr Tyr Ala Met Pro Ala Asn Gly Ser Val Val Ala Thr Ala Ala Gly
                325                 330                 335

Arg Gly Leu Ile Gln Val Ala Gln Gly Ala Ala Ser Leu Ala Gln Ala
            340                 345                 350

Ile Ser Asp Ala Ile Ala Val Leu Gly Arg Val Leu Ala Ser Ala Pro
        355                 360                 365

Ser Val Met Ala Val Gly Phe Ala Ser Leu Thr Tyr Ser Ser Arg Thr
    370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
            420                 425                 430

Asn Glu Ala Arg Gly Asn Thr Thr Thr Leu Ser Val Val Ser Thr Asp
        435                 440                 445

Gly Val Ser Val Pro Lys Ala Val Pro Val Arg Met Ala Ala Tyr Asn
    450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Pro Gly Asn
                485                 490                 495

Gln Asn Pro Ser Ser Thr Thr Pro Val Val Pro Lys Pro Val Pro Val
            500                 505                 510

Tyr Glu Gly Ala Thr Leu Thr Pro Val Lys Ala Thr Pro Glu Thr Tyr
        515                 520                 525

Pro Gly Val Ile Thr Leu Pro Glu Asp Leu Ile Ile Gly Phe Pro Ala
    530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
            580                 585                 590

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
    610                 615                 620

Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
                645                 650                 655

His Lys Val Arg Ile Ala Asp Gly Gly Gly Val Tyr Asn Met Gly Asn
            660                 665                 670
```

```
Leu Val Ala Val Thr Pro Lys Arg His Ile Glu Ile His Lys Gly Gly
        675                 680                 685

Lys


<210> SEQ ID NO 730
<211> LENGTH: 2070
<212> TYPE: DNA
<213> ORGANISM: Pseudomonas aeruginosa

<400> SEQUENCE: 730

atggctgtca atgattacga acctggttcg atggttatta cacatgtgca gggtggtggg      60

cgtgacataa tccagtatat tcctgctcga tcaagctacg gtactccacc atttgtccca     120

ccaggaccaa gtccgtatgt cggtactgga atgcaggagt acaggaagct aagaagtacg     180

cttgataagt cccattcaga actcaagaaa aacctgaaaa atgaaaccct gaaggaggtt     240

gatgaactca agagtgaagc ggggttgcca ggtaaagcgg tcagtgccaa tgacatccgc     300

gatgaaaaga gtatcgttga tgcactcatg gatgccaaag caaaatcgct aaaggccatt     360

gaggatcgcc cggccaatct ttatacggct tcagactttc ctcagaagtc agagtcgatg     420

taccagagtc agttgctggc cagccgaaaa ttctatggag agttcctgga tcgccatatg     480

agtgagctgg ccaaagcgta cagcgccgat atctataagg cgcaaatcgc tatcttgaaa     540

caaacgtctc aagagctgga gaataaagcc cggtcattgg aagcagaagc ccagcgagcc     600

gctgctgagg tggaggcgga ctacaaggcc aggaaggcaa atgtcgagaa aaaagtgcag     660

tccgagcttg accaggctgg gaatgctttg cctcaactga ccaatccaac gccagagcag     720

tggcttgaac gcgctactca actggttacg caggcgatcg ccaataagaa gaaattgcag     780

actgcaaaca atgccttgat tgccaaggca cccaatgcac tggagaaaca aaaggcaacc     840

tacaacgccg atctcctagt ggatgaaatc gccagcctgc aagcacggct ggacaagctg     900

aacgccgaaa cggcaaggcg caaggaaatc gctcgtcaag cggcgatcag ggctgccaat     960

acttatgcca tgccagccaa tggcagcgtt gtcgccaccg ccgcaggccg gggtctgatc    1020

caggtcgcac aaggcgccgc atcccttgct caagcgatct ccgatgcgat tgccgtcctg    1080

ggccgggtcc tggcttcagc accctcggtg atggccgtgg gctttgccag tctgacctac    1140

tcctcccgga ctgccgagca atggcaggac caaacgcccg atagcgttcg ttacgccctg    1200

ggcatggatg ccgctaaatt ggggcttccc ccaagcgtaa acctgaacgc ggttgcaaaa    1260

gccagcggta ccgtcgatct gccgatgcgc ctgaccaacg aggcacgagg caacacgacg    1320

accctttcgg tggtcagcac cgatggtgtg agcgttccga aagccgttcc ggtccggatg    1380

gcggcctaca atgccacgac aggcctgtac gaggttacgg ttccctctac gaccgcagaa    1440

gcgccgccac tgatcctgac ctggacgccg gcgagtcctc caggaaacca gaacccttcg    1500

agtaccactc cggtcgtacc gaagccggtg ccggtatatg agggagcgac ccttacaccg    1560

gtgaaggcta ccccggaaac ctatcctggg gtgattacac taccggaaga cctgatcatc    1620

ggcttcccgg ccgactcggg gatcaagccg atctatgtga tgttcaggga tccgcgggat    1680

gtacctggtg ctgcgactgg caagggacag cccgtcagcg gtaattggct cggcgccgcc    1740

tctcaaggtg agggggctcc aattccaagc cagattgcgg ataaactacg tggtaagaca    1800

ttcaaaaact ggcgggactt tcgggaacaa ttctggatag ctgtggctaa tgatcctgag    1860

ttaagtaaac agtttaatcc tggtagttta gctgtaatga gagatggagg ggctccttat    1920

gtcagagagt cagaacaggc tggcgggaga ataaagatcg aaatccacca caaggttcga    1980
```

atagcagatg gaggcggcgt ttacaatatg gggaaccttg ttgcagtaac gccaaaacgt 2040
catatagaaa tccacaaggg agggaagtga 2070

<210> SEQ ID NO 731
<211> LENGTH: 36
<212> TYPE: PRT
<213> ORGANISM: Lactobacillus plantarum

<400> SEQUENCE: 731

Lys Tyr Tyr Gly Asn Gly Leu Ser Cys Ser Lys Lys Gly Cys Thr Val
1 5 10 15

Asn Trp Gly Gln Ala Phe Ser Cys Gly Val Asn Arg Val Ala Thr Ala
20 25 30

Gly His Gly Lys
35

<210> SEQ ID NO 732
<211> LENGTH: 108
<212> TYPE: DNA
<213> ORGANISM: Lactobacillus plantarum

<400> SEQUENCE: 732
aaatattatg gcaacggcct gagctgcagc aaaaaaggct gcaccgtgaa ctggggccag 60
gcgtttagct gcggcgtgaa ccgcgtggcg accgcgggcc atggcaaa 108

<210> SEQ ID NO 733
<211> LENGTH: 30
<212> TYPE: PRT
<213> ORGANISM: Lactococcus lactis

<400> SEQUENCE: 733

Met Lys Thr Ile Leu Arg Phe Val Ala Gly Tyr Asp Ile Ala Ser His
1 5 10 15

Lys Lys Lys Thr Gly Gly Tyr Pro Trp Glu Arg Gly Lys Ala
20 25 30

<210> SEQ ID NO 734
<211> LENGTH: 93
<212> TYPE: DNA
<213> ORGANISM: Lactococcus lactis

<400> SEQUENCE: 734
atgaaaacaa tcctacgttt tgttgctggc tacgatattg ctagtcataa aaagaaaact 60
ggcggctatc catgggaacg tggaaaagct taa 93

<210> SEQ ID NO 735
<211> LENGTH: 24
<212> TYPE: PRT
<213> ORGANISM: Lactobacillus acidophilus

<400> SEQUENCE: 735

Gly Asn Pro Lys Val Ala His Cys Ala Ser Gln Ile Gly Arg Ser Thr
1 5 10 15

Ala Trp Gly Ala Val Ser Gly Ala
20

<210> SEQ ID NO 736
<211> LENGTH: 72
<212> TYPE: DNA
<213> ORGANISM: Lactobacillus acidophilus

<400> SEQUENCE: 736
ggcaacccga aagtggcgca ttgcgcgagc cagattggcc gcagcaccgc gtggggcgcg 60
gtgagcggcg cg 72

<210> SEQ ID NO 737
<211> LENGTH: 53
<212> TYPE: PRT
<213> ORGANISM: Lactobacillus salivarius cp400

<400> SEQUENCE: 737

Met Phe Phe Asn Phe Met Lys Lys Val Asp Val Lys Lys Asn Phe Gly
1 5 10 15

Tyr Lys Glu Val Ser Arg Lys Asp Leu Ala Lys Val Asn Gly Gly Lys
20 25 30

Arg Lys Lys His Arg Cys Arg Val Tyr Asn Asn Gly Met Pro Thr Gly
35 40 45

Met Tyr Arg Trp Cys
50

<210> SEQ ID NO 738
<211> LENGTH: 162
<212> TYPE: DNA
<213> ORGANISM: Lactobacillus salivarius cp400

<400> SEQUENCE: 738
atgtttttta attttatgaa aaaagtagat gtgaagaaga attttggata taaagaagtt 60
tctagaaaag atctagctaa agtaaatggt ggaaagagaa agaaacatcg ttgcagagtt 120
tataataatg gaatgcctac aggaatgtat cgttggtgct aa 162

<210> SEQ ID NO 739
<211> LENGTH: 5
<212> TYPE: PRT
<213> ORGANISM: Artificial Sequence
<220> FEATURE:
<223> OTHER INFORMATION: Caspase 2 consensus sequence

<400> SEQUENCE: 739

Asp Val Ala Asp Leu
1 5

<210> SEQ ID NO 740
<211> LENGTH: 5
<212> TYPE: PRT
<213> ORGANISM: Artificial Sequence
<220> FEATURE:
<223> OTHER INFORMATION: Caspase 2 consensus sequence

<400> SEQUENCE: 740

Asp Val Ala Asp Ile
1 5

<210> SEQ ID NO 741
<211> LENGTH: 12
<212> TYPE: PRT
<213> ORGANISM: Artificial Sequence
<220> FEATURE:
<223> OTHER INFORMATION: Synthetic RAP-binding peptide, RBP

<400> SEQUENCE: 741

Phe His Trp Trp Gln Thr Ser Pro Ala His Phe Ser
1 5 10

<210> SEQ ID NO 742
<211> LENGTH: 12
<212> TYPE: PRT
<213> ORGANISM: Artificial Sequence
<220> FEATURE:
<223> OTHER INFORMATION: Synthetic RAP-binding peptide, RBP

<400> SEQUENCE: 742

Trp Pro Phe Ala His Trp Pro Trp Gln Tyr Pro Arg
1               5                   10

<210> SEQ ID NO 743
<211> LENGTH: 9
<212> TYPE: PRT
<213> ORGANISM: Artificial Sequence
<220> FEATURE:
<223> OTHER INFORMATION: Synthetic AgrC ligand
<220> FEATURE:
<221> NAME/KEY: VARIANT
<222> LOCATION: 5, 9
<223> OTHER INFORMATION: Thiolacton linkage between C5 and F9

<400> SEQUENCE: 743

Gly Asp Ser Val Cys Ala Ser Tyr Phe
1               5

<210> SEQ ID NO 744
<211> LENGTH: 7
<212> TYPE: PRT
<213> ORGANISM: Artificial Sequence
<220> FEATURE:
<223> OTHER INFORMATION: Synthetic AgrC ligand
<220> FEATURE:
<221> NAME/KEY: VARIANT
<222> LOCATION: 3, 7
<223> OTHER INFORMATION: Thiolacton linkage between C3 and F7

<400> SEQUENCE: 744

Ser Val Cys Ala Ser Tyr Phe
1               5

<210> SEQ ID NO 745
<211> LENGTH: 5
<212> TYPE: PRT
<213> ORGANISM: Artificial Sequence
<220> FEATURE:
<223> OTHER INFORMATION: Synthetic Cry1Aa ligand

<400> SEQUENCE: 745

Ser Lys Ala Asp Thr
1               5

<210> SEQ ID NO 746
<211> LENGTH: 5
<212> TYPE: PRT
<213> ORGANISM: Artificial Sequence
<220> FEATURE:
<223> OTHER INFORMATION: Synthetic Cry1Aa ligand

<400> SEQUENCE: 746

Ser Lys Pro Ala Asp
1               5

<210> SEQ ID NO 747
<211> LENGTH: 11
<212> TYPE: PRT
<213> ORGANISM: Artificial Sequence
<220> FEATURE:
<223> OTHER INFORMATION: Synthetic Fsr ligand
<220> FEATURE:
<221> NAME/KEY: VARIANT
<222> LOCATION: 3, 11
<223> OTHER INFORMATION: Lacton linkage between S3 and A11

<400> SEQUENCE: 747

Gln Asn Ser Ala Ala Ala Phe Ala Ala Trp Ala
1 5 10

<210> SEQ ID NO 748
<211> LENGTH: 11
<212> TYPE: PRT
<213> ORGANISM: Artificial Sequence
<220> FEATURE:
<223> OTHER INFORMATION: Synthetic Fsr ligand
<220> FEATURE:
<221> NAME/KEY: VARIANT
<222> LOCATION: 3, 11
<223> OTHER INFORMATION: Lacton linkage between S3 and A11

<400> SEQUENCE: 748

Gln Asn Ser Ala Ala Ala Phe Gly Gln Trp Ala
1 5 10

<210> SEQ ID NO 749
<211> LENGTH: 7
<212> TYPE: PRT
<213> ORGANISM: Artificial Sequence
<220> FEATURE:
<223> OTHER INFORMATION: Synthetic AgrC1, AgrC2
<220> FEATURE:
<221> NAME/KEY: VARIANT
<222> LOCATION: 4, 7
<223> OTHER INFORMATION: Thiolacton linkage between C4 and M7)

<400> SEQUENCE: 749

Tyr Ser Thr Cys Phe Ile Met
1 5

<210> SEQ ID NO 750
<211> LENGTH: 7
<212> TYPE: PRT
<213> ORGANISM: Artificial Sequence
<220> FEATURE:
<223> OTHER INFORMATION: Synthetic AgrC1, AgrC2
<220> FEATURE:
<221> NAME/KEY: VARIANT
<222> LOCATION: 3, 7
<223> OTHER INFORMATION: Thiolacton linkage between C3 and M7

<400> SEQUENCE: 750

Ser Thr Cys Ala Phe Ile Met
1 5

ENGINEERING ANTIMICROBIAL PEPTIDES

REFERENCE TO RELATED APPLICATIONS

The present application is a U.S. national phase application under 35 U.S.C. § 371 of International Application No. PCT/US2019/035666, filed Jun. 5, 2019, which claims the benefit of U.S. Provisional Application No. 62/681,529, filed Jun. 6, 2018. Each of the aforementioned related applications is incorporated by reference herein in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled SYNG005WOSEQUENCE.TXT, created and last saved on Jun. 5, 2019, which is about 402,822 bytes in size. The information in the electronic format of the Sequence Listing is incorporated herein by reference in its entirety.

BACKGROUND

Microbial organisms such as bacteria can affect human and animal health, and participate in microbiota associated with a variety of animal organs and tissues. Microbial organism-mediated processes can be used in a variety of industrial processes for the manufacture of products of interest, for example for fermentation in a feedstock. Additionally, microbial organisms can be used to manufacture products in sterile environments, such as in the manufacture of pharmaceuticals, biologics, and cosmetics.

Tuning populations of microbial organisms, for example to reduce or eliminate undesired microbial organisms can be useful for maintaining the industrial processes and maintaining the health of tissues that comprise microbial organisms. Antimicrobial peptides such as bacteriocins can affect the growth or viability of microbial organisms.

FIELD

Embodiments herein relate to methods, systems and kits for engineering antimicrobial peptides such as bacteriocins, for example to have a desired range of activity in a desired range of culture conditions.

SUMMARY

Some embodiments include a method of engineering an antimicrobial peptide, such as a bacteriocin. The method can comprise (a) translating a candidate nucleic acid encoding a candidate antimicrobial peptide (e.g., bacteriocin) in vitro in a translation solution, so that the translation solution comprises the candidate antimicrobial peptide. The method can further comprise (b) combining the candidate antimicrobial peptide and a microbial organism in a solution environment. The method can further comprise (c) culturing the microbial organism and the candidate antimicrobial peptide in the solution environment under selected culture conditions. The method can further comprise (d) detecting inhibition of growth and/or reproduction, or a lack thereof, of the microbial organism in the solution environment. The method can further comprise (e) selecting the candidate nucleic acid upon detection of inhibition of growth and/or reproduction of the microbial organism in the solution environment under the selected culture conditions. The method can further comprise (f) producing a variant nucleic acid of the selected candidate nucleic acid, the variant nucleic acid encoding a variant of the candidate antimicrobial peptide. The method can further comprise repeating (a) (f) using one or more successive variant nucleic acids as the candidate nucleic acid, until a predetermined level of inhibition of growth and/or reproduction of the microbial organism in the solution environment under the selected culture conditions is achieved. Thus, the antimicrobial peptide has been engineered. In some embodiments, the method further comprises obtaining a sequence of the selected candidate nucleic acid. The method can further comprise indexing the sequence to the detected inhibition of growth and/or reproduction of the microbial organism in the solution environment of (d), wherein (f) comprises producing the variant nucleic acid based on the indexed sequence of the candidate nucleic acid. By way of example, the candidate nucleic acid can be amplified (such as by PCR), and one or more of the amplicons can be sequenced. In some embodiments, the method further comprises obtaining a sequence of an other candidate nucleic acid for which was detected a lack of inhibition of growth and/or reproduction of the microbial organism in another solution environment under the selected culture conditions. The method can further comprise indexing the sequence of the other candidate nucleic acid to the lack of inhibition of growth and/or reproduction of the microbial organism, wherein (f) comprises producing the variant nucleic acid of the selected candidate nucleic acid based on the indexed sequence of the other candidate nucleic acid. In some embodiments, the sequence of the other candidate nucleic acid is obtained if the other candidate nucleic acid produces a lower level of inhibition of growth and/or reproduction of the microbial organism in the solution environment under the selected culture conditions than the candidate nucleic acid. In some embodiments, producing the variant nucleic acid sequence based on the indexed sequence information comprises machine learning, such as automated machine learning. In some embodiments, the method further comprises confirming the inhibition of growth and/or reproduction of the microbial organism in the solution environment by the candidate antimicrobial peptide after (e), said confirming comprising repeating (a)-(d) for the candidate nucleic acid or a copy thereof, wherein the inhibition of growth and/or reproduction is confirmed when, in the repeat of (d), the quantity of microbial organism in the solution environment indicates inhibition of growth and/or reproduction of the microbial organism in the solution environment under the selected culture conditions. In some embodiments, detecting inhibition of growth and/or reproduction, or a lack thereof, of the microbial organism comprises quantifying the microbial organism in the solution environment, in which a decrease in a quantity of the microbial organism in the solution environment over a period of time indicates inhibition of growth and/or reproduction of the microbial organism. In some embodiments, the predetermined level of inhibition of growth and/or reproduction of the microbial organism in the solution environment under the selected culture conditions is a greater level of inhibition than that of a reference naturally-occurring or engineered antimicrobial peptide. In some embodiments, the engineered antimicrobial peptide and the candidate antimicrobial peptide of an earlier iteration of the method each have a potency. The potency of the engineered antimicrobial peptide can be greater than the potency of the candidate antimicrobial peptide. In some embodiments, the engineered antimicrobial peptide has a greater potency than the candidate antimicrobial peptide across a range of culture conditions and/or against a range of microbial organism strains and/or species. In some embodiments, repeating (b) of (a)-(f) comprises combining the translation solution with a different strain or species of microbial organism than that of a previous iteration of (b). In some embodiments, repeating (b) of (a) (f) comprises combining the translation solution with the same species or strain of microbial organism as a previous iteration of (b). In some embodiments, repeating (c) of (a)-(f) comprises culturing the microbial organism in a different culture environment than a previous iteration of (c). In some embodiments, repeating (c) of (a)-(f) comprises culturing the microbial organism in the same culture environment as a previous iteration of (c). In some embodiments, the candidate nucleic acid comprises DNA. The method can further comprise transcribing the candidate nucleic acid. In some embodiments, the translation solution further comprises a transcription solution, so that the translation solution is configured for transcription and translation of the candidate nucleic acid. In some embodiments, the translation solution comprises a translation reagent, such as a ribosome. In some embodiments, the translation solution comprises one or more post-translational modification enzymes. In some embodiments, the translation solution comprises no more than one candidate nucleic acid sequence encoding a candidate antimicrobial peptide. In some embodiments, the candidate nucleic acid encodes two or more different candidate antimicrobial peptides, so that the solution environment comprises two or more candidate antimicrobial peptides (for example, a cocktail of antimicrobial peptides). The variant nucleic acid can encode variants of at least one of the two or more candidate antimicrobial peptides. Thus, two or more antimicrobial peptides can be co-engineered to inhibit growth and/or reproduction of the microbial organism under the selected culture conditions. In some embodiments, the candidate antimicrobial peptide comprises a chimeric protein. In some embodiments, the selected culture conditions comprise conditions of an industrial process, a pharmaceutical manufacturing process, or a mammalian microbiota. In some embodiments, the mammalian microbiota is of a human gastrointestinal tract, skin, mammary gland, placenta, tissue, biofluid, seminal fluid, uterus, vagina, ovarian follicle, lung, saliva, oral cavity, mucosa, conjunctiva, or biliary tract. In some embodiments, the solution environment comprises two or more species of microbial organism. In some embodiments, the translation solution further comprises a substrate. The candidate nucleic acid can be immobilized on the substrate. The method can further comprise producing the variant nucleic acid immobilized on another substrate that is the same as or different from the substrate. In some embodiments, the substrate comprises a bead, nanoparticle, well, membrane, nitrocellulose, PVDF, nylon, acetate derivative, matrix, pore, plastic, metal, glass, polymer, polysaccharide, or paramagnetic compound. In some embodiments, said producing the variant nucleic acid comprises one or more of amplifying the selected candidate nucleic acid with a degenerate polymerase; amplifying the selected candidate nucleic acid in the presence of a degenerate primer; amplifying the selected candidate nucleic acid in the presence of a degenerate nucleotide; and mutagenesis reaction on the selected candidate nucleic acid. In some embodiments, a library of candidate nucleic acids is screened. In some embodiments, producing the variant nucleic acid comprises producing a library of variant nucleic acids, the method further comprising performing (a) (e) on the library of variant nucleic acids. In some embodiments, the method is performed in a microfluidic system. In some embodiments, the translation solution and/or the solution environment is microliter-scale. In some embodiments, the translation solution and/or the solution environment has a volume of 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl. In some embodiments, the solution environment comprises a microdrop. In some embodiments, the candidate antimicrobial peptide and the microbial organism in (b) are each in a microdrop, and said combining comprises combining microdrops into a solution environment comprising a microdrop. In some embodiments, said culturing in (c) comprises culturing a microdrop comprising the microbial organism and the candidate antimicrobial peptide in the solution environment. In some embodiments, a microdrop comprises a nanometer-scale droplet of solution. In some embodiments, the microbial organism comprises, consists essentially of, or consists of a bacteria. For example, the microbial organism can be a bacteria that is resistant to antibiotics, such as Methicillin-resistant *Staphylococcus aureus* (MRSA). In the method of some embodiments, the antimicrobial peptide comprises, consists essentially of, or consists of a bacteriocin. In some embodiments, the solution environment does not comprise any cells comprising nucleic acid encoding the antimicrobial peptide.

Some embodiments include a microfluidic system for engineering an antimicrobial peptide (e.g., bacteriocin). The microfluidic system can comprise a transcription station configured to perform in vitro transcription, the transcription station comprising a transcription reagent. The microfluidic system can further comprise a translation station in fluid communication with the transcription station, the translation station configured to perform in vitro translation, and comprising a translation reagent. The microfluidic system can further comprise a culture station in fluid communication with the translation station and configured to culture a microbial organism in a solution environment comprising the microbial organism, a candidate nucleic acid encoding a candidate antimicrobial peptide, and the candidate antimicrobial peptide under selected culture conditions. The microfluidic system can further comprise a detector in fluid communication with the culture station, and configured to detect inhibition of growth and/or reproduction, or a lack thereof, of the microbial organism in the solution environment. The microfluidic system can further comprise a variant station configured to produce a variant nucleic acid of the nucleic acid encoding the candidate antimicrobial peptide. The variant station can be in fluid communication with the transcription station. In some embodiments, the microfluidic system further comprises a processor. The variant station can further comprise a sequencing module configured to obtain sequence information from the candidate nucleic acid. The processor can be configured to index the sequence information to the detection of inhibition of growth and/or reproduction or the lack thereof for the microbial organism. In some embodiments, the processor is configured to select a sequence of the variant nucleic acid based on the indexed information by machine learning, such as automatic machine learning. In some embodiments, the variant station produces the variant nucleic acid only if the detector detects an inhibition of growth and/or reproduction of the microbial organism in the solution environment. In some embodiments, the variant station comprises a degenerate polymerase. In some embodiments, two or more of the transcription station, the translation station, the culture station, and/or the variant station are comprised within discrete chambers that are separate from each other. In some embodiments, the transcription station and the translation station are the same station or overlap with each other. In some embodiments, two or more of the transcription station, the translation station, the culture station, and the variant station, are comprised within a single chamber. In some embodiments, the single chamber is configured to expel a first set of reagents and subsequently receive a second set of reagents that is different from the first set. In some embodiments, the selected culture conditions of the culture station comprise conditions of an industrial process, pharmaceutical manufacturing process, or mammalian microbiota. In some embodiments, the translation station is in fluid communication with a substrate comprising the candidate nucleic acid immobilized thereon. In some embodiments, the substrate comprises a bead, nanoparticle, well, membrane, nitrocellulose, PVDF, nylon, acetate derivative, matrix, pore, plastic, metal, glass, polymer, polysaccharide, or paramagnetic compound. In some embodiments, the translation station comprises a chamber that is microliter-scale and/or the solution environment is microliter-scale. In some embodiments, the solution environment has a volume of about 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl. In some embodiments, the chamber of the translation station has a volume of about 1 μl-1000 μl, 1 μl-50 μl, 1 μl-100 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl. In some embodiments, the translation station comprises a mixture of different candidate antimicrobial peptides. In some embodiments, the microbial organism comprises multiple species of microbial organisms. In some embodiments, the translation station comprises one or more post-translational modification enzymes. In some embodiments, the solution environment comprises a microdrop. In some embodiments, the microfluidic system is configured to move and combine microdrops within the system. In some embodiments, the transcription reagent and/or the translation reagent are each in separate microdrops or in a combined microdrop. In some embodiments, the culture station is configured to culture a microbial organism in a microdrop. In some embodiments, a microdrop comprises a nanometer-scale droplet of solution. In some embodiments, for any microfluidic system described herein, the antimicrobial peptide comprises, consists essentially of, or consists of a bacteriocin. In some embodiments, the microfluidic system does not comprise any cells comprising nucleic acid encoding the antimicrobial peptide.

Some embodiments include a kit for engineering an antimicrobial peptide (e.g., bacteriocin). The kit can comprise a candidate nucleic acid encoding a candidate bacteriocin. The kit can further comprise a microfluidic system as described herein. In some embodiments, the kit further comprises a library of candidate nucleic acids. In some embodiments, the kit further comprises a microbial organism. In some embodiments, the microbial organism comprises a bacteria. In some embodiments, for any kit described herein, the antimicrobial peptide comprises, consists essentially of, or consists of a bacteriocin.

DETAILED DESCRIPTION

Figure 1:
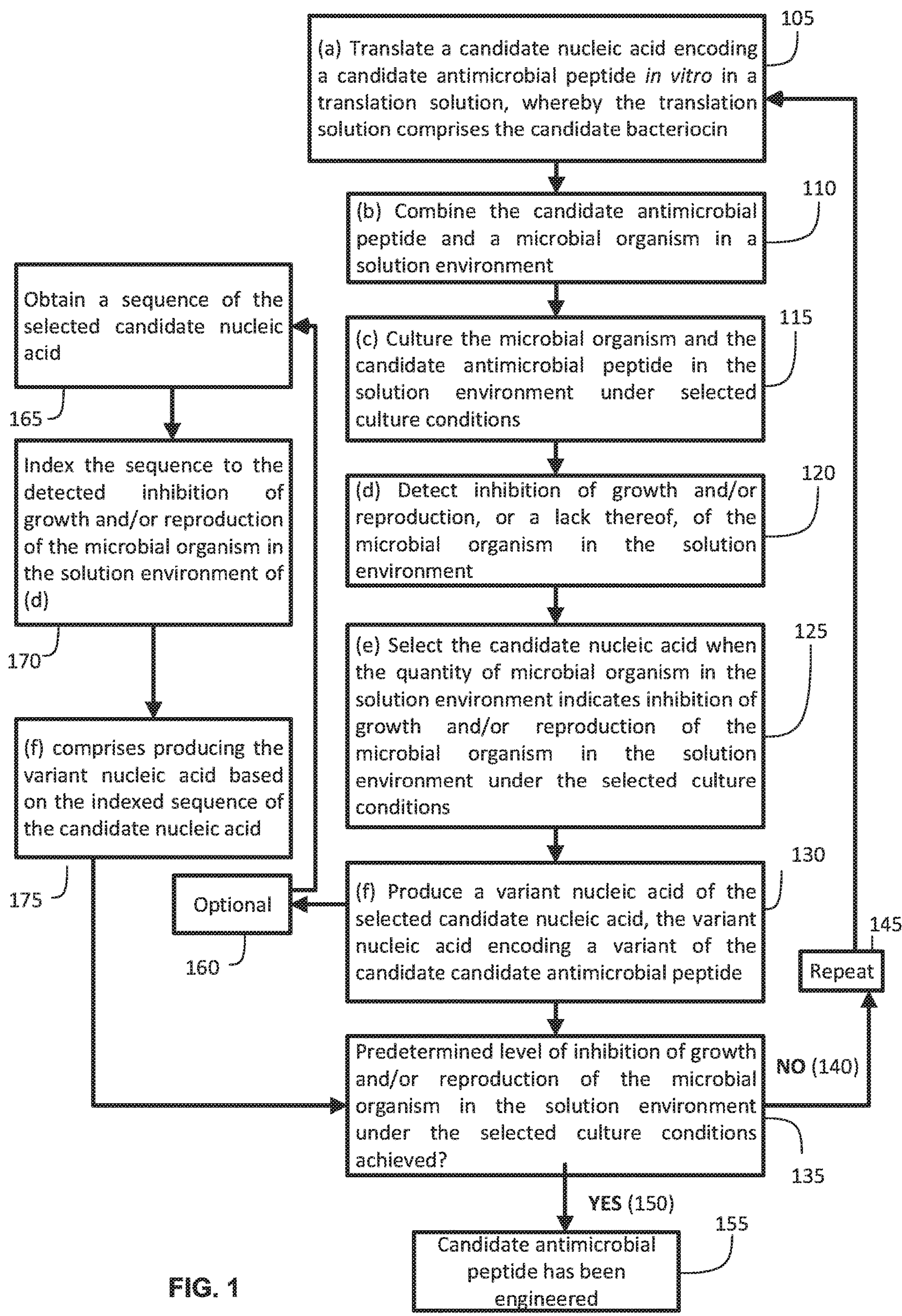
FIG. 1 is a flow diagram illustrating a method of engineering antimicrobial peptides (e.g., bacteriocins) according to some embodiments herein.

Described herein are methods, systems and kits for engineering antimicrobial peptides (e.g., bacteriocins). The antimicrobial peptides may be engineered to have a particular activity for a specified culture, environmental condition(s), and/or a range of conditions. For example, antimicrobial peptides can be engineered to have antimicrobial activity against pathogenic bacteria under conditions of a human gut microbiota. In some embodiments, an antimicrobial peptide is transcribed and translated in vitro and tested for effects on the viability or growth of a microbial organism under a specified set of conditions in a solution environment (for example, a droplet or microdrop in a microfluidic system). Based on the results of the testing, variants of the antimicrobial peptide can be designed, and the variants can be tested in an iterative process until a desired activity is achieved. In some embodiments, the iterative process for engineering antimicrobial peptides is performed by automated machine learning.

Translation Solutions and Translation Stations

Translation solutions can be useful for translating nucleic acids in accordance with the methods, microfluidic systems and kits of some embodiments described herein. Suitable translation solutions can comprise, consist essentially of, or consist of reagents for in vitro translation (which, for convenience, may be referred to herein as "translation reagents"), and as such can be configured for in vitro translation of a transcript such as an RNA. In some embodiments, a translation solution is comprised by a translation station of a microfluidic system as describe herein. In some embodiments, the translation solution further comprises a transcription solution comprising reagents for transcription (which, for convenience, may be referred to herein as "transcription reagents"), and thus is configured for in vitro transcription and translation, for example to transcribe and translate a candidate nucleic acid encoding a candidate antimicrobial peptide as described herein. It is contemplated that in vitro transcription and translation in a single solution (such as a transcription solution further comprising a translation solution as described herein) can facilitate efficient in vitro production of candidate antimicrobial peptides in accordance with methods, systems, and kits of some embodiments.

In accordance with the methods, systems and kits of some embodiments described herein, the translation solution comprises, consists essentially of, or consists of one or more translation reagents Examples of translation reagents include a ribosome, a buffer, an amino acid, a tRNA (which may be conjugated to an amino acid), a lysate or extract such as an *E. coli* lysate or *E. coli* extract, and a cofactor or metallic ion such as $Mg^{2+}$, or a combination of two or more of any of the listed items. In accordance with the methods, systems and kits of some embodiments described herein the translation solution further comprises a transcription solution, and thus is configured for in vitro transcription and translation. As described herein, a transcription solution further comprising a translation solution contemplates a single solution that is suitable for in vitro transcription and translation. As such, a transcription solution further comprising a translation solution encompasses a single transcription/translation solution, and well as translation solution with discrete sub-environments, at least some of which are suitable for transcription. It will be appreciated that some components of a transcription and/or translation solution, for example ribosomes, may not be liquids, and could potentially be isolated from the transcription and/or translation solution, for example by filtration and/or centrifugation. Translation solutions of methods, systems and kits of some embodiments described herein (and which can be comprised by translation solutions as described herein) can comprise, consist essentially or, or consist of one or more transcription reagents. Examples of transcription reagents include an RNA polymerase, a buffer, a nucleic acid mix (for example, NTPs including ATP, GTP, CTTP, and UTP), a cofactor or metallic ion such as $Mg^{2+}$, a transcription inducer (such as a transcription factor, IPTG, or lactose), a polyadenylation enzyme, a capping enzyme, a lysate or extract such as a bacterial lysate or extract such as an *E. coli* lysate or *E. coli* extract, an SP6 polymerase, a T3 polymerase, a T7 RNA polymerase, or a mixture of two or more of any of the listed items. The transcription solution can be useful for transcribing a template, such as a candidate nucleic acid as described herein. Translation solutions of methods, kits, and systems of some embodiments include one or more transcription reagents in combination with one or more translation reagents.

In some embodiments, the translation solution comprises a post-translational modification enzyme. Examples of post-translational modification enzymes include, but are not limited to a cleavage enzyme, a kinase, a phosphatase, a glycosyltransferase, or a mixture of any two of the listed items.

In some embodiments, a translation station of a microfluidic device comprises the translation solution. In some embodiments, the microfluidic device comprises a transcription station and a transcription solution, which may be the same station, or may be different stations. For example, in some embodiments, the transcription station comprises a single transcription/translation station configured for in vitro transcription and translation of a nucleic acid. In some embodiments, the translation station is configured to perform in vitro translation. In some embodiments, the transcription station is configured to perform in vitro transcription. In some embodiments, the translation station further comprises the transcription station (for example as a single environment, or as two discrete environments), and is configured to perform in vitro transcription and translation. In some embodiments, the microfluidic device comprises a transcription station comprising the transcription solution, and a separate translation station comprising the translation solution.

In some embodiments, the translation station is configured to receive a translation solution and/or one or more translation reagents and/or transcription reagents as described herein. In some embodiments, the transcription station is in fluid communication with one or more reservoirs comprising transcription reagents and/or translation reagents. As such, in some embodiments, a translation station initially does not include a translation solution, but is configured to receive a translation solution, or one or more reagents.

In accordance with the methods, systems and kits of some embodiments described herein, the translation solution comprises more than one candidate nucleic acid encoding a candidate antimicrobial peptide, for example encoding two or more different antimicrobial peptides that are being co-engineered together in accordance with some embodiments herein (so that a cocktail of bacteriocins can be engineered). In some embodiments, the translation solution comprises a candidate nucleic acid encoding no more than one candidate antimicrobial peptide.

It is contemplated that immobilizing a candidate nucleic acid on a substrate such as a bead can be useful for manipulation and analysis of a candidate nucleic acid and its corresponding candidate antimicrobial peptide in a microfluidic environment, for example in a microdroplet. In accordance with the methods, systems and kits of some embodiments described herein, the translation solution comprises a substrate. Examples of suitable substrates include a bead, a nanoparticle, a well, a membrane, nitrocellulose, PVDF, nylon, an acetate derivative, a matrix, a pore, plastic, metal, glass, a polymer, a polysaccharide, and a paramagnetic compound, or a combination of two or more of any of the listed items. In some embodiments, the candidate nucleic acid is immobilized on the substrate.

In accordance with the methods, systems and kits of some embodiments described herein, the translation solution is at a microliter-scale. For example, the translation solution may have a volume of 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl.

Bacteriocins and Antimicrobial Peptides

As used herein, "bacteriocin," and variations of this root term, has its customary and ordinary meaning as understood by one of skill in the art in view of this disclosure. It refers to a polypeptide that is secreted by a host cell and can neutralize at least one microbial organism other than the individual host cell in which the polypeptide is made, including cells clonally related to the host cell and other microbial cells. "Bacteriocin" also encompasses a cell-free or chemically synthesized version of such a polypeptide, for example an engineered bacteriocin in accordance with some embodiments herein. A host cell can exert cytotoxic or growth-inhibiting effects on one or a plurality of other microbial organisms by secreting bacteriocins. Example bacteriocins are set forth in SEQ ID NOS: 4-450 (even numbers) and 699-737 (odd numbers). Example nucleic acids encoding these bacteriocins are provided as SEQ ID NOs: 5-451 (odd numbers) and 700-738 (even numbers). Detailed descriptions of bacteriocins and some polynucleotide sequences that encode bacteriocins, including methods and compositions for using bacteriocins to control the growth of microbial cells can be found, for example, in U.S. Pat. No. 9,333,227, which is hereby incorporated by reference in its entirety. Some examples of suitable bacteriocins and categories of bacteriocins are taught in Tables 1.1 and 1.2 of U.S. Pat. No. 9,333,227. It is contemplated that any of these bacteriocins can be subject to further engineering. For example, variants and/or modifications of these bacteriocins can be candidate bacteriocins that can be used to engineer a bacteriocin having at least a specified activity in a solution environment under selected culture conditions in accordance with some embodiments herein. As used herein a "candidate bacteriocin" refers to a polypeptide that may have, but has not necessarily been confirmed to have bacteriocin activity. A candidate bacteriocin can be confirmed to inhibit growth and/or reproduction of a microbial organism under selected culture conditions in accordance with methods, systems, and kits of some embodiments herein. Accordingly, it is contemplated that that for any bacteriocin described herein, a "candidate bacteriocin" can comprise the noted structures, and/or can be a candidate for having the noted functionality (the functionality can subsequently be confirmed). A "variant antimicrobial peptide" or "variant bacteriocin" refers to an antimicrobial peptide (or bacteriocin, in particular) that has a different sequence and/or post-translational modification than a reference candidate bacteriocin. A "variant nucleic acid" refers to a nucleic acid that encodes the variant antimicrobial peptide (or bacteriocin, in particular). It will be appreciated that a variant of a candidate antimicrobial peptide (or candidate bacteriocin, in particular) may be selected as described herein, and as such, a variant nucleic acid of some embodiments is selected in order to encode the variant of the candidate antimicrobial peptide (or bacteriocin). If a variant antimicrobial peptide (e.g., variant bacteriocin) is tested, used, or cultured in accordance with methods, kits, and systems of some embodiments, the variant antimicrobial peptide itself can be a candidate antimicrobial peptide. For example, the variant antimicrobial peptide (e.g., variant bacteriocin) can comprise a point mutation, deletion (including a truncation), insertion (including a C- or N- terminal addition), rearrangement, or two or more of these compared to a candidate antimicrobial peptide.

Antimicrobial peptides are a class of peptides that kill or arrest the growth of microbial organisms. As used herein "antimicrobial peptide" (including variations of this root term) has its customary and ordinary meaning as would be understood by one of ordinary skill in the art in view of this disclosure. Classically, antimicrobial peptides have been described as peptides produced by the innate immune systems of invertebrates and vertebrates. Thus, while bacteriocins have classically been referred to a class of microbial gene products that target microbial organisms, antimicrobial peptides have classically been referred to as a class of invertebrate and vertebrate gene products that target microbial organisms. However, for conciseness "antimicrobial peptide" as used herein broadly encompasses classical antimicrobial peptides (e.g., that confer innate immune activity against microbial organisms) as well as bacteriocins.

Examples of classical antimicrobial peptides suitable for methods, systems, and kits of some embodiments herein are known in the art, and can be found, for example, at The Antimicrobial Peptide Database accessible on the world wide web at aps.unmc.edu/AP/, which is incorporated herein by reference in its entirety. Over 1000 antimicrobial peptides and variants thereof have been identified and cataloged. The Antimicrobial Peptide Database is described in Wang et al. (2016), *Nucleic Acids Res.* 44 (Database issue): D1087-D1093, which is incorporated herein by reference in its entirety. Examples of antimicrobial peptides include bacteriocins, antibacterial, antiviral, anti-HIV, antifungal, antiparasitic and anticancer peptides, such as Dermaseptin-B2, Abaecin, Ct-AMP1, Andropin, Aurein 1.1, Lactoferricin B, and Heliomicin. Methods, compositions, systems, and microfluidic devices of some embodiments comprise naturally-occurring antimicrobial peptides, or a nucleic acid encoding the same. Methods, compositions, systems, and microfluidic devices of some embodiments comprise non-naturally occurring antimicrobial peptides, or nucleic acids encoding the same. Methods, compositions, systems, and microfluidic devices of some embodiments include antimicrobial peptides that comprise a mutation or variation in a naturally-occurring antimicrobial peptides, or a nucleic acid encoding the same. Methods, compositions, systems, and microfluidic devices of some embodiments comprise antimicrobial peptides comprising, consisting essentially of, or consisting of non-naturally occurring peptide sequences, or nucleic acids encoding the same.

In accordance with the methods, systems and kits of some embodiments described herein, an antimicrobial peptide, for example, a bacteriocin to be engineered or that has been engineered (or a candidate antimicrobial peptide, and/or a variant of a candidate antimicrobial peptide as described herein) of some embodiments is initially produced in a pro-polypeptide, which can then be cleaved to produce the antimicrobial peptide. In some embodiments, the pro-polypeptide or antimicrobial peptide is chemically synthesized. In some embodiments, an antimicrobial peptide comprises a polypeptide that has undergone post-translational modifications, for example cleavage, or the addition of one or more functional groups. In some embodiments, an antimicrobial peptide is engineered. In some embodiments, the engineered antimicrobial peptide is engineered to have a modified activity or ability to kill or affect the growth of a microbial organism.

Some antimicrobial peptides (such as bacteriocins) have cytotoxic activity (e.g. "bacteriocide" effects), and thus can kill microbial organisms, for example bacteria, yeast, algae, synthetic microorganisms, and the like. Some antimicrobial peptides (such as bacteriocins) can inhibit the reproduction of microbial organisms (e.g. "bacteriostatic" effects), for example bacteria, yeast, algae, synthetic microorganisms, and the like, for example by arresting the cell cycle.

While many the bacteriocins are naturally-occurring (for example, naturally occurring bacteriocins set forth in SEQ ID NOS: 4-450 (even numbers) and 699-737 (odd numbers)), the skilled artisan will appreciate that in some embodiments of the methods, systems and kits described herein, a bacteriocin comprises a naturally-occurring bacteriocin other than the bacteriocins and encoding nucleotide sequences of SEQ ID SEQ ID NOS: 4-450 (even numbers) and 699-737 (odd numbers), or a non-naturally-occurring bacteriocin or a synthetic bacteriocin (such as an engineered bacteriocin), or a variant thereof (which can also be a kind of engineered bacteriocin of some embodiments). In some embodiments, an engineered bacteriocin has enhanced or decreased levels of cytotoxic or growth inhibition activity on the same or a different microorganism or species of microorganism relative to a wild-type bacteriocin. In some embodiments, the antimicrobial peptide (or bacteriocin) does not comprise a lantibiotic.

Several motifs have been recognized as characteristic of bacteriocins. For example, the motifYGXGV (SEQ ID NO: 2), wherein X is any amino acid residue, is an N-terminal consensus sequence characteristic of a class IIa bacteriocin. Accordingly, in some embodiments, a candidate (or variant) bacteriocin (e.g., an engineered bacteriocin) comprises an N-terminal sequence with at least about 50% identity to SEQ ID NO: 2), for example at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%. 83%, 84%, 85%, 86%, 87%, 88%, 89%, 90%, 91%, 92%. 93%, 94%, 95%, 96%, 97%, 98%, 99%, or 100% identity to SEQ ID NO: 2). In some embodiments, a candidate (or variant) bacteriocin (e.g., an engineered bacteriocin) comprises a N-terminal sequence comprising SEQ ID NO: 2). Additionally, some class IIb bacteriocins comprise a GxxxG motif. Without being limited by any particular theory, it is believed that the GxxxG motif can mediate association between helical proteins in the cell membrane, for example to facilitate bacteriocin-mediated neutralization through cell membrane interactions. As such, in some embodiments, the bacteriocin (e.g., the engineered bacteriocin) comprises a motif that facilitates interactions with the cell membrane. In some embodiments, the bacteriocin comprises a GxxxG motif. Optionally, the bacteriocin comprising a GxxxG motif can comprise a helical structure. In addition to structures described herein, "bacteriocin" as used herein also encompasses structures that have substantially the same effect on microbial cells as any of the bacteriocins explicitly provided herein.

In some embodiments, a fusion polypeptide comprising two or more antimicrobial peptides (such as bacteriocins) or portions thereof has a neutralizing activity against a broader range of microbial organisms than either individual antimicrobial peptide of the two or more antimicrobial peptides or portions thereof. For example, it has been shown that a hybrid antimicrobial peptide displays antimicrobial activity against pathogenic Gram-positive and Gram-negative bacteria (Acuña et al. (2012), *FEBS Open Bio,* 2: 12-19). It is noted that that Ent35-MccV fusion bacteriocin comprises, from N—terminus to C-terminus, an N-terminal glycine, Enterocin CRL35, a linker comprising three glycines, and a C-terminal Microcin V.

It is contemplated herein that an antimicrobial peptide (such as a bacteriocin) can comprise a fusion of two or more polypeptides, for example two or more polypeptides having antimicrobial (such as bacteriocin) activity. In some embodiments an antimicrobial peptide or a candidate antimicrobial peptide comprises a chimeric protein. In some embodiments, a variant antimicrobial peptide (such as a bacteriocin) or an engineered antimicrobial peptide (such as an engineered bacteriocin) comprises a fusion polypeptide comprising two or more antimicrobial peptides (such as bacteriocins). In some embodiments, a variant antimicrobial peptide (such as a bacteriocin) or an engineered antimicrobial peptide (such as a bacteriocin) comprises a chimeric protein comprising two or more antimicrobial peptides (such as bacteriocins), or fragments thereof. In some embodiments, the two or more antimicrobial peptides of the fusion comprise polypeptides of SEQ ID NOS: 4-450) (even numbers) and 699-737 (odd numbers), and or encoded by nucleic acids of SEQ ID NOs: 5-451 (odd numbers) and 700-738 (even numbers), or variants or modifications thereof. In some embodiments, the fusion polypeptide has a broader spectrum of activity than either individual antimicrobial peptide, for example having neutralizing activity against more microbial organisms, neutralizing activity under a broader range of environmental conditions, and/or a higher efficiency of neutralization activity. In some embodiments, the fusion polypeptide comprises two, three, four, five, six, seven, eight, nine, or ten antimicrobial peptides. In some embodiments, two or more antimicrobial peptide polypeptides are fused to each other via a covalent bond, for example a peptide linkage. In some embodiments, a linker is positioned between the two individual antimicrobial polypeptides of the fusion polypeptide. In some embodiments, the linker comprises one or glycines, for example about 1, 2, 3, 4, 5, 6, 7, 8, 9, 10, 11, 12, 13, 14, 15, 16, 17, 18, 19, or 20 glycines. In some embodiments, the linker is cleaved within the cell to produce the individual antimicrobial peptides (such as bacteriocins) included in the fusion protein. In some embodiments, a variant antimicrobial peptide (such as a variant bacteriocin) or engineered antimicrobial peptide (such as an engineered bacteriocin) as provided herein comprises a modification to provide a desired spectrum of activity relative to the unmodified or candidate antimicrobial peptide (e.g., bacteriocin). For example, the variant antimicrobial peptide (e.g., bacteriocin) or engineered antimicrobial peptide (e.g., bacteriocin) may have enhanced or decreased activity against the same organisms as the unmodified or candidate antimicrobial peptide (e.g., bacteriocin). Alternatively, the modified antimicrobial peptide (e.g., bacteriocin) may have enhanced activity against an organism against which the unmodified or candidate antimicrobial peptide (e.g., bacteriocin) has less activity or no activity.

In accordance with the methods, systems and kits of some embodiments described herein, an antimicrobial peptide (e.g., bacteriocin) is encoded by a polynucleotide. For example, a DNA sequence of an antimicrobial peptide (e.g., bacteriocin) gene may encode an mRNA transcript that is translated into a protein comprising, consisting essentially of, or consisting of an antimicrobial peptide (such as a bacteriocin). As used herein, a "candidate nucleic acid" refers to a nucleic acid that encodes a "candidate antimicrobial peptide (e.g., bacteriocin)" as described herein. In some embodiments, the polynucleotide encoding an antimicrobial peptide (such as a bacteriocin) comprises a variant nucleic acid. In some embodiments, the variant nucleic acid is produced by engineering or modifying the sequence of the candidate nucleic acid, for example by synthesis of the variant nucleic acid sequence, or by mutagenesis such a chemical mutagenesis, or degenerate polymerization.

Microbial Organisms

Engineered antimicrobial peptides in accordance with methods, microfluidic systems, and kits of some embodiments herein inhibit the growth and/or reproduction of microbial organisms. As used herein, "microbial organism," "microorganism," and variations of these root terms (such as pluralizations and the like), any naturally-occurring species or fully synthetic prokaryotic or eukaryotic unicellular organism, as well as Archaea species, as well as genetic modifications of any of these. Thus, this expression can refer to cells of bacterial species, fungal species, and algae.

Exemplary microorganisms that can be used in accordance with methods, kits, and microfluidic systems of some embodiments herein include, but are not limited to, bacteria, fungus, and algae, for example photosynthetic microalgae. In some embodiments, a microorganism is selected from the group consisting of bacteria and fungus (such as yeast). Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," *Science* 329: 52-56, hereby incorporated by reference in its entirety). As such, in some embodiments, the microorganism is fully synthetic. A desired combination of genetic elements, including elements that regulate gene expression, and elements encoding gene products (for example antimicrobial peptides (e.g., bacteriocins), immunity modulators, poison, antidote, and industrially useful molecules) can be assembled on a desired chassis into a partially or fully synthetic microorganism. Description of genetically engineered microbial organisms for industrial applications can also be found in Wright, et al. (2013) "Building-in biosafety for synthetic biology" *Microbiology* 159: 1221-1235. In the methods, microfluidic systems and kits of some embodiments, two or more different species and/or strains of microbial organism are contemplated, for example a solution environment can comprise two or more different species of microbial organisms, such as different members of a microbiota as described herein and/or two or more different species or strains that participate in an industrial fermentation process. For example, some embodiments include two or more different species and/or strains of bacteria, yeast, and/or algae.

A variety of bacterial species and strains can be used in accordance with methods, microfluidic systems, and kits of some embodiments herein, along with genetically modified variants, or synthetic bacteria based on a "chassis" of a known species. Exemplary bacteria with industrially applicable characteristics, which can be used in accordance with methods, systems, and kits of some embodiments herein include, but are not limited to, *Bacillus* species (for example *Bacillus coagulans, Bacillus subtilis*, and *Bacillus licheniformis*), *Paenibacillus* species, *Streptomyces* species, *Micrococcus* species, *Corynebacterium* species, *Acetobacter* species, *Cyanobacteria* species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellum, Staphylococcus* species such as *Staphylococcus aureus*, and *Escherichia coli*. In some embodiments, the bacterial species are species of a microbiota as described herein, for example the microbiota of a mammalian organ such as a gastrointestinal or skin micobiota. For example, in some embodiments, the bacterial species of a gastrointestinal microbiota include Firmicutes and/or *Bacteriodetes*.

A variety of yeast species and strains can be used in accordance with methods, microfluidic systems, and kits of some embodiments herein, and genetically modified variants, or synthetic yeast based on a "chassis" of a known species are also contemplated. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces japonicas*), *Pichia* or *Hansenula* species (for example, *Pichia pastoris* or *Hansenula polymorpha*) species, and *Brettanomyces* species (for example, *Brettanomyces claussenii*).

A variety of algae species and strains can be used in accordance with methods, microfluidic systems, and kits of some embodiments herein, and genetically modified variants, or synthetic algae based on a "chassis" of a known species are also contemplated. In some embodiments, the algae comprises photosynthetic microalgae. Exemplary algae species that can be useful for biofuels, and can be used in accordance with embodiments herein, include *Botryococcus braunii, Chlorella species, Dunaliella tertiolecta, Gracilaria species, Pleurochrysis carterae*, and *Sargassum* species. Additionally, many algaes can be useful for food products, fertilizer products, waste neutralization, environmental remediation, and carbohydrate manufacturing (for example, biofuels).

In clinical and industrial settings, undesired bacteria have developed resistance to one or more antibiotics, which can make it challenging to use conventional antibiotics to control the growth of these bacteria. Without being limited by theory, it is contemplated that mechanisms that confer antibiotic resistance (for example pumps or channels that transport drug compounds) are inapplicable to antimicrobial peptides such as bacteriocins, and thus, engineered antimicrobial peptides (e.g., engineered bacteriocins) in accordance with methods, systems, and kits of some embodiments herein can inhibit the growth or reproduction of a microbial organism that is resistant to antibiotics. In some embodiments, the microbial organism is resistant to an antimicrobial compound. For example, some embodiments include bacteria resistant to an antibiotic. In some embodiments, the microbial organism is Methicillin-resistant *Staphylococcus aureus* (MRSA). In some embodiments, the microbial organism is Vancomycin resistant.

Solution Environments

Solution environments can be useful for engineering antimicrobial peptides (such as bacteriocins) in accordance with the methods, microfluidic systems and kits of some embodiments described herein. For example, culture conditions in a solution environment can replicate or mimic conditions in a natural or synthetic environment in which a microbial organism may grow (for example a microbiota, an industrial process, and/or a sterile manufacturing process), and to engineer an antimicrobial peptide with selected characteristics in the natural or synthetic environment. Examples of culture conditions can include, but are not limited to temperature, pH, chemicals, the presence of other microbial organisms, and/or the presence of gene products such as proteases. Suitable solution environments can comprise, consist essentially of, or consist of one or more solutions and other ingredients that replicate or mimic the natural or synthetic environment. In some embodiments, a solution environment is comprised by a culture station of a microfluidic system as describe herein. In some embodiments, the solution environment comprises a microbial organism and a candidate antimicrobial peptide (e.g., candidate bacteriocin). The microbial organism can be cultured in the solution environment with the candidate antimicrobial peptide under selected culture conditions to replicate (or mimic) a natural or synthetic environment. In some embodiments, the solution environment is provided as a microdrop that is combined with a microdrop comprising the candidate antimicrobial peptide, so as to form a microdrop solution environment comprising the candidate antimicrobial peptide and microbial organism(s) in the solution environment.

In accordance with the methods, systems and kits of some embodiments described herein, the solution of the solution environment comprises an industrial feedstock, a pharmaceutical or cosmetic manufacturing solution, or a bodily fluid (for example, that of a microbiota). In accordance with the methods, systems and kits of some embodiments described herein, the solution of the solution environment comprises, consists essentially of, or consists of water, oil, acetic acid, methanol, ethanol, propanol, butanol, formic acid, propylene carbonate, nitromethane, dimethyl sulfoxide, acetonitrile, dimethylformamide, acetone, ethyl acetate, tetrahydrofuran, dichloromethane, diethyl ether, chloroform, 1,4-dioxane, toluene, benzene, cyclohexane, hexane, cyclopentane, pentane, a feedstock, a culture medium, a bodily fluid, or a combination of two or more of any of the listed items.

In accordance with the methods, systems and kits of some embodiments described herein, the selected culture conditions of the solution environment comprise, consists essentially of, or consist of conditions of an industrial process, a pharmaceutical manufacturing process, or a microbiota. Accordingly, the engineered antimicrobial peptide(s), when produced, can be integrated into the corresponding industrial process (which can be on an industrial scale).

Examples of industrial processes whose conditions may be replicated in a solution environment of some embodiments include fermentation (for example carbohydrate manufacturing such as biofuels), food production, decomposition, waste neutralization, and environmental remediation.

Examples of pharmaceutical or biologic or cosmetic manufacturing processes whose conditions may be replicated in solution environments of some embodiments include chemical synthesis, tissue culture, fermentation, extraction, isolation of chemical compounds, proportioning, and packaging, or a combination of two or more of any of the listed items. In some embodiments, a solution environment replicates a pharmaceutical or biologic product or component thereof, for example a buffer, a sterile solution, a saline solution, an ointment, a capsule, a container, and a vial, or a combination of two or more of any of the listed items. It can be advantageous for engineered antimicrobial peptides of some embodiments to maintain a sterile pharmaceutical or biologic or cosmetic manufacturing processes by targeting contaminating microbes.

The composition of microbial organisms in a solution environment of methods, microfluidic systems, and kits of some embodiments can be controlled so that a solution environment contains a specified species, quantities, and/or ratios of bacteria. By way of example, live bacteria can be sorted by flow cytometry, for example based on parameters such as membrane integrity (which can be measured, e.g, through labeling with a membrane-impermeable probe such as PI), membrane potential proton motive force (which can be measured, e.g., through labeling with membrane-permeable anionic or cationic dyes), enzyme activity (which can be measured, e.g., through labeling with of fluorogenic substrates that become fluorescent through enzyme activity), substrate turnover (which can be measured, e.g., through labeling with fluorescent substrates or analogs thereof), pump activity (which can be measured, e.g., through destaining in the presence of probes), gene expression activity (such as response to signaling, which can be measured, for example, by promoter-drive fluorescent protein synthesis), cell division (which can be measured, e.g., by counting fixed volumes against references particles), and/or cell proliferation (which can be measured, e.g., through DNA-specific staining). Example approaches for sorting live microbial cells are reviewed in detail in Miller et al. (2010), *FEMS Microbiol. Rev.* 34: 554-587, which is incorporated by reference in its entirety herein. In methods, microfluidic systems, and kits of some embodiments, the composition of microbial organisms in a solution environment is adjusted by flow cytometric sorting based on membrane integrity, membrane potential proton motive force, enzyme activity, substrate turnover, pump activity, gene expression activity, cell division, cell proliferation, or any combination of two or more of the listed items.

In methods, microfluidic systems, and kits of some embodiments, the cultures conditions of the solution environment replicate those of a microbiota, such as a plant microbiota or an animal microbiota such as a mammalian microbiota (e.g., a human microbiota). Examples of a mammalian microbiota include, but are not limited to, microbiota that of a gastrointestinal tract, skin, a mammary gland, a placenta, a tissue, a biofluid, a seminal fluid, a uterus, a vagina, an ovarian follicle, a lung, saliva, an oral cavity, a mucosa, a conjunctiva, and a biliary tract, or a combination of two or more of any of the listed items.

In some embodiments, the solution environment comprises, consists essentially of, or consists of a microbial organism. In some embodiments, the solution environment comprises at least two species or strains of microbial organism.

In some embodiments, the solution environment is at a microliter-scale. For example, the solution environment may have a volume of 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl. In some embodiments, the solution environment comprises substances such as trace metals, ions, and/or metabolites. In some embodiments, the solution environment comprises no such substances. In some embodiments, the solution environment comprises a media such as LB media or DMEM in a liquid form or in a gel or matrix form. In some embodiments, the solution environment is provided as a microdrop that is combined with a microdrop comprising the candidate antimicrobial peptide (e.g., candidate bacteriocin), so as to form a microdrop solution environment comprising the candidate antimicrobial peptide (e.g., candidate bacteriocin) and microbial organism(s) in the solution environment. Optionally, the solution environment can be provided as a single microdrop. Optionally, the solution environment can be provided as two or more mcirodrops (which contain the same or different components). For example, in some embodiments, two or more microdrops containing different components (e.g., a microbial organism, a culture medium, an industrial product or intermediate, or the like) are combined microdrop, and then the combined microdrop is contacted with a microdrop comprising the candidate antimicrobial peptide (e.g., candidate bacteriocin). For example, in some embodiments, two or more different microdrops (comprising the same or different components) can be added to a microdrop comprising the antimicrobial peptide, so as to form the solution environment comprising the microbial organism. Without being limited by theory, it is contemplated that some microbial organisms can inhibit in vitro transcription and/or in vitro translation. Accordingly, in accordance with methods, systems, and kits of some embodiments herein, an antimicrobial peptide (such as a bacteriocin) is produced by in vitro transcription before it is put in a solution environment with a microbial organism. For example, an antimicrobial peptide (such as a bacteriocin) can be transcribed/translated in a microdrop in vitro, and then the antimicrobial peptidecan be contacted or mixed with a microdrop comprising the microbial organism.

Examples of culture conditions that can be selected in the solution environment of methods, microfluidic devices, and kits some embodiments include, but are not limited to temperature, pH, viscosity, osmolality, salinity, humidity, culture time, wind, air flow, and turbidity, or a combination of two or more of any of the listed items. It is noted that the culture conditions can be selected for a particular setpoint (e.g., hold at or about 37° C.), threshold (e.g., no higher than 37° C.), or range (e.g., 0-37° C.). Examples of selected culture conditions of a solution environment include room temperature, body temperature, standard temperature and pressure, acidic conditions, alkaline conditions, pH (e.g., neutral pH), viscosity, salinity, humidity, darkness, turbidity, or a combination of two or more of any of the listed items. In some embodiments, the culture conditions comprise the presence of one or more other microbial organisms, which may be of the same species as each other, the same species (but different strains) from each other, different species from each other, and/or a combination of any of these. In some embodiments, the culture conditions comprise the presence of a gene product, for example a protease. It is contemplated that proteases or other gene products in solution environments can inhibit or prevent antimicrobial peptides (such as bacteriocins) from functioning, and accordingly, it can be useful in some embodiments to engineer antimicrobial peptides that are resistant to protease(s) in an a solution environment that comprises one or more proteases. Similarly, it is contemplated that the solution environment may comprise other gene products that may affect antimicrobial peptide function, for example post-translational modification enzymes, and in some embodiments, it can be useful to engineer antimicrobial peptides that function in the presence of these gene products. Accordingly, in some embodiments, the solution environment contains one or more gene products (for example a protease and/or a post-translational modification enzyme), and antimicrobial peptides are engineered to inhibit the growth or reproduction of microbial organisms in the presence of the gene product.

Detecting Inhibition of Growth and/or Reproduction, or a Lack Thereof

Inhibition of Growth and/or Reproduction

In some embodiments of the methods, systems and kits described herein, a candidate antimicrobial peptide (such as a bacteriocin) and/or an engineered antimicrobial peptide (such as a bacteriocin) inhibits the growth and/or reproduction of a microbial organism (for example a microbial organism as described herein), in a solution environment under selected culture conditions. Inhibition of growth or reproduction has its customary and ordinary meaning as understood by one of skill in the art in view of this disclosure. It refers to a decrease in or arrest of proliferation of microbial organisms (or a decrease in the rate of proliferation of microbial organisms), for example, arrest of the cell cycle and/or killing of microbial organisms. In accordance with methods, systems, and kits of some embodiments herein, an inhibition of growth and/or reproduction of a microbial organism represents a quantity of microbial organisms, and/or a rate of growth of the microbial organisms that does not exceed a reference level. In some embodiments of the methods, systems and kits described herein, inhibition of growth comprises a quantity of a microbial organism remaining constant or decreasing over time. The decrease can be compared to a reference level from an earlier point in time.

In some embodiments, inhibition of growth comprises a decrease in the size or amount of the microbial organism. In some embodiments, inhibition of growth comprises a decrease in an organelle of the microbial organism, for example a chloroplast or mitochondrion. In some embodiments, inhibition of growth comprises killing the microbial organism, for example through lysis, apoptosis, and/or necrosis. In some embodiments, inhibition of reproduction of a microbial organism comprises a decrease or a cessation in the rate of cell division or cell doubling. In some embodiments, inhibition of reproduction of a microbial organism comprises a decrease or a cessation in an increase in an amount of the microbial organism.

Detecting Inhibition of Growth and/or Reproduction

Inhibition of growth and/or reproduction, or a lack thereof, of a microbial organism can be detected directly or indirectly via a number of suitable approaches and apparatuses in accordance with methods, microfluidic systems, and kits of some embodiments herein. By way of example, inhibition of growth or reproduction of one or more microbial organisms can indicate whether a candidate antimicrobial peptide (such as a bacteriocin) has a suitable activity in a particular solution environment under selected culture conditions in accordance with the methods, microfluidic systems and kits of some embodiments described herein. Detecting inhibition of growth and/or reproduction, or a lack thereof, can be performed by any number of suitable methods, for example as described herein.

In methods, kits, and microfluidic systems of some embodiments, inhibition of growth and/or reproduction is detected when a quantity, growth rate, or reproduction rate of a microbial organism is less than, or is less than or equal to a predetermined level. The predetermined level can be a reference point. For example, the predetermined level of some embodiments can be a growth rate or quantity of the microbial organism prior to culturing the microbial organism with the antimicrobial peptide (such as a bacteriocin). For example, the predetermined level of some embodiments can be or the growth rate or quantity of a control microbial organism that is cultured in a control solution environment under the selected culture conditions in the absence of the candidate antimicrobial peptide (and/or in the presence of a sham antimicrobial peptide such as a sham bacteriocin that is known to be inactive). In some embodiments, the predetermined level of inhibition of growth and/or reproduction of the microbial organism in the solution environment under the selected culture conditions is a greater level of inhibition than that of a reference naturally-occurring or engineered antimicrobial peptide (such as an engineered bacteriocin) in a corresponding control solution environment containing the same microbial organism under the same culture conditions.

In accordance with the methods, systems and kits of some embodiments described herein detecting inhibition of growth and/or reproduction, or a lack thereof, of the microbial organism comprises quantifying the microbial organism in the solution environment. A decrease (or arrest) in a quantity of the microbial organism in the solution environment over a period of time can indicate inhibition of growth and/or reproduction of the microbial organism. Quantifying the microbial organism may be performed by any method known in the art. In some embodiments of the methods, systems and kits described herein, quantifying the microbial organism comprises detecting and/or measuring the light absorbance of a bacterial culture. In some embodiments, the quantity of the microbial organism is detected by measuring an optical density with a spectrophotometer (for example at $OD_{600}$). In some embodiments, quantifying the microbial organism comprises determining the amount of a microbial marker such as a protein, RNA sequence or DNA sequence. For example, in some embodiments, quantifying the microbial organism comprises performing RNA or DNA sequencing or qPCR. In some embodiments, quantifying the microbial organism comprises optically, chemically, and/or electromagnetically quantifying the marker (for example, by performing an immunoassay, by performing an enzymatic assay, via chromatography, via mass spectrometry, or the like). In some embodiments, quantifying the microbial organism comprises visually detecting the microbial organism. In some embodiments, a detector such as an optical sensor detects inhibition of growth and/or reproduction, or a lack thereof, of a microbial organism as described herein.

Sequencing Candidate Nucleic Acids, Indexing, and Variant Antimicrobial Peptides In accordance with the methods, systems and kits of some embodiments described herein, candidate nucleic acids are sequenced. Sequencing candidate nucleic acids can facilitate the selection of variant antimicrobial peptides (such as bacteriocins) and variant nucleic acids as described herein. Sequencing can be performed by any method known in the art, for example chain termination sequencing (which may also be referred to as "Sanger sequencing"), and/or next generation sequencing using a platform such as Roche 454, Illumina Solexa, ABI-SOLiD, Ion Torrent, Complete Genomics, Pacific Bioscience, Helicos, and/or the Polonator platform. In methods, microfluidic systems, and kits of some embodiments, sequencing comprises chain termination sequencing, pyrosequencing, sequencing by synthesis, sequencing by ligation, nanopore sequencing, ion semiconductor sequencing or single-molecule real-time sequencing.

It is further contemplated that as successive rounds of culturing and detection are performed on candidate antimicrobial peptides (such as candidate bacteriocins) and/or variant antimicrobial peptides (such as variant bacteriocins), structural features of the candidate antimicrobial peptides and/or variant antimicrobial peptides that positively (or negatively) correlate with inhibition of growth of a microbial organism in a solution environment under selected culture conditions can guide the design of variant antimicrobial peptides such as variant bacteriocins (and thus variant nucleic acids) having desired activity. By way of example, data can be collected and indexed through successive iterations of engineering candidate nucleic acids, and automated machine learning can identify structures such as domains and structural motifs that correlate with desired inhibition of growth or reproduction (and can be included). For example, as discussed herein, certain domains and motifs have shown to be correlates of certain antimicrobial peptide (e.g., bacteriocin) activities, for example the motif YGXGV motif associated with the N-termini of class IIa bacteriocins. By way of example, domains and structural motifs that negatively correlate with desired inhibition of growth or reproduction can be avoided.

Accordingly, methods, systems and kits of some embodiments described herein comprise indexing or correlating the sequence of a candidate nucleic acid with inhibition of growth and/or reproduction, or a lack thereof, of a microbial organism. As such, structure-function correlations can be identified, which can guide the selection of variant antimicrobial peptides (such as variant bacteriocins). By way of example, particular classes of amino acids (e.g., hydrophobic, hydrophilic) and particular positions or ranges of positions, or known or canonical structural domains or motifs can be correlated with inhibition of growth or reproduction. In some embodiments, a candidate antimicrobial peptide (e.g., candidate bacteriocin) that yields inhibition of growth or reproduction that meets or exceeds a particular threshold can be aligned (for example using a ClustalW tool), and consensus sequences can be identified. As such, in accordance with methods and microfluidic systems and kits of some embodiments, a sequence of a selected candidate nucleic acid (encoding a candidate antimicrobial peptide that yields detection of inhibition of growth or reproduction of the microbial organism in the solution environment under the selected culture conditions) can be obtained. The sequence can be indexed to the detected inhibition of growth and/or reproduction of the microbial organism in a solution environment. Based on the sequence, one or more variant antimicrobial peptides (such as variant bacteriocins) can be identified (as described herein), and a variant nucleic acid encoding the variant antimicrobial peptide (such as a variant bacteriocin) as described herein can be produced.

In accordance with the methods, systems and kits of some embodiments described herein, designing a variant antimicrobial peptide (such as a variant bacteriocin)(and therefore producing a variant nucleic acid sequence) based on the indexed sequence information comprises machine learning, such as automated machine learning.

Variant nucleic acids in accordance with methods, systems, and kits of some embodiments herein can be performed by any suitable method known in the art, for example chemical synthesis, or mutagenesis of a candidate nucleic acid. In some embodiments, the variant nucleic acid is immobilized on a substrate such as a bead as described herein.

In methods, systems and kits of some embodiments, producing a variant nucleic acid comprises one or more of amplifying a selected candidate nucleic acid with a degenerate polymerase; amplifying the selected candidate nucleic acid in the presence of a degenerate primer; amplifying the selected candidate nucleic acid in the presence of a degenerate nucleotide; and a mutagenesis reaction on the selected candidate nucleic acid.

In some embodiments, producing the variant nucleic acid comprises chemical synthesis of the variant nucleic acid. In some embodiments, the chemical synthesis comprises synthesis with random nucleotides. In some embodiments, the chemical synthesis produces a specified sequence, for example a variant nucleic acid designed based on indexing the sequence of a candidate nucleic acid to inhibition of growth and/or reproduction as described herein. The specified variant nucleic acid sequence of some embodiments is designed by automated machine learning. In some embodiments, the variant nucleic acid is codon-optimized. In some embodiments, producing the variant nucleic acid comprises degenerate or mutagenesis replication or amplification of a candidate nucleic acid. In some embodiments, producing the variant nucleic acid comprises mutating a candidate nucleic acid, for example using ionizing radiation, a chemical mutagen such as an intercalating agent, or via incorporation of a synthetic nucleotide. In some embodiments, the mutagen reacts with the candidate nucleic acid and results in mutations upon replication or amplification of the candidate nucleic acid. In some embodiments, the mutagen interacts with a polymerase or a reagent involved in the replication or amplification of the candidate nucleic acid, and thereby causes the polymerase to insert incorrect nucleic acids during the replication or amplification, and results in the variant nucleic acid. In some embodiments, a degenerate polymerase produces replicates of a candidate nucleic acid that include variations.

In methods, systems and kits of some embodiments, the candidate nucleic acid or the variant nucleic acid is transcribed and translated via in vitro translation. In methods, systems and kits of some embodiments, the candidate nucleic acid or the variant nucleic acid is inserted into a vector for cellular or cell-free transcription and translation. In some embodiments, the vector is cultured to produce quantities of the candidate nucleic acid or the variant nucleic acid. Some embodiments comprise harvesting and/or isolating the quantities of the candidate nucleic acid and/or variant nucleic acid produced by the vector. In some embodiments, the vector is configured to express a candidate antimicrobial peptide (such as a candidate bacteriocin) from the candidate nucleic acid or an engineered antimicrobial peptide (such as an engineered bacteriocin) from the variant nucleic acid. In some embodiments, the candidate antimicrobial peptide (e.g., candidate bacteriocin) or the engineered antimicrobial peptide (e.g., engineered bacteriocin) encoded by the vector is harvested or isolated from the vector. In some embodiments, the vector comprises bacteria such as *E coli*. Thus, some embodiments comprise growing up quantities of a candidate nucleic acid or a variant nucleic acid in a vector such as bacteria, and isolating the candidate nucleic acid, the variant nucleic acid, a candidate antimicrobial peptide (e.g., candidate bacteriocin) produced by the candidate nucleic acid, or an engineered antimicrobial peptide (e.g., engineered bacteriocin) produced by the variant nucleic acid, from the vector.

Methods of Engineering Antimicrobial Peptides

In some embodiments, a method of engineering an antimicrobial peptide is provided. For example, the method may include engineering an antimicrobial peptide to have a desired range of activity in a desired range of culture conditions. In some embodiments, one or more of the methods of engineering an antimicrobial peptide (e.g., bacteriocin) are performed on a microfluidic system as described herein, and/or using components of a kit as described herein.

In some embodiments, the method comprises translating a candidate nucleic acid to produce a candidate antimicrobial peptide (e.g., candidate bacteriocin), culturing the candidate antimicrobial peptide with a microbial organism in a solution environment, and detecting inhibition of growth and/or reproduction (or a lack thereof) of the microbial organism. Portions of, or all of the method can be repeated on successive variants of candidate antimicrobial peptides (e.g., candidate bacteriocins) until a candidate antimicrobial peptide exhibiting a desired inhibition of growth and/or reproduction is identified, which can represent an engineered antimicrobial peptide (e.g., engineered bacteriocin).

In some embodiments, a method of engineering an antimicrobial peptide (e.g., bacteriocin) is provided. The method can comprise (a) translating a candidate nucleic acid encoding a candidate antimicrobial peptide (e.g., bacteriocin) in vitro in a translation solution, whereby the translation solution comprises the candidate antimicrobial peptide (e.g., bacteriocin), (b) combining the candidate antimicrobial peptide (e.g., bacteriocin) and a microbial organism in a solution environment, (c) culturing the microbial organism and the candidate antimicrobial peptide (e.g., bacteriocin) in the solution environment under selected culture conditions, (d) detecting inhibition of growth and/or reproduction, or a lack thereof, of the microbial organism in the solution environment, (e) selecting the candidate nucleic acid upon detection of inhibition of growth and/or reproduction of the microbial organism in the solution environment under the selected culture conditions, (f) producing a variant nucleic acid of the selected candidate nucleic acid, the variant nucleic acid encoding a variant of the candidate antimicrobial peptide (e.g., bacteriocin). Steps (a)-(f) can be repeated using one or more successive variant nucleic acids as the candidate nucleic acid, until a predetermined level of inhibition of growth and/or reproduction of the microbial organism in the solution environment under the selected culture conditions is achieved, whereby the antimicrobial peptide (e.g., bacteriocin) has been engineered.

FIG. 1 is a flow diagram illustrating a method of engineering an antimicrobial peptide (e.g., bacteriocin) according to some embodiments herein. The method can comprise (a) translating a candidate antimicrobial peptide (e.g., candidate bacteriocin) encoding an antimicrobial peptide (e.g., candidate bacteriocin) in vitro in a translation solution, so that the translation solution thus comprises the candidate antimicrobial peptide (e.g., candidate bacteriocin) 105. The method can comprise (b) combining the candidate antimicrobial peptide (e.g., candidate bacteriocin) and a microbial organism in a solution environment 110, for example by mixing microdroplets comprising the candidate antimicrobial peptide (e.g., candidate bacteriocin) and microbial organism, respectively to form a microdroplet of the solution environment. The method can comprise (c) culturing the microbial organism and the candidate antimicrobial peptide (e.g., candidate bacteriocin) in the solution environment under selected culture conditions 115 as described herein, for example temperature, pH, nutrient content, microbiota flora, in vivo conditions, and/or industrial feedstock. The method can comprise (d) detecting inhibition of growth and/or reproduction, or a lack thereof, of the microbial organism in the solution environment 120. The detecting can be performed as described herein. The method can comprise (e) selecting the candidate nucleic acid when the quantity of microbial organism in the solution environment indicates inhibition of growth and/or reproduction of the microbial organism in the solution environment under the selected culture conditions 125, for example if the quantity of, or growth rate of the microbial organism does not exceed a reference level as described herein. The method can comprise (f) producing a variant nucleic acid of the selected candidate nucleic acid, the variant nucleic acid encoding a variant of the candidate antimicrobial peptide 130, for example by chemical synthesis, and/or by mutagenesis or degenerate polymerase as described herein. The method can comprise comparing the detected inhibition of growth and/or reproduction, or a lack thereof, to a predetermined level of inhibition of growth and/or reproduction 135. If the predetermined level of inhibition of growth and/or reproduction of the microbial organism in the solution environment under the selected culture conditions is again not achieved 140, the method can comprise repeating the cycle 145 using a different candidate antimicrobial peptide (e.g., different candidate bacteriocin). In some embodiments, the sequence of the different candidate antimicrobial peptide (e.g., different candidate bacteriocin) is selected based on indexing the sequence information of the candidate antimicrobial peptide to the detected of inhibition of growth and/or reproduction (or the lack thereof) for the microbial organism. If the predetermined level of inhibition of growth and/or reproduction of the microbial organism in the solution environment under the selected culture conditions is achieved 150, the method can indicate that a desired antimicrobial peptide (e.g., bacteriocin) has been engineered 155. In some embodiments, the cycle is repeated 145 using iteratively different candidate antimicrobial peptides (e.g., different candidate bacteriocins) until the predetermined level of inhibition of growth and/or reproduction of the microbial organism in the solution environment under the selected culture conditions is achieved 150. This result can indicate that the desired antimicrobial peptide (e.g., bacteriocin) has been engineered 155. In some embodiments, one or more of the steps is performed in a different order than is shown, one or more additional steps are added, or one or more step is omitted. For example, in some embodiments, (e) is omitted.

In some embodiments, the method comprises producing the variant nucleic acid based on the indexed sequence of the candidate nucleic acid. It is contemplated that such indexing can advantageously identify antimicrobial peptide (e.g., bacteriocin) structures that positively (or negatively) correlate with inhibition of growth and/or reproduction of a microbial organism in a solution environment, and thus can guide the selection of variants of candidate antimicrobial peptides (e.g., bacteriocins) so as to select sequences, motifs, and/or other structures that are predicted to yield enhanced inhibition of growth and/or reproduction of the microbial organism in the solution environment. Accordingly, with continued reference to FIG. 1, some embodiments of the method comprise one or more optional steps 160. In some embodiments, a sequence of the selected candidate nucleic acid is obtained 165. In some embodiments, the sequence is obtained 165 after (f) 130. In some embodiments, the method comprises indexing the sequence to the detected inhibition of growth and/or reproduction of the microbial organism in the solution environment of (d) 170. The indexing can be performed as described herein, for example using a processor as described herein. In some embodiments, (f) comprises producing the variant nucleic acid based on the indexed sequence of the candidate nucleic acid 175. The variant nucleic acid can be produced as described herein, for example by chemical synthesis of a variant nucleic acid encoding a specified variant of a candidate antimicrobial peptide (e.g., bacteriocin). Accordingly, in some embodiments, the producing the selecting of the sequence of the variant candidate antimicrobial peptide (e.g., bacteriocin) (and the variant nucleic acid sequence) is based on the indexed sequence information comprises machine learning, such as automated machine learning.

It is further contemplated that sequences of candidate antimicrobial peptides (e.g., bacteriocin) that do not yield inhibition of growth and/or reproduction of the microbial organism in the sequence environment (or that yield inhibition of growth and/or reproduction that falls short of a predetermined level) can inform the selection of variants of candidate antimicrobial peptides (e.g., bacteriocin). In accordance with some embodiments, the method comprises obtaining the sequence of an other candidate nucleic acid (encoding an other candidate antimicrobial peptide) for which was detected a lack of inhibition of growth and/or reproduction of the microbial organism in another solution environment under the selected culture conditions (in addition to an absence of inhibition of growth and/or reproduction, this method also contemplates other candidate nucleic acids for which inhibition of growth and/or reproduction of the microbial organism is less than that of the candidate nucleic acid, and/or falls short of a predetermined level). The method can further comprise indexing the sequence of the other candidate nucleic acid to the lack of inhibition of growth and/or reproduction of the microbial organism. In accordance with this method, producing a variant nucleic acid comprises producing the variant nucleic acid of the selected candidate nucleic acid based on the indexed sequence of the other candidate nucleic acid. Thus, the inhibition of growth and/or reproduction, or a lack thereof, is indexed, and the indexed information is used to produce a variant nucleic acid. In some embodiments the sequence of the other candidate nucleic acid is obtained if the other candidate nucleic acid produces a lower level of inhibition of growth and/or reproduction of the microbial organism in the solution environment under the selected culture conditions than the candidate nucleic acid. In some embodiments, producing the variant nucleic acid comprises one or more of amplifying the selected candidate nucleic acid with a degenerate polymerase; amplifying the selected candidate nucleic acid in the presence of a degenerate primer; amplifying the selected candidate nucleic acid in the presence of a degenerate nucleotide; and mutagenesis reaction on the selected candidate nucleic acid.

It is further contemplated that if a candidate antimicrobial peptide (e.g., bacteriocin) is determined to yield a suitable inhibition of reproduction and/or growth of the microbial organism in the solution environment, the method of some embodiments can further comprise confirming the inhibition of reproduction and/or growth by repeating at least portions of the method using the same candidate antimicrobial peptide (e.g., bacteriocin). In some embodiments, the method comprises confirming the inhibition of growth and/or reproduction of the microbial organism in the solution environment by the candidate antimicrobial peptide (e.g., bacteriocin) after (e). The confirming can comprise repeating (a)-(d) for the candidate nucleic acid or a copy thereof. The inhibition of growth and/or reproduction can be confirmed when, in the repeat of (d), the quantity of microbial organism in the solution environment indicates inhibition of growth and/or reproduction of the microbial organism in the solution environment under the selected culture conditions.

In accordance with the methods, systems and kits of some embodiments described herein, an engineered antimicrobial peptide (e.g., bacteriocin) and a candidate antimicrobial peptide (e.g., bacteriocin) of an early iteration of a method as described herein each have a potency. A "potency" refers to an amount by which the engineered antimicrobial peptide (e.g., bacteriocin) or candidate antimicrobial peptide (e.g., bacteriocin) inhibits growth and/or reproduction of a microbial organism, for example a change in growth or reproduction rate, or a change in the number of microbial organisms in the solution environment. In some embodiments, the potency of the engineered antimicrobial peptide (e.g., bacteriocin) is greater than the potency of the candidate antimicrobial peptide (e.g., bacteriocin) (from an earlier iteration of the method). In some embodiments, the engineered antimicrobial peptide (e.g., bacteriocin) has a greater potency than the candidate antimicrobial peptide (e.g., bacteriocin) across a range of culture conditions and/or against a range of microbial organism strains and/or species.

It is contemplated that many industrial, pharmaceutical, cosmetic, and microbiota environments will contain more than one type of microbial organism that can be regulated. Accordingly, in methods, systems, and kits of some embodiments, the candidate antimicrobial peptide (e.g., bacteriocin) inhibits the growth and/or reproduction of more than one type of microbial organism, such as more than one species and/or strain of microbial organism. It is further contemplated that it can be desirable in many industrial, pharmaceutical, cosmetic, and microbiota environments to inhibit the growth and/or reproduction of one or more kinds of undesired microbial organisms (e.g., pathogenic and/or contaminating strains and/or species), while preserving one or more microbial organisms unaffected by the antimicrobial peptides (e.g., bacteriocin) (e.g., commensal, industrially useful, and/or otherwise desirable microbial organisms may be preserved). Accordingly, in some embodiments, the candidate antimicrobial peptide (e.g., bacteriocin) does not inhibit the growth and/or reproduction of one or more microbial organisms in the solution environment. In some embodiments, the candidate antimicrobial peptide (e.g., bacteriocin) inhibits the growth and/or reproduction of at least one type of microbial organism in the solution environment, but does not inhibit the growth and/or reproduction of one or more other types of microbial organisms in the solution environment. In some embodiments, one candidate antimicrobial peptide (e.g., bacteriocin) inhibits the growth and/or reproduction of a microbial organism, and another candidate antimicrobial peptide (e.g., bacteriocin) does not inhibit the growth and/or reproduction of the microbial organism. In some embodiments, a candidate antimicrobial peptide (e.g., bacteriocin) inhibits the growth and/or reproduction of a microbial organism, but does not inhibit the growth and/or reproduction of a second microbial organism.

In some embodiments of the method one or more portions of the method are repeated and/or performed in a different order than is shown in FIG. 1. In some embodiments of the method, (b) is repeated. In some embodiments of the method, repeating (b) of (a)-(f) comprises combining the translation solution with a different strain or species of microbial organism than that of a previous iteration of (b). For example, it may be desired to engineer an antimicrobial peptide (e.g., bacteriocin) to be effective against one microbial organism and also another microbial organism. In some embodiments, repeating (b) of (a)-(f) comprises combining the translation solution with the same species or strain of microbial organism as a previous iteration of (b). For example, multiple iterations of the method to produce and test multiple variant candidate antimicrobial peptides (e.g., variant candidate bacteriocins) may result in an engineered antimicrobial peptide (e.g., engineered bacteriocins) with enhanced properties against a microbial organism compared to just one iteration of (a)-(f). In some embodiments, (c) is repeated. In some embodiments, repeating (c) of (a)-(f) comprises culturing the microbial organism in a different solution environment and/or under different culture conditions than a previous iteration of (c). For example, it may be desired to engineer an antimicrobial peptide (e.g., bacteriocin) to be effective in multiple solution environments. In some embodiments, repeating (c) of (a) (f) comprises culturing the microbial organism in the same culture environment as a previous iteration of (c).

In some embodiments of the method, the candidate nucleic acid comprises DNA. In some embodiments, the method comprises transcribing the candidate nucleic acid (e.g., DNA). The candidate nucleic acid can be transcribed in a transcription solution as described herein. In the method of some embodiments, the translation solution comprises a transcription solution, in which the translation solution is configured for transcription and translation of the candidate nucleic acid (e.g., DNA). In the method of some embodiments, the translation solution comprises a translation reagent, such as a ribosome. In the method some embodiments, the translation solution comprises one or more post-translational modification enzymes. In some embodiments, the translation solution further comprises a substrate, and the candidate nucleic acid is immobilized on the substrate. In the method of some embodiments, the translation solution and/or the solution environment is microliter-scale. In the method of some embodiments, the translation solution and/or the solution environment has a volume of 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl. In some embodiments, the solution environment is a microdrop. In methods, kits, and systems of some embodiments, the solution environment is hydrophilic. In methods, kits, and systems of some embodiments, the solution environment is hydrophobic. In methods, kits, and systems of some embodiments, the solution environment comprises a hydrogel. In methods, kits, and systems of some embodiments, the solution environment is hydrophilic. In methods, kits, and systems of some embodiments, the solution environment does not comprise any cells comprising nucleic acid encoding the antimicrobial peptide.

It is further contemplated that in methods, kits, and systems of some embodiments, two or more antimicrobial peptides (e.g., bacteriocin) are co-engineered to inhibit growth and/or reproduction of the microbial organism under the selected culture conditions. In some embodiments of the method, the candidate nucleic acid encodes two or more different candidate antimicrobial peptides (e.g., candidate bacteriocins) so that a cocktail of candidate antimicrobial peptides is encoded. For example, the two or more different candidate nucleic acids can each have their own promoter, and/or the downstream candidate nucleic acid can contain an IRES, and/or the candidate nucleic acid can comprise a sequence encoding 2A or a proteolytic site between the sequences encoding the candidate antimicrobial peptides (e.g., candidate bacteriocins). Accordingly, the solution environment in the method, system, and/or kit of some embodiments can comprise two or more candidate antimicrobial peptides (e.g., candidate bacteriocins). Additionally, the variant nucleic acid can encode variants of at least one of the two or more candidate antimicrobial peptides (e.g., bacteriocin), for example both of the candidates. Thus, two or more antimicrobial peptides (e.g., bacteriocin) can be co-engineered to inhibit growth and/or reproduction of the microbial organism under the selected culture conditions. For example, more than one candidate nucleic acids may be co-engineered together to have synergistic effects. In some embodiments, the translation solution comprises no more than one candidate nucleic acid sequence encoding a candidate antimicrobial peptide (e.g., bacteriocin). In some embodiments of the method, the candidate antimicrobial peptide (e.g., bacteriocin) comprises a chimeric protein.

In some embodiments of the method, a candidate nucleic acid is immobilized on a substrate, for example a bead as described herein. Example of suitable substrates suitable for methods, systems, and kits of some embodiments include a bead, nanoparticle, well, membrane, nitrocellulose, PVDF, nylon, acetate derivative, matrix, pore, plastic, metal, glass, polymer, polysaccharide, or paramagnetic compound. In some embodiments, the method comprises immobilizing the candidate nucleic acid on the substrate. In some embodiments, the method comprises producing the variant nucleic acid immobilized on another substrate, which this is the same as, or different from the substrate that the candidate nucleic is or was immobilized on.

In some embodiments of the method, a library of candidate nucleic acids is screened. For example, two or more candidate nucleic acids of a library can be screened in parallel (for example, in different microfluidic devices, or in different portions of the same microfluidic device), and/or can be screened in serial (for example, on the same microfluidic devices, one-at-a-time). In some embodiments, producing the variant nucleic acid comprises producing a library of variant nucleic acids, and the method further comprises performing (a)-(e) on the library of variant nucleic acids. For example, several antimicrobial peptides (e.g., bacteriocins) may be engineered at the same time, or several variant antimicrobial peptides (e.g., bacteriocins) may be tested at the same time, and one(s) that yield inhibition of growth and/or reproduction of a microbial organism are selected for producing variant nucleic acids. By way of example, in some embodiments, a library of candidate nucleic acids (or variant nucleic acids) comprises at least 5, 10, 100, 500, 1000, 5000, 10,000, 50,000, 100000 candidate nucleic acids (or variant nucleic acids).

In some embodiments, the method is performed in a microfluidic system as described herein.

Microfluidic Systems for Engineering Antimicrobial Peptides (e.g., Bacteriocins)

A microfluidic system can be useful to determine if a candidate antimicrobial peptide (e.g., bacteriocin) inhibits growth and/or reproduction of a microbial organism in a solution environment under selected culture conditions, and to engineer an antimicrobial peptide (e.g., bacteriocin) in accordance with some embodiments herein. In some embodiments, multiple components of the system work together to produce engineered antimicrobial peptides (e.g., bacteriocin) with desired activities that are tested in one or more of industrial, pharmaceutical, or physiological (e.g., microbiota) culture conditions.

In some embodiments, a microfluidic system for engineering an antimicrobial peptide (e.g., bacteriocin) is provided. In some embodiments, the microfluidic system comprises a transcription station configured to perform in vitro transcription of a candidate nucleic acid. The transcription station can comprise transcription reagent. The microfluidic system can further comprise a translation station in fluid communication with the transcription station. The translation station can be configured to perform in vitro translation. The translation station can further comprise a translation reagent. The system can further comprise a culture station in fluid communication with the translation station and configured to culture a microbial organism in a solution environment comprising the microbial organism, a candidate nucleic acid encoding a candidate antimicrobial peptide (e.g., candidate bacteriocin), and the candidate antimicrobial peptide. The culture can be under selected culture conditions as described herein. The system can further comprise a detector in fluid communication with the culture station. The detector can be configured to detect inhibition of growth and/or reproduction (or a lack thereof) of the microbial organism in the solution environment. The system can further comprise a variant station configured to produce a variant nucleic acid of the nucleic acid encoding the candidate antimicrobial peptide (e.g., candidate bacteriocin). The variant station is in fluid communication with the transcription station. In some embodiments, the variant station is in data communication with the detector (either directly, or via processor). Accordingly, the system (for example via the processor) can be configured to index (for example, via the processor) the sequence information to the detection of inhibition of growth and/or reproduction or the lack thereof for the microbial organism.

Figure 2:
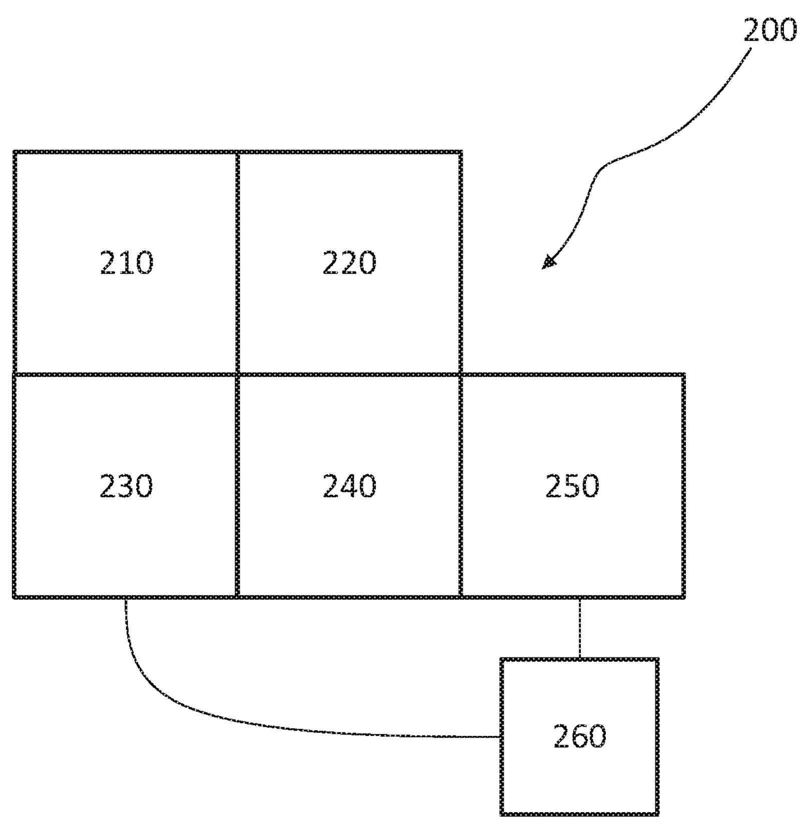
FIG. 2 is a schematic diagram of a system for engineering antimicrobial peptides (e.g., bacteriocins) according to some embodiments herein.

FIG. 2 is a schematic diagram of a system 200 for engineering antimicrobial peptides (e.g., bacteriocin) according to some embodiments herein. The system can comprise a transcription station 210 and/or a translation station 220 as provided herein (which can be comprised by a single transcription/translation station, or can be separate stations). The translation station 220 can be in fluid communication with the transcription station 210. The system can further comprise a culture station 240 as described herein. The culture station 240 can be in fluid communication with the translation station 220 (for example, directly, and/or via a transcription station). The system comprise a detector 250 as described herein. The detector 250 can be in fluid communication with the culture station 240, and can be configured to detect inhibition of growth and/or reproduction of a microbial organism, or a lack thereof. The system can further comprise a variant station 230 in fluid communication with the transcription station 210 and/or translation station 220. In some embodiments, the variant station comprises a sequencing module as described herein. The system of some embodiments further comprises a processor 260. In some embodiments, the processor 260 is in data communication with the detector 250 and/or the variant station 230. For example, the processor can be configured to index sequence information of a candidate antimicrobial peptide (e.g., bacteriocin) to the detection of inhibition of growth and/or reproduction or the lack thereof for the microbial organism as described herein. In some embodiments, the detector 250 detects inhibition of growth or reproduction of the microbial organism in the solution environment in the culture station 240. In some embodiments, the detector 250 detects inhibition of growth or reproduction of the microbial organism at a location outside of the culture station 240. In some embodiments, the microfluidic system comprises a microdrop system, and is configured to move mircrodrops comprising candidate nucleic acids, candidate antimicrobial peptides (e.g., bacteriocin) and/or microbial organisms to the applicable station(s), and/or to move the applicable station(s) to the microdrop. In some embodiments, the microfluidic system comprise a microfluidic channel, for example a network of microfluidic channels.

In some embodiments, two or more of the transcription station, the translation station, the culture station, and/or the variant station are comprised within discrete chambers that are separate from each other. In some embodiments, the transcription station and the translation station are the same station or overlap with each other (e.g., a single transcription/translation station). In some embodiments, two or more of the transcription station, the translation station, the culture station, and the variant station, are comprised within a single chamber. Optionally, the single chamber can be configured to expel a first set of reagents and subsequently receive a second set of reagents that is different from the first set so that a single location can be used for two or more functions (for example, transcription and translation, and/or culture and detection).

Transcription Stations

Some embodiments of the microfluidic system comprise a transcription station. In some embodiments, the transcription station is configured to perform in vitro transcription. In some embodiments, the transcription station comprises a transcription solution as described herein. In some embodiments, the transcription station comprises one or more transcription reagents. In some embodiments, the transcription station is part of a single transcription/translation station. In some embodiments, the transcription station is the same station as the translation station. In some embodiments, the transcription station is separate from the translation station, for example separated by a wall, barrier, valve, or the like.

Translation Stations

The microfluidic system of some embodiments comprises a translation station. In some embodiments, the translation station is configured to perform in vitro translation of a candidate nucleic acid encoding a candidate antimicrobial peptide (e.g., candidate bacteriocin). In some embodiments, the translation station comprises a translation solution as described herein. In some embodiments, the translation station comprises one or more translation reagents. In some embodiments, the translation station comprises one or more post-translational modification enzymes.

In some embodiments, the translation station is in fluid communication with a substrate comprising the candidate nucleic acid immobilized thereon, for example when variant nucleic acids are synthesized on a substrate in the variant station. In some embodiments, the substrate comprises a bead, nanoparticle, well, membrane, nitrocellulose, PVDF, nylon, acetate derivative, matrix, pore, plastic, metal, glass, polymer, polysaccharide, or paramagnetic compound.

In some embodiments, the translation station comprises a chamber (e.g., an in vitro translation chamber) that is microliter-scale and/or the solution environment is microliter-scale. In some embodiments, the chamber of the translation station has a volume of about 1 μl-1000 μl, 1 μl-50 μl, 1 μl-100 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl.

In some embodiments, the translation station comprises a mixture of different candidate antimicrobial peptides (e.g., candidate bacteriocins).

Culture Stations

Some embodiments of the microfluidic system comprise a culture station. In some embodiments, the culture station is configured to culture one or more microbial organisms in a culture environment under selected culture conditions as described herein, for example conditions of an industrial process, chemical or pharmaceutical manufacturing process, fermentation process, and/or a microbiota (such as a mammalian microbiota). In some embodiments, the culture station comprises a solution environment as described herein. In some embodiments, the culture station is configured to culture a microbial organism in a solution environment. In some embodiments, the solution environment comprises the microorganism, a candidate nucleic acid encoding a candidate antimicrobial peptide (e.g., candidate bacteriocin), and the candidate antimicrobial peptide under selected culture conditions.

In some embodiments, the selected culture conditions of the culture station comprise conditions of an industrial process, pharmaceutical manufacturing process, or microbiota (e.g., mammalian microbiota) as described herein.

In some embodiments, the solution environment in the culture station has a volume of about 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl. In some embodiments, the solution environment is a microdrop.

Detectors

The microfluidic system of some embodiments comprises a detector as described herein. The detector can be configured to detect inhibition of growth and/or reproduction of a microbial organism in solution environment as described herein. In some embodiments, the detector comprises an optical detector such as a spectrophotometer. The spectrophotometer can be configured to measure an optical density (for example at $OD_{600}$), which can indicate an amount (and/or rate of change in an amount) of microbial organisms in the solution environment. In some embodiments, the detector comprises a camera. In some embodiments, the detector is in fluid communication with a culture station as described herein. In some embodiments, the detector is configured to detect inhibition of growth and/or reproduction of a microbial organism in a culture station as described herein. In some embodiments, the detector is configured to detect growth and/or reproduction of a microbial organism in a culture station as described herein, but is not in fluid communication with the culture station. In some embodiments, the detector is configured to detect a lack of growth and/or reproduction of a microbial organism in a culture station. In some embodiments, the detector is configured to detect inhibition of growth and/or reproduction, or a lack thereof, of a microbial organism in a culture station. In some embodiments, the detector is connected to a processor.

Variant Stations

The microfluidic system of some embodiments comprises a variant station. In some embodiments, the variant station is configured to produce a variant nucleic acid of a nucleic acid encoding a candidate antimicrobial peptide (e.g., bacteriocin) as described herein. In some embodiments, the variant station is in data communication with a processor as described herein. The variant station can produce a selected variant nucleic acid encoding a variant of the candidate antimicrobial peptide (e.g., bacteriocin) based on an index of sequence information of the candidate antimicrobial peptide (e.g., bacteriocin) to inhibition of growth and/or reproduction of the microbial organism (or a lack thereof). The indexing can be performed by a processor as described herein. In some embodiments, the variant station is configured to perform a mutagenesis reaction to produce the variant nucleic acid. In some embodiments, the variant station comprises a degenerate polymerase, a degenerate primer, and/or a degenerate nucleotide, which can produce the variant nucleic acid.

In some embodiments, the variant station comprises a sequencing module configured to obtain sequence information from a candidate nucleic acid. The sequencing module can perform sequencing as described herein. In some embodiments, the microfluidic system is configured to index the sequence information to a detection of inhibition of growth and/or reproduction or the lack thereof for a microbial organism in the solution environment. In some embodiments, the microfluidic system is configured to select a sequence of the variant nucleic acid based on the indexed information by machine learning, for example automatic machine learning. In some embodiments, a processor is configured to index the sequence information, and/or select the sequence of the variant nucleic acid (for example, based on a selected sequence of a variant of the candidate antimicrobial peptide (such as a candidate bacteriocin).

In some embodiments, the variant station produces the variant nucleic acid only if the detector detects an inhibition of growth and/or reproduction of the microbial organism in the solution environment.

Kits

In some embodiments, a kit for engineering an antimicrobial peptide (e.g., bacteriocin) is provided. In some embodiments, the kit comprises a candidate nucleic acid encoding a candidate antimicrobial peptide (such as a candidate bacteriocin), and a microfluidic system as described herein. In some embodiments, the kit comprises a library of candidate nucleic acids. In some embodiments, the kit comprises a microbial organism. In some embodiments, the kit further comprises instructions that the kit is to be used for engineering an antimicrobial peptide (e.g., bacteriocin).

Example 1—Screening and Selection of Variant Antimicrobial Peptides with Desired Properties A library of candidate nucleic acids comprising point mutations of a nucleotide sequence encoding wild-type microcin V bacteriocin (SEQ ID NO: 65) is engineered by the following method. The library is prepared by introducing point mutations in SEQ ID NO: 65 with a degenerate DNA polymerase. Each candidate nucleic acid of the library comprises a point mutations of SEQ ID NO: 65. Each candidate nucleic acid is transcribed and translated in vitro in a translation solution that includes reagents for in vitro transcription and in vitro translation. After the in vitro transcription and translation is complete, each translation solution is a microdrop of about 10 μl in volume, which comprises a candidate antimicrobial peptide (that is a variant of microcin V).

Each translation solution comprising a candidate antimicrobial peptide is combined with a microliter-scale solution environment inoculated with *Salmonella enterica*. The solution environment is designed to mimic an industrial process involved in the production of chicken broth, and contains chicken broth at room temperature and a pH of 7.2, with preservatives and additives specific to the chicken broth. Once combined, the microliter-scale solution environment containing the *Salmonella enterica* and candidate antimicrobial peptide is a microdrop having a volume of about 500 μl.

The solution environment is incubated at room temperature for 24 hours. *Salmonella* growth is monitored during the incubation period using a spectrophotometer, and a final measurement of *Salmonella* density is determined at the end of the incubation period. The measurements include a spectrophotometric reading at $OD_{600}$. The *Salmonella* growth rate in each solution environment is compared to *Salmonella* growth in a control solution environment that includes the wild-type microcin V antimicrobial peptide without any point mutations (encoded by SEQ ID NO: 65). Candidate nucleic acids encoding candidate antimicrobial peptides (e.g., bacteriocin) in solution environments with 50% or less of the *Salmonella* growth rate of the control solution environment.

The selected candidate nucleic acids are amplified by PCR with a degenerate DNA polymerase to produce variant nucleic acids. The variant nucleic acids are then transcribed and translated in vitro, and variant antimicrobial peptides (variant bacteriocins) produced by the in vitro transcription and translation of the variant nucleic acids are combined with solution environments containing *Salmonella enterica* and chicken broth. The variant nucleic acids and variant antimicrobial peptides (variant bacteriocins) are considered candidate nucleic acids and candidate antimicrobial peptides (candidate bacteriocins) in another round of screening selection. In another round of screening selection, the solution environments containing the new candidate antimicrobial peptides are incubated, and *Salmonella* growth is monitored as with the prior solution environments containing the prior candidate antimicrobial peptides (candidate bacteriocins), and the new candidate antimicrobial peptides (candidate bacteriocins) that limit *Salmonella* growth the most (for example by at least 75% compared to the control wild-type microcin V bacteriocin) are selected. By this method the microcin V bacteriocin is engineered to more effectively inhibit *Salmonella* growth. More rounds of making variants, and screening and selection are performed if desired to further engineer the antimicrobial peptide (bacteriocin) and enhance its properties.

Example 2-Engineering Antimicrobial Peptides with Machine Learning

A method similar to that of Example 1 is used to engineer the library of candidate nucleic acids comprising point mutations of the microcin V bacteriocin, except that machine learning is used to select and modify the bacteriocins. Additionally, the nucleotide sequence of each candidate nucleic acid is obtained by DNA sequencing.

The library is screened, and *Salmonella* growth is measured in each solution environment comprising a candidate antimicrobial peptides (candidate bacteriocins). A processor stores information relating to the *Salmonella* growth in each solution environment in a database. Information relating to the growth inhibition is stored for each candidate antimicrobial peptide (e.g., bacteriocin) regardless of the amount of growth inhibition it exerted on the *Salmonella*. The stored information is tabulated by the processor, and is indexed with the sequence information for each point mutation in microcin V. The indexing by the processor associates each point mutation with the detected level of growth inhibition (or lack thereof) for that point mutant. The processor performs structure function correlation, so as to select point mutations that yielded inhibition of growth and/or reproduction of the *Salmonella*, while avoiding those that did not. Thus, the processor selects variants of the candidate antimicrobial peptide (e.g., bacteriocin), and corresponding sequences of variant nucleic acids to be tested in further iterations of the screening. Some of the variant nucleic acids include multiple point mutations. Thus, the processor selects candidate antimicrobial peptide (e.g., bacteriocin) sequences by automated machine learning.

Variant nucleic acids with the sequences designed by the processor via machine learning are then chemically synthesized, and transcribed and translated in vitro to produce variant antimicrobial peptides (e.g., bacteriocins). The variant antimicrobial peptides (e.g., bacteriocin) produced by the in vitro transcription and translation are screened in solution environments containing *Salmonella*. The *Salmonella* growth is monitored, and a processor again performs a structure function-analysis based on the indexing of variant sequences to growth inhibition information for each variant. Information from the first analysis is used to inform this second structure function analysis, and thus the processor learns an optimized sequence for inhibiting *Salmonella* growth in the solution environment. Thus, the processor engineers a new antimicrobial peptide (e.g., bacteriocin) that is engineered to inhibit *Salmonella* growth in the solution environment under culture conditions of an industrially-relevant process.

Example 3—Microdroplet Apparatus for Screening and Selection of Variant Antimicrobial Peptides A kit containing a microfluidic system is provided. The microfluidic system comprises a microdroplet apparatus configured to perform in vitro transcription and translation of a candidate nucleic acid encoding a candidate antimicrobial peptide such as a candidate bacteriocin) on a bead in a first microdroplet. The microdroplet apparatus is configured to contact the first microdroplet (containing the translated candidate antimicrobial peptide such as a candidate bacteriocin) with a second microdroplet that includes a bacteria. Contacting the first microdroplet with the second microdroplet produces a combined microdroplet that comprises a culture environment comprising the combined contents of the first and second microdroplets. The microfluidic apparatus is configured to culture the third microdroplet for a period of time at selected culture conditions (for example 14 hours at 37° C.). The microdroplet device includes a detector configured to measure reproduction of the bacteria, or a lack thereof, in the third microdroplet. The microdroplet device includes a processor configured to receive and process information relating to the detected reproduction, or lack thereof. Thus, the microfluidic system is suitable for engineering an antimicrobial peptide (e.g., bacteriocin) in accordance with some embodiments herein.

In at least some of the embodiments described herein, one or more elements used in an embodiment can interchangeably be used in another embodiment unless such a replacement is not technically feasible. It will be appreciated by those skilled in the art that various other omissions, additions and modifications may be made to the methods and structures described herein without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more," or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed herein. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method of generating an antimicrobial peptide with a predetermined level of antimicrobial activity, the method comprising:

(1) providing a library of candidate nucleic acids encoding a plurality of candidate antimicrobial peptides;

(2) for each of the plurality of candidate antimicrobial peptides encoded by nucleic acids of the library, in a microfluidic device:

(a) translating a candidate nucleic acid encoding the candidate antimicrobial peptide from the library in vitro, thereby producing the candidate antimicrobial peptide; and (b) detecting antimicrobial activity, or a lack thereof, of the candidate antimicrobial peptide against a microbial organism under selected culture conditions, wherein the antimicrobial activity comprises inhibition of growth and/or reproduction of the microbial organism;

(3)

(a) obtaining the sequence of one or more of the translated candidate nucleic acids from the library for which antimicrobial activity of the encoded antimicrobial peptide is detected, and indexing the obtained sequences to the detected antimicrobial activity, and/or (b) obtaining the sequence of one or more of the translated candidate nucleic acids from the library for which a lack of antimicrobial activity of the encoded antimicrobial peptide is detected, and indexing the obtained sequences to the lack of antimicrobial activity;

(4) introducing one or more mutations or variations in one or more of the candidate nucleic acids of the library of candidate nucleic acids for which antimicrobial activity by the candidate antimicrobial peptide(s) encoded by the one or more candidate nucleic acids is detected, based on the indexed sequences of (3)(a) and/or based on the indexed sequence of (3)(b), to produce a library of variant nucleic acids, each of the variant nucleic acids encoding a variant antimicrobial peptide having a different sequence from the candidate antimicrobial peptide;

(5) for a plurality of variant antimicrobial peptides encoded by variant nucleic acids of the library of variant nucleic acids, in the microfluidic device:

(a) translating in vitro the variant nucleic acid encoding the variant antimicrobial peptide, thereby producing the variant antimicrobial peptide;

(b) detecting antimicrobial activity, or a lack thereof, of the variant antimicrobial peptide against the microbial organism under selected culture conditions, wherein the antimicrobial activity comprises inhibition of growth and/or reproduction of the microbial organism; and (6) performing one or more iterations of (3)-(5) using variant nucleic acids of the library of variant nucleic acids from an earlier iteration as the candidate nucleic acid in each successive iteration, and detecting a predetermined level of antimicrobial activity against the microbial organism under the selected culture conditions by one or more variant antimicrobial peptides, thereby generating an antimicrobial peptide with the predetermined level of antimicrobial activity, wherein the predetermined level of antimicrobial activity against the microbial organism under the selected culture conditions is a level of antimicrobial activity greater than a reference naturally-occurring antimicrobial peptide, a reference engineered antimicrobial peptide, or the antimicrobial activity detected in (2)(b).

2. The method of claim 1, wherein the generated antimicrobial peptide and the candidate antimicrobial peptide or the variant antimicrobial peptide of an earlier iteration of the method each have a potency, and wherein the potency of the generated antimicrobial peptide is greater than the potency of the candidate antimicrobial peptide and the potency of the variant antimicrobial peptide.

3. The method of claim 1, wherein the one or more iterations of (3)-(5) comprises detecting the antimicrobial activity, or a lack thereof, of the variant antimicrobial peptide against a different strain or species of microbial organism than that of (2)(b) or a previous iteration of (5)(b).

4. The method of claim 1, wherein the one or more iterations of (3)-(5) comprises detecting the antimicrobial activity, or a lack thereof, of the variant antimicrobial peptide in a different culture condition than (2)(b) or a previous iteration of (5)(b).

5. The method of claim 1, comprising, in (2)(a) transcribing a DNA molecule encoding the candidate nucleic acid in vitro to generate the candidate nucleic acid; and translating the transcribed candidate nucleic acid in vitro to produce the candidate antimicrobial peptide.

6. The method of claim 1, wherein the selected culture conditions replicate conditions of:

an industrial process selected from a feedstock, fermentation, food production, decomposition, waste neutralization, environmental remediation;

a pharmaceutical or cosmetic manufacturing process selected from chemical synthesis, tissue culture, extraction, isolation of chemical compounds, proportioning, and packaging; or a mammalian microbiota selected from microbiota of a gastrointestinal tract, skin, a mammary gland, a placenta, a tissue, a biofluid, a seminal fluid, a uterus, a vagina, an ovarian and B follicle, a lung, saliva, an oral cavity, a mucosa, a conjunctiva, and a biliary tract.

7. The method of claim 1, wherein the microbial organism comprises a bacterial organism.

8. The method of claim 1, wherein the antimicrobial peptide comprises a bacteriocin.

9. The method of claim 1, wherein detecting antimicrobial activity, or a lack thereof in (2)(b) comprises contacting a translation solution comprising the translated candidate antimicrobial peptide with a microdrop comprising the microbial organism.

10. The method of claim 1, wherein the translating in (2)(a) comprises translating the candidate nucleic acid encoding the candidate antimicrobial peptide in vitro in a translation solution, thereby producing the candidate antimicrobial peptide in the translation solution, wherein the translation solution comprises no more than one candidate nucleic acid sequence encoding the candidate antimicrobial peptide.

11. The method of claim 1, wherein the one or more mutations or variations introduced in one or more of the translated candidate nucleic acids comprises: a point mutation; a deletion; an insertion; a rearrangement; or any combination thereof.

12. The method of claim 1, wherein the variant antimicrobial peptide in a second or later iteration of (3)-(5) comprises a different sequence than the variant antimicrobial peptide of any earlier iteration.

13. The method of claim 1, comprising detecting antimicrobial activity, or a lack thereof, of the variant antimicrobial peptide in (5)(b) against the same microbial organism as the microbial organism against which antimicrobial activity, or a lack thereof, of the candidate antimicrobial peptide is detected in (2)(a).

14. The method of claim 1, wherein the selected culture conditions of (2)(b) and (5)(b) are the same.

15. The method of claim 1, wherein the predetermined level of antimicrobial activity against the microbial organism under the selected culture conditions is:

at least a 75% greater level of antimicrobial activity than a reference naturally-occurring or a reference engineered antimicrobial peptide;

at least a 50% greater level of antimicrobial activity than the candidate antimicrobial peptide, or the variant antimicrobial peptide in an earlier iteration; or inhibition of growth of the microbial organism under the selected culture conditions, if the candidate antimicrobial peptide does not inhibit growth of the microbial organism under the selected culture conditions.

* * * * *